US009725419B2

(12) United States Patent
Li et al.

(10) Patent No.: US 9,725,419 B2
(45) Date of Patent: Aug. 8, 2017

(54) CYCLOALKYL SUBSTITUTED PYRIMIDINEDIAMINE COMPOUNDS AND THEIR USES

(71) Applicant: Rigel Pharmaceuticals, Inc., South San Francisco, CA (US)

(72) Inventors: Hui Li, Santa Clara, CA (US); Ankush Argade, Foster City, CA (US); Rajinder Singh, Belmont, CA (US); Sambaiah Thota, Fremont, CA (US); David Carroll, San Francisco, CA (US); Kin Tso, San Francisco, CA (US); Vanessa Taylor, San Francisco, CA (US); John McLaughlin, San Francisco, CA (US); Vadim Markovtsov, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 793 days.

(21) Appl. No.: 13/757,262

(22) Filed: Feb. 1, 2013

(65) Prior Publication Data
US 2013/0210814 A1   Aug. 15, 2013

Related U.S. Application Data

(63) Continuation of application No. 12/951,949, filed on Nov. 22, 2010, now Pat. No. 8,410,093, which is a continuation of application No. 11/567,506, filed on Dec. 6, 2006, now Pat. No. 7,868,013, which is a continuation of application No. 11/133,419, filed on May 18, 2005, now Pat. No. 7,754,714.

(60) Provisional application No. 60/572,534, filed on May 18, 2004, provisional application No. 60/572,507, filed on May 18, 2004, provisional application No. 60/580,765, filed on Jun. 18, 2004, provisional application No. 60/628,496, filed on Nov. 15, 2004, provisional application No. 60/628,199, filed on Nov. 15, 2004, provisional application No. 60/650,195, filed on Feb. 3, 2005.

(51) Int. Cl.
| | | |
|---|---|---|
| C07D 403/12 | (2006.01) |
| A61K 31/505 | (2006.01) |
| C07D 239/48 | (2006.01) |
| A61K 31/506 | (2006.01) |
| C07D 205/12 | (2006.01) |
| C07D 239/42 | (2006.01) |
| C07D 401/12 | (2006.01) |
| C07D 405/12 | (2006.01) |
| C07D 413/12 | (2006.01) |
| C07D 487/08 | (2006.01) |
| C07D 295/155 | (2006.01) |
| C07D 417/12 | (2006.01) |
| C07D 471/08 | (2006.01) |

(52) U.S. Cl.
CPC .......... *C07D 239/48* (2013.01); *A61K 31/505* (2013.01); *A61K 31/506* (2013.01); *C07D 205/12* (2013.01); *C07D 239/42* (2013.01); *C07D 295/155* (2013.01); *C07D 401/12* (2013.01); *C07D 403/12* (2013.01); *C07D 405/12* (2013.01); *C07D 413/12* (2013.01); *C07D 417/12* (2013.01); *C07D 471/08* (2013.01); *C07D 487/08* (2013.01)

(58) Field of Classification Search
CPC .. C07D 239/42; C07D 239/48; C07D 401/12; C07D 403/12; A61K 31/505; A61K 31/506
USPC ...... 514/230.5, 252.19, 252.2, 275; 544/105, 544/295, 324
See application file for complete search history.

(56) References Cited

U.S. PATENT DOCUMENTS

| | | |
|---|---|---|
| 5,962,312 A | 10/1999 | Plowman et al. |
| 5,972,676 A | 10/1999 | Plowman et al. |
| 6,207,401 B1 | 3/2001 | Plowman et al. |
| 6,342,503 B1 | 1/2002 | Aldrich et al. |
| 6,593,326 B1 | 7/2003 | Bradbury et al. |
| 6,841,579 B1 | 1/2005 | Plowman et al. |
| 6,908,920 B2 | 6/2005 | Thomas et al. |
| 7,060,827 B2 | 6/2006 | Singh et al. |
| 7,173,028 B2 | 2/2007 | Dahmann et al. |
| 7,459,301 B2 | 12/2008 | Argade |
| 7,511,137 B2 | 3/2009 | Li |
| 7,858,633 B2 | 12/2010 | Li et al. |
| 7,868,013 B2 | 1/2011 | Li et al. |
| 2003/0139435 A1 | 7/2003 | Ahmed et al. |
| 2003/0162802 A1 | 8/2003 | Guo |

(Continued)

FOREIGN PATENT DOCUMENTS

| | | |
|---|---|---|
| WO | WO 95/10506 | 4/1995 |
| WO | WO 00/03032 | 1/2000 |

(Continued)

OTHER PUBLICATIONS

Caravajal et al., Aurora Kinases: New Targets for Cancer Therapy, Clin Cancer Res 2006:12(23), pp. 6869-6875, Dec. 1, 2006.*

(Continued)

*Primary Examiner* — Deepak Rao
(74) *Attorney, Agent, or Firm* — Travis Young; McDonnell Boehnen Hulbert & Berghoff LLP

(57) ABSTRACT

The present disclosure provides 2,4-pyrimidinediamine compounds having antiproliferative activity, compositions comprising the compounds and methods of using the compounds to inhibit cellular proliferation and to treat proliferate diseases such as tumorigenic cancers.

3 Claims, 4 Drawing Sheets

(56) References Cited

U.S. PATENT DOCUMENTS

Figure 1:
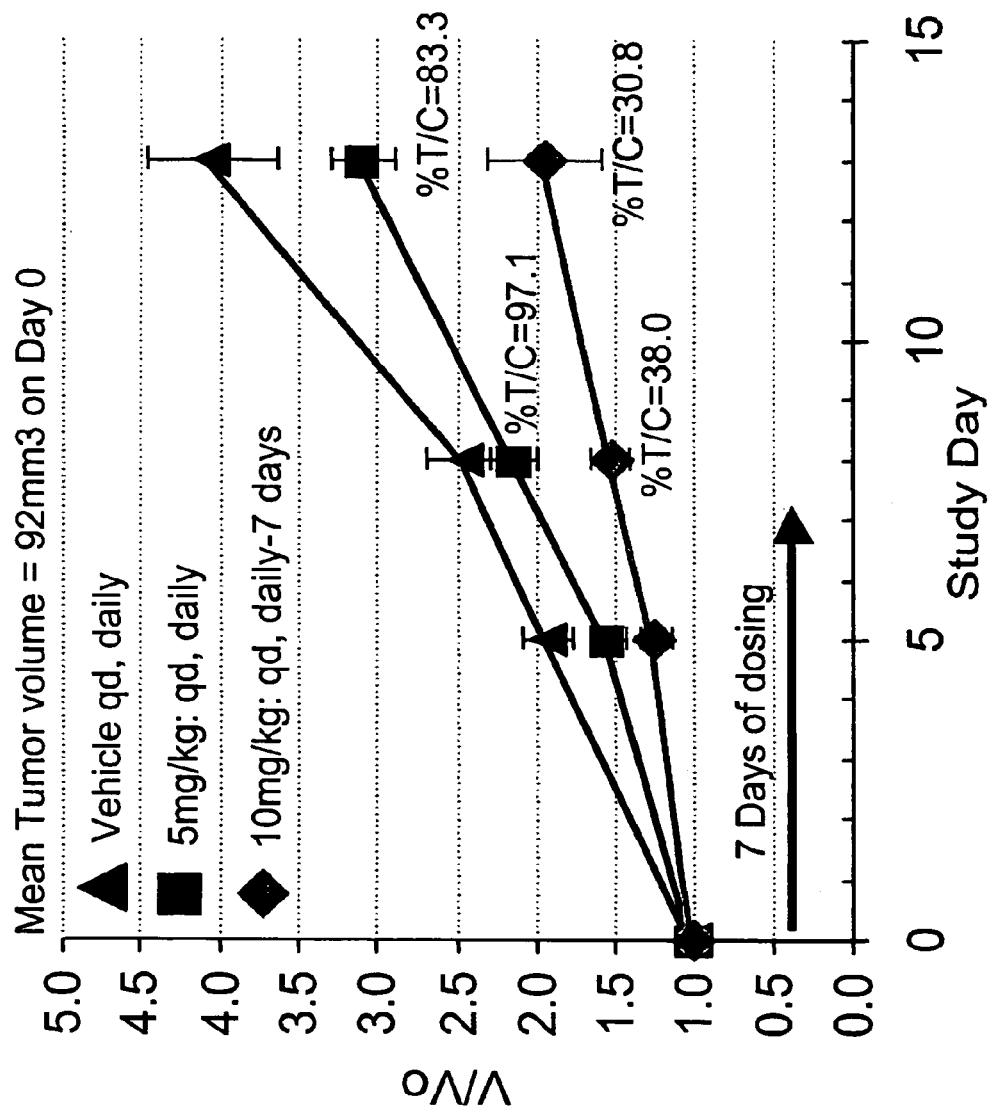

| | | |
|---|---|---|
| 2004/0029902 A1 | 2/2004 | Singh et al. |
| 2004/0102630 A1 | 5/2004 | Brumby |
| 2004/0224966 A1 | 11/2004 | Brumby et al. |
| 2004/0265852 A1 | 12/2004 | Plowman et al. |
| 2005/0002938 A1 | 1/2005 | Plowman et al. |
| 2005/0113398 A1 | 5/2005 | Argade et al. |
| 2005/0176743 A1 | 8/2005 | Luecking et al. |
| 2005/0192301 A1 | 9/2005 | Li et al. |
| 2005/0203114 A1 | 9/2005 | Armistead et al. |
| 2005/0209221 A1 | 9/2005 | Nunes et al. |
| 2005/0209224 A1 | 9/2005 | Singh et al. |
| 2005/0209230 A1 | 9/2005 | Singh et al. |
| 2005/0234049 A1 | 10/2005 | Singh et al. |
| 2006/0025410 A1 | 2/2006 | Singh et al. |
| 2006/0035891 A1 | 2/2006 | Li et al. |
| 2006/0035916 A1 | 2/2006 | Singh et al. |
| 2006/0040955 A1 | 2/2006 | Singh et al. |
| 2006/0058292 A1 | 3/2006 | Singh et al. |
| 2006/0058525 A1 | 3/2006 | Singh et al. |
| 2006/0135543 A1 | 6/2006 | Singh et al. |
| 2006/0166308 A1 | 7/2006 | Argade |
| 2006/0167254 A1 | 7/2006 | Cooper et al. |
| 2006/0270694 A1 | 11/2006 | Wong |
| 2007/0032514 A1 | 2/2007 | Zhan et al. |
| 2007/0179140 A1 | 8/2007 | Argade et al. |
| 2007/0299060 A1 | 12/2007 | Li et al. |
| 2008/0009494 A1 | 1/2008 | Li et al. |

FOREIGN PATENT DOCUMENTS

| | | |
|---|---|---|
| WO | WO 02/04429 | 1/2002 |
| WO | WO 02/059110 | 8/2002 |
| WO | WO 02/096888 | 12/2002 |
| WO | WO 02/102313 | 12/2002 |
| WO | WO 03/002544 | 1/2003 |
| WO | WO 03/026664 | 4/2003 |
| WO | WO 03/030909 | 4/2003 |
| WO | WO 03/032997 | 4/2003 |
| WO | WO 03/040141 | 5/2003 |
| WO | WO 03/055489 | 7/2003 |
| WO | WO 01/60816 | 8/2004 |
| WO | WO 2005/035507 | 4/2005 |
| WO | WO 2005/037800 | 4/2005 |
| WO | WO 2005/063722 | 7/2005 |
| WO | WO 2005/118544 | 12/2005 |
| WO | WO 2006/078846 | 7/2006 |
| WO | WO 97/22702 | 6/2009 |

OTHER PUBLICATIONS

Pearce et al., Failure modes in anticancer drug discovery and development, Cancer Drug Design and Discovery Edited by Stephen Neidle, Chapter 18, pp. 424-435 (2008).*

Lu et al., Aurora A is essential for early embryonic development and tumor suppression, Journal of Biological Chemistry, vol. 283, No. 46, pp. 31785-31790, 2008.*
Harrington et al., VX-680, a potent and selective small-molecule inhibitor of the Aurora kinases, suppresses tumor growth in vivo, Nature Medicine, vol. 10, No. 3, Mar. 2004, pp. 262-267.*
Forro et al.: "Vapor-assisted enzymatic hydrolysis of beta-lactams in a solvent-fee system," Tetrahedron: Asymmetry, 2008, pp. 1005-1009, vol. 19, Elsvier, Oxford, United Kingdom.
Ulrich, Chapter 4: Crystallization, Kirk-Othmer Encyclopedia of Chemical Technology, Aug. 2002.
Vippagunta et al., Crystalline Solids, Advanced Drug Delivery Reviews, 48, pp. 3-26, 2001.
West, Solid Solutions, Solid State Chemistry and its applications, pp. 358 & 365, 1988.
Gura, systems for identifying New Drugs Are Often Faulty, Cancer Models, Science, vol. 278, No. 5340, pp. 1041-1042, (1997).
Johnson et al., Relationships between drug activity in NCI preclinical in vitro and in vivo models and early clinical trials, British Journal of Cancer (2001) 64(10):1424:1431.
Simone, Oncology: Introduction, Cecil Textbook of Medicine, 20th Edition, vol. 1, pp. 1004-1010, 1996.
Rogers et al., PubMed Abstract (J Cell Biol. 157(2):219:29, Epub) Apr. 2002.
Tanaka et al., PubMed Abstract (Cell 108(3):317-29) Feb. 2002.
Cuiper, Ann Dite: "Molecular docketing with Candida Antarctica Lipase B1," Enantioselecetive Synthesis of Lactams and Lactones: A Chemo-Enzymatic Approach, Chapter 10, 1999, pp. 133-10, http://dissertations. Ub.rug.ni/oal.
Adam et al. Synthesis of Optically Active x-Methyklene beta-lactams through lipase-catalyzed Kinetic Resolutions J. Org. Chem. 65a:4919-4922, 2000.
Forro et al.: "Direct and Indirect Enzymatic Methods for the Preparation of Enatiopure Cyclic beta-amino acids and Derivative from beta-lactams", Mini-Reviews in Organic Chemistry, 1(1):93-102, 2004.
Kurokawa et al. "Both Enantiomers of N-oc_indoline-2-carboxylic Esters", Bull, Chem. Soc. Jpn. 77L1021-1025, 2004.
Parker et al.: "Enhancement of Candida Antarctica Lipase B Eantioseleceivity and Activity in Organic Solvents," Chem. Commun, pp. 2247-2248, 1998.
Torre et al., 2004, "Lipase Catalysed Michael Addition of Secondary Amines to Acrylonitrile," Chem. Commun. pp. 1724-1725.
Lin-Yu Lu et al.: "Aurora A Is essential for Early Embryonic Development and Tumor Suppression," Journal of Biological Chemistry, vol. 283, No. 46, Nov. 14, 2008, pp. 31785-31790.
Elizabeth A. Harrington et al.: "VX-680, a potent and selective small-molecule inhibitor of the aurora kinases, suppresses tumor growth in vivo," Nature Medicine, vol. 10, No. 3, Mar. 2004, pp. 262-267.

* cited by examiner ated to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long-term health of the patient.

CYCLOALKYL SUBSTITUTED PYRIMIDINEDIAMINE COMPOUNDS AND THEIR USES

1. CROSS-REFERENCE TO RELATED APPLICATIONS

This application is a continuation of U.S. application Ser. No. 12/951,949 filed Nov. 22, 2010, now U.S. Pat. No. 8,410,093, which is a continuation of U.S. application Ser. No. 11/567,506 filed Dec. 6, 2006 now U.S. Pat. No. 7,868,013, which is a continuation of U.S. application Ser. No. 11/133,419 filed May 18, 2005, now U.S. Pat. No. 7,754,714, which claims priority from U.S. Provisional application Ser. No. 60/572,534 filed May 18, 2004, U.S. Provisional Application No. 60/572,507 filed May 18, 2004, U.S. Provisional Application No. 60/580,765 filed Jun. 18, 2004, U.S. Provisional Application No. 60/628,496 filed Nov. 15, 2004, U.S. Provisional Application No. 60/628,199 filed Nov. 15, 2004, and U.S. Provisional Application No. 60/650,195 filed Feb. 3, 2005, the contents of which are incorporated herein by reference.

2. FIELD

The present disclosure provides 2,4-pyrimidinediamine compounds that exhibit antiproliferative activity, prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of proliferative disorders, such as tumors and cancers.

3. BACKGROUND

Cancer is a group of varied diseases characterized by uncontrolled growth and spread of abnormal cells. Generally, all types of cancers involve some abnormality in the control of cell growth and division. The pathways regulating cell division and/or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. This process of mutation and natural selection is enhanced by genetic instability displayed by many types of cancer cells, an instability which is gained either from somatic mutations or by inheritance from the germ line. The enhanced mutability of cancerous cells increases the probability of their progression towards formation of malignant cells. As the cancer cells further evolve, some become locally invasive and then metastasize to colonize tissues other than the cancer cell's tissue of origin. This property along with the heterogeneity of the tumor cell population makes cancer a particularly difficult disease to treat and eradicate.

Traditional cancer treatments take advantage of the higher proliferative capacity of cancer cells and their increased sensitivity to DNA damage. Ionizing radiation, including γ-rays and x-rays, and cytotoxic agents, such as bleomycin, cis-platin, vinblastine, cyclophosphamide, 5'-fluorouracil, and methotrexate rely upon a generalized damage to DNA and destabilization of chromosomal structure which eventually lead to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long-term health of the patient.

Although more selective chemotherapeutic treatments have been developed based on knowledge of how cancer cells develop, for example, the anti-estrogen compound tamoxifen, the effectiveness of all chemotherapeutic treatments are subject to development of resistance to the drugs. In particular, the increased expression of cell membrane bound transporters, such as MdrI, produces a multidrug resistance phenotype characterized by increased efflux of drugs from the cell. These types of adaptations by cancer cells severely limit the effectiveness of certain classes of chemotherapeutic agents. Consequently, identification of other chemotherapeutic agents is critical for establishing therapies effective for attacking the heterogeneous nature of proliferative disease and for overcoming any resistance that may develop over the course of therapy with other compounds. Moreover, use of combinations of chemotherapeutic agents which may have differing properties and cellular targets, increases the effectiveness of chemotherapy and limits the generation of drug resistance.

4. SUMMARY

In one aspect, the present disclosure provides 2,4-pyrimidinediamine compounds that exhibit biological activities, such as the ability to inhibit proliferation of numerous types of cancer cells in in vitro assays. The compounds generally comprise a 2,4-pyrimidinediamine according to structural formula (I):

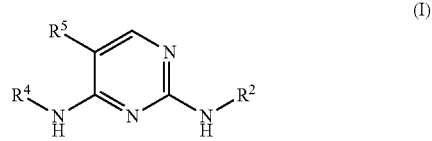

including the salts, hydrates, solvates and N-oxides thereof. In the compounds of structural formula (I), $R^4$ represents a saturated or unsaturated, optionally bridged cycloalkyl that includes an amide or ester $R^7$ substituent, although in instances in which the cycloalkyl ring includes two or more bridgehead carbon atoms or is unsaturated, this $R^7$ substituent is optional. The $R^7$ substituent can be positioned at any carbon atom on the cycloalkyl ring, including on a bridgehead or bridging carbon atom. In some embodiments, the $R^7$ substituent is positioned on the carbon atom attaching the cycloalkyl ring to the remainder of the molecule. In some embodiments, the substituent is positioned on the carbon atom adjacent to the carbon atom attaching the cycloalkyl ring to the remainder of the molecule, or on its next-nearest neighbor.

The nature of the $R^2$ group can vary widely. For example, the $R^2$ group can be an optionally substituted aryl, heteroaryl, arylalkyl or heteroarylalkyl group. In some embodiments, $R^2$ is a phenyl group that includes from one to three of the same or different substituents. The substituents can be selected from virtually any substituent group, including, but not limited to, branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities may be protected or unprotected, as is well-known in the art. In some embodiments, at least one of the substituents is a water-solubilizing group.

$R^5$ is hydrogen, an optionally substituted lower alkyl group or an electronegative group. Typical electronegative groups suitable for substituting the 2,4-pyrimidinediamine compounds at the $R^5$ position include, but are not limited to, cyano (—CN), isonitrile (—NC), nitro (—NO$_2$), halo, bromo, chloro, fluoro, (C1-C3) haloalkyl, (C1-C3) perhaloalkyl, (C1-C3) fluoroalkyl, (C1-C3) perfluoroalkyl, —CF$_3$, (C1-C3) haloalkoxy, (C1-C3) perhaloalkoxy, (C1-C3) fluoroalkoxy, (C1-C3) perfluoroalkoxy, —OCF$_3$, —C(O)R$^a$, —C(O)OR$^a$, —C(O)CF$_3$ and —C(O)OCF$_3$.

As will be appreciated by skilled artisans, the $R^4$ ring can contain chiral centers. For example, the carbon atom connecting the $R^4$ ring to the remainder of the molecule and the carbon atom including the $R^7$ substituent can be chiral centers. If the $R^4$ ring includes, for example, non-equivalent bridges, the bridgehead carbon atoms can also be chiral centers. As a consequence of these (and other) chiral centers, the 2,4-pyrimidinediamine compounds can include various diastereomers in racemic or enriched forms. For example, when the $R^4$ ring is an unbridged saturated or unsaturated cycloalkyl ring that includes an $R^7$ substituent on the carbon atom adjacent to the carbon atom attaching the cycloalkyl ring to the remainder of the molecule, the compounds of formula (I) include two racemates, a cis racemate and a trans racemate, that together comprise four diastereomers, represented by structural formulae (IIa)-(IId), below (absolute configuration assignments determined assuming $R^7$ is an ester or amide group, and $R^7$ resides on carbon two of the cycloalkyl ring, the pyrimidine 4-nitrogen resides on carbon one of the cycloalkyl ring):

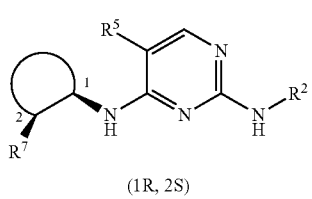

(IIa)

(1R, 2S)

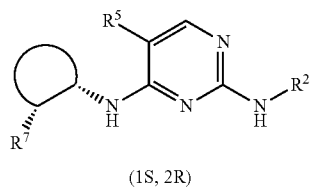

(IIb)

(1S, 2R)

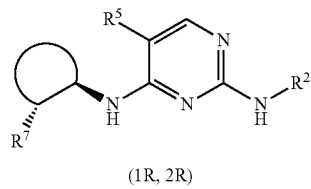

(IIc)

(1R, 2R)

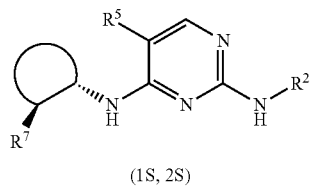

(IId)

(1S, 2S)

In structures (IIa)-(IId), the illustrated ring including the $R^7$ substituent could be any lower unbridged, saturated or unsaturated cycloalkyl ring. Moreover, while the $R^7$ substitutent is illustrated at a specific location, it could be at other locations.

When $R^4$ is a saturated or unsaturated bridged cycloalkyl that includes bridges that allow for exo-endo geometries and an $R^7$ substituent on a carbon atom adjacent to the carbon atom attaching the cycloalkyl ring to the remainder of the molecule, the compounds of formula (I) include two cis racemates, an exo-exo and an endo-endo, and two trans racemates, an exo-endo and an endo-exo. For example, when $R^4$ comprises a norbornyl or norbornenyl bonded to the remainder at the molecule at its 2-position, then these racemates are represented by structural formulae (IIIa)-(IIId), below:

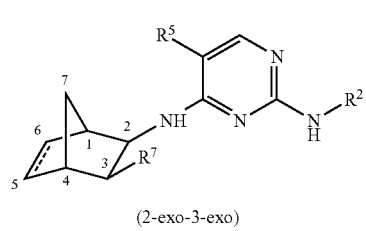

(IIIa)

(2-exo-3-exo)

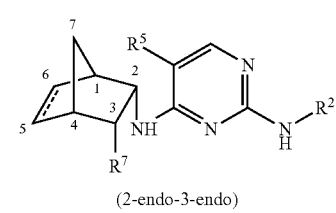

(IIIb)

(2-endo-3-endo)

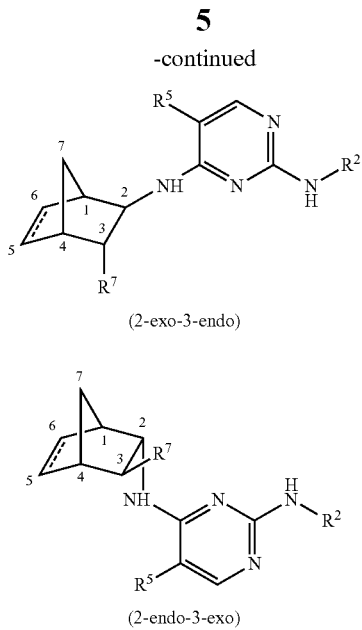

(IIIc) (2-exo-3-endo)

(IIId) (2-endo-3-exo)

Together these four racemates comprise eight diastereomers, represented by structural formuale (IVa)-(IVh), below (absolute configuration assignments determined assuming $R^7$ is an ester or amide group):

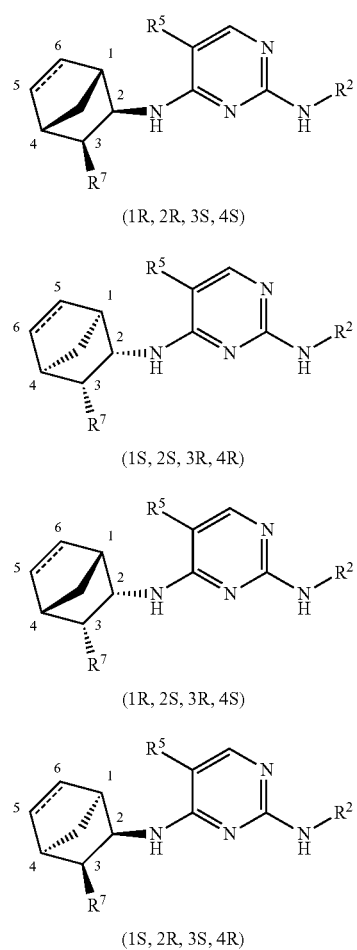

(IVa) (1R, 2R, 3S, 4S)

(IVb) (1S, 2S, 3R, 4R)

(IVc) (1R, 2S, 3R, 4S)

(IVd) (1S, 2R, 3S, 4R)

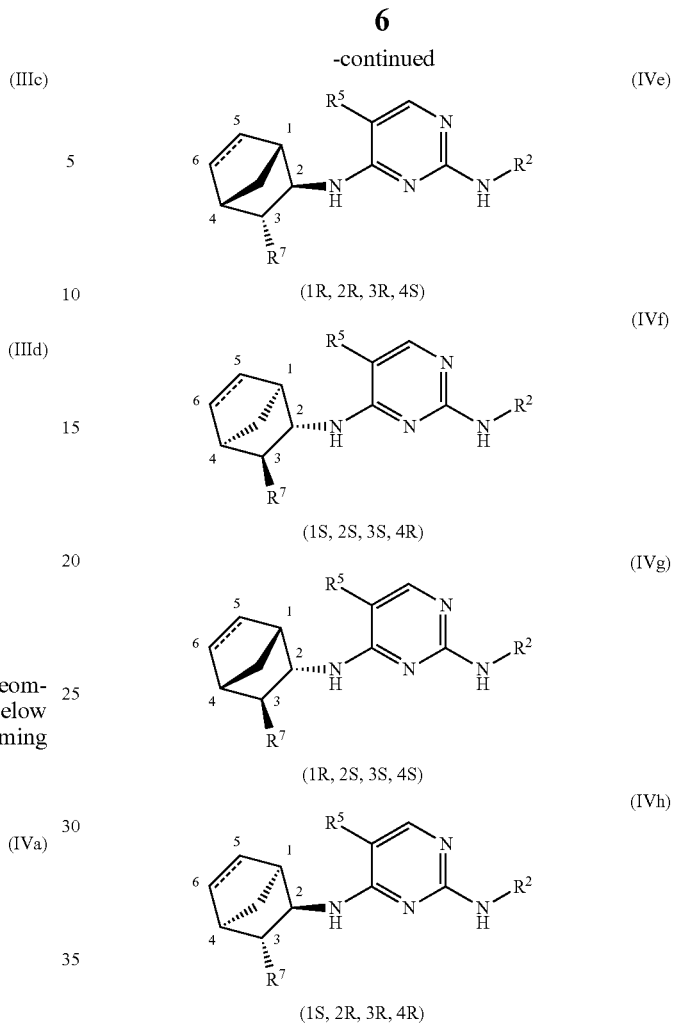

(IVe) (1R, 2R, 3R, 4S)

(IVf) (1S, 2S, 3S, 4R)

(IVg) (1R, 2S, 3S, 4S)

(IVh) (1S, 2R, 3R, 4R)

In structural formulae (IIIa)-(IIId) and (IVa)-(IVh), the bond including the dotted line can be a single bond or a double bond.

Although the racemates of structural formulae (IIIa)-(IIId) and the diastereomers of structural formulae (IVa)-(IVh) are illustrated with a specific bridged cycloalkyl $R^4$ ring, it should be appreciated that the $R^4$ ring could be virtually any saturated or unsaturated bridged cycloalkyl in which, for example, the carbon atoms corresponding to the illustrated 1-, 2-, 3- and 4-carbon atoms are chiral centers. Moreover, although the illustrated ring includes a specified bridge position and a single bridging carbon atom, the ring could include more bridging atoms, and the bridgehead carbon atoms could be positioned at different locations within the cycloalkyl ring. In addition, the ring could include additional bridgehead and bridging carbon atoms such that it contains more than one bridge. Also, depending on it's structure, additional chiral centers can be in the saturated or unsaturated bridged cycloalkyl.

For compounds according to structural formulae (IIa)-(IId) in which the $R^4$ cycloalkyl ring is cyclopentyl, $R^7$ is —C(O)NH$_2$ and $R^2$ is 4-(1-methylpiperazin-4-yl)-3-methylphenyl, it has been discovered that the two cis (1S,2R) and (1R,2S) diastereomers and the trans (1R,2R) diastereomer exhibit antiproliferative activity against a variety of different tumor cell types in vitro assays, where as the trans (1S,2S) diastereomer is relatively inactive against these same tumor cells. Based on this observation, it is expected that the cis racemate, two cis diastereomers and trans diastereomer of other 2,4-pyrimidinediamine compounds described herein that correspond in absolute stereochemical configuration to the active cis and trans diastereomers according to structural formulae (IIa), (IIb) and (IIc), respectively, will exhibit similar antiproliferative activity.

For compounds according to structural formulae (IVc)-(IVh) in which $R^7$ is —C(O)NH$_2$ and $R^2$ is 4-(1-methylpiperazin-4-yl)-3-methylphenyl, both cis racemates exhibit significant antiproliferative activity against tumor cells in in vitro assays. However, the exo-exo racemate is approximately twenty-fold more potent than the endo-endo racemate. Moreover, for the exo-exo racemate, the enantiomer corresponding to structural formula (IVa), i.e., the (1R,2R,3S,4S) diastereomer, is largely responsible for the potency of the racemate, being approximately 1000-fold more potent than its corresponding enantiomer, i.e., the (1S,2S,3R,4R) diastereomer (IVb). This (1R,2R,3S,4S) diastereomer is also approximately 20-50 times more potent than the endo-endo racemate (mixture of (IVc) and (IVd).).

Based on this observation, it is expected that the racemates and diastereomers of other 2,4-pyrimidinediamine compounds described herein that correspond in absolute stereochemical configuration to the exo-exo and endo-endo cis racemates of structural formulae (IIIa) and (IIIb), and to the (1R,2R,3S,4S) diastereomer of structural formula (IVa), will exhibit similar antiproliferative activity. Moreover, it is expected that any diastereomer corresponding in absolute stereochemical configuration to the diastereomer of structural formula (IVa) will exhibit similar superior potency as compared to the other diastereomers.

When the $R^4$ cycloalkyl ring is a norbornyl or norbornenyl, synthesizing the trans racemates and diastereomers may be difficult owing to steric constraints. However, where trans diastereomers of bridged cycloalkyl groups are possible, the diastereomers corresponding to structural formulae (IVf) and (IVg), supra, are expected to exhibit antiproliferative activity.

Thus, in another aspect, the present disclosure provides 2,4-pyrimidinediamine compounds that are enriched in one or more of the active diastereomers corresponding to those described above. In some embodiments, the stereoisomerically enriched compounds are cis racemates. In a specific embodiment, the stereoisomerically enriched compounds are exo-exo or endo-endo cis racemates corresponding to structural formulae (IIIa) and (IIIb)). In some embodiments, the stereoisomerically enriched compounds are enriched in one or more cis diastereomers. In some embodiments, the stereoisomerically enriched compounds are enriched in one or more diastereomers corresponding to structural formula (IIa), (IIb) and (IIc). In a specific embodiment, the stereoisomerically enriched compound is a diastereomer according to structural formula (IIa), (IIb) or (IIc) that is substantially free of all other diastereomers. In some embodiments, the stereoisomerically enriched compounds are enriched in the diastereomer corresponding to structural formula (IVa). In a specific embodiment, the stereoisomerically enriched compound is a diastereomer corresponding to structural formula (IVa) that is substantially free of all other diastereomers.

In still another aspect, prodrugs of the compounds and/or stereoisomerically enriched compounds (referred to collectively herein as "compounds") are provided. Such prodrugs may be active in their prodrug form, or may be inactive until converted under physiological or other conditions of use to an active drug form. In the prodrugs, one or more functional groups of the compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs include special types of protecting groups, termed "progroups," masking one or more functional groups of the compounds that cleave under the conditions of use to yield an active drug compound. Functional groups within the compounds that may be masked with progroups for inclusion in a promoiety include, but are not limited to, amines (primary and secondary), hydroxyls, sulfanyls (thiols), carboxyls, carbonyls, etc. Myriad progroups suitable for masking such functional groups to yield promoieties that are cleavable under the desired conditions of use are known in the art. All of these progroups, alone or in combination, may be included in the prodrugs. Specific examples of promoieties that yield primary or secondary amine groups that can be included in the prodrugs include, but are not limited to amides, carbamates, imines, ureas, phosphenyls, phosphoryls and sulfenyls. Specific examples of promoieties that yield sulfanyl groups that can be included in the prodrugs include, but are not limited to, thioethers, for example S-methyl derivatives (monothio, dithio, oxythio, aminothio acetyls), silyl thioethers, thioesters, thiocarbonates, thiocarbamates, asymmetrical disulfides, etc. Specific examples of promoieties that cleave to yield hydroxyl groups that can be included in the prodrugs include, but are not limited to, sulfonates, esters, carbonates, phosphates (phosphonoxy) and their salts with organic bases and metals. Specific examples of promoieties that cleave to yield carboxyl groups that can be included in the prodrugs include, but are not limited to, esters (including silyl esters, oxamic acid esters and thioesters), amides and hydrazides.

In another aspect, the present disclosure provides intermediates useful for synthesizing the compounds and/or prodrugs described herein. In an illustrative embodiment, the intermediates are compounds according to structural formula (V):

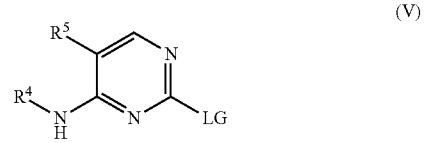

(V)

wherein $R^4$ and $R^5$ are as defined for structural formula (I) and LG represents a leaving group. Suitable leaving groups include, but are not limited to, quaternary ammonium salts, —S(O)$_2$Me, —SMe and halo (e.g., F, Cl, Br, I). In a specific embodiment, the leaving group LG is chloro.

The intermediates of structural formula (V) may be stereoisomerically enriched in one or more diastereomers such that they can be used to synthesize compounds enriched in one or more of the various diastereomers discussed above. In a specific embodiment of the intermediates, $R^4$ is not

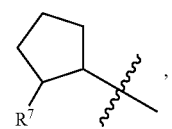

or a stereoisomerically enriched diastereomer thereof, where $R^7$ is —C(O)NH$_2$. In another specific embodiment, the intermediate is not any compound described in application Ser. No. 11/016,403, filed Dec. 17, 2004 and/or U.S. Ser. No. 2004/042971, filed Dec. 17, 2004, the disclosures of which are incorporated herein by reference.

In still another aspect, compositions comprising one or more of the compounds described herein are provided. The compositions generally comprise the compound(s), and/or prodrugs, salts, hydrates, solvates and/or N-oxides thereof, and an appropriate carrier, excipient and/or diluent. The exact nature of the carrier, excipient and/or diluent will depend upon the desired use for the composition, and may range from being suitable or acceptable for in vitro uses, to being suitable or acceptable for veterinary uses, to being suitable or acceptable for use in humans.

The compounds described herein are potent inhibitors of the proliferation abnormal cells, such as tumor cells, in in vitro assays. Thus, in still another aspect, methods of inhibiting proliferation of abnormal cells, and in particular tumor cells, are provided. The methods generally involve contacting an abnormal cell such as a tumor cell, with an amount of one or more compounds described herein, and/or prodrugs, salts, hydrates, solvates and/or N-oxides thereof, effective to inhibit proliferation of the cell. The cells can be contacted with the compound per se, or the compound can be formulated into a composition. The methods may be practiced in in vitro contexts, or in in vivo contexts as a therapeutic approach towards the treatment or prevention of proliferative disorders, such as tumorigenic cancers.

In still another aspect, methods of treating proliferative disorders are provided. The methods may be practiced in animals in veterinary contexts or in humans. The methods generally involve administering to an animal or human subject an amount of one or more compounds described herein, and/or prodrugs, salts, hydrates, solvates and/or N-oxides thereof, effective to treat or prevent the proliferative disorder. The compound(s) per se can be administered to the subject, or the compound(s) can be administered in the form of a composition. Proliferative disorders that can be treated according to the methods include, but are not limited to, tumorigenic cancers.

The compounds described herein are also potent inhibitors of Aurora kinases. Aurora kinases are a family of enzymes known to be key regulators of cell division. Elevated levels of Aurora kinases have been found in several types of human cancer cells, such as breast, colon, renal, cervical, neuroblastomer, melanoma, lymphoma, pancreatic, prostate and other types of solid tumors (see, e.g., Bischott et al., 1998, EMBO J. 17:3052-3065; Geopfert & Brinkley, 2000, Curr. Top. Dev. Biol. 49:331-342; Sakakura et al., 2001, Br. J. Cancer 84:824-831), and overexpression of Aurora kinases has been shown to result in cell transformation, a process by which normal cells become cancers. Although not intending to be bound by any particular theory of operation, it is believed that the compounds described herein, as well as the active prodrugs, salts, hydrates, solvates and/or N-oxides thereof, exert their antiproliferative activity by inhibiting one or more Aurora kinases.

Thus, in yet another aspect, methods of inhibiting an activity of an Aurora kinase are provided. The methods generally involve contacting an Aurora kinase with an amount of one or more compounds described herein, and/or active prodrugs, salts, hydrates, solvates and/or N-oxides thereof, effective to inhibit its activity. The methods can be practiced in in vitro contexts with purified or partially purified Aurora kinase enzymes (e.g., with extracts of cells expressing an Aurora kinase), in in vitro contexts with intact cells expressing an Aurora kinase, or in in vivo contexts to inhibit an Aurora kinase-mediated process (for example cellular mitosis) and/or as a therapeutic approach towards the treatment or prevention of diseases or disorders that are mediated, at least in part, by an Aurora kinase activity.

In still another aspect, methods of treating or preventing Aurora kinase-mediated diseases or disorders are provided. The methods generally involve administering to an animal or human subject an amount of one or more compounds described herein, and/or active prodrugs, salts, hydrates, solvates and/or N-oxides thereof, effective to treat or prevent the Aurora kinase-mediated disease or disorder. Aurora kinase-mediated diseases and disorders include any disease, disorder, or other deleterious condition in which a member of the Aurora kinase family of enzymes plays a role. Specific examples of such Aurora kinase-mediated diseases or disorders include, but are not limited to, melanoma, leukemia, and solid tumor cancers, such as, for example, colon, breast, gastric, ovarian, cervical, melanoma, renal, prostate, lymphoma, neuroblastoma, pancreatic and bladder cancers.

Other aspects include, but are not limited to, intermediates and methods useful for synthesizing the stereoisomerically enriched compounds and prodrugs, as will be described in more detail herein below.

5. BRIEF DESCRIPTION OF THE DRAWINGS

FIGS. 1-4 illustrate the inhibitory effect of compound 234 (enantiomer E3) on the growth of various different types of tumors in standard xenograft treatment and regression models.

6. DETAILED DESCRIPTION

6.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Cyclic alkyls can include zero bridgehead carbon atoms or two or more bridgehead carbon atoms. Thus, cyclic alkyls can be monocyclic, bicyclic or polycyclic in structure. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to an alkyl group containing from 1 to 8 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkenyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group containing 1 to 8 carbon atoms. In some embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. A "lower alkylene" group is an alkylene group containing from 1 to 8 carbon atoms. In some embodiments, the alkylene group is a straight-chain saturated alkano group, e.g., methano, ethano, propano, butano, and the like.

"Cycloalkyl" by itself or as part of another substituent refers to a cyclic version of an "alkyl" group. A cycloalkyl group may include zero bridgehead carbon atoms or two or more bridgehead carbon atoms. Thus, a cycloalkyl may be monocyclic, bicyclic or polycyclic, depending upon the number of bridgehead and bridging carbon atoms. Cycloalkyl groups that include zero bridgehead carbon atoms are referred to herein as "monocyclic cycloalkyls" or "unbridged cycloalkyls." Cycloalkyls that include at least two bridgehead carbon atoms and at least one bridging carbon atom are referred to herein as "bridged cycloalkyls." Bridged cycloalkyls that include two bridgehead carbon atoms are referred to herein as "bicyclic bridged cycloalkyls." Bridged cycloalkyls that include more than two bridgehead carbon atoms are referred to herein as "polycyclic bridged cycloalkyls." Typical unbridged cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical bridged cycloalkyls include, but are not limited to, adamantyl, noradamantyl, bicyclo[1.1.0]butanyl, norboranyl (bicyclo[2.2.1]heptanyl), norbornenyl (bicyclo[2.2.1]heptanyl), norbornadienyl (bicyclo[2.2.1]heptadienyl), tricyclo[2.2.1.0]heptanyl, bicyclo[3.2.1]octanyl, bicyclo[3.2.1]octadienyl, bicyclo[2.2.2]octanyl, bicyclo[2.2.2]octenyl, bicyclo[2.2.2]octadienyl, bicyclo[5,2,0]nonanyl, bicyclo[4.3.2]undecanyl, tricyclo[5.3.1.1]dodecanyl, and the like. Where specific levels of saturation are intended, the nomenclature cycloalkanyl and cycloalkenyl is used. A "lower" unbridged cycloalkyl contains from 3 to 8 carbon atoms. A "lower" bridged cycloalkyl contains from 5 to 16 carbon atoms.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is (C5-C15) aryl, with (C5-C10) being more typical. Specific examples are phenyl and naphthyl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

The above-defined groups may include prefixes and/or suffixes that are commonly used in the art to create additional well-recognized substituent groups. As examples, "alkyloxy" or "alkoxy" refers to a group of the formula —OR, "alkylamine" refers to a group of the formula —NHR and "dialkylamine" refers to a group of the formula —NRR, where each R is independently an alkyl. As another example, "haloalkoxy" or "haloalkyloxy" refers to a group of the formula —OR', where R' is a haloalkyl.

"Prodrug" refers to a derivative of an active compound (drug) that may require a transformation under the conditions of use, such as within the body, to release the active drug. Prodrugs are frequently, but not necessarily, pharmacologically inactive until converted into the active drug. Prodrugs are typically obtained by masking a functional group in the drug compound believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active stereoisomerically enriched compounds described herein to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active stereoisomerically enriched drug compound to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Proliferative disorder" refers to a disease or disorder characterized by aberrant cell proliferation, for example, where cells divide more than their counterpart normal cells. The aberrant proliferation may be caused by any mechanism of action or combination of mechanisms of action. For example, the cell cycle of one or more cells may be affected such that cell(s) divide more frequently than their counterpart normal cells, or as another example, one or more cells may bypass inhibitory signals, which would normally limit their number of divisions. Proliferative diseases include, but are not limited to, slow or fast growing tumors and cancers.

"Antiproliferative compound" refers to a compound that inhibits the proliferation of a cell as compared to an untreated control cell of a similar type. The inhibition can be brought about by any mechanism or combination of mechanisms, and may operate to inhibit proliferation cytostatically or cytotoxically. As a specific example, inhibition as used herein includes, but is not limited to, arrest of cell division, a reduction in the rate of cell division, proliferation and/or growth, and/or induction of cell death, by any mechanism of action, including, for example apoptosis.

"Aurora kinase" refers to a member of the family of serine/threonine protein kinases that are generally referred to as "Aurora" kinases. The Aurora family of serine/threonine protein kinases are essential for cell proliferation (see, e.g., Bischhoff & Plowman, 1999, Trends Cell Biol. 9:454-459; Giet & Prigent, 1999, J. Cell Science 112:3591-3601; Nigg, 2001, Nat. Rev. Mol. Cell. Biol. 2:21-32; Adams et al., 2001, Trends Cell Biol. 11:49-54). Presently, there are three known mammalian family members: Aurora-A ("2"), Aurora-B ("1") and Aurora-C ("3") (see, e.g., Giet & Prigent, 1999, J. Cell Sci. 112:3591-3601; Bischoff & Plowman, 1999, Trends Cell Biol. 9:454-459, the disclosure of which is incorporated herein by reference). As used herein, "Aurora kinase" includes not only these three known mammalian family members, but also later-discovered mammalian family members and homologous proteins from other species and organisms (for non-limiting examples of homologous members of the Aurora kinase family from other species and organisms see Schumacher et al., 1998, J. Cell Biol. 143:

1635-1646; Kimura et al., 1997, J. Biol. Chem. 272:13766-13771), the disclosure of which is incorporated herein by reference.

"Aurora kinase-mediated process" or "Aurora kinase-mediated disease or disorder" refers to a cellular process, disease or disorder in which an Aurora kinase plays a role. The Aurora kinases are believed to play a key role in protein phosphorylation events that regulate the mitotic phase of the cell cycle. The human Aurora kinases display distinct subcellular locations during mitosis. For example, Aurora-A is upregulated during the M phase of the cell cycle and localizes to the spindle pole during mitosis, suggesting involvement in centrosomal functions. While Aurora-A activity is maximized during prophase, Aurora-B is believed to play an important role during chromatid separation and formation of the cleavage furrow in anaphase and telophase. The role of Aurora-C is less clear, but it has been shown to localize to centrosomes during mitosis from anaphase to cytokinesis. Moreover, inhibition of Aurora kinase activity in mammalian cells leads to abnormal cell growth and polyploidy (Terada et al., 1998, EMBO J. 17:667-676). Thus, Aurora kinases are thought to regulate cell division, chromosome segregation, mitotic spindle formation, and cytokinesis. As used herein, all of these various processes are within the scope of "Aurora kinases-mediated process."

Moreover, since its discovery in 1997, the mammalian Aurora kinase family has been closely linked to tumorigenesis. The most compelling evidence for this is that over-expression of Aurora-A transforms rodent fibroblasts (Bischoff et al., 1998, EMBO J. 17:3052-3065). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the Aurora-A locus and chromosomal instability in mammary and gastric tumors has been observed (Miyoshi et al., 2001, Int. J. Cancer 92:370-373; Sakakura et al., 2001, Brit. J. Cancer 84:824-831).

The Aurora kinases have been reported to be over-expressed in a wide range of human tumors. Elevated expression of Aurora-A has been detected in over 50% of colorectal (Bischoff et al., 1998, EMBO J. 17:3052-3065; Takahashi et al., 2000, Jpn. J. Cancer Res. 91:1007-1014), ovarian (Gritsko et al., 2003, Clinical Cancer Research 9:1420-1426, and gastric tumors (Sakakura, 2001, Brit. J. Cancer 84:824-831), and in 94% of invasive duct adenocarcinomas of the breast (Tanaka, 1999, Cancer Research 59:2041-2044). High levels of Aurora-A have also been reported in renal, cervical, neuroblastoma, melanoma, lymphoma, pancreatic and prostate tumor cell lines (Bischoff et al., 1998, EMBO J. 17:3052-3065; Kimura et al., 1999, J. Biol. Chem. 274:7334-7340; Zhou et al., 1998, Nature Genetics 20:189-193; Li et al., 2003, Clin Cancer Res. 9(3):991-7). Amplification/overexpression of Aurora-A is observed in human bladder cancers and amplification of Aurora-A is associated with aneuploidy and aggressive clinical behavior (Sen et al, 2002, J Natl Cancer Inst. 94(17):1320-9). Moreover, amplification of the Aurora-A locus (20q13) correlates with poor prognosis for patients with node-negative breast cancer (Isola et al., 1995, American Journal of Pathology 147:905-911). Aurora-B is highly expressed in multiple human tumor cell lines, including leukemic cells (Katayama et al., 1998, Gene 244:1-7). Levels of this enzyme increase as a function of Duke's stage in primary colorectal cancers (Katayama et al., 1999, J. Nat'l Cancer Inst. 91:1160-1162). Aurora-C, which is normally only found in germ cells, is also over-expressed in a high percentage of primary colorectal cancers and in a variety of tumor cell lines including cervical adenocarcinoma and breast carcinoma cells (Kimura et al., 1999, J. Biol. Chem. 274:7334-7340; Takahashi et al., 2000, Jpn. J. Cancer Res. 91:1007-1014).

In contrast, the Aurora kinase family is expressed at a low levels in the majority of normal tissues, the exceptions being tissues with a high proportion of dividing cells such, as the thymus and testis (Bischoff et al., 1998, EMBO J., 17:3052-3065). For a further review of the role(s) Aurora kinases play in proliferative disorders, see Bischhoff & Plowman, 1999, Trends Cell Biol. 9:454-459; Giet & Prigent, 1999, J. Cell Science 112:3591-3601; Nigg, 2001, Nat. Rev. Mol. Cell Biol. 2:21-32; Adams et al., 2001, Trends Cell Biol. 11:49-54 and Dutertre et al., 2002, Oncogene 21:6175-6183.

Although over-expression of proteins by cancer cells is not always indicative that inhibition of the protein activity will yield anti-tumor effect, it has been confirmed in functional assays that at least the following types of tumor cells are sensitive to inhibition of Aurora kinase activity: prostate (DU145), cervical (Hela), pancreatic (Mia-Paca2, BX-PC3), histological leukemia (U937), lung adenocarinoma, lung epidermoid, small lung cell carcinoma, breast, renal carcinoma, MolT3 (all) and Molt4 (all).

Based on the established role of Aurora kinases in a variety of cancers, examples of "Aurora kinases-mediated diseases and disorders" include, but are not limited to, melanoma, leukemia, and solid tumor cancers, such as, for example, the various solid tumor cancers listed above.

"Therapeutically effective amount" refers to an amount of a compound sufficient to treat a specified disorder or disease, or one or more of its symptoms. In reference to tumorigenic proliferative disorders, a therapeutically effective amount comprises an amount sufficient to, among other things, cause the tumor to shrink, or to decrease the growth rate of the tumor.

In many situations, standard treatments for tumorigenic proliferative disorders involve surgical intervention to remove the tumor(s), either alone or in combination with drug (chemo) and/or radiation therapies. As used herein, a "therapeutically effect amount" of a compound is intended to include an amount of compound that either prevents the recurrence of tumors in subjects that have had tumor(s) surgically removed, or slows the rate of recurrence of tumor(s) in such subjects.

Accordingly, as used herein, amounts of compounds that provide therapeutic benefit adjunctive to another type of therapy, such as surgical intervention and/or treatment with other antiproliferative agents, including, for example, 5-fluorouracil, vinorelbine, taxol, vinblastine, cisplatin, topotecan, etc.), are included within the meaning of "therapeutically effective amount."

"Prophylactically effective amount" refers to an amount of a compound sufficient to prevent a subject from developing a specified disorder or disease. Typically, subjects in which prophylaxis is practiced are not suffering from the specified disorder or disease, but are recognized as being at an elevated risk for developing this disease or disorder based factors such as, but not limited to, diagnostic markers and family history.

6.2 The Compounds

As discussed in the Summary section, the present disclosure provides 2,4-pyrimidinedianine compounds that have myriad useful biological activities, including antiproliferative activity against a variety of different tumor cell types in in vitro assays. In an illustrative embodiment, the compounds are 2,4-pyrimidinediamines according to structural formula (I):

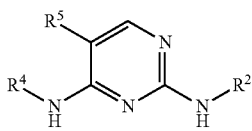
(I)

including the active salts, hydrates, solvates and N-oxides thereof wherein:

$R^2$ is selected from a (C6-C20) aryl optionally substituted with one or more of the same or different $R^8$ groups, a 5-20 membered hetaroaryl optionally substituted with one or more of the same or different $R^8$ groups, a (C7-C28) arylalkyl optionally substituted with one or more of the same or different $R^8$ groups and a 6-28 membered heteroarylalkyl optionally substituted with one or more of the same or different $R^8$ groups;

$R^5$ is selected from hydrogen, lower alkyl optionally substituted with one or more of the same or different $R^8$ groups, and an electronegative group;

$R^4$ is a saturated or unsaturated, bridged or unbridged cycloalkyl containing a total of from 3 to 16 carbon atoms that is substituted with an $R^7$ group, with the proviso that when $R^4$ is an unsaturated unbridged cycloalkyl, or a saturated bridged cycloalkyl, this $R^7$ substituent is optional;

$R^7$ is an ester or amide group, which in some embodiments is selected from —C(O)OR$^d$ and —C(O)NR$^d$R$^d$;

each $R^8$ group is, independently of the others, selected from a water-solubilizing group, $R^a$, $R^b$, lower cycloalkyl optionally substituted with one or more of the same or different $R^a$ and/or $R^b$ groups, lower heterocycloalkyl optionally substituted with one or more of the same or different $R^a$ and/or $R^b$ groups, lower alkoxy optionally substituted with one or more of the same or different $R^b$ groups and —O—(CH$_2$)$_x$—R$^b$, where x is an integer ranging from 1 to 6;

each $R^a$ is, independently of the others, selected from hydrogen, lower alkyl, lower cycloalkyl, (C6-C14) aryl, phenyl, naphthyl, (C7-C20) arylalkyl and benzyl;

each $R^b$ is, independently of the others, selected from =O, —OR$^a$, (C1-C3) haloalkyloxy, —OCF$_3$, =S, —SR$^a$, =NR$^a$, =NOR$^a$, —NR$^c$R$^c$, halogen, —CF$_3$, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^c$R$^c$, —S(O)$_2$NR$^c$R$^c$, —OS(O)R$^a$, —OS(O)$_2$R$^a$, —OS(O)$_2$OR$^a$, —OS(O)$_2$R$^a$, —OS(O)$_2$NR$^c$R$^c$, —C(O)R$^a$, —C(O)OR$^a$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NH)NR$^c$R$^c$ and —OC(NR$^a$)NR$^c$R$^c$;

each $R^c$ is, independently of the others, selected from $R^a$ or, alternatively, two $R^c$ that are bonded to the same nitrogen atom may be taken together with this nitrogen atom to form a 5-8 membered heterocycloalkyl group which may optionally include from 1 to 3 additional heteroatomic groups selected from O, S, N—(CH$_2$)$_y$—R$^a$, N—(CH$_2$)$_y$C(O)R$^a$, N—(CH$_2$)$_y$—C(O)OR$^a$, N—(CH$_2$)$_y$—S(O)$_2$R$^a$, N—(CH$_2$)$_y$—S(O)$_2$OR$^a$ and N—(CH$_2$)$_y$—C(O)NR$^a$R$^a$, where y is an integer ranging from 0 to 6, and which may optionally include one or more of the same or different $R^8$ and/or lower alkyl substituents; and each $R^d$ is, independently of the others, selected from $R^a$, $R^c$ and a chiral auxiliary group.

As can be seen from structural formula (I), the compounds described herein comprise three "main" features or moieties: (i) an optionally substituted, saturated or unsaturated, bridged or unbridged cycloalkyl ring (substituent $R^4$); (ii) an optionally 5-substituted 2,4-pyrimidinediamine ring; and (iii) an optionally substituted aryl, heteroaryl, arylalkyl or heteroarylalkyl moiety (substituent $R^2$). Various specific embodiments of these three main features, which can be combined with one another, are described in more detail, below.

In many embodiments of the compounds, the pyrimidinediamine moiety is substituted at the 5-position with an electronegative substituent ($R^5$ substituent). The exact identity of this electronegative substituent is not critical. Thus, the $R^5$ substituent can include virtually any substituent group that has electronegative character. Specific examples of suitable electronegative groups include, but are not limited to, cyano (—CN), isonitrile (—NC), nitro (—NO$_2$), halo (e.g., Br, Cl, F), (C1-C3) haloalkyl, (C1-C3) perhaloalkyl, (C1-C3) fluoroalkyl, (C1-C3) perfluoroalkyl, trifluoromethyl (—CF$_3$), (C1-C3) haloalkoxy, (C1-C3) perhaloalkoxy, (C1-C3) fluoroalkoxy, (C1-C3) perfluoroalkoxy, trifluoromethoxy (—OCF$_3$), —C(O)R$^a$, —C(O)OR$^a$, —C(O)CF$_3$ and —C(O)OCF$_3$, where $R^a$ is as defined for structural formula (I). In a specific embodiment, $R^5$ is selected from cyano, nitro, halo, bromo, chloro, fluoro, trifluoromethyl and trifluoromethoxy. In another specific embodiment, $R^5$ is fluoro.

The $R^2$ substituent or moiety can comprise virtually any substituted or unsubstituted aryl, heteroaryl, arylalkyl or heteroarylalkyl group. Moreover, the nature of any present optional substituents can vary widely. Many 2,4-pyrimidinediamine compounds having optionally substituted aryl, heteroaryl, arylalkyl and heteroarylalkyl $R^2$ substituent groups that exhibit biological activity have been reported in the literature (see, e.g., U.S. application Ser. No. 10/355,543 filed Jan. 31, 2003 (US 2004/0029902), WO 03/063794, U.S. application Ser. No. 10/631,029 filed Jul. 29, 2003, WO 2004/014382, U.S. application Ser. No. 10/903,263 filed Jul. 30, 2004, international application no. PCT/US2004/24716 filed Jul. 30, 2004, and U.S. Pat. No. 6,235,746, the disclosures of which are incorporated herein by reference). All of these $R^2$ substitutents are expected to be useful in the 2,4-pyrimidinediamine compounds described herein.

In some embodiments, the $R^2$ moiety is a substituted aryl, heteroaryl, arylalkyl or heteroaryl group in which at least one of the substituents is a water-solubilizing group. Such water-solubilizing groups are especially useful when the $R^2$ moiety has significant hydrophobic character, such as when $R^2$ is an aryl, for example phenyl or naphthyl, or an arylalkyl, for example benzyl.

As used herein, a "water-solubilizing" group is a group that has hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acides, amines, etc.); groups that include permanent charges (e.g., quaternary ammonium groups); and/or heteroatoms or heteroatomic groups (e.g., O, S, N, NH, N—(CH$_2$)$_y$—R$^a$, N—(CH$_2$)$_y$—C(O)R$^a$, N—(CH$_2$)$_y$—C(O)OR$^a$, N—(CH$_2$)$_y$—S(O)$_2$R$^a$, N—(CH$_2$)$_y$—S(O)$_2$OR$^a$, N—(CH$_2$)$_y$—C(O)NR$^a$R$^a$, etc., where $R^a$ and y are as previously defined for structural formula (I)). In some embodiments, the water-solubilizing group is a cycloheteroalkyl that optionally includes from 1 to 5 substituents, which may themselves be water-solubilizing groups. In a specific embodiment, the water-solubilizing group is of the formula

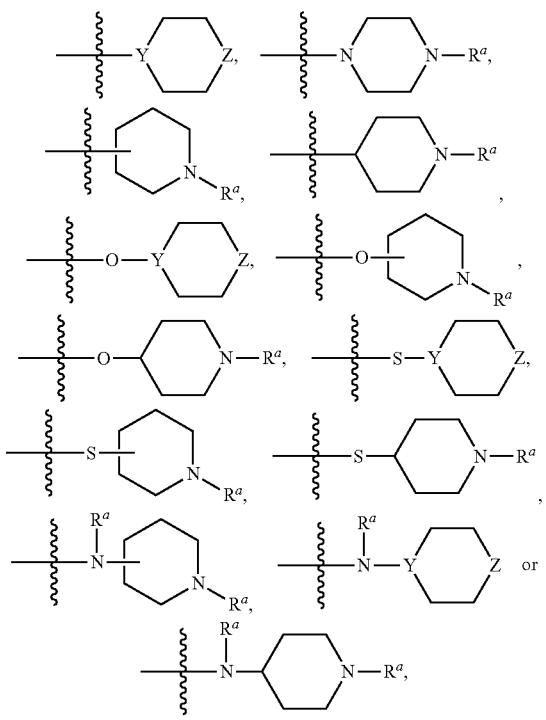

where Y is selected from CH and N, Z is selected from CH$_2$, O, S, N, NH, N—(CH$_2$)$_y$—R$^a$, N—(CH$_2$)$_y$—C(O)R$^a$, N—(CH$_2$)$_y$—C(O)OR$^a$, N—(CH$_2$)$_y$—S(O)$_2$R$^a$, N—(CH$_2$)$_y$—S(O)$_2$OR$^a$ and N—(CH$_2$)$_y$—C(O)NR$^c$R$^c$, where R$^a$, R$^c$ and y are as previously defined for structural formula (I), with the proviso that Y and Z are not both simultaneously CH and CH$_2$, respectively. In another specific embodiment, the water-solubilizing group is selected from morpholino, piperidinyl, (C1-C6) N-alkyl piperidinyl, N-methyl piperidinyl, piperazinyl, (C1-C6) N-alkylpiperazinyl, N-methylpiperazinyl, N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, imidazoyl, and the like.

In a specific embodiment of the 2,4-pyrimidinediamine compound described herein, R$^2$ is a substituted phenyl of the formula:

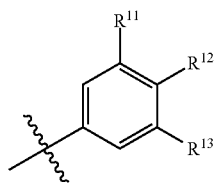

where one of R$^{11}$, R$^{12}$ or R$^{13}$ is a water-solubilizing group, and the other two of R$^{11}$, R$^{12}$ and R$^{13}$ are each, independently of one another, selected from hydrogen, lower alkyl, (C1-C3) alkyl, methyl, halo, chloro, fluoro, hydroxy, (C1-C3) hydroxyalkyl, —O(CH$_2$)$_x$—R$^b$, —NR$^c$R$^c$, —C(O)NR$^c$R$^c$, —C(O)NHR$^a$ and —C(O)NHCH$_3$, where R$^a$, R$^b$, R$^c$, and x are as previously defined for structural formula (I). In a specific exemplary embodiment, R$^{11}$ is hydrogen; R$^{12}$ is the water-solubilizing group, preferably selected from one of the specific embodiments of water-solubilizing groups described above; and R$^{12}$ is selected from methyl, halo, chloro, fluoro, (C1-C3) alkoxy, —CH$_2$OR$^e$ and —C(O)NHR$^e$, where R$^e$ is selected from hydrogen, methyl and (C1-C3) alkyl.

In another specific exemplary embodiment, R$^{11}$ is selected from hydrogen, lower alkyl, —(CH$_2$)$_n$—OH, —OR$^a$, —O(CH$_2$)$_n$—R$^a$, —O(CH$_2$)$_n$—R$^b$, —C(O)OR$^a$, halo, —CF$_3$ and —OCF$_3$; and R$^{12}$ and R$^{13}$ are each, independently of one another, selected from hydrogen, lower alkyl, —OR$^a$, —O(CH$_2$)$_x$—R$^a$, —O—(CH$_2$)$_x$—R$^b$, —NH—C(O)R$^a$, halo, —CF$_3$, —OCF$_3$,

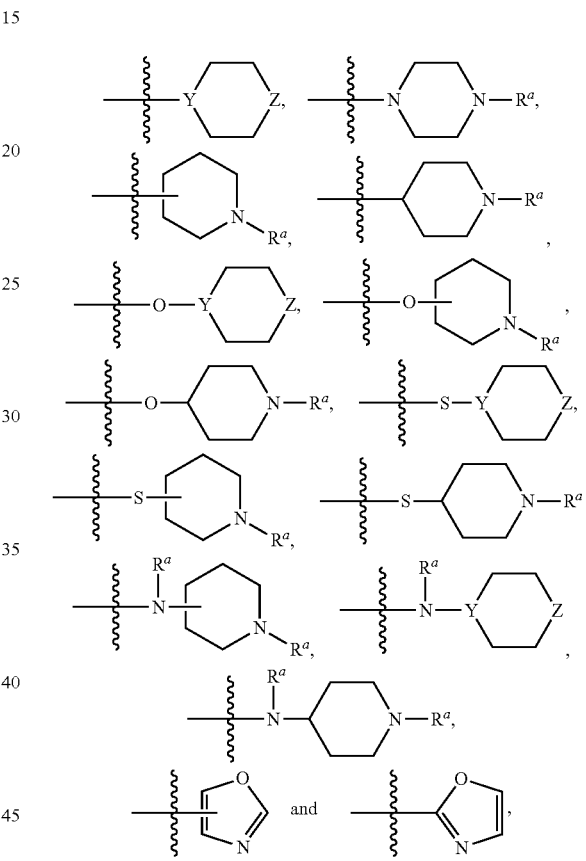

where R$^a$, R$^b$, R$^c$, and x are as previously defined for structural formula (I) and Y and Z are as defined supra.

In a specific embodiment, R$^{11}$ is hydrogen; R$^{12}$ is selected from,

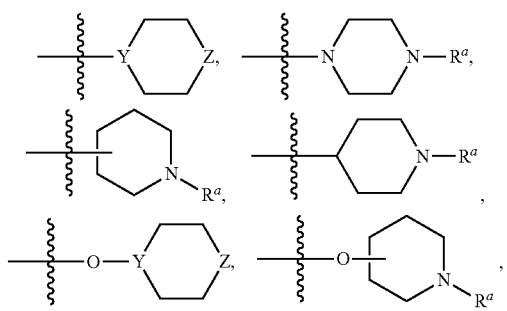

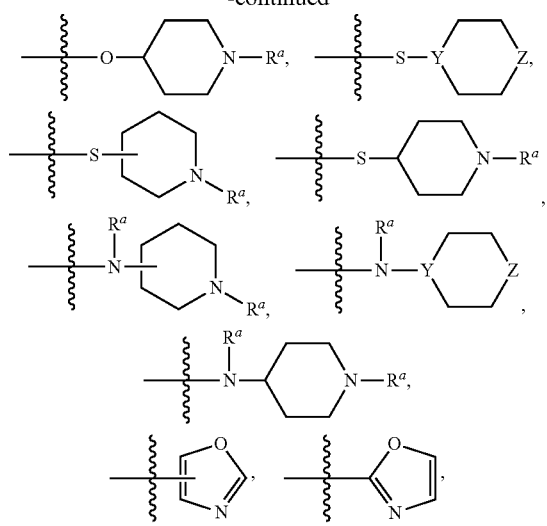

morpholino, piperidinyl, (C1-C3) N-alkyl piperidinyl, N-methyl piperidinyl, piperazinyl, (C1-C3) N-alkylpiperazinyl, N-methylpiperazinyl, N-ethyl piperidinyl, N-ethyl piperazinyl, pyrrolidinyl, N-alkyl pyrrolidinyl, N-methylpyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazoyl; and $R^{13}$ is other than,

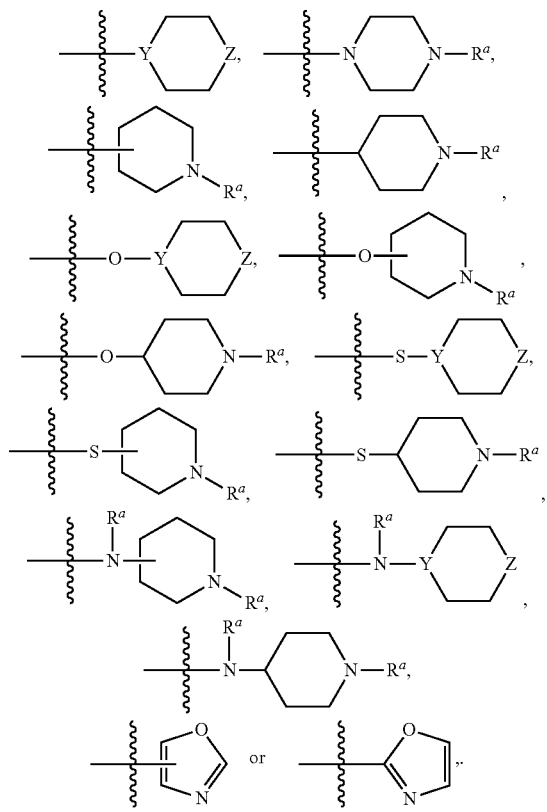

In another specific embodiment, $R^{11}$ is hydrogen; $R^{12}$ is selected from,

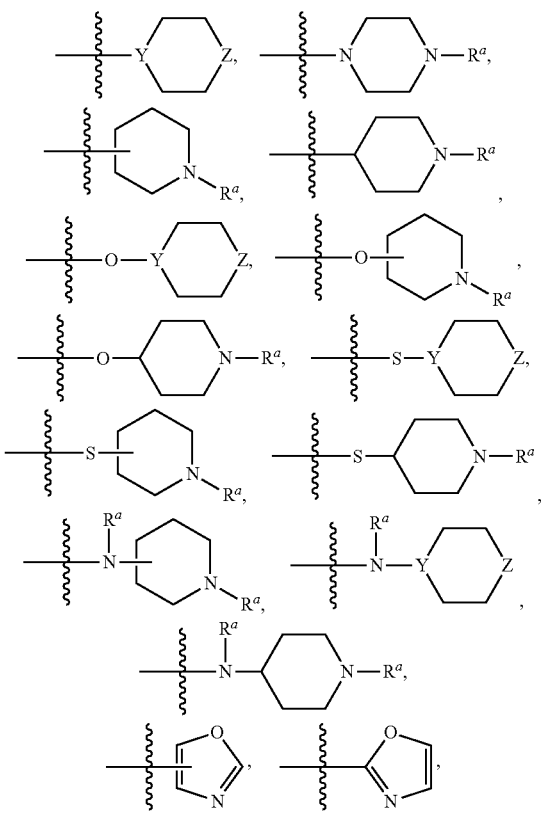

morpholino, piperidinyl, (C1-C3) N-alkyl piperidinyl, N-methyl piperidinyl, piperazinyl, (C1-C3) N-alkylpiperazinyl, N-methylpiperazinyl, N-ethyl piperidinyl, N-ethyl piperazinyl, pyrrolidinyl, N-alkyl pyrrolidinyl, N-methylpyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazoyl; and $R^{13}$ is selected from hydrogen, methyl, methoxy, trifluoromethyl and chloro.

In still another specific embodiment, $R^{11}$ is hydrogen; $R^{12}$ is other than,

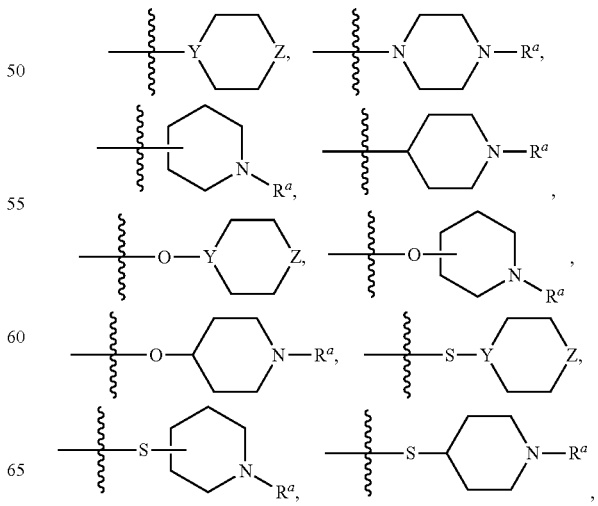

-continued

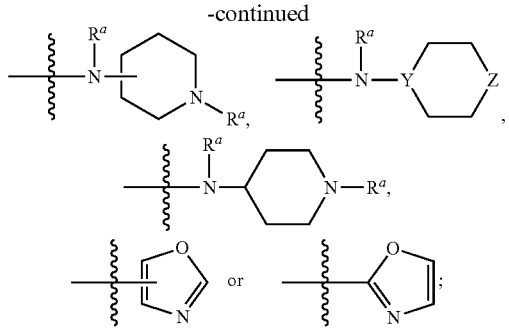

and R[13] is selected from,

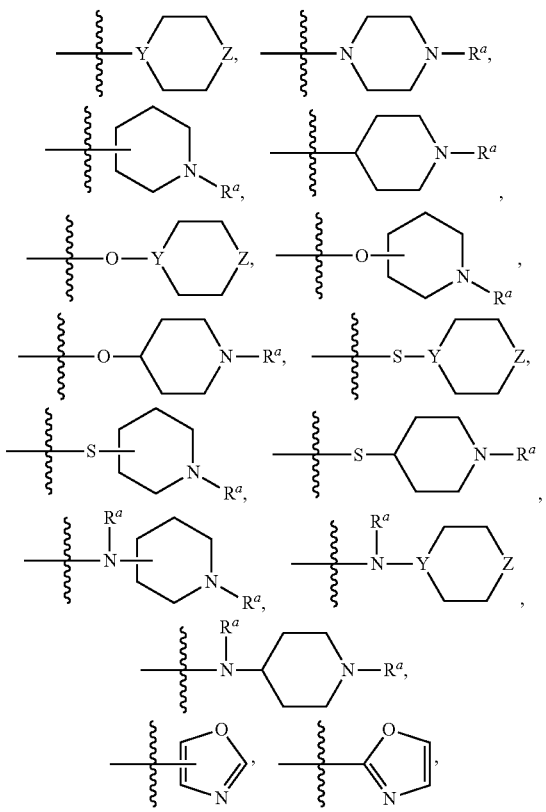

morpholino, piperidinyl, (C1-C3) N-alkyl piperidinyl, N-methyl piperidinyl, piperazinyl, (C1-C3) N-alkylpiperazinyl, N-methylpiperazinyl N-ethyl piperidinyl, N-ethyl piperazinyl, pyrrolidinyl, N-alkyl pyrrolidinyl, N-methylpyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazoyl.

In still another specific embodiment, R[11] is hydrogen; and R[12] and R[13] are each other than,

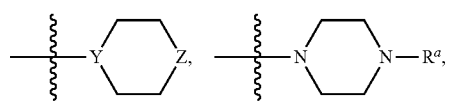

-continued

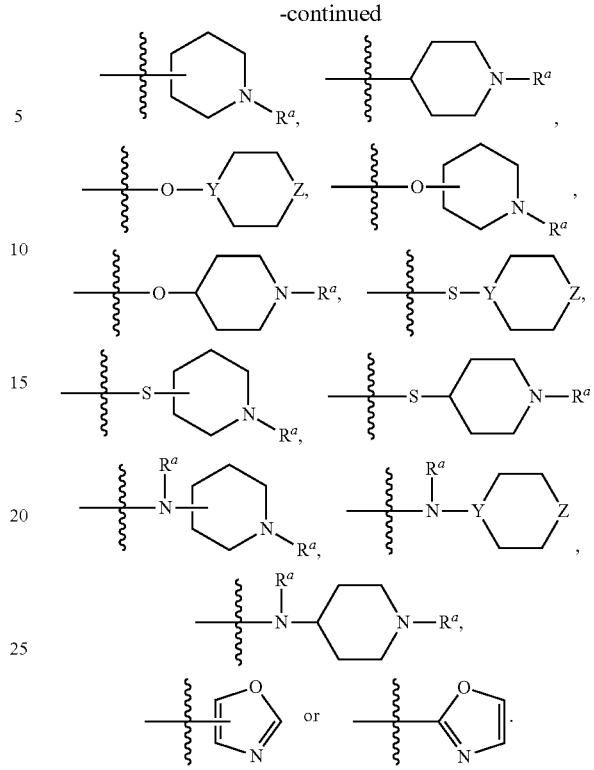

In still another specific embodiment, R[11] and R[12] are each hydrogen and R[13] is —OCH$_2$NHR$^a$.

In still other embodiments, R[11], R[12] and R[13] are each, independently of one another, selected from hydrogen, methyl, methoxy, trifluoromethyl and chloro, with the proviso that at least two of R[11], R[12] and R[13] are other than hydrogen.

In still other embodiments, R[11] is hydrogen; R[12] is selected from hydrogen,

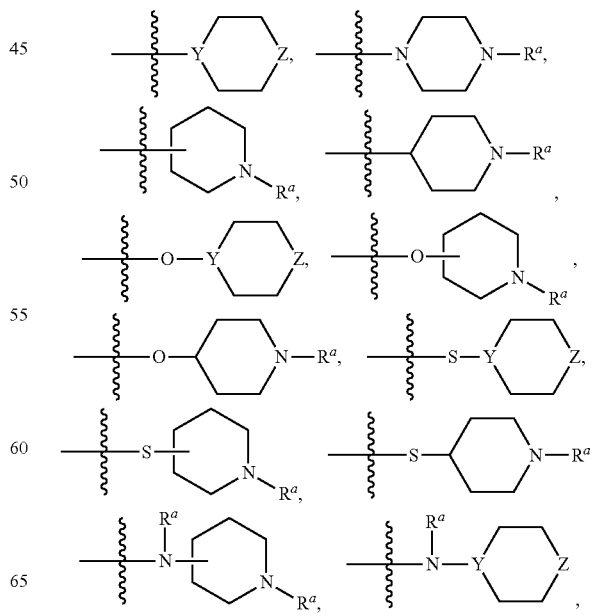

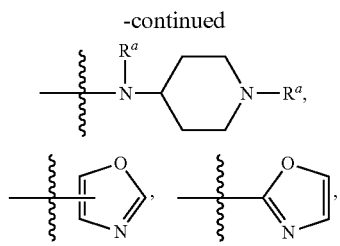

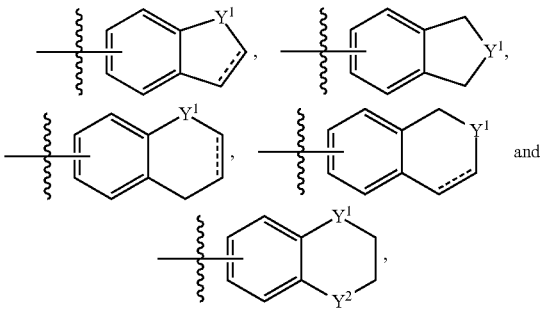

morpholino, piperidinyl, (C1-C3) N-alkyl piperidinyl, N-methyl piperidinyl, piperazinyl, (C1-C3) N-alkylpiperazinyl and N-methylpiperazinyl N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazoyl; and $R^{13}$ is selected from hydrogen, lower alkyl, halo and —$CF_3$. In a specific embodiment, $R^{13}$ is selected from the hydrogen, methyl, chloro and —$CF_3$.

In yet another specific embodiment, $R^{11}$ is hydrogen; $R^{12}$ is hydrogen; and $R^{13}$ is selected from,

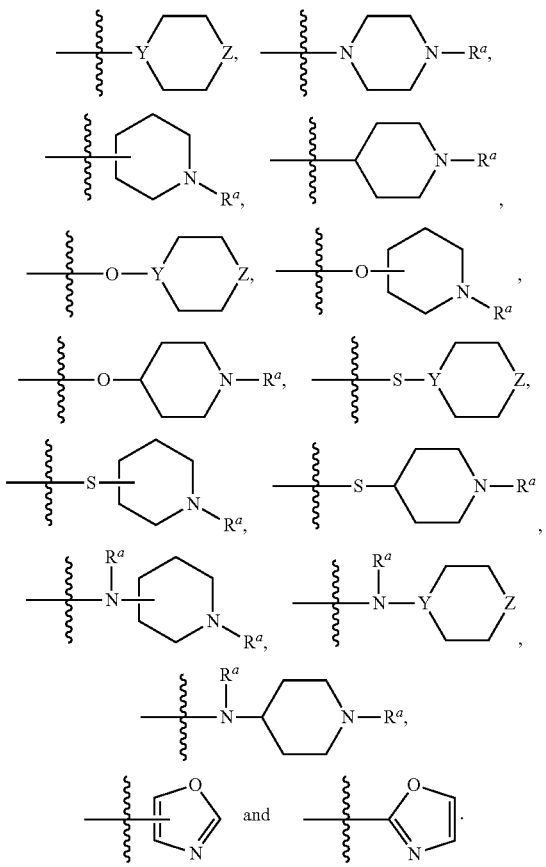

In yet another specific embodiment, $R^{11}$ is hydrogen; $R^{12}$ is selected from (C1-C3) N-alkyl piperazinyl and N-methyl piperazinyl; and $R^{13}$ is methyl.

In some other exemplary embodiments, $R^2$ is an optionally substituted heteroaryl group. In a specific exemplary embodiment, $R^2$ is selected from where $Y^1$ is selected from O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2OR^a$ and N—$(CH_2)_y$—$C(O)NR^cR^c$, where $R^a$, $R^c$ and y are as previously defined, $Y^2$ us selected from O, S and $S(O)_2$, and the bonds including the dotted line can be single bonds or double bonds.

While not intending to be bound by any theory of operation, it is believed that the antiproliferative activity of the compounds described herein, as well as their ability to inhibit Aurora kinases, derives in large part from the $R^4$ moiety, although $R^2$ is also believed to be important for selectivity, but to a lesser extent. In many embodiments of the compounds described herein, the $R^4$ group is a saturated or unsaturated, bridged or unbridged cycloalkyl that includes an $R^7$ substituent at one of the carbon atoms. The $R^7$ substituent can be attached to any carbon atom, but in specific embodiments is attached to the carbon atom connecting the $R^4$ group to the N4-nitrogen atom, the carbon atom adjacent to this carbon atom, or its next-nearest neighbor. Thus, in some embodiments, the compounds of structural formula (I) are selected from structural formulae (I.1), (I.2) and/or (I.3):

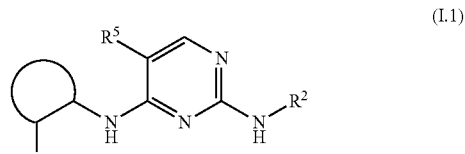

(I.1)

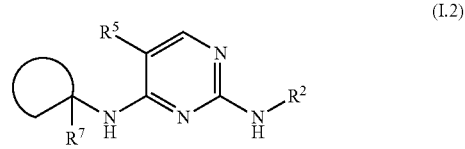

(I.2)

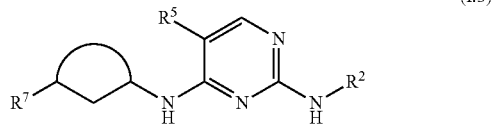

(I.3)

where the illustrated ring including the $R^7$ substituent represents a saturated or unsaturated, bridged or unbridged cycloalkyl ring, and $R^2$, $R^5$ and $R^7$ are as previously defined for structural formula (I).

When the $R^4$ group in the compounds of structural formula (I) comprises an unbridged cycloalkyl, it will typically contain from 3 to 8 carbon atoms. When the unbridged cycloalkyl is unsaturated, the ring may include one, two or more double bonds, which may be positioned at any ring positions, but are most commonly positioned such that they do not include the carbon atom attaching the $R^4$ ring to the remainder of the molecule. In many embodiments, saturated rings and unsaturated rings including a single double bond are preferred. Specific examples of $R^4$ groups that comprise an unbridged saturated, or singly unsaturated, cycloalkyl ring include, but are not limited to,

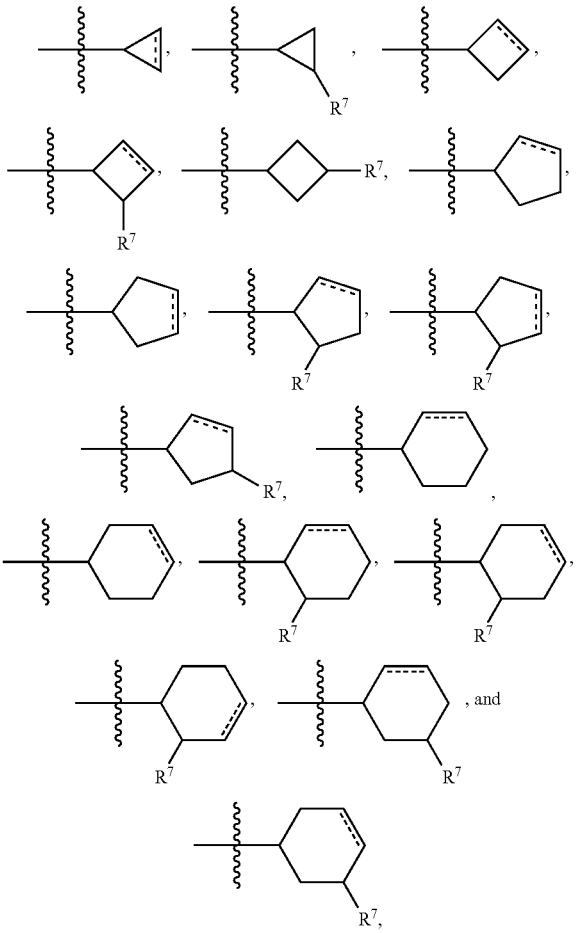

where $R^7$ is as previously defined for structural formula (I) and the dotted lines represent a single bond or a double bond.

When the $R^4$ group comprises a bridged cycloalkyl, it will typically contain from 5 to 16 carbon atoms. When the bridged cycloalkyl is unsaturated, it may include one, two or more double bonds, which may be positioned at any ring positions, but are most commonly positioned so that they do not include the carbon atom attaching the $R^4$ ring to the remainder of the molecule, or a bridgehead carbon atom. In many embodiments, of unsaturated bridged cycloalkyls, those including a single double bond are preferred. Specific examples of $R^4$ groups that comprise a bridged cycloalkyl ring include, but are not limited to,

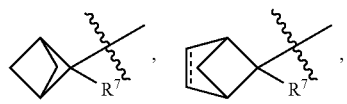

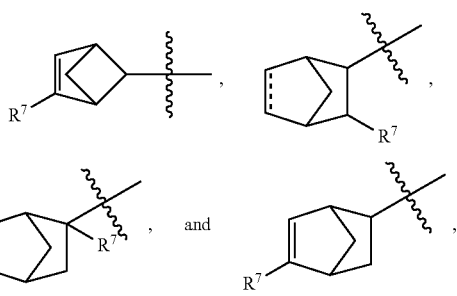

where $R^7$ is as previously defined for structural formula (I) and the dotted lines represent a single bond or a double bond.

$R^7$ is an ester or amide group. In some embodiments, $R^7$ is an amide of the formula $-C(O)NHR^d$ or an ester of the formula $-C(O)OR^d$, where $R^d$ is as previously described for structural formula (I). In some embodiments, $R^d$ is hydrogen. In some embodiments, $R^d$ is lower alkyl. In some embodiments, $R^d$ is a chiral auxiliary group. Examples of suitable chiral auxiliary groups include, but are not limited to;

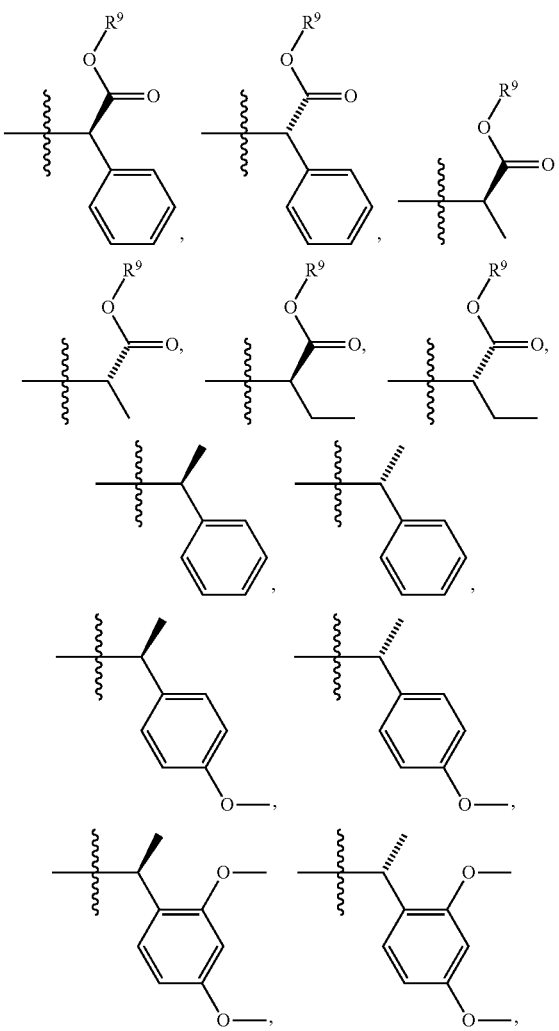

-continued

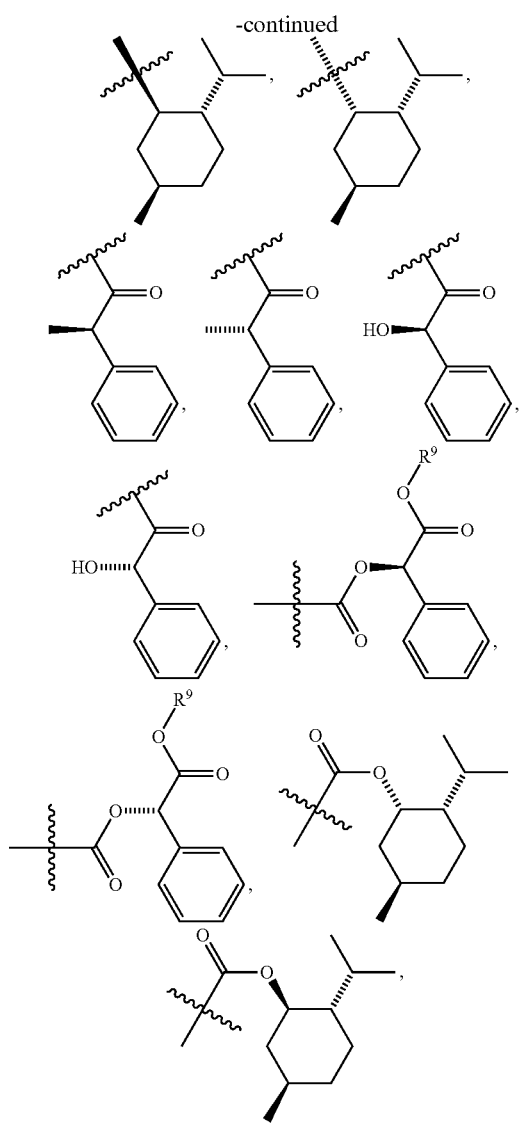

where $R^9$ is selected from hydrogen and lower alkyl (e.g. methyl, ethyl, isopropyl, cyclopropyl, $CH_2$-cyclopropyl, cyclobutyl, —$CH_2$-cyclobutyl, etc.).

In still other embodiments, $R^7$ is an amide of the formula —C(O)$NR^cR^c$ where $R^c$ is as previously defined for structural formula (I). In yet other embodiments, $R^7$ is an amide of the formula —C(O)$NHR^a$, where $R^a$ is as previously defined for structural formula (I). In a specific embodiment, $R^a$ is hydrogen.

6.3 Stereoisomerically Enriched and Stereoisomerically Pure Compounds

As will be appreciated by skilled artisans, in many embodiments of the compounds according to structural formula (I), the $R^4$ group includes chiral centers. For example, embodiments of compounds in which $R^4$ is an unbridged cycloalkyl substituted at the carbon atom adjacent to the carbon atom attaching the $R^4$ group to the remainder of the molecule includes two chiral carbon atoms: the carbon atom attaching the $R^4$ group to the remainder of the molecule, and the carbon atom including the $R^7$ substituent. Such compounds include two racemates, a cis racemate and a trans racemate, that together comprise four diastereomers, represented by structural formulae (IIa)-(IId), below (absolute configuration assignments determined assuming $R^7$ is an ester or amide group, and $R^7$ resides on carbon two of the cycloalkyl ring, the pyrimidine 4-nitrogen resides on carbon one of the cycloalkyl ring):

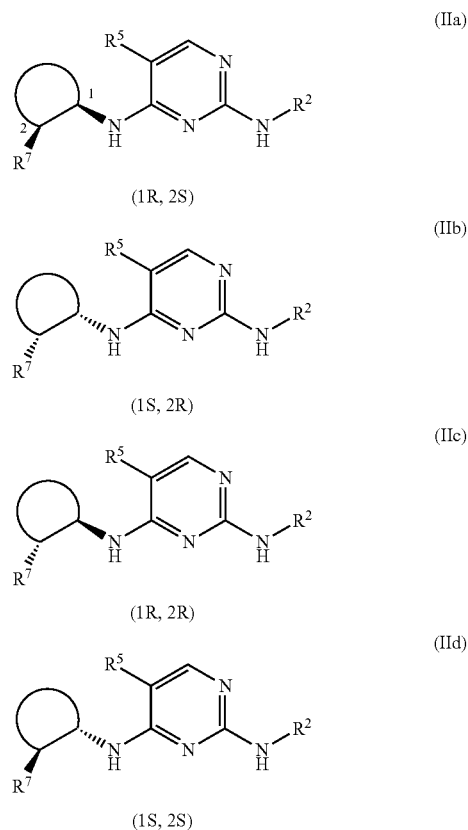

In structures (IIa)-(IId), the illustrated ring including the $R^7$ substituent could be any lower unbridged, saturated or unsaturated cycloalkyl ring, such as one of the exemplary rings illustrated previously. Moreover, while the $R^7$ substituent is illustrated at a specific location, it could be other locations.

For a specific compound, N4-(2-aminocarbonylcyclopent-1-yl)-5-fluoro-N2-[4-(4-methylpiperazin-1-yl)-3-methylphenyl]-2,4-pyrimidinediamine, it has been discovered that the trans (1R,2R) diastereomer and the two cis diastereomers, cis (1S,2R) and cis (1R,2S) inhibit the proliferation of a variety of tumor cell lines in in vitro assays, whereas the trans (1S,2S) diastereomer is relatively inactive in this same assay (see, e.g., Section 7.16, infra). Based on the activity of this compound, it is expected that the various diastereomers of all of the compounds according to structural formula (I) that correspond in absolute configuration to the cis racemate, and the cis and trans diastereomers of structural formulae (IIa)-(IIc) will exhibit similar differences in antiproliferative active activity.

Compounds in which $R^4$ is a substituted bridged cycloalkyl can include two cis racemates, exo-exo and endo-endo, represented by structural formulae (IIIa) and (IIIb), below, and two trans racemates, exo-endo and endo-exo, illustrated by structural formulae (IIIc) and (IIId), below:

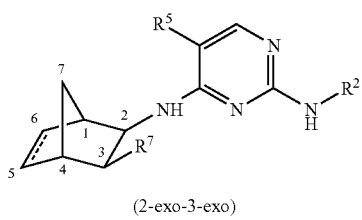
(IIIa)
(2-exo-3-exo)

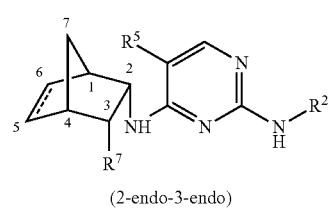
(IIIb)
(2-endo-3-endo)

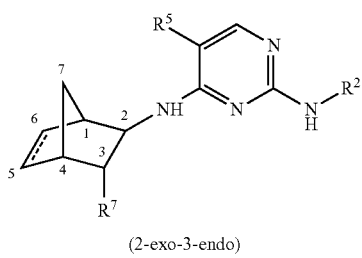
(IIIc)
(2-exo-3-endo)

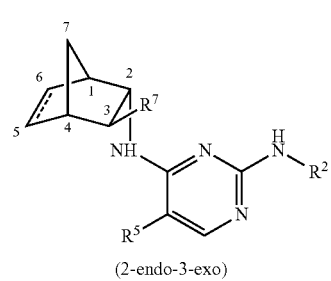
(IIId)
(2-endo-3-exo)

Together, these four racemates comprise eight diastereomers, illustrated as structures (IVa)-(IVh), below:

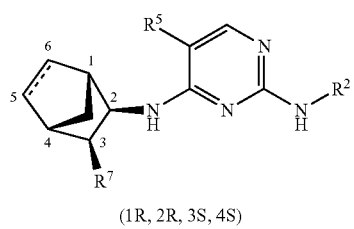
(IVa)
(1R, 2R, 3S, 4S)

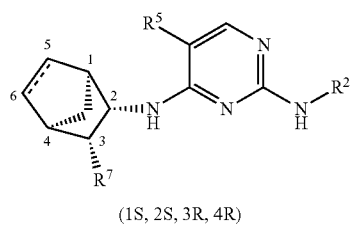
(IVb)
(1S, 2S, 3R, 4R)

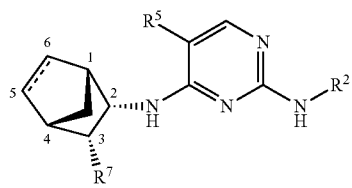
(IVc)
(1R, 2S, 3R, 4S)

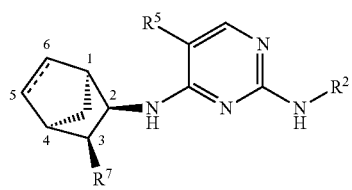
(IVd)
(1S, 2R, 3S, 4R)

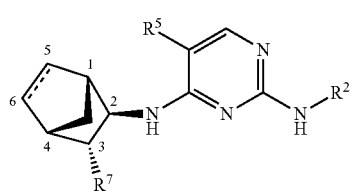
(IVe)
(1R, 2R, 3R, 4S)

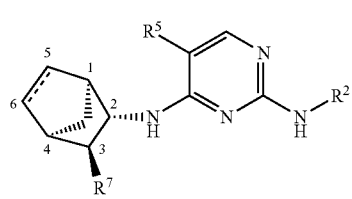
(IVf)
(1S, 2S, 3S, 4R)

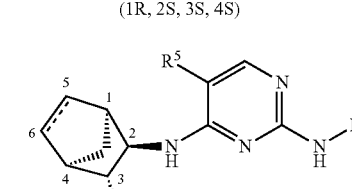
(IVg)
(1R, 2S, 3S, 4S)

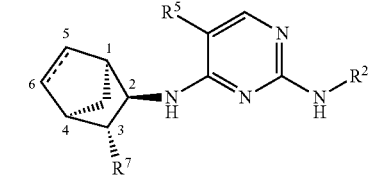
(IVh)
(1S, 2R, 3R, 4R)

In structural formulae (IIIa)-(IIId) and (IVa)-(IVh), the bond including the dotted line can be either a single bond or a double bond. It should be noted that while the racemates and diastereomers of structures (IIIa)-(IIId) and (IVa)-(IIh) are illustrated with reference to a specific bridged $R^4$ ring, these structural diagrams are for illustrative purposes only to exemplify the absolute stereochemistry of the chiral centers with respect to one another, and are not intended to be limiting with respect to the identity of the bridged $R^4$ ring, the location of the bridge, the number of carbon atoms comprising bridge and/or the location of the $R^7$ substituent. Thus, these structures are intended to be illustrative of any bridged $R^4$ ring which includes racemates and diastereomers corresponding in stereospecific configuration to the structures of structural formulae (IIIa)-(IIId) and (IVa)-(IVh). In this application, the terms "exo" and "endo" are used as a matter of convenience to name compounds where $R^4$ comprises a bicyclo[2.2.1]heptane or heptene. The exo and endo nomenclature was initially developed to describe preferential attack by reagents on a double bond of bicyclo[2.2.1] heptene ring systems, which happen to have chemically distinct bridges (a —CH$_2$— bridge and a —CH=CH— bridge). For example, there are eight diastereomers represented by formulae (IVa)-(IVh), in part, because of the chirality imparted to the $R^4$ ring system by virtue of these chemically distinct bridges. When $R^4$ is a bi- or tricyclic system where the bridges are chemically distinct, then analogous racemates and diastereomers exist. Specific examples of $R^4$ rings that have such corresponding racemates and diastereomers include, but are not limited to bicyclo[2.2.1]heptane, bicyclo[2.2.1]heptene, bicyclo[2.2.2] octene, bicyclo[3.2.1]octane, bicyclo[3.2.1]octene, and the like.

For a specific molecule, N4-(3-aminocarbonylbicyclo [2.2.1]hept-5-en-2-yl)-5-fluoro-N2-[3-methyl-4-(4-methyl-piperazin-1-yl)phenyl]-2,4-pyrimidinediamine, it has been discovered that the two cis racemates exhibit antiproliferative activity against a variety of tumor cell types in in vitro assays. However, the cis exo-exo racemate is approximately twenty-fold more potent than the cis endo-endo racemate in all cell lines tested. Moreover, it has been discovered that the enantiomer corresponding to the (1R,2R,3S,4S) diastereomer of structural formula (IVa) is largely responsible for the potency of the exo-exo cis racemate. When tested as isolated stereoisomers, the (1R,2R,3S,4S) diastereomer of this compound exhibited IC$_{50}$s in the nanomolar range, whereas the (1S,2S,3R,4R) diastereomer of this compound generally exhibited IC$_{50}$s in the micromolar range against the same cell lines. Thus, in general, the (1R,2R,3S,4S) diastereomer of this compound is approximately 1000-fold more potent than the (1S,2S,3R,4R) diastereomer. The (1R, 2R,3S,4S) diastereomer exhibited similarly superior results compared to the (1S,2S,3R,4R) diastereomers in cell-based inhibition assays against Aurora kinase B.

Based on the observed potency of this (1R,2R,3S,4S) diastereomer, it is expected that the full range of diastereomers corresponding to the diastereomer of structural formula (IVa) will exhibit similarly superior potencies as compared to their enantiomers, the exo-exo and endo-endo cis racemates, and their other diastereomers.

Thus, additional specific embodiments of the compounds include compounds that are enriched in one or more of the active diastereomers, or in one or more of the diastereomers that exhibit superior potencies in in vitro and/or in vivo antiproliferation assays, and/or that are substantially free of inactive diastereomers.

In some embodiments, the stereoisomerically enriched compounds are compounds according to structural formula (I) in which $R^4$ comprises an unbridged saturated or unsaturated cycloalkyl that is enriched one or more of the diastereomers corresponding to structural formulae (IIa), (IIb) and/or (IIc). In a specific embodiment, the compound is substantially free of the diastereomer corresponding to structural formula (IId). In another specific embodiment, the compound is a mixture, including a racemic mixture, of the diastereomers corresponding to structural formulae (IIa) and (IIb). In still another specific embodiment, the compound is a substantially pure diastereomer corresponding to structure (IIa), (IIb) or (IIc).

In some embodiments, the stereoisomerically enriched compounds are compounds according to structural formula (I) in which $R^4$ comprises a bridged saturated or unsaturated cycloalkyl, or a saturated or unsaturated bicycloalkyl, that are enriched in a diastereomer corresponding to structural formula (IVa), (IVb), (IVc) and/or (IVd). In a specific embodiment, the compound is a racemic mixture of cis isomers corresponding to structural formulae (IIIa) or (IIIb). In another specific embodiment, the compound is substantially pure in the diastereomer corresponding to structural formula (IVa).

In one illustrative embodiment, the stereoisomerically enriched compounds are compounds according to structural formula (VI):

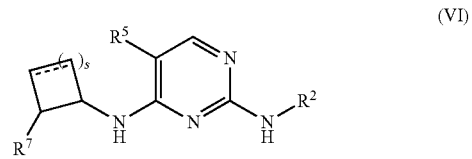

(VI)

including the salts, hydrates, solvates and N-oxides thereof, that are enriched in one or more diastereomers according to structural formula (VIa), (VIb) and/or (VIc):

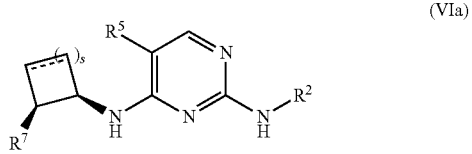

(VIa)

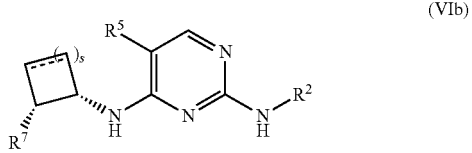

(VIb)

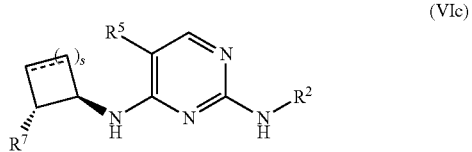

(VIc)

wherein s is an integer ranging from 0 to 5; $R^2$, $R^5$ and $R^7$ are as previously defined for structural formula (I); and the dotted line represents one or more optional double bonds, the positions of which can vary, with the proviso that when S is 0, the ring does not include a double bond. In a specific embodiment, S is 1, 2, 3 or 4 and the bond including the dotted line is a single bond.

In another illustrative embodiment, the stereoisomerically enriched compounds are compounds according to structural formula (VII):

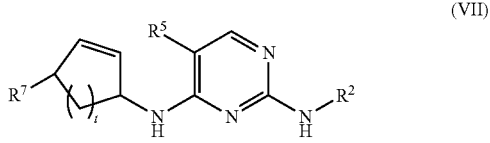

(VII)

including the salts, hydrates, solvates and N-oxides thereof, that is enriched in one or more diastereomers according to structural formula (VIIa), (VIIb) or (VIIc):

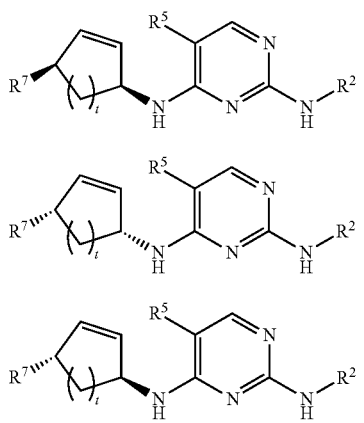

(VIIa)

(VIIb)

(VIIc)

wherein t is an integer ranging from 1 to 3 and $R^2$, $R^5$ and $R^7$ are as previously defined for structural formula (VI). In a specific embodiment, t is 1 or 2.

In still another illustrative embodiment, the stereoisomerically enriched compounds are compounds according to structural formula (VI) that are substantially free of the diastereomer of structural formula (VId):

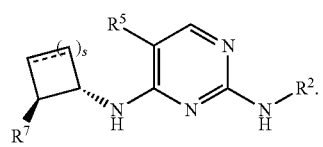

(VId)

In still another illustrative embodiment, the stereoisomerically enriched compounds are compounds according to structural formula (VII) that are substantially free of the diastereomer of structural formula (VIId):

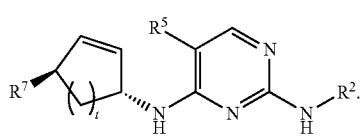

(VIId)

In still another illustrative embodiment, the stereoisomerically enriched compounds are compounds according to structural formulae (VIa) or (VIIa) that are substantially free of all other enantiomers and/or diastereomers.

In yet another illustrative embodiment, the stereoisomerically enriched compounds are compounds according to structural formula (VIII):

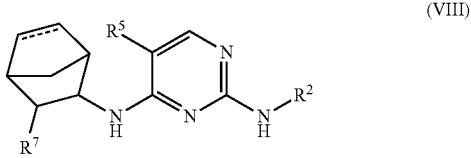

(VIII)

including the salts, hydrates, solvates and N-oxides thereof, that are enriched in the diastereomer of structural formula (VIIIa):

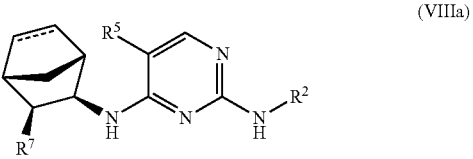

(VIIIa)

wherein $R^2$, $R^5$ and $R^7$ are as previously defined for structural formula (I), and the dotted line represents a single bond or double bond.

In still another illustrative embodiment, the stereoisomerically enriched compounds are compounds according to structural formula (VIIIa) that are substantially free of any other enantiomers and diastereomers.

In some specific embodiments of the stereoisomerically enriched compounds described herein, $R^7$ is one of the previously defined specific embodiments and $R^2$ is a phenyl of the formula

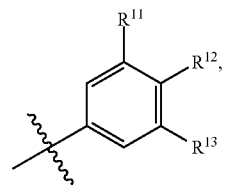

where $R^{11}$ and $R^{12}$ and $R^{13}$ are as previously defined in connection with any of the previously-discussed specific embodiments.

As used herein, a compound is "enriched" in a particular diastereomer when that diastereomer is present in excess over any other diastereomer present in the compound. The actual percentage of the particular diastereomer comprising the enriched compound will depend upon the number of other diastereomers present. As a specific example, a racemic mixture is "enriched" in a specified enantiomer when that enantiomer constitutes greater than 50% of the mixture. Regardless of the number of diastereomers present, a compound that is enriched in a particular diastereomer will typically comprise at least about 60%, 70%, 80%, 90%, or even more, of the specified diastereomer. The amount of enrichment of a particular diastereomer can be confirmed using conventional analytical methods routinely used by those of skill in the art, as will be discussed in more detail, below.

Some embodiments of stereoisomerically enriched compounds are substantially free of specified enantiomers and/or diastereomers. By "substantially free of" is meant that the compound comprises less than about 10% of the undesired diastereomers and/or enantiomers as established using conventional analytical methods routinely used by those of skill in the art (discussed in more detail below). In some embodiments, the amount of undesired stereoisomers may be less than 10%, for example, 9%, 8%, 7%, 6%, 5%, 4%, 3%, 2%, 1% or even less. Stereoisomerically enriched compounds that contain about 95% or more of a desired stereoisomer are referred to herein as "substantially pure" stereoisomers. Stereoisomerically enriched compounds that contain about 99% or more of a desired stereoisomer are referred to herein as "pure" stereoisomers. The purity of any stereoisomerically enriched compound (diastereoisomeric purity; % de) can be confirmed using conventional analytical methods, as will be described in more detail, below.

Various specific exemplary embodiments of the compounds described herein are provided in TABLE 1, in the Examples section. In this table, compounds that were either synthesized or isolated as specific diastereomers are illustrated showing the absolute stereochemistry about the chiral centers of the $R^4$ ring. Compounds having chiral centers in the $R^4$ ring that are not illustrated with a specified stereochemical configuration were synthesized as racemates.

Those of skill in the art will appreciate that the compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, compounds that include ester moieties may be considered prodrugs of their corresponding carboxylic acid, regardless of whether the ester form is pharmacologically active.

Included within the scope of the invention are prodrugs of the various compounds described herein. In such prodrugs, any available functional moiety may be masked with a progroup to yield a prodrug. Functional groups within the compounds described herein that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs described herein.

In one illustrative embodiment, the prodrugs are compounds according to structural formulae (I), supra, in which $R^a$, $R^b$ and $R^c$ may be, in addition to their previously-defined alternatives, a progroup.

Those of skill in the art will appreciate that many of the compounds and prodrugs described herein, as well as the various compound species specifically described and/or illustrated herein, may exhibit the phenomena of tautomerism and conformational isomerism. For example, the compounds and prodrugs may exist in several tautomeric forms, including the enol form, the keto form and mixtures thereof. The compounds may also include chiral centers in addition to those specifically discussed herein, and may therefore exist as optical isomers. As the various compound names, formulae and compound drawings within the specification and claims can represent only one of the possible tautomeric or conformational forms, it should be understood that the invention encompasses any tautomers, conformational or optical isomers, of the compounds or prodrugs having one or more of the utilities described herein, as well as mixtures of these various different isomeric forms. In cases of limited rotation around the 2,4-pyrimidinediamine core structure, atrop isomers are also possible and are also specifically included in the compounds and/or prodrugs of the invention.

Depending upon the nature of the various substituents, the compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, adipic acid, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an inorganic or organic base (e.g., ammonia, ethanolamine, diethanolamine, triethanolamine, N-methylglucamine, morpholine, piperidine, dimethylamine, diethylamine, etc.).

The compounds and prodrugs, as well as the salts thereof, may also be in the form of hydrates, solvates and/or N-oxides, as are well-known in the art.

For embodiments of compounds that are enriched in particular diastereomers, the stereoisomeric enrichment and/or purity may be established by conventional analytical methods well known to those of skill in the art. For example, use of chiral NMR shift reagents, gas chromatographic analysis using chiral columns, high pressure liquid chromatographic analysis using chiral columns, formation of diastereomeric derivatives through reaction with chiral reagents and conventional analysis may be used to establish the stereoisomeric enrichment and/or purity of a specific stereoisomer. Alternatively, synthesis using starting materials of known stereoisomeric enrichment and/or purity may be used to establish the stereoisomeric enrichment and/or purity of the compounds described herein. Other analytical methods for demonstrating stereoisomeric homogeneity are well within the ambit of the skilled artisan.

6.4 Methods of Synthesis

The compounds and prodrugs described herein may be synthesized via a variety of different synthetic routes using commercially available starting materials and/or starting materials prepared by conventional synthetic methods. A variety of exemplary synthetic routes that can be used to synthesize the compounds and prodrugs are described in WO 03/063794 and US 2004-0029902, the disclosures of which are incorporated herein by reference.

For purposes of illustration, an exemplary synthetic scheme that can be used to synthesize the full range of compounds described herein is illustrated in Scheme (I), below:

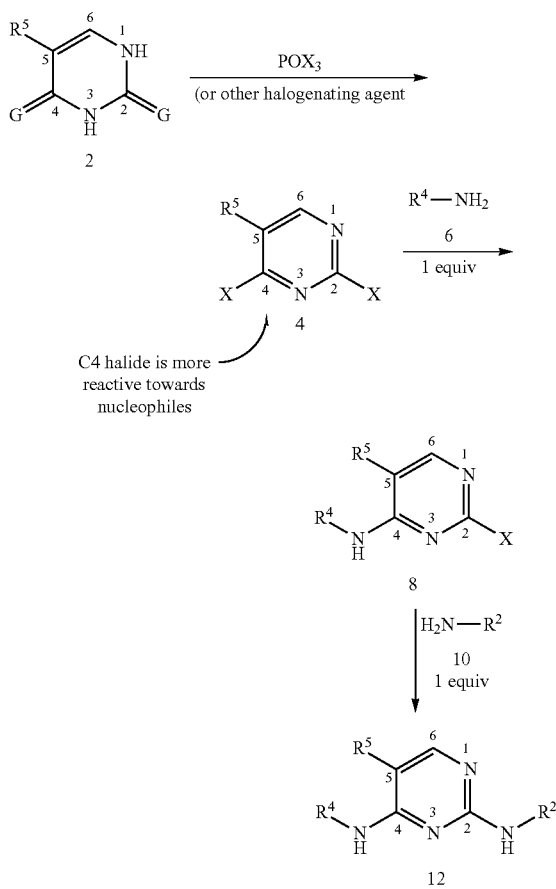

In Scheme (I), $R^2$, $R^4$ and $R^5$ are as previously defined for structural formula (I), supra, X is a halogen (e.g., F, Cl, Br or I), and each G is, independently of the other, selected from O and S.

Referring to Scheme (I), uracil or thiouracil 2 is dihalogenated at the 2- and 4-positions using the standard halogenating agent $POX_3$ (or other standard halogenating agents) under standard conditions to yield 2,4-bis-halo pyrimidine 4. The halide at the C4 position is more reactive towards nucleophiles than the halide at the C2 position in pyrimidine 4. This differential reactivity can be exploited to synthesize the compounds and prodrugs described herein by first reacting 2,4-bis-halopyrimidine 4 with one equivalent of amine 6, yielding 8, followed by reaction with amine 10 to yield compounds according to structural formula (I) (12).

In most situations, the C4 halide is more reactive towards nucleophiles, as illustrated in the Scheme. However, as will be recognized by skilled artisans, the identity of the $R^5$ substituent may alter this reactivity. For example, when $R^5$ is trifluoromethyl, a 50:50 mixture of 4N-substituted-4-pyrimidineamine 8 and the corresponding 2N-substituted-2-pyrimidineamine is obtained. Regardless of the identity of the $R^5$ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry, Biotage AB, Sweden) in a sealed tube (at 20 bar pressure).

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13, 078-8; CAS Registry 66-22-8); 2-thio-uracil (Aldrich #11, 558-4; CAS Registry 141-90-2); 2,4-dithiouracil (Aldrich #15, 846-1; CAS Registry 2001-93-6); 5-bromouracil (Aldrich #85, 247-3; CAS Registry 51-20-7; 5-fluorouracil (Aldrich #85, 847-1; CAS Registry 51-21-8); 5-iodouracil (Aldrich #85, 785-8; CAS Registry 696-07-1); 5-nitrouracil (Aldrich #85, 276-7; CAS Registry 611-08-5); 5-(trifluoromethyl)-uracil (Aldrich #22, 327-1; CAS Registry 54-20-6). Additional 5-substituted uracils and/or thiouracils are available from General Intermediates of Canada, Inc., Edmonton, Calif. (http://www-.generalintermediates.com) and/or Interchim, Cedex, France (http://www.interchim.com), or may be prepared using standard techniques. Myriad textbook references teaching suitable synthetic methods are provided infra.

Amines 6 and 10 may be purchased from commercial sources or, alternatively, may be synthesized utilizing standard techniques. For example, amines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances amines 6 and/or 10 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Prodrugs as described herein may be prepared by routine modification of the above-described methods.

Compounds that are enriched, substantially pure and/or pure in specified diastereomers may be isolated by chiral separation or by other standard techniques. Methods for chirally resolving specific diastereomers are described in more detail in the Examples section.

Alternatively, stereoisomerically enriched, substantially stereoisomerically pure and/or stereoisomerically pure compounds may be synthesized from amine 6 starting materials having the desired stereochemistry, or that include chiral auxiliaries to aid chiral separation. For example, specified racemic mixtures can be synthesized using the appropriate racemic amine 6. As another specific example, stereoisomerically pure compounds can be synthesized from the appropriate stereoisomerically pure amine 6.

In one exemplary embodiment, illustrated in Scheme (II), below, the desired diastereomer is resolved chemically using (R)-methyl-p-methoxybenzylamine as a chiral auxiliary.

18, yielding a mixture of diastereomers 20a and 20b. This diastereomeric mixture is treated with an acid such as TFA to cleave the Boc group, yielding a mixture of diastereomers 22a and 22b, which can be reacted with 2,4-dihalopyrmidine 4 to afford a racemic mixture of compounds 24a and 24b. At

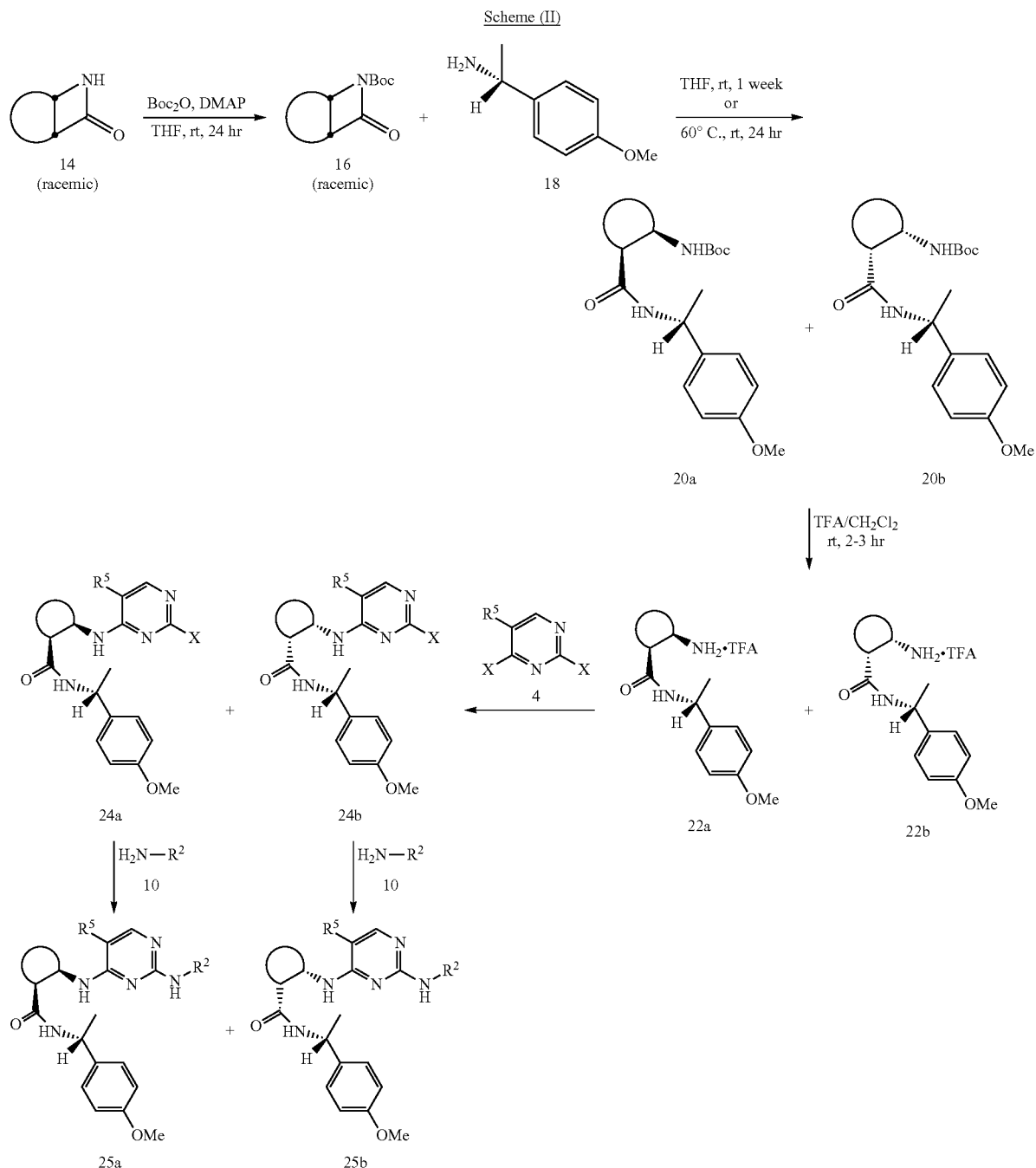

In Scheme (II), 2-exo-3-exo racemic β-lactam 14 (prepared as described in Stajar et al., 1984, Tetrahedron 40(12): 2385) is protected with a Boc group, yielding the corresponding racemic Boc-protected β-lactam 16. In β-lactams 14 and 16, the ring represents any saturated or unsaturated, bridged or unbridged cycloalkyl. Boc-protected racemate 16 is then reacted with (R)-methyl-para-methoxybenzylamine this stage, compounds 24a and 24b can be resolved from one another by crystallization, each isolated diastereomer reacted with amine 10, and the chiral auxiliary cleaved to afford isolated diastereomers 25a and 25b. The chiral auxiliaries from isolated diasteromers 25a and 25b can then be cleaved, and the compounds further derivatized, if desired. Alternatively, the chiral auxiliaries need not be cleaved, as 2,4-pyrimidinediamine compounds including the chiral auxiliaries have antiproliferative activity.

For compounds in which $R^5$ is fluoro and $R^2$ is

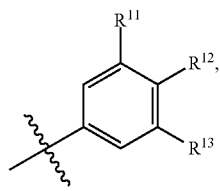

where $R^{11}$ is hydrogen, $R^{12}$ is 4-methyl-piperazin-2-yl, and $R^{13}$ is methyl, cleavage of the chiral auxiliary proved difficult. For these and other compounds where such cleavage proves difficult, the chiral auxiliary can be cleaved from compounds 24a and 24b, and the resultant isolated compounds reacted with amine 10.

Compounds that are stereoisomerically enriched, substantially stereoisomerically pure and/or stereoisomerically pure in specified diastereomers can also be synthesized from stereoisomerically enriched, substantially stereoisomerically pure, and/or stereoisomerically pure β-lactams. Such stereoisomerically enriched and/or (substantially) stereoisomerically pure β-lactams can be enzymatically resolved and isolated. In one exemplary embodiment, (substantially) stereoisomerically pure β-lactams can be resolved and isolated from a racemic mixture of 2-exo-3-exo β-lactam 14 using an immobilized lipolase (available from Sigma Chemical Co., catalog no. L4777) as described in Eniko et al., 2004, Tetrahedron Asymmetry 15:573-575. In another exemplary embodiment, (substantially) stereoisomerically pure β-lactams can be resolved and isolated from 2-exo-3-exo Boc-protected racemic β-lactam 16 using resin bound, immobilized chirazyme L-2-type B, c.f. enzyme (Candida Antarctica Type B, c-f, available from Biocatalytics, Inc., Pasadena, Calif.) as described in copending application Ser. No. 60/628,401, filed Nov. 5, 2004. A specific example of the use of this enzyme to resolve specified diastereomers of β-lactams is described in the Examples section, as is a method of synthesizing 2-exo-3-exo racemic β-lactam 16.

Examples of synthesizing specified diastereomers utilizing enzyme reactions are illustrated in Schemes (III) and (IV), below. In Schemes (III) and (IV), stereoisomerically enriched, substantially stereoisomerically pure and/or stereoisomerically pure compounds in which $R^7$ is an N-substituted amide can be prepared from the corresponding carboxamide using standard techniques. The carboxamide can be converted to the corresponding acids and/or esters via acidic hydrolysis or treatment with basic alkoxide, respectively. A specific example of the use of Novozyme 435 enzyme as illustrated in Scheme (IV), which like the Chirazyme enzyme discussed supra and illustrated in Scheme (III), can be used to resolve enantiomers from racemic β-lactams, is described in the Examples section.

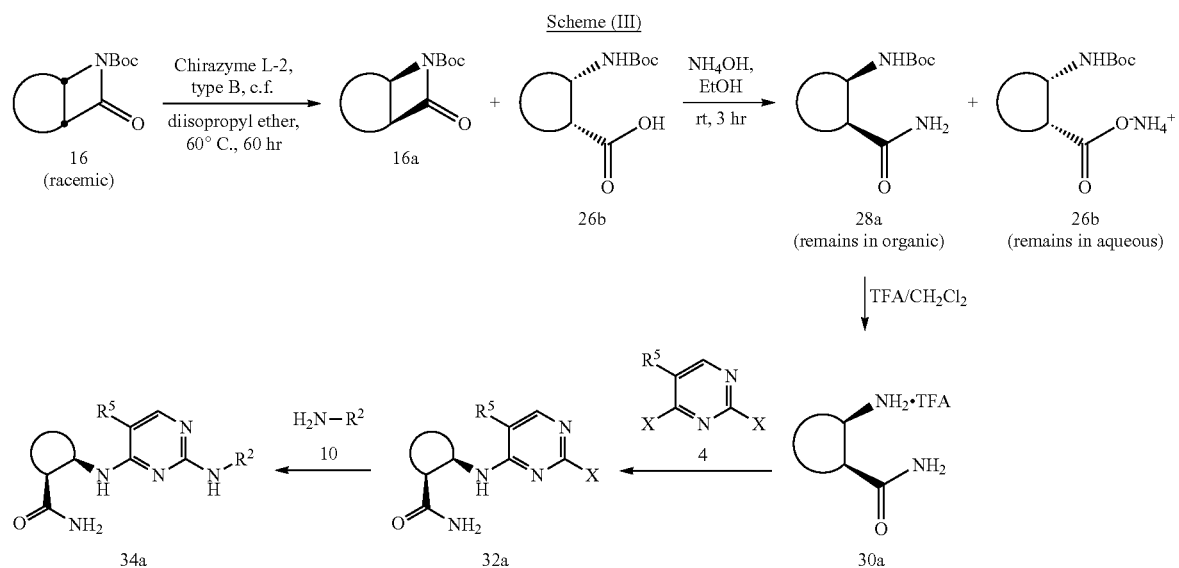

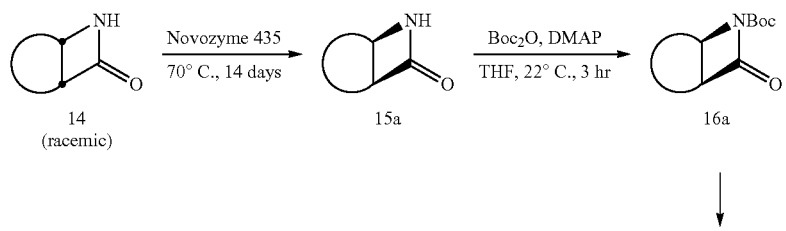

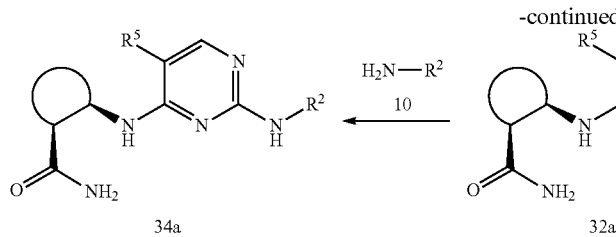
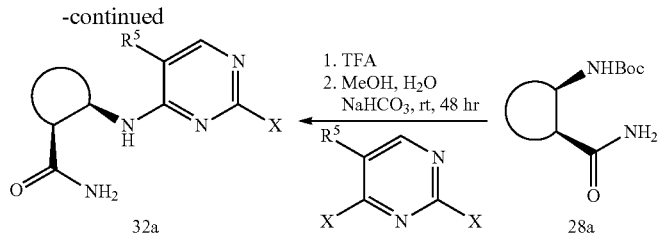

6.5 Activity of the Antiproliferative Compounds

Active compounds typically inhibit proliferation of desired cells, such as tumor cells, with an $IC_{50}$ in the range of about 20 µM or less, as measured in a standard in vitro cellular proliferation assay. Of course, skilled artisans will appreciate that compounds which exhibit lower $IC_{50}$'s, for example on the order of 10 µM, 1 µM, 500 nM, 100 nM, 10 nM, 1 nM, or even lower, may be particularly useful in therapeutic applications. The antiproliferative activity may be cytostatic or it may be cytotoxic. In instances where antiproliferative activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

Active compounds also typically inhibit an activity of an Aurora kinase with an $IC_{50}$ in the range of about 20 µM or less, typically in the range of about 10 µM, 1 µM, 500 nM, 100 nM, 10 nM, 1 nM, or even lower. The $IC_{50}$ against an Aurora kinase can be determined in a standard in vitro assay with an isolated aurora kinase, or in a functional cellular assay. A suitable enzyme-coupled assay that can be used to determine the degree of Aurora kinase activity is described in Fox et al., 1998, Protein Sci. 7:2249-2255. Kemptide peptide sequence LRRASLG (Bochem Ltd., UK) can be used as a substrate for Aurora kinase-A Aurora kinase-B and/or Aurora kinase-C, and reactions can be carried out at 30° C. in a solution containing 100 mM HEPES (pH 7.5), 10 mM Mg $Cl_2$, 25 mM NaCl, 1 mM DTT. $IC_{50}$ values can be determined using computerized non-linear regression with commercially-available software (e.g., Prism 3.0, GraphPed Software, San Diego, Calif.). A suitable cell-based functional assay is described in the Examples section.

6.6 Uses of the Antiproliferative Compounds

The active compounds, including the various prodrugs, salts, hydrates and/or N-oxide forms thereof, may be used to inhibit Aurora kinases, Aurora kinase-mediated processes, and/or cell proliferation in a variety of contexts. According to some embodiments, a cell or population of cells is contacted with an amount of such a compound effective to inhibit an activity of an Aurora kinase, an Aurora kinase-mediated process and/or proliferation of the cell or cell population. When used to inhibit cellular proliferation, the compound may act cytotoxically to kill the cell, or cytostatically to inhibit proliferation without killing the cell.

In some embodiments, the methods may be practiced in vivo as a therapeutic approach towards the treatment or prevention of Aurora kinase-mediated diseases or disorders, and in particular proliferative disorders. Thus, in a specific embodiment, the stereoisomerically enriched compounds described herein, (and the various forms described herein) may be used to treat or prevent proliferative disorders in animal subjects, including humans. The method generally comprises administering to the subject an amount of a stereoisomerically enriched compound, or a prodrug, salt, hydrate or N-oxide thereof, effective to treat or prevent the disorder. In one embodiment, the subject is a mammal, including, but not limited to, bovine, horse, feline, canine, rodent, or primate. In another embodiment, the subject is a human.

A variety of cellular proliferative disorders may be treated or prevented with the compounds described herein. In some embodiments, the compounds are used to treat various cancers in afflicted subjects. Cancers are traditionally classified based on the tissue and cell type from which the cancer cells originate. Carcinomas are considered cancers arising from epithelial cells while sarcomas are considered cancers arising from connective tissues or muscle. Other cancer types include leukemias, which arise from hematopoietic cells, and cancers of nervous system cells, which arise from neural tissue. For non-invasive tumors, adenomas are considered benign epithelial tumors with glandular organization while chondomas are benign tumor arising from cartilage. In the present invention, the described compounds may be used to treat proliferative disorders encompassed by carcinomas, sarcomas, leukemias, neural cell tumors, and non-invasive tumors.

In a specific embodiment, the compounds are used to treat solid tumors arising from various tissue types, including, but not limited to, cancers of the bone, breast, respiratory tract, brain, reproductive organs, digestive tract, urinary tract, bladder, eye, liver, skin, head, neck, thyroid, parathyroid, kidney, pancreas, blood, ovary, colon, germ/prostate, and mestastatic forms thereof.

Specific proliferative disorders include the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial edema, pleuropulmonary blastoma, and malignant mesothelioma; d) proliferative disorders of the brain include, but are not limited to, brain stem and hyptothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer- Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and neck cancers can include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkins lymphoma, cutaneous T cell lymphoma, renal tumors and carcinomas T-cell lymphomas and leukemias, and lymphoma of the central nervous system; l) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The compounds of the present invention may be tested for effectiveness against the disorders described herein, and a therapeutically effective regimen established. Effectiveness, as further described below, includes reduction or remission of the tumor, decreases in the rate of cell proliferation, or cytostatic or cytotoxic effect on cell growth.

6.7 Combination Therapies

The compounds described herein may be used alone, in combination with one another, or as an adjunct to, or in conjunction with, other established antiproliferative therapies. Thus, the compounds may be used with traditional cancer therapies, such as ionization radiation in the form of γ-rays and x-rays, delivered externally or internally by implantation of radioactive compounds, and as a follow-up to surgical removal of tumors.

In another aspect, the compounds may be used with other chemotherapeutic agents useful for the disorder or condition being treated. These compounds may be administered simultaneously, sequentially, by the same route of administration, or by a different route.

In some embodiments, the present compounds are used with other anti-cancer or cytotoxic agents. Various classes of anti-cancer and anti-neoplastic compounds include, but are not limited to, alkylating agents, antimetabolites, vinca alkyloids, taxanes, antibiotics, enzymes, cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agents include L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tamoxifen.

These and other useful anti-cancer compounds are described in *Merck Index,* 13th Ed. (O'Neil M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1387, McGraw Hill, (2001), both of which are incorporated by reference herein.

Additional anti-proliferative compounds useful in combination with the compounds described herein include, by way of example and not limitation, antibodies directed against growth factor receptors (e.g., anti-Her2); antibodies for activating T cells (e.g., anti-CTLA-4 antibodies); and cytokines such as interferon-α and interferon-γ, interleukin-2 and GM-CSF.

6.8 Formulations and Administration

When used to treat or prevent such diseases, the active compounds and prodrugs may be administered singly, as mixtures of one or more active compounds, or in mixture or combination with other agents useful for treating such diseases and/or the symptoms associated with such diseases. The active compounds and prodrugs may also be administered in mixture or in combination with agents useful to treat other disorders or maladies, such as steroids, membrane stabilizers. The active compounds or prodrugs may be administered per se, or as pharmaceutical compositions comprising an active compound or prodrug.

Pharmaceutical compositions comprising the active compounds (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see *Remington's Pharmaceutical Sciences,* 15$^{th}$ Ed., Hoover, J. E. ed., Mack Publishing Co. (2003)

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known in the art.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) or other vehicles such as CREMOPHOR (a class of non-ionic solubilizers and emulsifiers manufactured by BASF Corporation, Florham Park, N.J.), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.9 Effective Dosages

The active compound(s) or prodrug(s), or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an IC$_{50}$ of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, latest edition, supra, and the references cited therein.

Initial dosages may also be estimated from in vivo data, such as animal models. Animal models useful for testing the efficacy of compounds to treat or prevent the various diseases described above are well-known in the art. Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) LD$_{50}$/ED$_{50}$ effect is the therapeutic index (LD$_{50}$ is the dose lethal to 50% of the population and ED$_{50}$ is the dose therapeutically effective in 50% of the population). Compounds(s) that exhibit high therapeutic indices are preferred.

6.10 Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

7. EXAMPLES

The inventions are further defined by reference to the following examples, which describe the preparation of several exemplary embodiments of the compounds described herein, methods for assaying their biological activity, and methods for their use. It will be apparent to the skilled artisan that many modifications, both to the materials and methods, may be practiced without departing from the scope of the inventions.

7.1 Preparation of 4-(4-methylpiperazinyl)-3-methylnitrobenzene

Reaction:

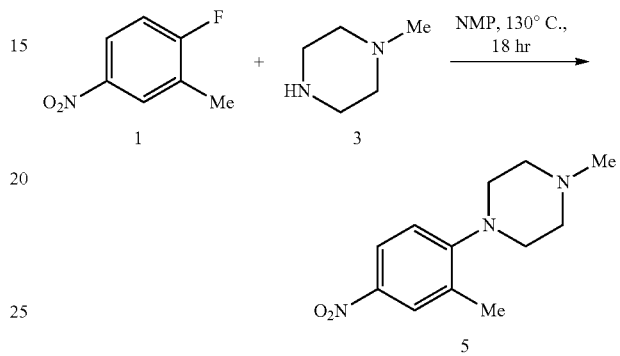

Procedure: A homogeneous mixture of 4-fluoro-3-methylnitrobenzene 1 (20 g, 129 mmol) and N-methylpiperazine 3 (25.82 g, 258 mmol) in N-methylpyrrolidone (NMP) (10 mL) was refluxed (120° C.) under N$_2$ for 24 hours. The reaction mixture upon cooling to room temperature was poured over a saturated NaCl solution (100 mL). The resulting solid was sonicated for approx. 30 seconds, filtered, washed with ice-cold water (2×10 mL) and dried under high vacuum to obtain 4-(4-methylpiperazinyl)-3-methylnitrobenzene 5 (28 g, 92%). $^1$H NMR (CD$_3$OD): δ 8.02 (m, 2H), 7.13 (d, 1H, J=9.3 Hz), 3.08 (m, 4H), 2.66 (m, 4H), 2.38 (s, 6H); LCMS: purity: 99%, MS (m/e): 236

7.2 Preparation of 4-(4-Methylpiperazinyl)-3-Methylaniline

Reaction:

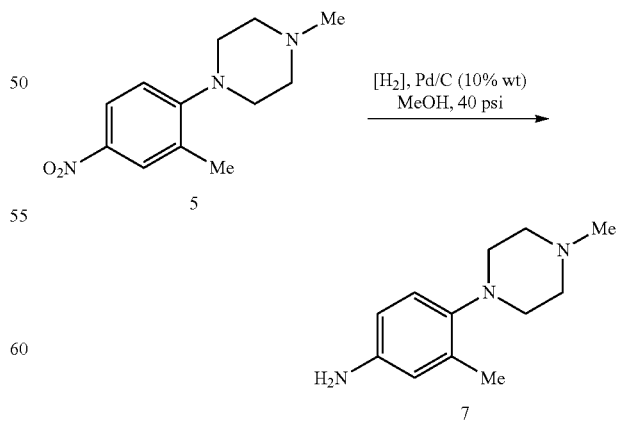

Procedure: A heterogeneous mixture of 4-(4-methylpiperazinyl)-3-methylnitrobenzene 5 (20 g, 85 mmol), 10% Pd/C (1.3 g) in methanol (1.2 liter) was hydrogenated [H$_2$] at 40

PSI for 3 hours. The palladium catalyst was filtered through a pad of celite, washed with methanol (3×50 mL) and the combined filtrate was concentrated to afford 4-(4-methyl-piperazinyl)-3-methylaniline 7 (15 g, 86%). $^1$H NMR (CD$_3$OD): δ 6.83 (d, 1H, J=8.7 Hz), 6.59 (d, 1H, J=2.7 Hz), 6.54 (dd, 1H, J=8.4 and 2.7 Hz), 2.84 (t, 4H, J=4.8 Hz), 2.60 (bm, 4H), 2.34 (s, 3H), 2.20 (s, 3H); LCMS: purity: 99.9%, MS (m/e): 206 (MH$^+$).

7.3 Synthesis of (1S,2R)-N4-(2-Aminocarbonylcy-clopent-1-yl)-5-fluoro-N-2-[4-(4-methylpiperazin-1-yl)-3-methylphenyl]-2,4-pyrimidinediamine

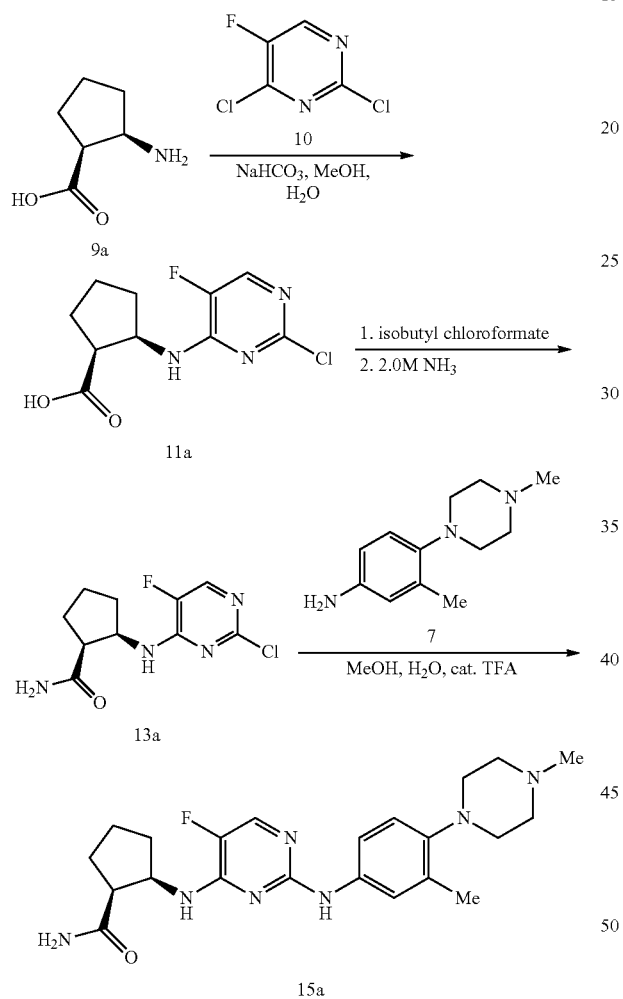

A mixture of (1S,2R)-2-aminocyclopentanecarboxylic acid HCl salt (100 mg) 9a, 2,4-dichloro-5-fluoropyrimidine (200 mg) 10, sodium bicarbonate (50 mg), methanol (5 mL) and water (1 mL) was stirred, with warming, from room temperature to 60° C. overnight. The reaction solution was evaporated to give (1S,2R)-cyclopentanecarboxylic acid 11a.

The crude residue 11a was dissolved in dichloromethane (10 mL) and isobutyl chloroformate (0.15 mL) and diiso-propylethylamine (0.27 mL) were added. The reaction mixture was stirred at ambient temperature for 30 minutes, quenched with 2.0M ammonia in methanol (10 ml), stirred at room temperature for 30 minutes, diluted with water (100 mL) and extracted with ethyl acetate (2×100 mL). The combined organic layers were evaporated to provide crude (1S,2R)-carboxamide 13a.

(1S,2R)-carboxamide 13a was reacted with 3-methyl-4-(4-methyl)piperazinoaniline 7 in a solution of methanol (5 mL) and water (0.5 mL) with catalytic amount of trifluoro-acetic acid at 100° C. overnight. The reaction mixture was evaporated and purified by flash chromotography (2.0 MNH$_3$ in methanol in CH$_2$Cl$_2$=1-5%). Recrystallization from ethyl acetate and hexanes gave the title (1S,2R) car-boxamide 15a (30 mg) as a white solid.

7.4 Synthesis of (1R,2S)-N4-(2-Aminocarbonylcy-clopent-1-yl)-5-fluoro-N-2-[4-(4-methylpiperazin-1-yl)-3-methylphenyl]-2,4-pyrimidinediamine

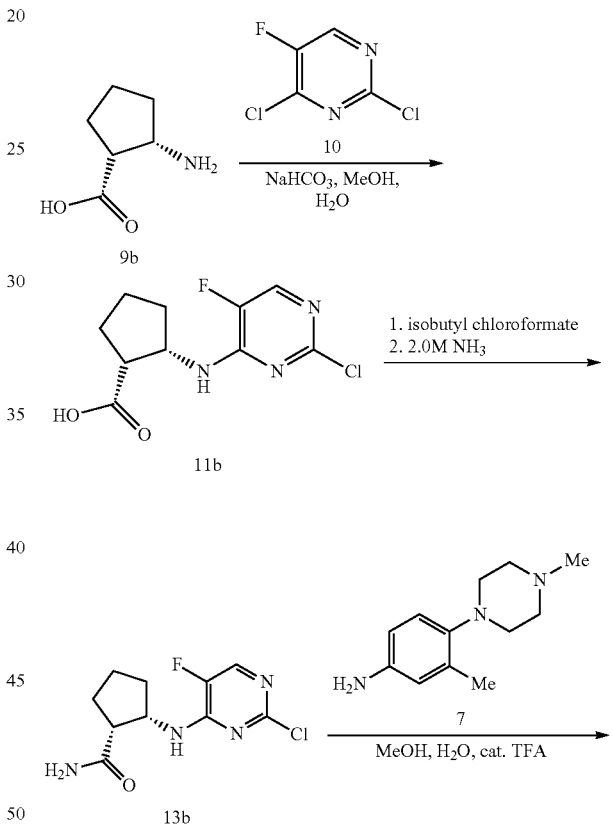

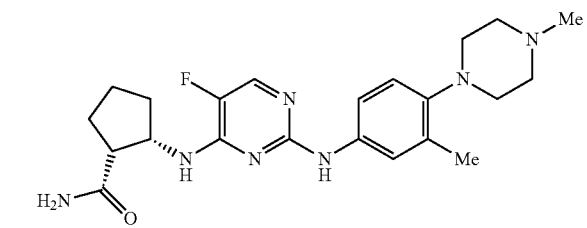

Using the method of Section 7.3, and starting with (1R, 2S)-2-aminocyclopentane carboxylic acid 9a (250 mg) gave the title compound 15b as a white solid (10 mg).

7.5 Synthesis of (1S,2S) N4-(2-Aminocarbonylcyclopent-1-yl)-5-fluoro-N2-[4-(4-methylpiperazin-1-yl)-3-methylphenyl]-2,4-pyrimidinediamine

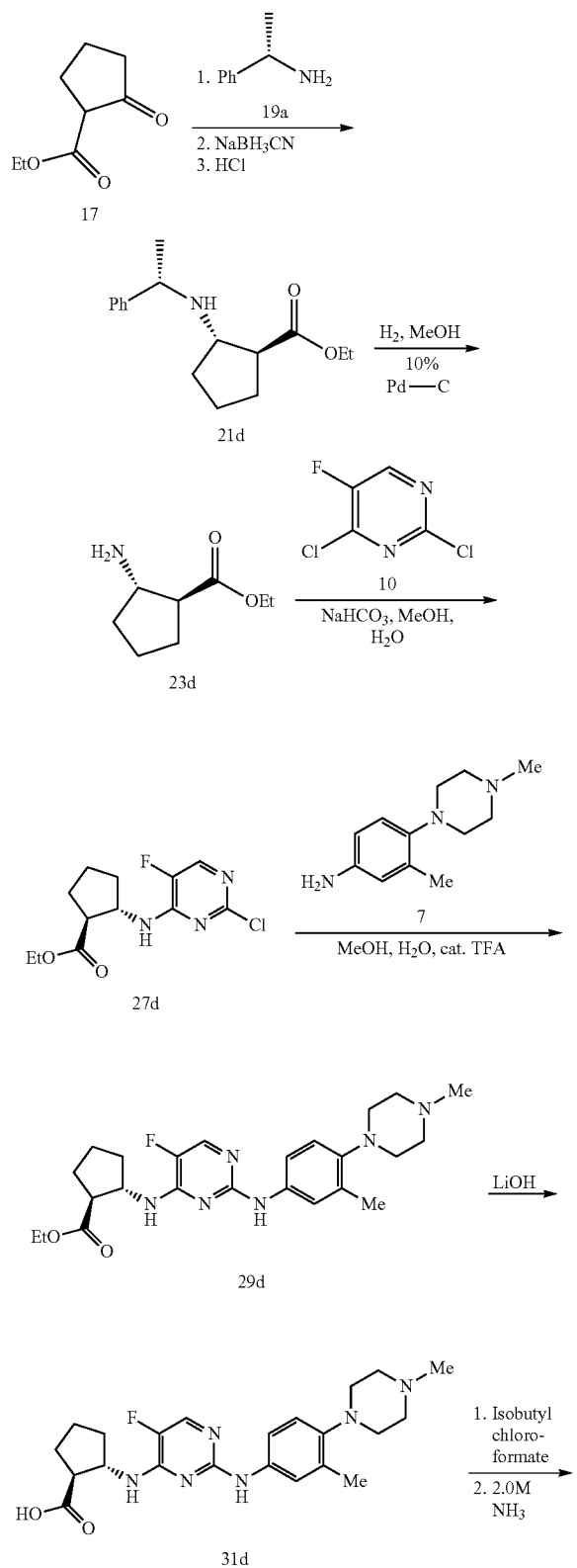

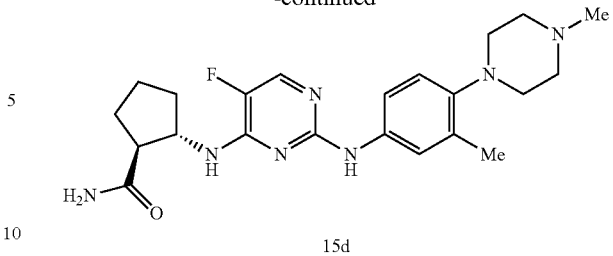

Ethyl (1S,2S)-2-aminocyclopentanecarboxylate 23d was made according to the procedure of Gellman et al., *J. Org. Chem.* 2001, 66, 5629-5632. The ethyl ester of 2-carboxy cyclopentanone 17 (4 mL), (S)-(-)-methylbenzylamine (6.96 mL) 19a and glacial acetic acid (3.08 mL) were dissolved in ethanol (32 mL) and stirred at room temperature overnight. The reaction solution was diluted with ethanol (64 ml) and heated to 72° C. Then NaBH$_3$CN (4.24 g) was added in portions and mixture was stirred at 72° C. for 5 h. Water (150 mL) was added and ethanol was removed in vacuo. The remaining aqueous solution was extracted with ether (2×150 mL) and the ether layer was passed through a silica plug, which was eluted with ether (150 mL). The filtrate was evaporated and the residual oil was dissolved in ethyl acetate (120 mL). Then 4.0 N HCl in dioxane (6.5 mL) was added dropwise with stirring. The solution was kept at 0° C. for 1 h, the white precipitate was then filtered and washed with ethyl acetate. The resulting white solid was recrystallized from ethanol (6.5 g in 40 mL ethanol). The product was further recrystallized from acetonitrile to give the HCl salt of the ethyl ester of benzylated β-aminocyclopentanecarboxylate 21d.

The HCl salt of the ethyl ester of benzylated β-amino cyclopentane carboxylate 21d (300 mg) was dissolved in methanol and 10% Pd—C was added. The solution was shaken under H$_2$ at 50 psi for 3 days, filtered through Celite and washed with methanol. The filtrate was evaporated to give the ethyl (1S,2S)-2-aminocyclopentane carboxylate 23d.

A mixture of the HCl salt of carboxylate 23d, 2,4-dichloro-5-fluoropyrimidine 10 (200 mg), sodium bicarbonate (100 mg), methanol (5 mL) and water (1 mL) were stirred at room temperature overnight. The reaction solution was diluted with water (100 mL). The aqueous solution was extracted with ethyl acetate (2×100 mL) and the organic layers were evaporated to give the mono-SNAr product 27d.

The mono-SNAr product 27d was reacted with 3-methyl-4-(4-methyl)piperazinoaniline 7 in a solution of methanol (1 mL) and water (0.2 mL) with catalytic amount of trifluoroacetic acid at 100° C. overnight. The reaction mixture was evaporated and purified by flash column chromatography (2.0 MNH$_3$ in methanol in CH$_2$Cl$_2$=1-3%) to give ethyl (1S,2S)-cyclopentanecarboxylate 29d.

Ethyl (1S,2S)-cyclopentanecarboxylate 29d (100 mg) was dissolved in a solution of THF/MeOH/H$_2$O 6:3:1 and LiOH (46 mg) was added. The reaction solution was stirred at room temperature overnight, neutralized with 1N HCl and the pH of the aqueous solution was adjusted to pH 6. The solvent was evaporated and the solid recrystallized from methanol and ethyl acetate to give (1S,2S)-cyclopentanecarboxylic acid 31d.

(1S,2S)-cyclopentanecarboxylic acid 31d (100 mg) in dichloromethane (10 mL) was treated with diisopropylethylamine (0.08 mL) and isobutyl chloroformate (0.045 mL)

and the reaction mixture stirred at room temperature for 30 minutes, quenched with 2.0 M NH₃ in methanol (10 mL), stirred at room temperature for 30 minutes and then evaporated. The residue was purified by flash chromatography (2.0 M NH₃ in methanol in CH₂Cl₂=1-5%). Recrystallization from ethyl acetate and hexanes gave the title compound (1S,2S)-1-(2,4-pyrimidinediamino)-2-cyclopentanecarboxamide 15d as a white solid.

7.6 Synthesis of (1R,2R)-N4-(2-Aminocarbonylcyclopent-1-yl)-5-fluoro-N2-[4-(4-methylpiperazin-1-yl)-3-methylphenyl]-2,4-pyrimidinediamine

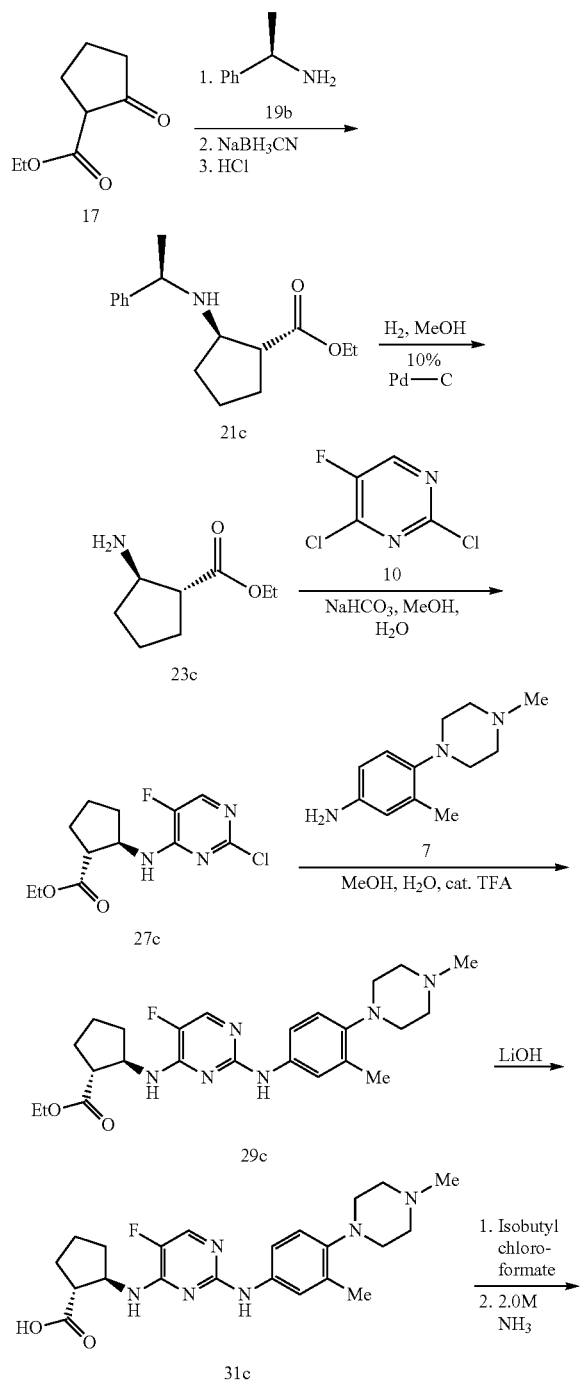

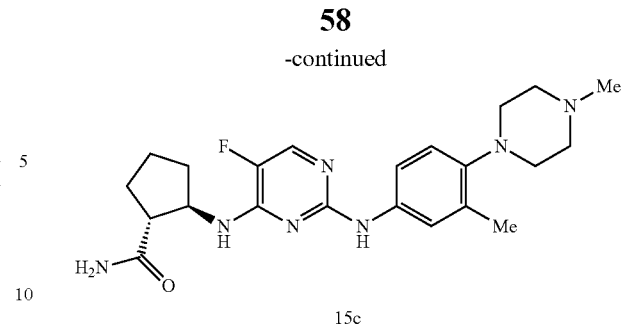

Using (R)-(−)-methylbenzylamine (6.96 mL) instead of (S)-(+)-methylbenzylamine in the first step and following the procedure of Section 7.5 gave the title compound (1R, 2R)-1-(2,4-pyrimidinediamino)-2-cyclopentanecarboxamide 15c (30 mg).

7.7 Synthesis of (1S,2R)-N4-(2-Aminocarbonylcyclopent-1-yl)-5-fluoro-N2-[4-(4-methylpiperazin-1-yl)-3-methylphenyl]-2,4-pyrimidinediamine

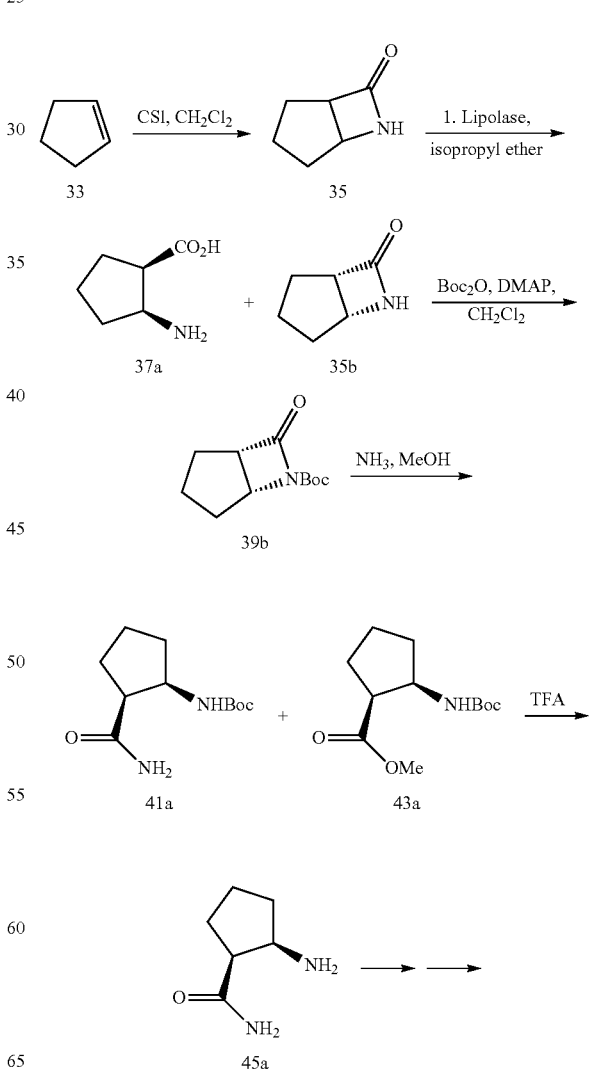

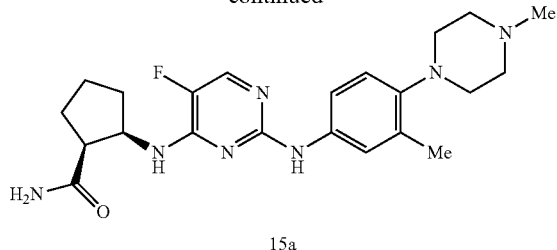

15a

Cyclopentene 33 (18.7 mL) and chloro sulfonyl isocyanate (18.4 mL) were dissolved in dichloromethane (30 mL) at 0° C. and stirred for 1 h. The reaction mixture was heated to 40° C. for 24 h, quenched slowly with cold water in an ice bath and then added dropwise to a solution of $Na_2SO_3$ (13.36 g) in water (40 mL) at 0° C. Meanwhile, 20% NaOH aqueous solution (125 mL) was added to keep the pH of the solution at 5-7. The temperature was the solution was controlled to remain below 25° C. After addition, the solution was stirred for 1 h at 0° C. and extracted with dichloromethane (2×200 mL). The dichloromethane solution was evaporated and recrystallized from ether and hexanes to give the racemic β-lactam of cyclopentane 35 as a solid (10 g).

Racemic 35 (4 g) was dissolved in isopropyl ether (80 mL). Lipolase (lipase on acrylic resin, 4 g) and water (0.32 mL) was added. The reaction solution was stirred at 60° C. for 10 days. Solid was 37a filtered off and washed with isopropyl ether. The filtrate was evaporated and recrystallized from isopropyl ether and hexanes to give a light yellow solid as product 35b (2 g).

Compound 35b (2 g) was dissolved in dichloromethane (20 mL) followed by addition of $Boc_2O$ (4.4 g) 4-dimethylaminopyridine ("DMAP") (0.22 g). The reaction mixture was stirred at room temperature overnight, diluted with ethyl acetate (100 mL), washed with water (100 mL) and brine (100 mL). Ethyl acetate was evaporated and the resulting mixture was passed through a short silica gel column, eluting with 1:1 ethyl acetate and hexanes. The solvent was removed in vacuo and recrystallized from hexanes to give white solid 39b as product.

Compound 39b was dissolved in 2.0M $NH_3$ in methanol (30 mL) and reacted at room temperature overnight. The solution was evaporated and recrystallized from ethyl acetate/hexanes to give white solid 41a (800 mg). The filtrate was evaporated to give the corresponding methyl ester of 43a as an oil.

Compound 43a (800 mg) was reacted in 4.0 M HCl in dioxane (10 mL) at room temperature for 2 h and the solution was evaporated to give the HCl salt of 45a.

The HCl salt of 45a was dissolved in methanol (10 mL) and water (1 mL).

2,4-dichloro-5-fluoropyrimidine (1 g) and sodium bicarbonate (500 mg) were added to the solution and stirred at room temperature overnight. The solution was diluted with water (100 mL) and extracted with ethyl acetate (3×100 mL). The organic layers were evaporated and recrystallized from ethyl acetate/hexanes to give a white solid as mono-SNAr product (750 mg).

4-Fluoro-3-methylnitrobenzene (4 g) was dissolved in methanol (10 mL) and methylpiperazine (4 mL) was added to the solution, which was heated at 100° C. overnight and then diluted with water (100 mL). The solution was extracted with ethyl acetate (2×100 mL), the organic extracts were evaporated and recrystallized from ethyl acetate/hexanes to give as yellow solid 3-methyl-4-(4-methyl)piperazinonitrobenzene. The solid was dissolved in methanol (50 mL) and 10% Pd—C was added. The reaction solution was reacted under 40 psi $H_2$ for 1 h. The catalyst was removed by filtration and washed with methanol. The filtrate was evaporated to give 3-methyl-4-(4-methyl)piperazinoaniline.

The mono-SNAr product (700 mg) was reacted with 3-methyl-4-(4-methyl)piperazinoaniline in a solution of methanol (5 mL) and water (0.5 mL) with catalytic amount of trifluoroacetic acid at 100° C. overnight. The reaction mixture was evaporated and purified by flash column chromatography (2.0 $MNH_3$ in methanol in $CH_2Cl_2$=1-7%). Recrystallization from ethyl acetate and hexanes gave a white solid 15a (700 mg). Compound 15a was dissolved in methanol (10 mL) and reacted with 4.0M HCl in dioxane (0.9 mL) at room temperature for 30 min. The solution was evaporated and dried to solid. Recrystallization from cold methanol and ethyl acetate gave the HCl salt of 15a.

7.8 Preparation of 3-Aza-4-oxo-tricyclo[4.2.1.0(2,5)]non-7-ene

Reaction:

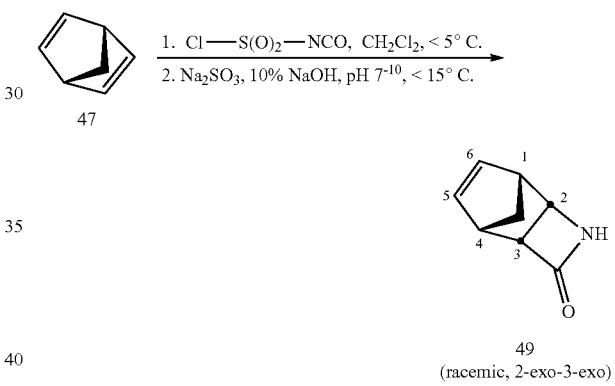

49
(racemic, 2-exo-3-exo)

Procedure: Part 1: A solution of 2,5-norbornadiene 47 (25.0 mL, 0.246 mole) in $CH_2Cl_2$ (110 mL, fresh bottle) was cooled in an ice/NaCl bath (−10° C.). To this was added drop-wise a solution of CSI (21.4 mL, 0.246 mole) in $CH_2Cl_2$ (45 mL, fresh bottle) at a rate to maintain the temperature below 5° C. (the addition took approx. 1.25 hr.). Upon completion of the addition, the reaction mixture was stirred for 1 hour at 0-5° C. and then removed from the cooling bath and allowed to warm to 20° C. The reaction mixture was quenched with water (60 mL) and vigorously stirred for several minutes. The organic layer was separated, washed with brine, and dried with $Na_2SO_4$. Concentration gave light brown oil.

Part 2: A mixture of $Na_2SO_3$ (24.5 g), water (70 mL), and $CH_2Cl_2$ (30 mL) was cooled in an ice/NaCl bath. The oil from Part 1 was diluted to 100 mL with $CH_2Cl_2$ and added dropwise to the above mixture at a rate to maintain the temperature below 15° C. (the addition took approx. 1.75 hr). The pH of the reaction mixture was monitored with a pH meter and kept basic (pH 7-10) by adjusting with 10% NaOH (w/v) (as needed). Upon completion of the addition, the reaction mixture was stirred for 1 hour at 5-10° C. (final pH was 8.5). The reaction mixture was poured into a separatory funnel and the $CH_2Cl_2$ layer separated. This organic phase was a thick and gelatinous solid suspension.

It was diluted with water (approx. 400 mL) to make a more free flowing solution. The aqueous layer was further extracted with CH$_2$Cl$_2$ (4×100 mL). (Alternatively, the solids can be separated from the CH$_2$Cl$_2$ by centrifugation. The solids can then be diluted with water (until almost all dissolved) and extracted with CH$_2$Cl$_2$). The aqueous layer was further extracted with CH$_2$Cl$_2$ (10×100 mL). The CH$_2$Cl$_2$ extracts were monitored by TLC for the presence of product. The combined organic extracts were washed with brine, dried with MgSO$_4$, and filtered through celite. Removal of solvent gave the desired product, racemic-2-exo-3-endo 3-aza-4-oxo-tricyclo[4.2.1.0(2,5)]non-7-ene 49 as white solid (20.5 g, 62%). $^1$H NMR (DMSO-d$_6$): δ 8.01 (bs, 1H), 6.22 (dd, J=3.3 and 5.4 Hz, 1H), 6.12 (dd, J=3.3 and 5.4 Hz, 1H), 2.88 (dd, J=1.5 and 3.3, 1H), 2.79 (bs, 1H), 2.74 (bs, 1H), 1.58 (d, J=9.3 Hz, 1H), and 1.47 (d, J=9.3 Hz, 1H).

7.9 Preparation of 4-oxo-3-tert-butoxycarbonylaza-tricyclo[4.2.1.0(2,5)]non-7-ene Reaction:

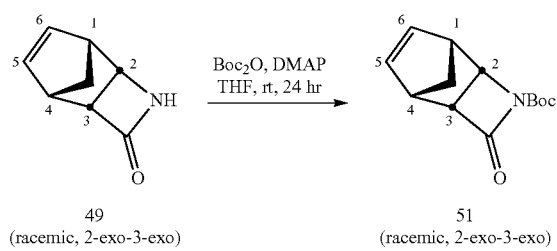 [SMILES: O=C1N[C@@H]2[C@H]1[C@@H]1C=C[C@H]2C1 ; CC(C)(C)OC(=O)N1C(=O)[C@H]2[C@@H]1[C@H]1C=C[C@@H]2C1]

Procedure: A homogeneous mixture of 3-aza-4-oxo-tricyclo[4.2.1.0(2,5)]non-7-ene (49; racemic-2-exo-3-exo; 10.0 g, 74 mmol), (BOC)$_2$O (16.1 g, 74 mmol) and DMAP (1.1 g) in CH$_2$Cl$_2$ was stirred under N$_2$ at room temperature for 24 hours. To this reaction mixture were added EtOAc (100 mL) followed by H$_2$O (100 mL) and stirred for additional 1 hour. The organic layer was separated and washed with H$_2$O (2×100 mL). The organic layer was dried over anhydrous Na$_2$SO$_4$ and solvent was removed under a reduced pressure to afford 4-oxo-3-tert-butoxycarbonylaza-tricyclo[4.2.1.0(2,5)]non-7-ene (51; racemic-2-exo-3-exo) (16.5 g, 70%); $^1$H NMR (DMSO-d$_6$): δ 6.29 (dd, J=3.3 and 5.4 Hz, 1H), 6.19 (dd, J=3.3 and 5.4 Hz, 1H), 3.77 (d, J=4.5 Hz, 1H), 3.13 (bs, 1H), 3.08-3.04 (m, 1H), 2.93 (bs, 1H), 1.45 (s, 9H). LCMS: 95%.

7.10 Preparation of, and Isolation of, Stereoisomerically Pure Diastereomers From (±) Racemic (2-exo-3-exo)-N4-(3-aminocarbonylbicyclo[2.2.1]hept-5-en-2-yl)-5-fluoro-N2-[3-methyl-4-(4-methylpiperazin-1-yl)phenyl]-2,4-pyrimidinediamine A racemic mixture of the title compound was prepared from the 2-exo-3-exo racemate of 2-aminobicylco[2.2.1]hept-5-en-3-carboxamide as follows.

Reaction:

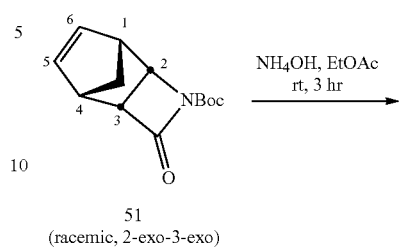

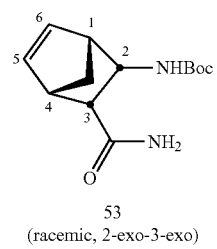

Procedure: A round bottom flask equipped with a rubber septum and a magnetic stirring bar was charged with racemic N-BOC-β-lactam 51 (2.0 g) under a positive pressure of nitrogen. To this were added ethyl acetate (25 mL) followed by 30% ammonia in water (25 mL) and stirred at room temperature for 3 hours. The ethyl acetate layer was separated and washed with 5% aqueous solution of NaHCO$_3$ (20 mL), dried over anhydrous Na$_2$SO$_4$ and solvent was evaporated to afford 1.10 gm of racemic N-BOC carboxyamide 53.

Reaction:

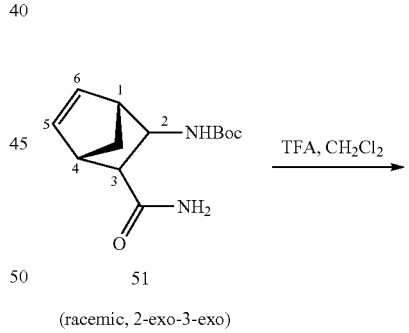

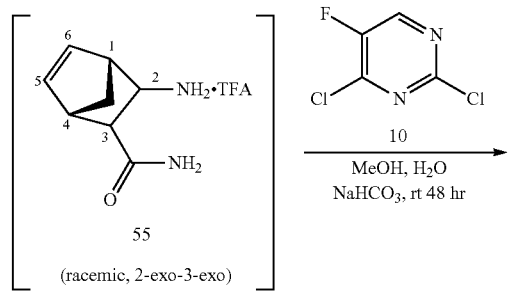

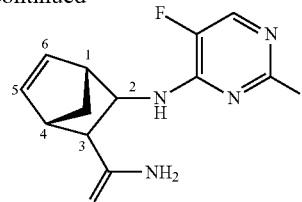

57

(racemic, 2-exo-3-exo)

Procedure: A round bottom flask equipped with N₂ inlet and a magnetic stirring bar was charged with racemic N-BOC lactam 51 (2.00 g, 7.9 mmol) and then treated with 20% of TFA in CH₂Cl₂ at room temperature for 2 hours. The resulting solution was concentrated under a reduced pressure. The trace of TFA was removed under high vacuum for several hours to afford the intermediate, TFA salt (55, racemic). The resulting racemic TFA salt 55 was treated with 2,4-dichloro-5-fluoropyrimidine 10 (1.58 g, 9.51 mm) in MeOH:H₂O (20:10 mL) in the presence of NaHCO₃ (1.33 g, 15.84 mmol) at room temperature for 48 hours. The reaction mixture was diluted with H₂O (25 mL), saturated with NaCl and extracted with EtOAc (3×50 mL). upon drying over anhydrous Na₂SO₄, the solvent was evaporated and the residue was chromatographed (silica gel, CH₂Cl₂ then 2-4% 2N NH₃/MeOH in CH₂Cl₂) to afford 1.3 g of racemic mono-SNAr product 57.

Reaction:

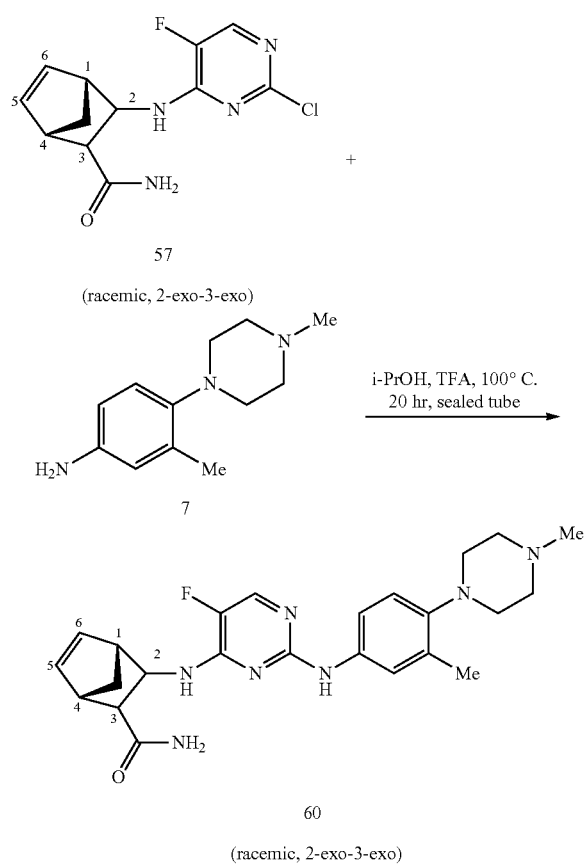

Procedure: A sealed tube charged with racemic mono-SNAr product 57 (1.1 g, 8 mmol), aniline 7 (0.90 g, 4.4 mmol), TFA (0.6 mL) and methanol (9 mL) was stirred at 100° C. for 24 hours. The resulting viscous homogeneous solution was concentrated and the residue was chromatographed (silica gel, CH₂Cl₂ then 2-5% 2N NH₃/MeOH in CH₂Cl₂) to afford the expected 2-exo-3-exo racemic 2,4-diaminopyrimidine derivative 60 (1.12 g; purity: 95%):

Isolation of Enantionmers: The diastereomers were resolved and isolated from racemate R1 by chiral preparative HPLC chromatography Phenomenex Chirex 3020 250×10 mm column), eluting with a 35:63:2 (vol:vol:vol) mixture of hexane:dichloromethane:methanol at a flow rate of 6 mL/min. The enantiomer eluting at 9.44 min. was designated the E1 enantiomer and the enantiomer eluting at 12.74 min. was designated the E2 enantiomer.

7.11 Enzymatic Preparation of Stereoisomerically Pure (1R,2R,3S,4S)-N4-(3-Aminocarbonylbicyclo [2.2.1]hept-5-en-2-yl)-5-fluoro-N2-[3-methyl-4-(4-methylpiperazin-1-yl)phenyl]-2,4-pyrimidinediamine Using Chirazyme 7.11.1 Preparation of Stereochemically Pure N-Boc-β-Lactam Reaction

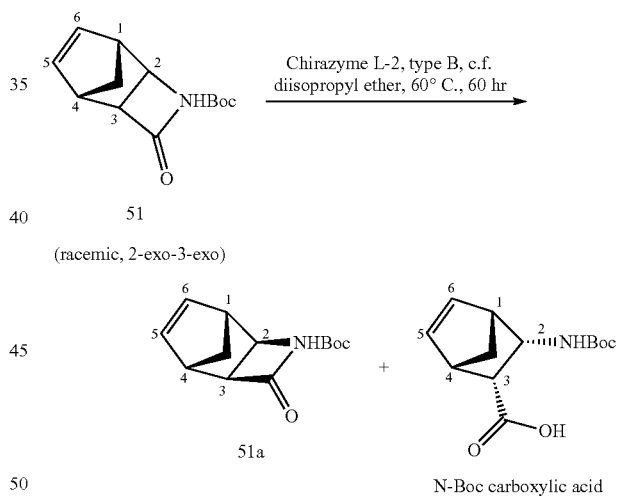

Procedure: A dry sealed tube charged with 4-oxo-3-tert-butoxycarbonylaza-tricyclo[4.2.1.0(2,5)]non-7-ene (51; racemic-2-exo-3-exo) (4.0 g, 17.02 mmol), resin bound/immobilized chirazyme L-2, type B, c.f. (8.0 g, purchased from BioCatalytics Inc., Pasadena, Calif.) and diisopropyl ether (80 mL) was gently shaken in an incubator at 60° C. for 60 hours. (The enzymatic resolution of racemic N-BOC β-lactam 51 was followed by proton NMR. The integration of tert-butyl group of enantiomerically pure N-BOC lactam 51a and N-BOC carboxylic acid was seen in 1:1 ratio). The resulting reaction mixture was filtered and the solid resin was washed with diisopropyl ether (2×40 mL). The filtrate was concentrated to afford a mixture of enantiomerically pure N-BOC-β-lactam 51a and N-BOC carboxylic acid (total mass: 4.0 gm).

Reaction:

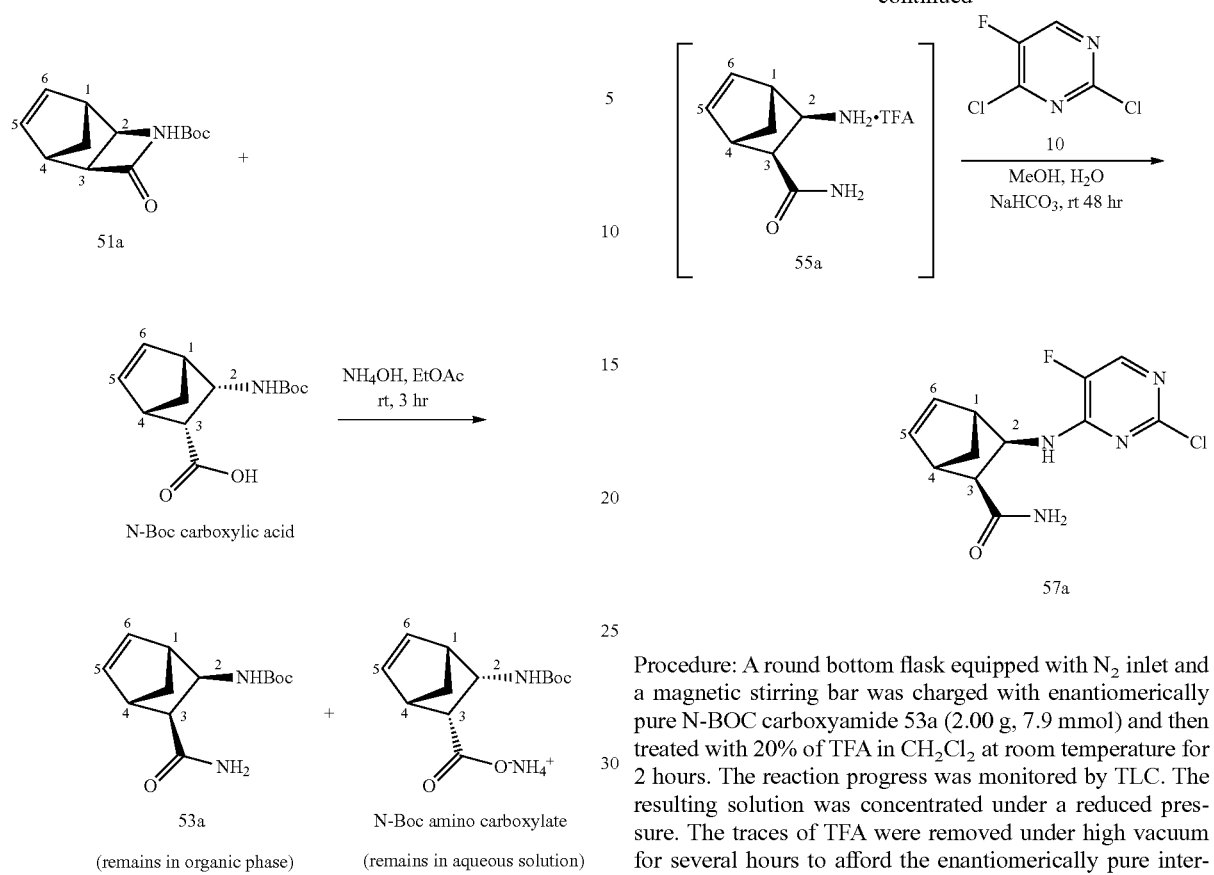

N-Boc carboxylic acid 53a
(remains in organic phase)

N-Boc amino carboxylate
(remains in aqueous solution)

Procedure: A round bottom equipped with a rubber septum and a magnetic stirring bar was charged with a mixture of enantiomerically pure N-BOC-lactam 7a and N-BOC carboxylic acid (4.0 g) under a positive pressure of nitrogen. To this were added ethyl acetate (50 mL) followed by 25% ammonia in water (50 mL) and stirred at room temperature for 3 hours. The reaction progress was monitored by TLC. The ethyl acetate layer was separated and washed with 5% aqueous solution of NaHCO$_3$ (40 mL), dried over anhydrous Na$_2$SO$_4$ and solvent was evaporated to afford 2.00 gm of desired enantiomerically pure N-BOC carboxy amide 53a keeping behind the N-BOC ammonium carboxylate in aqueous solution.

7.11.2 Preparation of Stereoisomerically Pure Mono SNAr Product

Reaction:

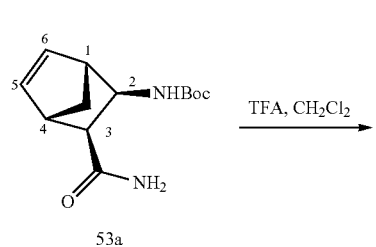

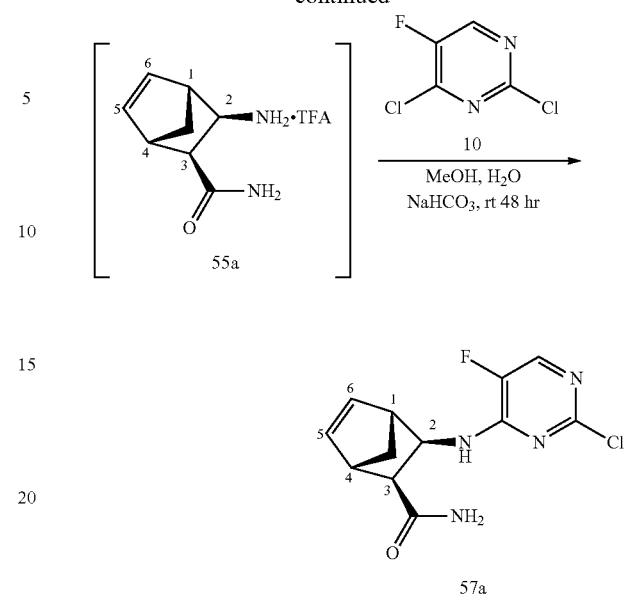

Procedure: A round bottom flask equipped with N$_2$ inlet and a magnetic stirring bar was charged with enantiomerically pure N-BOC carboxyamide 53a (2.00 g, 7.9 mmol) and then treated with 20% of TFA in CH$_2$Cl$_2$ at room temperature for 2 hours. The reaction progress was monitored by TLC. The resulting solution was concentrated under a reduced pressure. The traces of TFA were removed under high vacuum for several hours to afford the enantiomerically pure intermediate, TFA salt 55a. The resulting TFA salt 55a was treated with 2,4-dichloro-5-fluoropyrimidine 10 (1.58 g, 9.51 mmol) in MeOH:H$_2$O (20:10 mL) in the presence of NaHCO$_3$ (1.33 g, 15.84 mmol) at room temperature for 48 hours. The reaction mixture was diluted with H$_2$O (25 mL), saturated with NaCl and extracted with EtOAc (3×50 mL). Upon drying over anhydrous Na$_2$SO$_4$ the solvent was evaporated and the residue was chromatographed (silica gel, CH$_2$Cl$_2$ then 2-4% 2N NH$_3$/MeOH in CH$_2$Cl$_2$) to afford 1.2 g (54%) of desired mono-SNAr product 57a. The enantiomeric purity was greater than 99% as determined by chiral HPLC; [α]$_D$+61.10° (c 1.0, MeOH).

7.11.3 Preparation of Stereoisomerically Pure (1R, 2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Reaction:

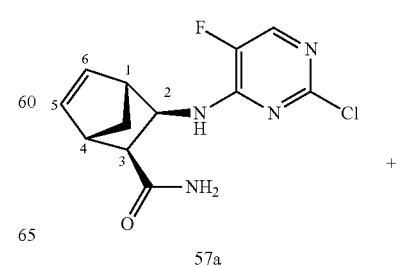

+

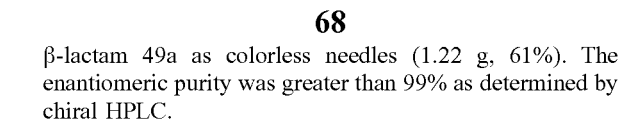

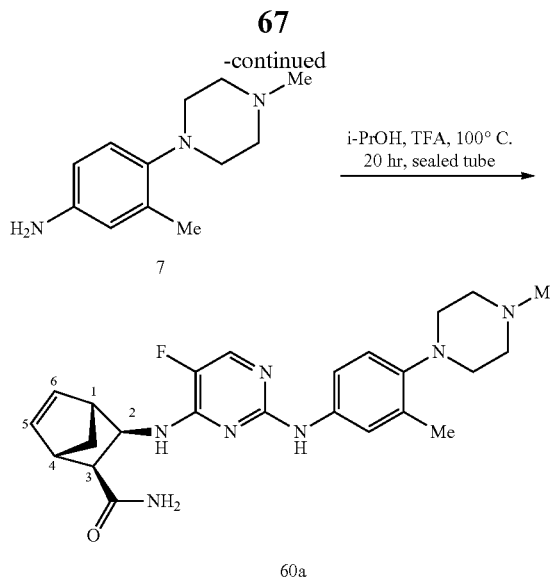

Procedure: A sealed tube charged with enantiomerically pure mono-SNAr product 57a (2.25 g, 8 mmol), aniline 7 (1.80 g, 8.8 mmol), TFA (1.12 mL) and methanol (18 mL) was stirred at 100° C. for 24 hours. The resulting viscous but homogeneous solution was concentrated and the residue was chromatographed (silica gel, $CH_2Cl_2$ then 2-5% 2N $NH_3$/MeOH in $CH_2Cl_2$) to afford the expected 2,4-diaminopyrimidine derivative 60a (2.28 g, 63%; purity: 95% AUC; enantiomeric purity: greater than 99% as determined by chiral HPLC. The chiral analytical data, $^1H$ NMR and LCMS analyses were found to be identical with the enantiomer designated E1; $[\alpha]_D^{RT}$+44.4° (c 1.0, MeOH).

7.12 Enzymatic Preparation of Stereoisomerically Pure (1R,2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Using Novazyme 435 Enzyme

7.12.1 Preparation of Stereoisomerically Pure β-Lactam

Reaction:

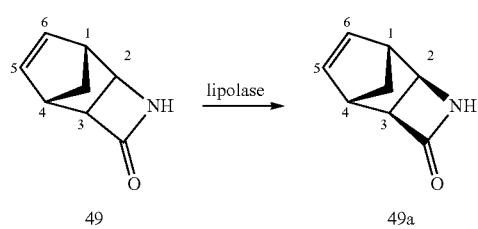 [SMILES: O=C1NC2C1[C@@H]1C=C[C@H]2C1 ; O=C1N[C@H]2[C@@H]1[C@@H]1C=C[C@H]2C1]

Procedure: Immobilized Lipolase (8.0 g, from Sigma, order number L4777), β-lactam 49 (racemic: 2-exo-3-exo) (4.0 g, 7.4 mmol) and water (0.13 ml, 7.4 mmol) were added to 250 ml diisopropyl ether in a pressure flask. The mixture was degassed with nitrogen for 20 minutes and the flask was sealed and incubated for 14 days at 70° C. The mixture was cooled to room temperature, filtered over celite and washed with 300 ml diisopropyl ether. The combined filtrate was concentrated to dryness and the residue was crystallized from diisopropyl ether to give the enantiomerically pure β-lactam 49a as colorless needles (1.22 g, 61%). The enantiomeric purity was greater than 99% as determined by chiral HPLC.

7.12.2 Preparation of Stereoisomerically Pure 2-N-Boc-amino-3-aminocarbonyl-bicyclo[2.2.1]hept-5-ene Reaction:

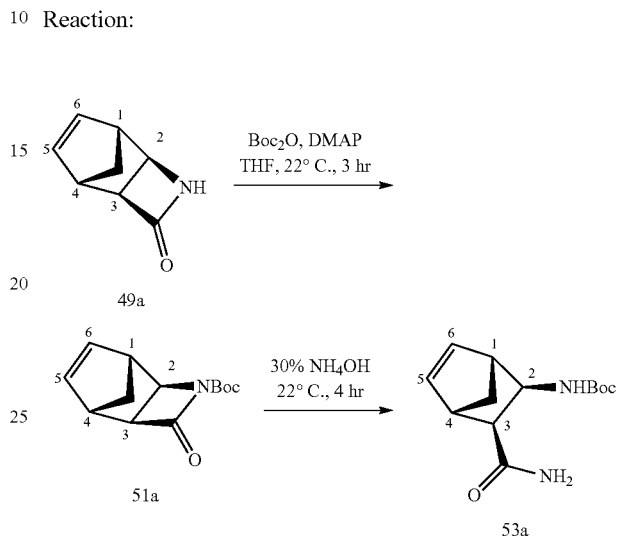

Procedure: A homogeneous mixture of enantiomerically pure 3-aza-4-oxo-tricyclo[4.2.1.0(2,5)]non-7-ene 49a (1.1 g, 8.2 mmol), $(BOC)_2O$ (2.76 g, 12.3 mmol) and DMAP (100 mg) in $CH_2Cl_2$ was stirred under $N_2$ at room temperature for 3 hours to give enantiomerically pure N-BOC lactam 51a, which was used further without isolation. To this reaction mixture was added 20 ml of 25% aqueous ammonium hydroxide and stirring was continued for another 4 hours. Water was added and the reaction mixture was extracted with dichloromethane (2×50 ml). The combined organic phase was washed with aqueous HCl (5%), dried over sodium sulfate and reduced to dryness under reduced pressure to give enantiomerically pure N-BOC carboxyamide 53a (2.51 g) as a white solid, which was used in the next step without further purification.

7.12.3 Preparation of Stereoisomerically Pure Mono SNAr Product (1R,2R,3S,4S)-N4-(3-Aminocobonylbicyclo[2.2.1]hept-5-en-2-yl)-2-chloro-5-fluoro-4-aminopyridine Reaction:

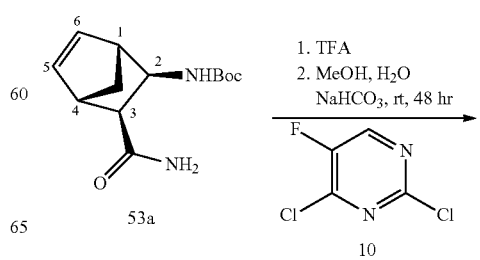

-continued

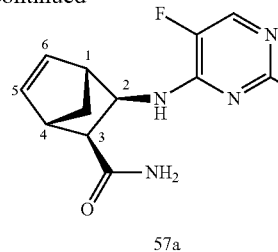

57a

Procedure: The enantiomerically pure N-BOC carboxyamide 53a (2.51 g) was dissolved in 10 ml dichloromethane and treated with 10 ml TFA. The mixture was stirred for 1 hour at room temperature and concentrated to dryness under reduced pressure. The residue was suspended in toluene and again concentrated to dryness. The resulting solid was dissolved in methanol:water (30 ml:3 ml) and treated with 1.5 g sodium bicarbonate. The 5-fluoro-2,4-dichloropyrimidine (3 g, 17.9 mmol) was added and the mixture was stirred for 2 days at room temperature. The volatiles were removed under vacuum and the residue was suspended in brine. The precipitate was filtered, dried and subjected to column chromatography (silica gel, dichloromethane-methanol, 20:1) to give the desired enantiomerically pure mono-SNAr product 57a as a white solid (1.7 g, 74%).

7.12.4 Preparation of Stereoisomerically Pure (1R, 2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Reaction:

Procedure: A homogeneous mixture of aniline 7 (400 mg, 1.95 mmol), enantiomerically pure mono-SNAr product 57a (400 mg, 1.41 mmol) and 0.2 ml TFA in 4 ml isopropanol in a sealed tube was stirred at 100° C. for 20 hours. The mixture was cooled to room temperature, diluted with 2 ml diethylether and the resulting precipitate was filtered and washed with diethylether. The remaining solids were dissolved in water and treated with aqueous 25% ammonium hydroxide solution. The resulting precipitate was filtered, washed with water and dried to give 527 mg (83%) of desired product, 2,4-diaminopyrimidine derivative 60a as an off-white solid. Purity was determined by LCMS to be greater than 97% and the enantiomeric purity was determined by chiral HPLC to be greater than 99%. The chiral analytical data, $^1$H NMR and LCMS analyses were identical with the enantiomer that was designated E1.

7.13 Preparation of Stereoisomerically Pure Compounds Using (R)-Methyl-p-Methoxybenzylamine as a Chiral Auxiliary 7.13.1 Preparation of 2-Exo-3-Exo Racemic Amines Reaction:

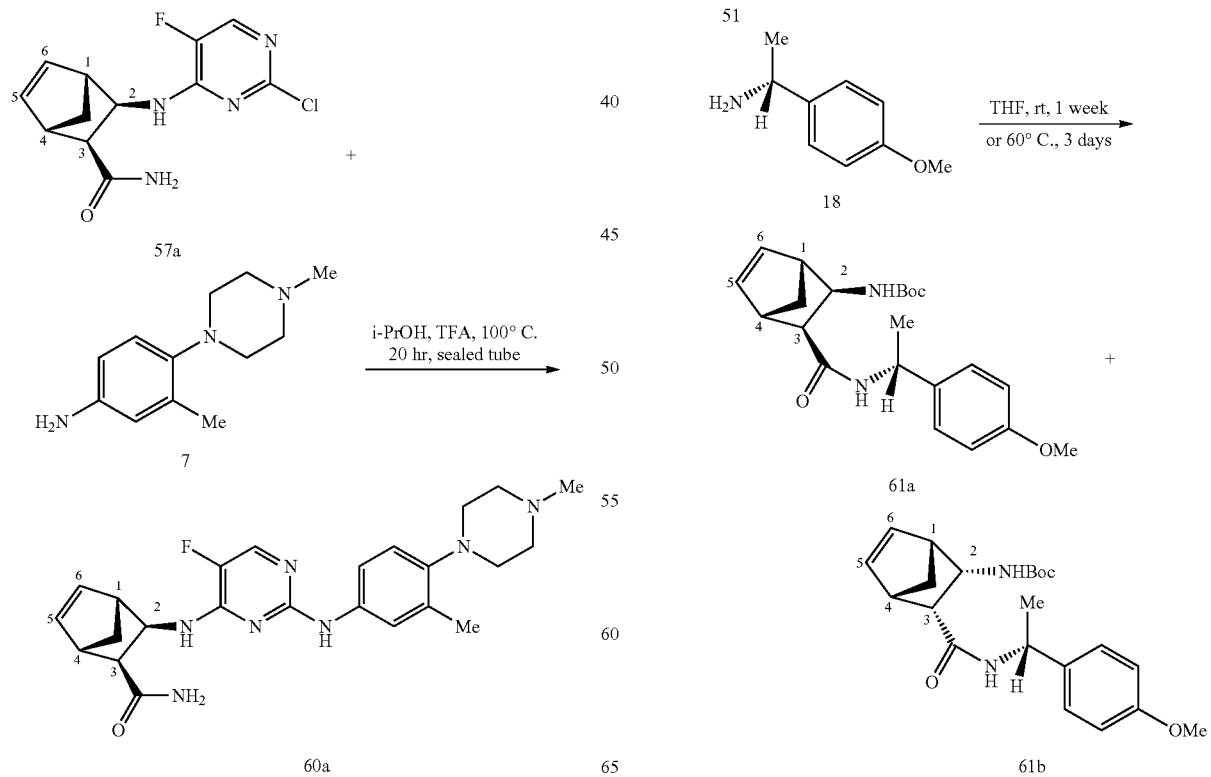

Procedure: A homogeneous mixture of 4-oxo-3-tert-butoxy-carbonylaza-tricyclo[4.2.1.0(2,5)]non-7-ene (51; racemic-2-exo-3-exo) (9.2 g, 40 mmol) and (R)-methyl-4-methoxyl-benzylamine 13 (18, 24 g, 48 mmol) in dry THF (75 mL) was stirred at room temperature for 48 hours. The reaction mixture was concentrated, suspended in hexanes (5 mL), sonicated and the solid was separated by filtration to give mixture of diasterisomers 61a and 61b (12 mg). Alternatively, the purification can be done using column chromatography (silica gel, hexanes then 5%, 10%, 20% and 50% EtOAc in hexanes).

7.13.2 Preparation of 2-Exo-3-Exo Racemic Mono SNAr Products Followed By Separation of Isomerically Pure Compounds by Crystallization Reaction:

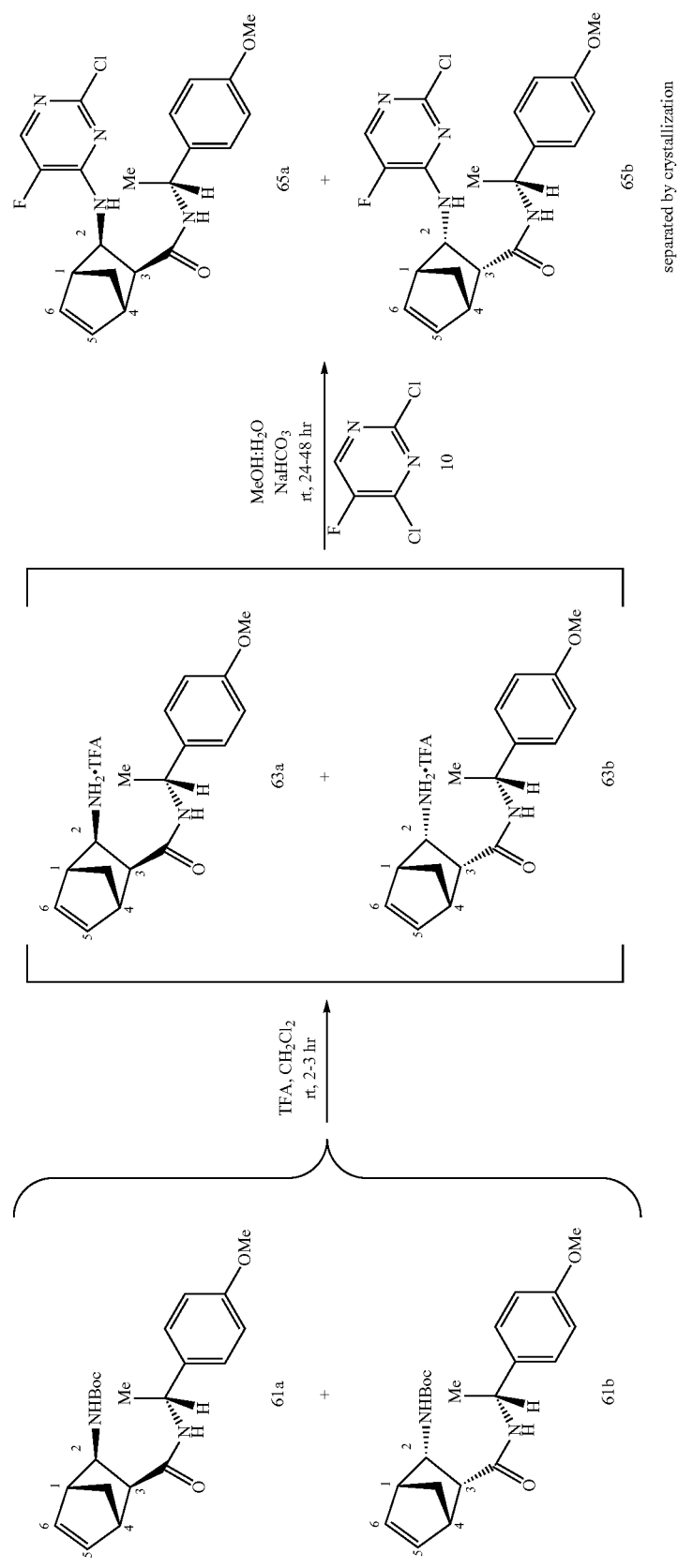

Procedure: A heterogeneous mixture of diasterisomers 61a and 61b (6.0 g g, 17 mmol), TFA (20 mL) in CH$_2$Cl$_2$ was stirred at room temperature for 2 hours. TLC was used to monitor the progress of the reaction. The resulting reaction was concentrated to dryness and dried under a high vacuum for several hours to afford a diasterisomeric mixture of intermediates 63a and 63b. This mixture was then reacted with 2,4-dichloro-5-fluoropyrimidine 10 (3.4 g, 20 mmol) in the presence of NaHCO$_3$ (5.7 g, 68 mmol) in MeOH:H$_2$O (50 mL, each) at room temperature for 24 hours. The reaction mixture was then diluted with NaCl-saturated water (50 mL) and extracted with CH$_2$Cl$_2$. The extract upon drying over anhydrous Na$_2$SO$_4$ followed by removal of solvent under reduced pressure gave a residue, which was chromatographed (silica gel, CH$_2$Cl$_2$ then 2% 2N NH$_3$/MeOH in CH$_2$Cl$_2$). The chromatographic purification gave a mixture diasterisomers 65a and 65b (4.0 g) (1:1 ratio can be seen with a clear separation on reverse phase LCMS). The resulting 4.0 grams upon crystallization using EtOAc: hexanes (30:150 mL; v/v) afforded crystalline material of intermediate 65a, which was confirmed by X-ray crystal structure; chemical purity: 96% and % de: 96%. [α]$_D$-36.7° (c, 0.18 MeOH). The mother liquor containing the other isomer had poor % de (70-80%), which is assumed to be diastereoisomer 65b.

7.13.3 Preparation of Stereoisomerically Pure Product Including the Chiral Auxiliary Reaction:

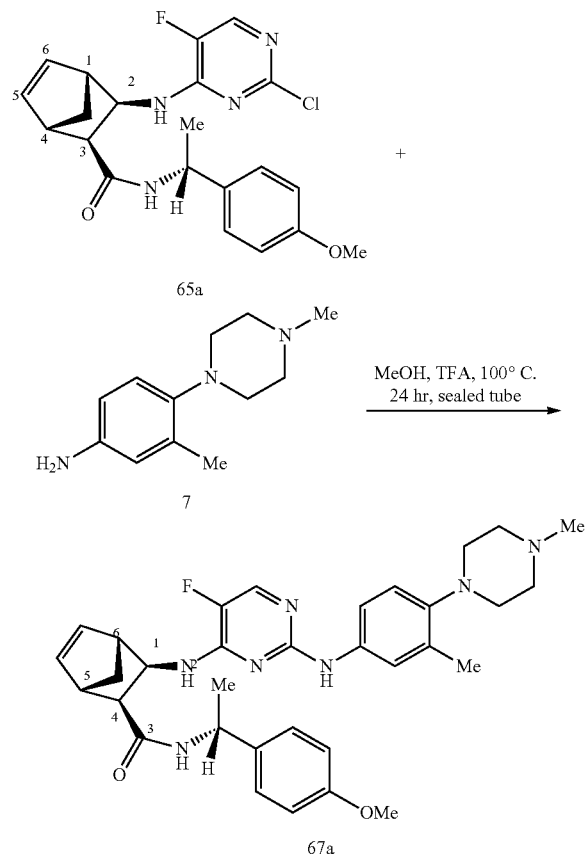

Procedure: A mixture of diastereoisomer 65a (1.42 g, 3.4 mmol), aniline 7 (0.834 g, 4.0 mmol) and TFA (700 mg) in MeOH (10 mL) was heated in a sealed tube at 100° C. for 24 hours. The resulting residue was chromatographed (silica gel, CH$_2$Cl$_2$ then 2% 2N NH$_3$/MeOH in CH$_2$Cl$_2$) to afford product 67a as colorless solid, chemical purity: 96%.

7.13.4 Cleavage of the Chiral Auxiliary

The cleavage of chiral auxiliary from 17a was found to be difficult, therefore the cleavage of chiral auxiliary from intermediate compounds 16a and 16b followed by the second SNAr reaction with aniline 4 was carried as follows.

7.13.5 Cleavage of the Chiral Auxiliary From Stereoisomerically Pure Intermediate 65a and Preparation of Stereoisomerically Pure (1R,2R,3S,4S)-N4-(3-Aminocarbonylbicyclo[2.2.1]hept-5-en-2-yl)-5-fluoro-N2-[3-methyl-4-(4-methylpiperazin-1-yl) phenyl]-2,4-pyrimidinediamine Reaction

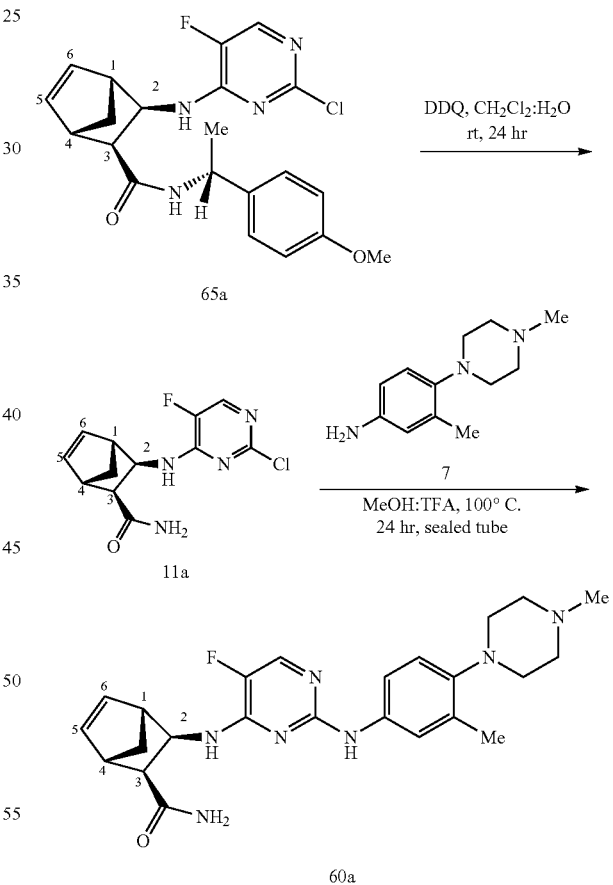

Procedure: The mono-SNAr product with chiral auxiliary 65a was allowed to react with DDQ (3 equivalents) in CH$_2$Cl$_2$:H$_2$O at room temperature to obtain the desired mono-SNAr product 11a. The mono-SNAr product was purified by column chromatography and found to be same as compound 11a obtained via enzymatic route, which was confirmed by chiral analytical HPLC, LCMS and $^1$H NMR. Further, the reaction of mono-SNAr product 11a with aniline 7 in MeOH:TFA at 100° C. in a sealed tube for 24 h gave the desired product 60a. It was purified by column chromatography and analyzed by ¹H NMR, LCMS and chiral analytical HPLC. The chiral analytical HPLC, LCMS and ¹H NMR analyses indicated that the data for the product 60a was matching with the enantiomer designated E1.

7.13.6 Cleavage of the Chiral Auxiliary From Intermediate 65b and Preparation of Stereoisomerically Pure (1S,2R,3S,4R)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Reaction:

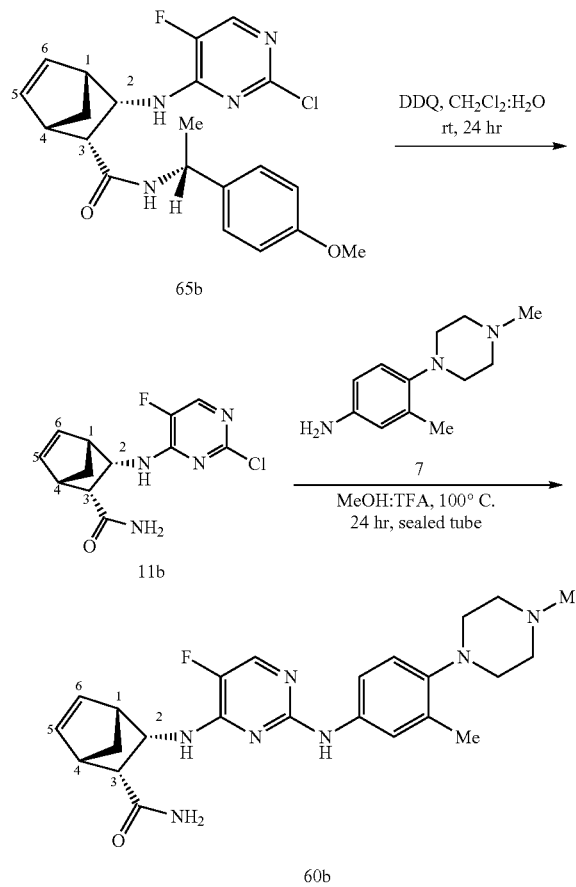

Procedure: The mono-SNAr product 65b was allowed to react with DDQ (3 equivalents) in $CH_2Cl_2$:$H_2O$ at room temperature to obtain the desired mono-SNAr product 11b (after the cleavage of chiral auxiliary). The mono-SNAr product was purified by column chromatography and found to be a different diastereoisomer than that was obtained via enzymatic route, and this was confirmed by chiral analytical HPLC. Further, the reaction of mono-SNAr product 11b with aniline 7 in MeOH:TFA at 100° C. in a sealed tube for 24 h gave the desired product 60b. It was purified by column chromatography and analyzed by ¹H NMR, LCMS and chiral analytical HPLC. The chiral analytical HPLC, LCMS and ¹H NMR analyses indicated that the data for product 60b was identical with the enantiomer designed E2. $[\alpha]_D$ -85.9° (c, 1.17 MeOH).

7.14 Preparation of HCl Salts

HCl salts of the 2-exo-3-exo racemate R1Compound 60 and stereoisomerically pure enantiomer E1 Compound 60a were prepared by as described below. These HCl salts were designated racemate R3 (Compound 228) and enantiomer E3 (Compound 234), respectively.

7.14.1 Preparation of Racemic N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Hydrogen Chloride Salt To a solution of 2-exo-3-exo racemic N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine (racemate R1; compound 60) (0.140 g, 0.3 mmol) in MeOH (3 mL) at 0° C. was added HCl (4M, dioxane, 0.170 mL, 0.681 mmol) dropwise and then stirred at ° C. for 1 h and room temperature for 15 minutes. The clear homogeneous solution was filtered, concentrated and redissolve in EtOH. The ethanolic solution upon precipitation with anti-solvent (EtOAC) gave the precipitate, which was isolated to give 2-exo-3-exo racemic N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine bis hydrogen chloride salt (racemate R2; Compound 185). LCMS: purity: 98%; MS (m/e): 453 (MH⁺).

7.14.2 Preparation of Stereoisomerically pure (1R, 2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Hydrogen Chloride Salt In like manner to the preparation of racemate R1 (Compound 60), supra, the interaction of 2 equivalents of HCl (4M, dioxane) with stereoisomerically pure (1R,2R, 3 S, 4S)-N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine (enantiomer E1; Compound 60a) gave stereoisomerically pure (1R,2R,3S,4S)-N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine Hydrogen Chloride Salt (enantiomer E3) (Compound 234). LCMS: purity: 97%; MS (m/e): 453 (MH⁺); $[\alpha]_D$ +46.3° (c, 0.04 MeOH).

7.15 Preparation of Other Compounds

Various other compounds according to structural formula (I) were prepared by routine adaptation of the above-described syntheses and/or Scheme (I). These compounds, along with their chromatographic, NMR and/or spectral data, are provided in TABLE 1, below. Compounds for which no physical characterization data are provided were not synthesized or purified as single diastereomers.

7.16 Inhibition of Cellular Proliferation In Vitro

Many of the various compounds described herein were tested against A549 and H1299 cells for their ability to inhibit proliferation using standard in vitro antiproliferation assays. The $IC_{50}$ values measured in a 6 point assay are provided in TABLE 1. In TABLE 1, a "+" indicates an $IC_{50}$ value of ≤10 μM, a "++" indicates an $IC_{50}$ value of ≤1 μM, "+++" indicates an $IC_{50}$ value of ≤100 nM, and a "-" indicates an $IC_{50}$ value of >10 μM. A blank indicates that the compound was not tested against the specific cell line.

TABLE 1

| Compound No. | Structure | Name |
|---|---|---|
| 100 | 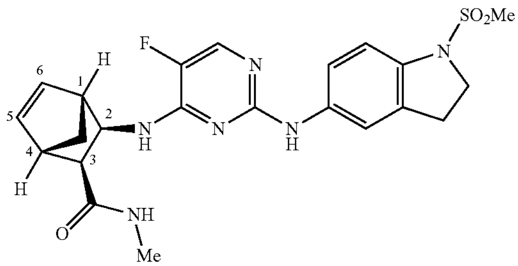 [SMILES: CNC(=O)[C@@H]1[C@H](Nc2nc(Nc3ccc4c(c3)CCN4S(C)(=O)=O)ncc2F)[C@H]2C=C[C@@H]1C2] | (1R,2R,3S,4S)-5-fluoro-N4-[3-methylaminocarbonylbicyclo[2.2.1]hept-5-en-2-yl)-N2-[1-methysulfonyl-2,3-dihydroindol-5-yl]-2,4-pyrimidinediamine |
| 101 | 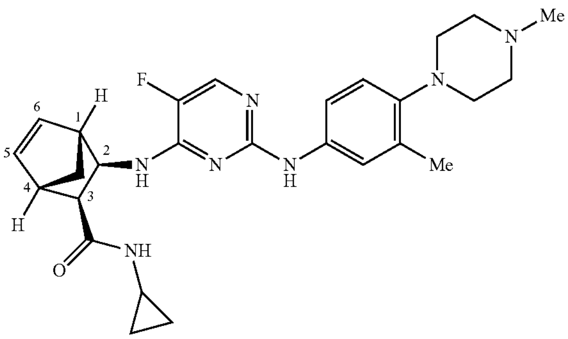 [SMILES: Cc1cc(Nc2ncc(F)c(N[C@H]3[C@@H](C(=O)NC4CC4)[C@@H]4C=C[C@H]3C4)n2)ccc1N1CCN(C)CC1] | (1R,2R,3S,4S)-N4-(3-N-cyclopropylaminocarbonylbicyclo[2.2.1]hept-2-yl)-5-fluoro-N2-[3-methyl-4-(4-methylpiperazin-1-yl)phenyl]-2,4-pyrimidinediamine |
| 102 | 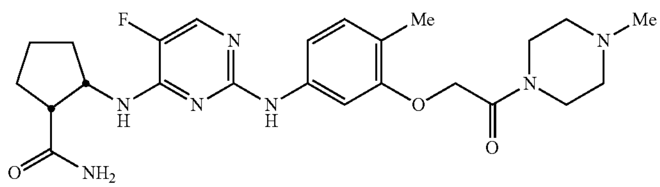 [SMILES: Cc1ccc(Nc2ncc(F)c(N[C@H]3CCC[C@H]3C(N)=O)n2)cc1OCC(=O)N1CCN(C)CC1] | Racemic-cis-N4-(2-aminocarbonylcyclopent-1-yl)-5-fluoro-N2-[4-methyl-3-(4-methylpiperazin-1-yl)carbonylmethyleneoxyphenyl]-2,4-pyrimidinediamine |
| 103 | Mixture of IVa + IVb type | Racemic-(2-exo, 3-exo)-N4-(3-aminocarbonylbicyclo[2.2.1]hept-5-en-2-yl)-5-fluoro-N2-[4-methy-3-(N-morpholinyl)carbonylmethyleneoxyphenyl]-2,4-pyrimidinediamine |
| 104 | Mixture of IVa + IVb type | Racemic-(2-exo, 3-exo)-N4-(3-aminocarbonylbicyclo[2.2.1]hept-5-en-2-yl)-5-fluoro-N2-[4-methyl-3-(N-morpholinyl)-2-ethyleneoxyphenyl]-2,4-pyrimidinediamine |
| 105 | 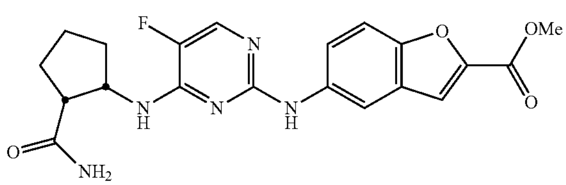 [SMILES: COC(=O)c1cc2cc(Nc3ncc(F)c(N[C@H]4CCC[C@H]4C(N)=O)n3)ccc2o1] | Racemic-cis-N4-(2-aminocarbonylcyclopent-1-yl)-5-fluoro-N2-(2-methoxycarbonylbenzofuran-5-yl)-2,4-pyrimidinediamine |

TABLE 1-continued

| | | |
|---|---|---|
| 106 | 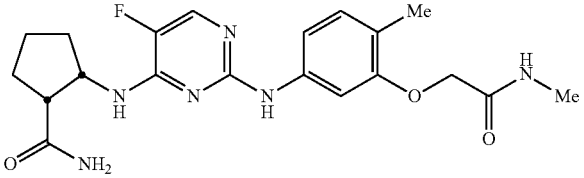 [SMILES: CNC(=O)COc1cc(Nc2ncc(F)c(N[C@H]3CCC[C@H]3C(N)=O)n2)ccc1C] | Racemic-cis-N4-(2-aminocarbonylcyclopent-1-yl)-5-fluoro-N2-[4-methyl-3-(N-methylamino)carbonylmethyleneoxyphenyl]-2,4-pyrimidinediamine |
| 107 | 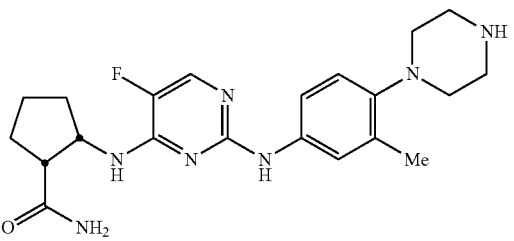 [SMILES: Cc1cc(Nc2ncc(F)c(N[C@H]3CCC[C@H]3C(N)=O)n2)ccc1N1CCNCC1] | Racemic-cis-N4-(2-aminocarbonylcyclopent-1-yl)-5-fluoro-N2-[3-methyl-4-(piperazin-1-yl)phenyl]-2,4-pyrimidinediamine |
| 108 | Mixture of IVa + IVb type<br />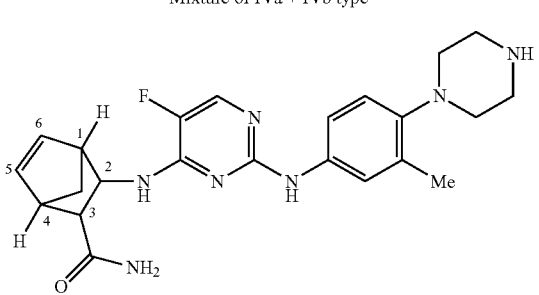 | Racemic-(2-exo, 3-exo)-N4-(3-Aminocarbonylbicyclo[2.2.1]hept-5-en-2-yl)]-5-fluoro-N2-[3-methyl-4-(piperazin-1-yl)phenyl]-2,4-pyrimidinediamine |
| 109 | 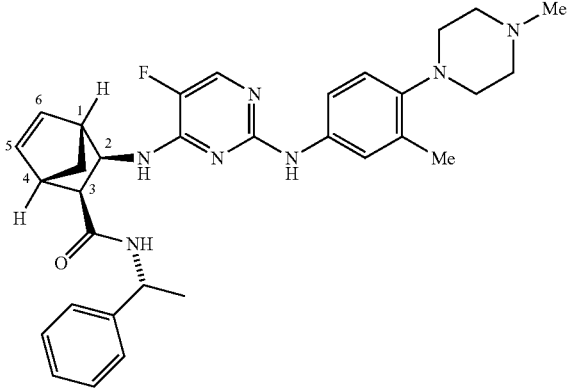 | (1R,2R,3S,4S)-N4-5-Fluoro-N4-(3-(R)-alpha-methylbenzylaminocarbonylbicyclo[2.2.1]hept-5-en-2-yl)-N2-[3-methyl-4-(4-methylpiperazin-1-yl)phenyl]-2,4-pyrimidinediamine |
| 110 | 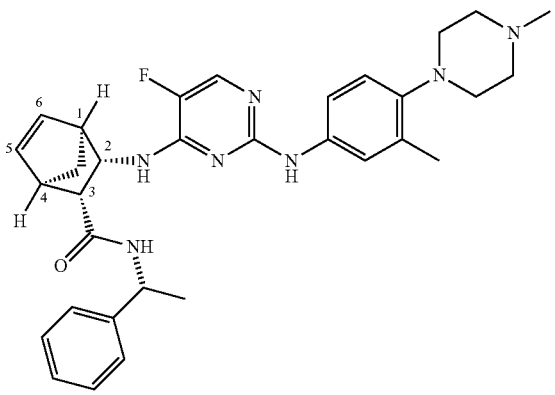 | (1S,2S,3R,4R)-N4-5-Fluoro-N4-(3-(R)-alpha-methylbenzyl-aminocarbonylbicyclo[2.2.1]hept-5-en-2-yl)-N2-[3-methyl-4-(4-methylpiperazin-1-yl)phenyl]-2,4-pyrimidinediamine |

TABLE 1-continued

| | | | |
|---|---|---|---|
| 111 | Mixture of IVa + IVb type | 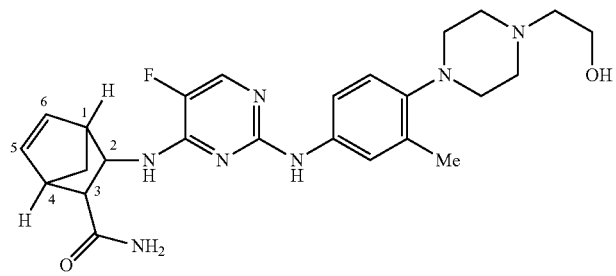 | Racemic-(2-exo, 3-exo)-N4-[3-amino-carbonylbicyclo[2.2.1]hept-5-en-2-yl)]-5-fluoro-N2-{3-methyl-4-[4-(2-hydroxyethyl)piperazin-1-yl]phenyl}-2,4-pyrimidinediamine |
| 112 | Mixture of IVa + IVb type | 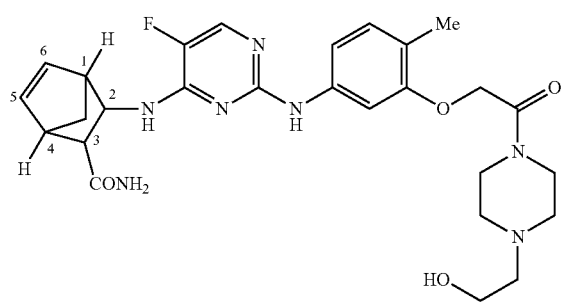 | Racemic-(2-exo, 3-exo)-N4-(3-amino-carbonylbicyclo[2.2.1]hept-5-en-2-yl)-5-fluoro-N2-{4-methyl-3-[4-(2-hydroxyethyl)piperazin-1-yl]carbonylmethyleneoxyphenyl}-2,4-pyrimidinediamine |
| 113 | Mixture of IVa + IVb type | 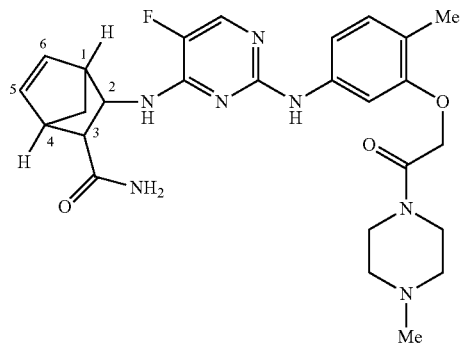 | Racemic-(2-exo, 3-exo)-N4-(3-amino-carbonylbicyclo[2.2.1]hept-5-en-2-yl)-5-fluoro-N2-[(4-methyl-3-(4-methylpiperazin-1-yl)carbonylmethyleneoxyphenyl]-2,4-pyrimidinediamine |
| 114 | Mixture of type IVa + IVb | 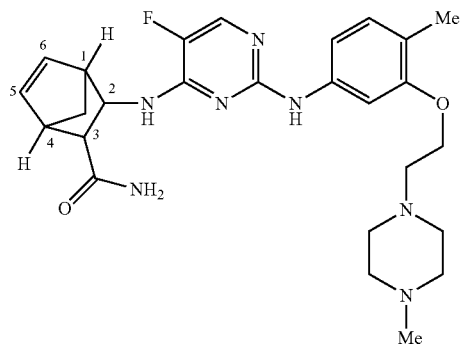 | Racemic-(2-exo, 3-exo)-N4-(3-amino-carbonylbicyclo[2.2.1]hept-5-en-2-yl)-5-fluoro-N2-[4-methyl-3-[(4-methylpiperazin-1-yl-ethyloxy)phenyl]-2,4-pyridinediamine |

TABLE 1-continued

| | | |
|---|---|---|
| 115 | 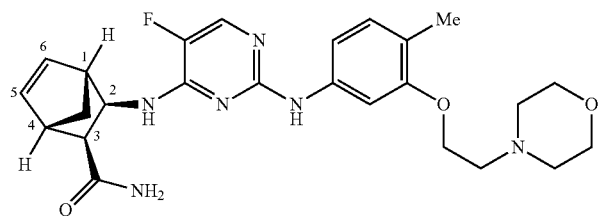 [SMILES: Cc1ccc(Nc2ncc(F)c(N[C@H]3[C@@H](C(N)=O)[C@@H]4C=C[C@H]3C4)n2)cc1OCCN1CCOCC1] | (1R,2R,3S,4S)-N4-(3-Amino-carbonylbicyclo[2.2.1]hept-5-en-2-yl)-5-fluoro-N2-[4-methyl-3-(2-morpholinoethyloxy)phenyl]-2,4-pyrimidinediamine |
| 116 | 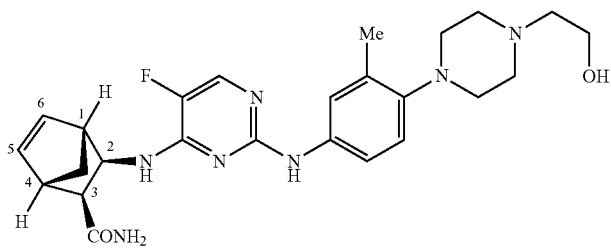 [SMILES: Cc1cc(Nc2ncc(F)c(N[C@H]3[C@@H](C(N)=O)[C@@H]4C=C[C@H]3C4)n2)ccc1N1CCN(CCO)CC1] | (1R,2R,3S,4S)-N4-(3-Amino-carbonylbicyclo[2.2.1]hept-5-en-2-yl)-5-fluoro-N2-{4-[4-(2-hydroxyethyl)piperazin-1-yl]-3-methylphenyl}-2,4-pyrimidinediamine |
| 117 | 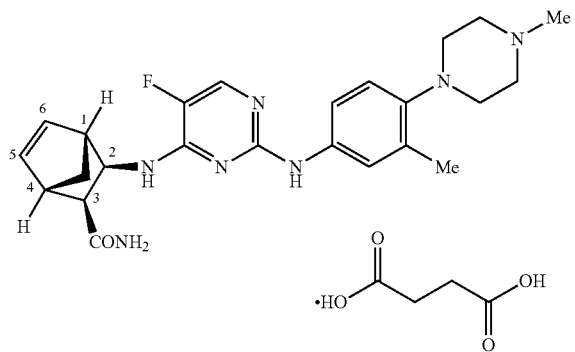 | (1R,2R,3S,4S)-N4-(3-Amino-carbonylbicyclo[2.2.1]hept-5-en-2-yl)-5-fluoro-N2-[3-methyl-4-(4-methylpiperazin-1-yl)phenyl]-2,4-pyrimidinediamine Succinic Acid Salt |
| 118 | 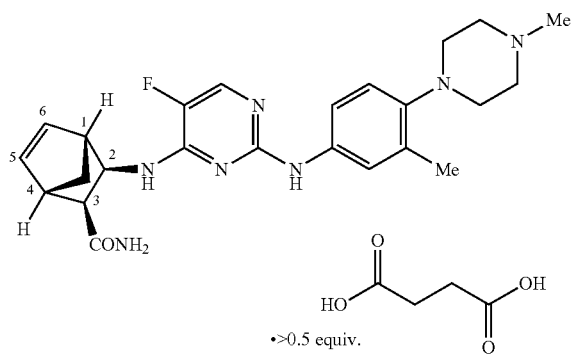 [SMILES: Cc1cc(Nc2ncc(F)c(N[C@H]3[C@@H](C(N)=O)[C@@H]4C=C[C@H]3C4)n2)ccc1N1CCN(C)CC1 ; O=C(O)CCC(=O)O] | (1R,2R,3S,4S)-N4-(3-Amino-carbonylbicyclo[2.2.1]hept-5-en-2-yl)-5-fluoro-N2-[3-methyl-4-(4-methylpiperazin-1-yl)phenyl]-2,4-pyrimidinediamine Succinic Acid Salt |
| 119 | 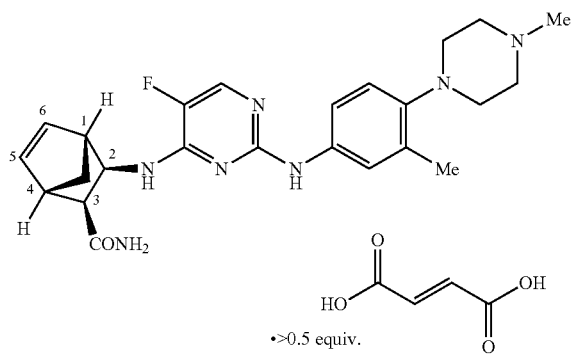 [SMILES: Cc1cc(Nc2ncc(F)c(N[C@H]3[C@@H](C(N)=O)[C@@H]4C=C[C@H]3C4)n2)ccc1N1CCN(C)CC1 ; O=C(O)/C=C/C(=O)O] | (1R,2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Fumaric Acid Salt |

TABLE 1-continued

| | | |
|---|---|---|
| 120 | 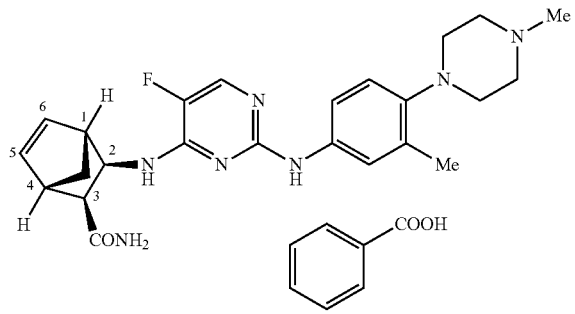 [SMILES: Cc1cc(Nc2ncc(F)c(N[C@H]3[C@@H](C(N)=O)[C@@H]4C=C[C@H]3C4)n2)ccc1N1CCN(C)CC1 ; O=C(O)c1ccccc1] | (1R,2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Benzoic Acid Salt |
| 121 | 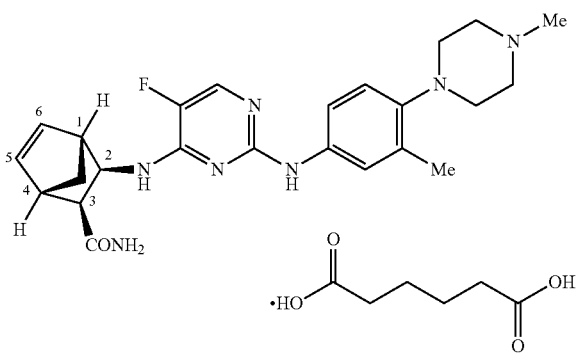 | (1R,2R,3S,4S)-N4-(3-Aminocarbonylbicyclo[2.2.1]hept-5-ene-2-yl)-5-fluoro-N2-[3-methyl-4-(4-methylpiperazin-1-yl)phenyl]-2,4-pyrimidinediamine Adipic Acid Salt |
| 122 | 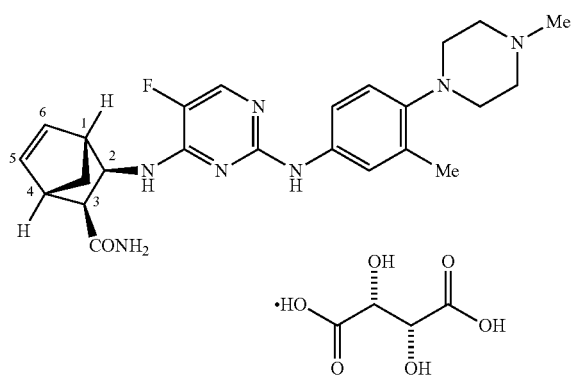 | (1R,2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Tartaric Acid Salt |
| 123 | 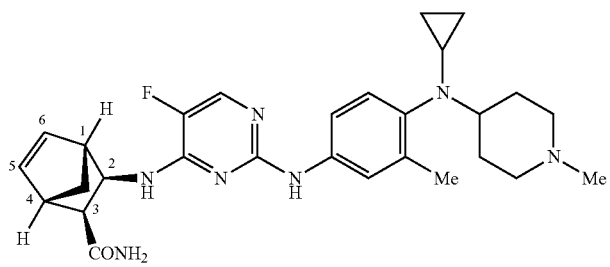 [SMILES: Cc1cc(Nc2ncc(F)c(N[C@H]3[C@@H](C(N)=O)[C@@H]4C=C[C@H]3C4)n2)ccc1N(C1CC1)C1CCN(C)CC1] | (1R,2R,3S,4S)-N4-(3-Aminocarbonylbicyclo[2.2.1]hept-5-en-2-yl)-5-fluoro-N2-{4-[N-cyclopropyl-(1-methylpiperidin-4-yl)]-3-methylphenyl}-2,4-pyrimidinediamine |

TABLE 1-continued

| 124 | 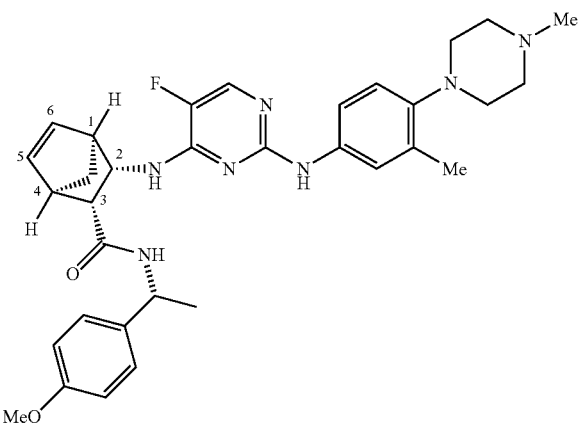 | (1S,2S,3R,4R)-5-Fluoro-N4-(3-(R)-4-methoxy-alpha-methylbenzylamino carbonylbicyclo[2.2.1]hept-5-en-2-yl)-N2-[3-methyl-4-(4-methylpiperazin-1-yl)phenyl]-2,4-pyrimidinediamine |
| --- | --- | --- |
| 125 | 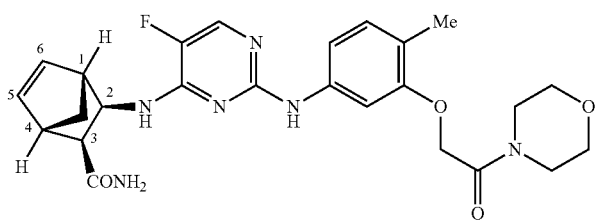 [SMILES: Cc1ccc(Nc2ncc(F)c(N[C@H]3[C@@H](C(N)=O)[C@@H]4C=C[C@H]3C4)n2)cc1OCC(=O)N1CCOCC1] | (1R,2R,3S,4S)-N4-(3-Aminocarbonylbicyclo[2.2.1]hept-5-en-2-yl)-5-fluoro-N2-[4-methyl-3-(morpholin-4-ylcarbonylmethyleneoxy)phenyl]-2,4-pyrimidinediamine |
| 126 | 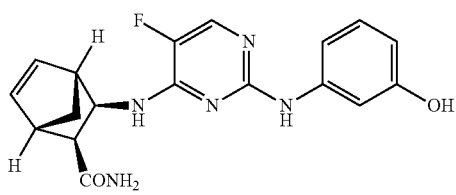 [SMILES: NC(=O)[C@@H]1[C@H](Nc2nc(Nc3cccc(O)c3)ncc2F)[C@H]2C=C[C@@H]1C2] | (1R,2R,3S,4S)-N4-[3-Aminocarbonylbicyclo[2.2.1]hept-5-en-2-yl]-5-fluoro-N2-(3-hydroxyphenyl)-2,4-pyrimidinediamine |
| 127 | 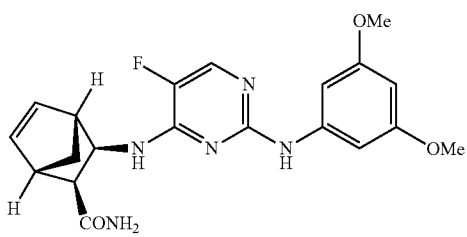 [SMILES: COc1cc(Nc2ncc(F)c(N[C@H]3[C@@H](C(N)=O)[C@@H]4C=C[C@H]3C4)n2)cc(OC)c1] | (1R,2R,3S,4S)-N4-[3-Aminocarbonylbicyclo[2.2.1]hept-5-en-2-yl]-N2-(3,5-dimethoxyphenyl)-5-fluoro-2,4-pyrimidinediamine |
| 128 | 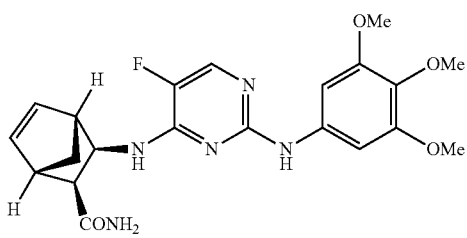 [SMILES: COc1cc(Nc2ncc(F)c(N[C@H]3[C@@H](C(N)=O)[C@@H]4C=C[C@H]3C4)n2)cc(OC)c1OC] | (1R,2R,3S,4S)-N4-[3-Aminocarbonylbicyclo[2.2.1]hept-5-en-2-yl]-5-fluoro-N2-(3,4,5-trimethoxyphenyl)-2,4-pyrimidinediamine |
| 129 | 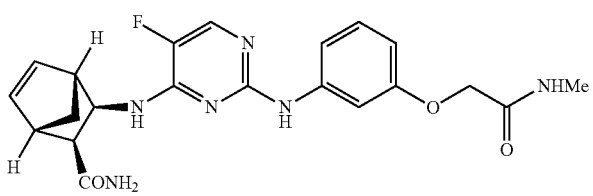 [SMILES: CNC(=O)COc1cccc(Nc2ncc(F)c(N[C@H]3[C@@H](C(N)=O)[C@@H]4C=C[C@H]3C4)n2)c1] | (1R,2R,3S,4S)-N4-[3-Aminocarbonylbicyclo[2.2.1]hept-5-en-2-yl]-N2-[3-(N-methylaminocarbonyl)methyleneoxyphenyl]-5-fluoro-2,4-pyrimidinediamine |

TABLE 1-continued

| 130 | 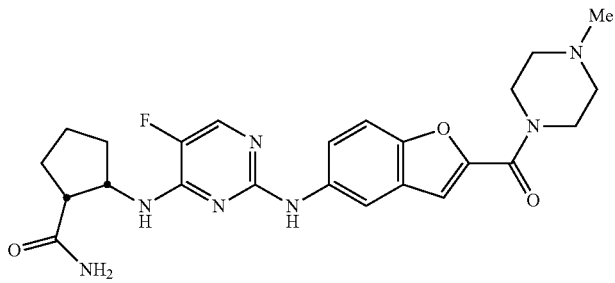 [SMILES: CN1CCN(C(=O)c2cc3cc(Nc4ncc(F)c(N[C@H]5CCC[C@H]5C(N)=O)n4)ccc3o2)CC1] | Racemic-cis-N4-(2-aminocarbonylcyclopent-1-yl)-5-fluoro-N2-[2-(4-methylpiperazin-1-ylcarbonyl)benzofuran-5-yl]-2,4-pyrimidinediamine |
|---|---|---|
| 131 | 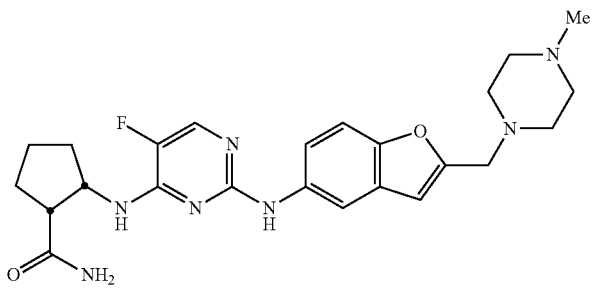 [SMILES: CN1CCN(Cc2cc3cc(Nc4ncc(F)c(N[C@H]5CCC[C@H]5C(N)=O)n4)ccc3o2)CC1] | Racemic-cis-N4-(2-aminocarbonylcyclopent-1-yl)-5-fluoro-N2-[2-(4-methylpiperazin-1-ylmethylene)benzofuran-5-yl]-2,4-pyrimidinediamine |
| 132 | 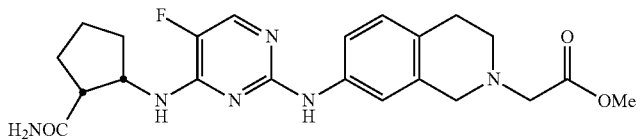 [SMILES: COC(=O)CN1CCc2ccc(Nc3ncc(F)c(N[C@H]4CCC[C@H]4C(N)=O)n3)cc2C1] | Racemic-cis-N4-(2-aminocarbonylcyclopent-1-yl)-5-fluoro-N2-[2-(methoxycarbonylmethylene)-1,2,3,4-tetrahydroisoquin-7-yl]-2,4-pyrimidinediamine |
| 133 | Mixture of IVa + IVb type 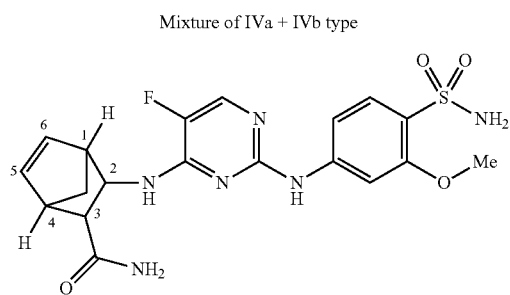 [SMILES: COc1cc(Nc2ncc(F)c(NC3C4C=CC(C4)C3C(N)=O)n2)ccc1S(N)(=O)=O] | Racemic-(2-exo,3-exo)-N4-(3-aminocarbonylbicyclo[2.2.1]hept-5-en-2-yl)-N2-(4-aminosulfonyl-3-methoxyphenyl)-5-fluoro-2,4-pyrimidinediamine |
| 134 | Mixture of IVa + IVb type 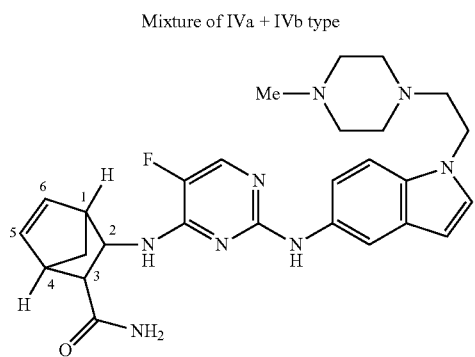 [SMILES: CN1CCN(CCn2ccc3cc(Nc4ncc(F)c(NC5C6C=CC(C6)C5C(N)=O)n4)ccc32)CC1] | Racemic-(2-exo,3-exo)-N4-(3-aminocarbonylbicyclo[2.2.1]hept-5-en-2-yl)-5-fluoro-N2-{1-[2-(4-methyl-piperazin-1-yl)ethyl]indol-5-yl}-2,4-pyrimidinediamine |

TABLE 1-continued

| | | | |
|---|---|---|---|
| 135 | Mixture of IVa + IVb type | 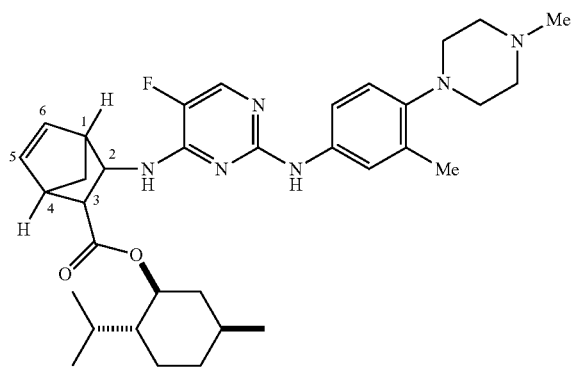 | Racemic (2-exo,3-exo)-5-Fluoro-N4-[3-(1R,2S,5R)-(−)-menthyloxycarbonyl bicyclo[2.2.1]hept-5-en-2-yl]-N2-[3-methyl-4-(4-methylpiperazin-1-yl)phenyl]-2,4-pyrimidinediamine |
| 136 | | 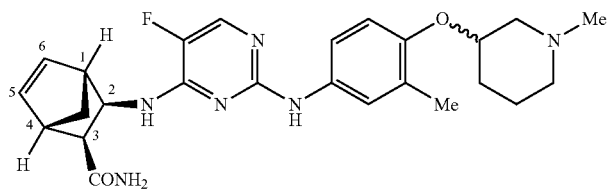 [SMILES: Cc1cc(Nc2ncc(F)c(N[C@H]3[C@@H](C(N)=O)[C@@H]4C=C[C@H]3C4)n2)ccc1OC1CCCN(C)C1] | (1R,2R,3S,4S)-N4-(3-aminocarbonylbicyclo[2.2.1]hept-5-en-2-yl)-5-fluoro-N2-[4-((±)-1-methyl-piperidin-3-yloxy)phenyl]-2,4-pyrimidinediamine |
| 137 | | 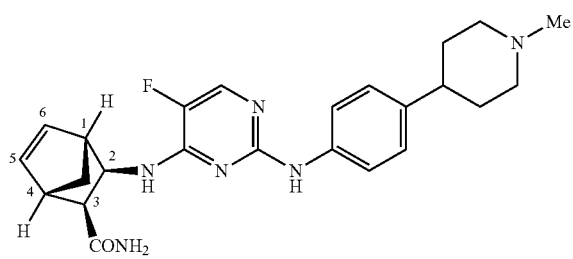 [SMILES: CN1CCC(c2ccc(Nc3ncc(F)c(N[C@H]4[C@@H](C(N)=O)[C@@H]5C=C[C@H]4C5)n3)cc2)CC1] | (1R,2R,3S,4S)-N4-(3-aminocarbonyl bicyclo[2.2.1]hept-5-en-2-yl)-5-fluoro-N2-[4-(1-methylpiperidin-4-yl)phenyl]-2,4-pyrimidinediamine |
| 138 | | 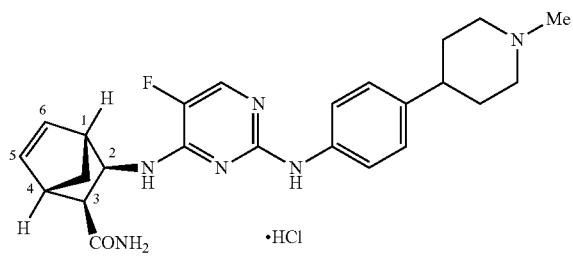 [SMILES: CN1CCC(c2ccc(Nc3ncc(F)c(N[C@H]4[C@@H](C(N)=O)[C@@H]5C=C[C@H]4C5)n3)cc2)CC1 ; Cl] | (1R,2R,3S,4S)-N4-(3-Aminocarbonyl bicyclo[2.2.1]hept-5-en-2-yl)-5-fluoro-N2-[4-(1-methylpiperidin-4-yl)phenyl]-2,4-pyrimidinediamine Hydrochloric Acid Salt |
| 139 | | 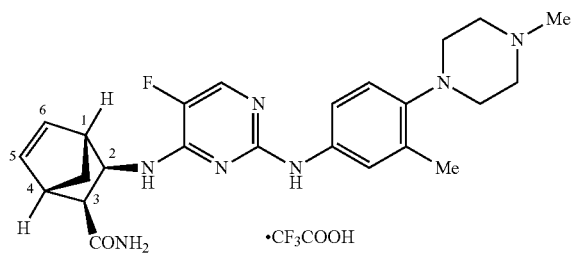 [SMILES: Cc1cc(Nc2ncc(F)c(N[C@H]3[C@@H](C(N)=O)[C@@H]4C=C[C@H]3C4)n2)ccc1N1CCN(C)CC1 ; "·CF3COOH"] | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine Trifluoroacetic Acid Salt |
| 140 | | 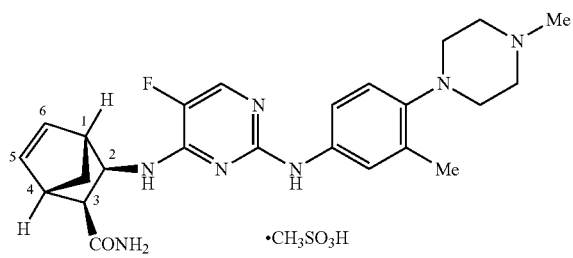 | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine Methanesulfonic Acid Salt |

TABLE 1-continued

| | | |
|---|---|---|
| 141 | 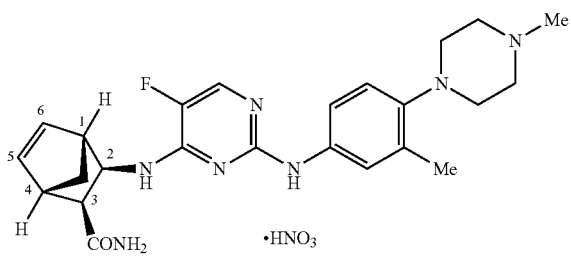 | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine Nitric Acid Salt |
| 142 | 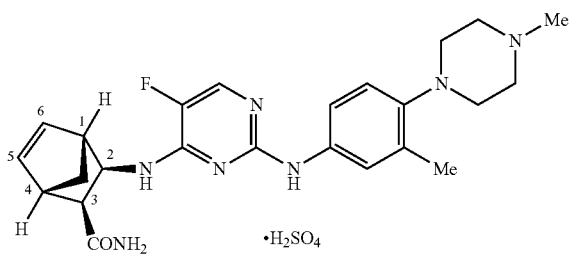 | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine Sulfuric Acid Salt |
| 143 | 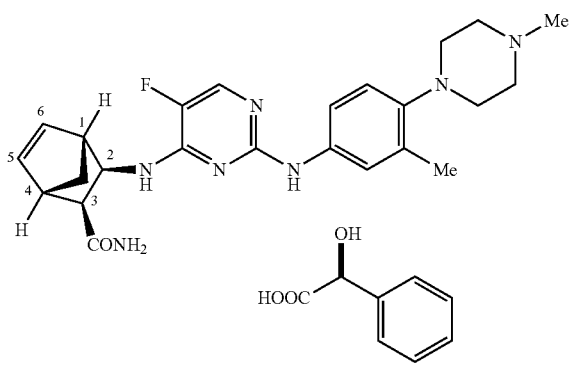 [SMILES: Cc1cc(Nc2ncc(F)c(N[C@H]3[C@@H](C(N)=O)[C@@H]4C=C[C@H]3C4)n2)ccc1N1CCN(C)CC1 ; O=C(O)[C@@H](O)c1ccccc1] | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine (S)-Mandelic Acid Salt |
| 144 | 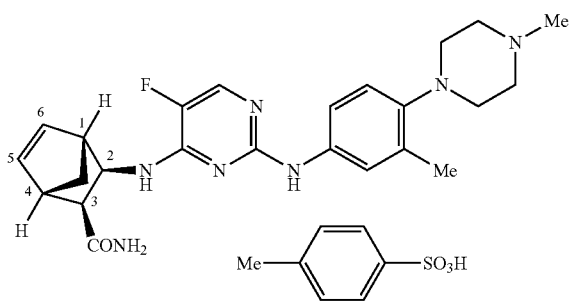 | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine p-Toluenesulfonic Acid Salt |
| 145 | 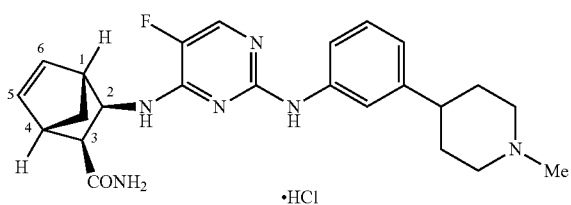 [SMILES: CN1CCC(c2cccc(Nc3ncc(F)c(N[C@H]4[C@@H](C(N)=O)[C@@H]5C=C[C@H]4C5)n3)c2)CC1 ; Cl] | (1R,2R,3S,4S)-N4-(3-Aminocarbonyl bicyclo[2.2.1]hept-5-en-2-yl)-5-fluoro-N2-[3-(1-methylpiperidin-4-yl)phenyl]-2,4-pyrimidinediamine Mono-Hydrochloric Acid Salt |
| 146 | 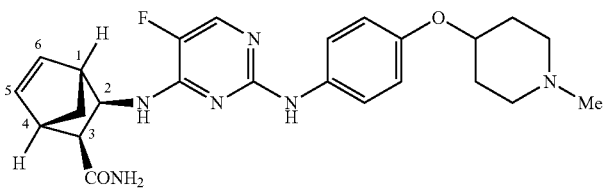 [SMILES: CN1CCC(Oc2ccc(Nc3ncc(F)c(N[C@H]4[C@@H](C(N)=O)[C@@H]5C=C[C@H]4C5)n3)cc2)CC1] | (1R,2R,3S,4S)-N4-(3-Aminocarbonyl bicyclo[2.2.1]hept-5-en-2-yl)-5-fluoro-N2-[4-(1-methylpiperidin-4-yloxy)phenyl]-2,4-pyrimidinediamine |

TABLE 1-continued

| | | |
|---|---|---|
| 147 | 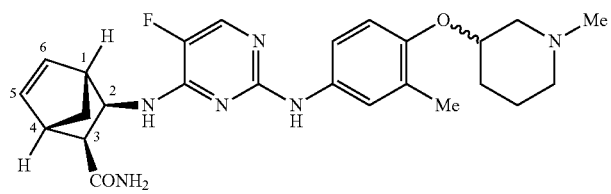 [SMILES: Cc1cc(Nc2ncc(F)c(N[C@H]3[C@@H](C(N)=O)[C@@H]4C=C[C@H]3C4)n2)ccc1OC1CCCN(C)C1] | (1R,2R,3S,4S)-N4-(3-Aminocarbonyl bicyclo[2.2.1]hept-5-en-2-yl)-5-fluoro-N2-[3-methyl-4-(1-methylpiperidin-3(±)-yloxy)phenyl]-2,4-pyrimidinediamine |
| 148 | 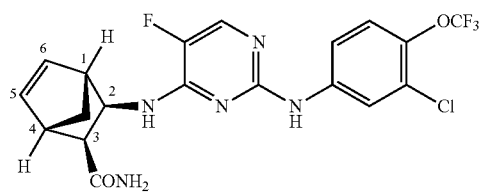 [SMILES: NC(=O)[C@@H]1[C@H](Nc2nc(Nc3ccc(OC(F)(F)F)c(Cl)c3)ncc2F)[C@H]2C=C[C@@H]1C2] | (1R,2R,3S,4S)-N4-(3-Aminocarbonyl bicyclo[2.2.1]hept-5-en-2-yl)-N2-(3-chloro-4-trifluoromethoxyphenyl)-5-fluoro-2,4-pyrimidinediamine |
| 149 | 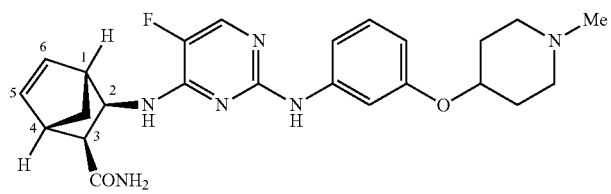 [SMILES: CN1CCC(Oc2cccc(Nc3ncc(F)c(N[C@H]4[C@@H](C(N)=O)[C@@H]5C=C[C@H]4C5)n3)c2)CC1] | (1R,2R,3S,4S)-N4-(3-Aminocarbonyl bicyclo[2.2.1]hept-5-en-2-yl)-5-fluoro-N2-[3-(1-methylpiperidin-4-yloxy)phenyl]-2,4-pyrimidinediamine |
| 150 | 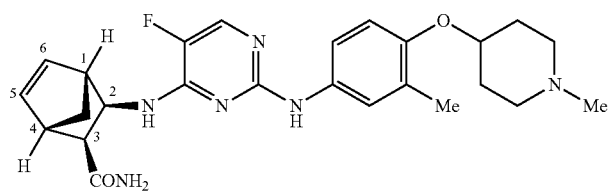 [SMILES: Cc1cc(Nc2ncc(F)c(N[C@H]3[C@@H](C(N)=O)[C@@H]4C=C[C@H]3C4)n2)ccc1OC1CCN(C)CC1] | (1R,2R,3S,4S)-N4-(3-Aminocarbonyl bicyclo[2.2.1]hept-5-en-2-yl)-5-fluoro-N2-[3-methyl-4-(1-methylpiperidin-4-yloxy)phenyl]-2,4-pyrimidinediamine |
| 151 | 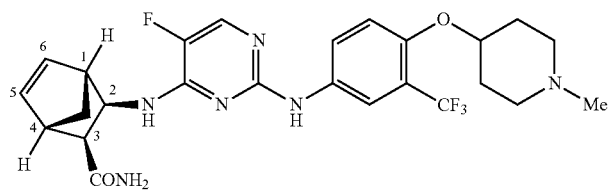 | (1R,2R,3S,4S)-N4-(3-Aminocarbonyl bicyclo[2.2.1]hept-5-en-2-yl)-5-fluoro-N2-[4-(1-methylpiperidin-4-yloxy)-3-trifluoromethylphenyl]-2,4-pyrimidinediamine |
| 152 | 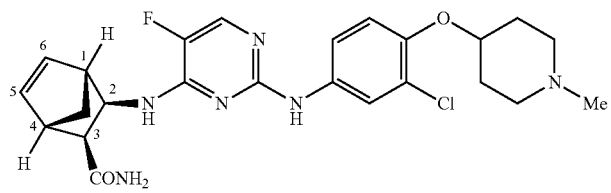 [SMILES: CN1CCC(Oc2ccc(Nc3ncc(F)c(N[C@H]4[C@@H](C(N)=O)[C@@H]5C=C[C@H]4C5)n3)cc2Cl)CC1] | (1R,2R,3S,4S)-N4-(3-Aminocarbonyl bicyclo[2.2.1]hept-5-en-2-yl)-N2-[3-chloro-4-(1-methylpiperidin-4-yloxy)phenyl]-5-fluoro-2,4-pyrimidinediamine |
| 153 | 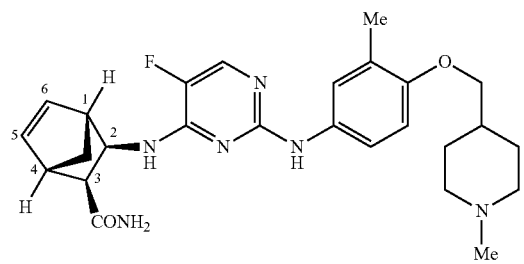 [SMILES: Cc1cc(Nc2ncc(F)c(N[C@H]3[C@@H](C(N)=O)[C@@H]4C=C[C@H]3C4)n2)ccc1OCC1CCN(C)CC1] | (1R,2R,3S,4S)-N4-(3-Aminocarbonyl bicyclo[2.2.1]hept-5-en-2-yl)-5-fluoro-N2-[4-(1-methylpiperidin-4-ylmethyleneoxy)-3-methylphenyl]-2,4-pyrimidinediamine |

TABLE 1-continued

| | | |
|---|---|---|
| 154 | 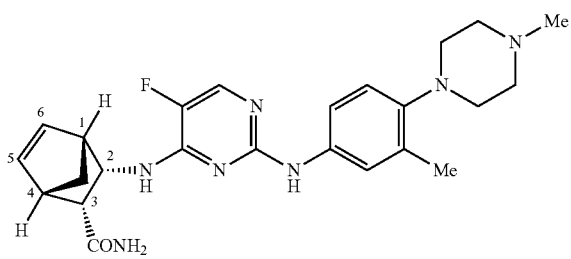 [SMILES: Cc1cc(Nc2ncc(F)c(N[C@@H]3[C@H](C(N)=O)[C@@H]4C=C[C@H]3C4)n2)ccc1N1CCN(C)CC1] | (1R,2S,3R,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine |
| 155 | 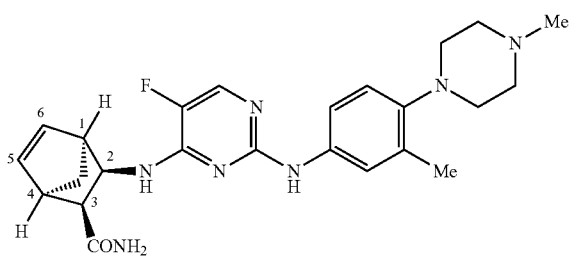 [SMILES: Cc1cc(Nc2ncc(F)c(N[C@H]3[C@@H](C(N)=O)[C@H]4C=C[C@@H]3C4)n2)ccc1N1CCN(C)CC1] | (1S,2R,3S,4R)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine |
| 156 | 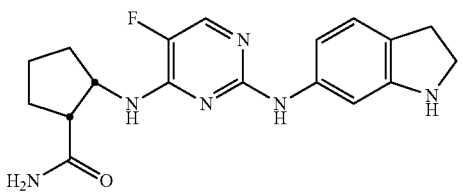 [SMILES: NC(=O)[C@@H]1CCC[C@@H]1Nc1nc(Nc2ccc3c(c2)NCC3)ncc1F] | Racemic-cis-N4-(2-aminocarbonyl cyclopent-1-yl)-N2-(2,3-dihydroindol-6-yl)-5-fluoro-2,4-pyrimidinediamine |
| 157 | 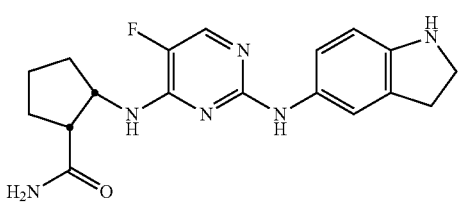 [SMILES: NC(=O)[C@@H]1CCC[C@@H]1Nc1nc(Nc2ccc3c(c2)CCN3)ncc1F] | Racemic-cis-N4-(2-aminocarbonyl cyclopent-1-yl)-N2-(2,3-dihydroindol-5-yl)-5-fluoro-2,4-pyrimidinediamine |
| 158 | 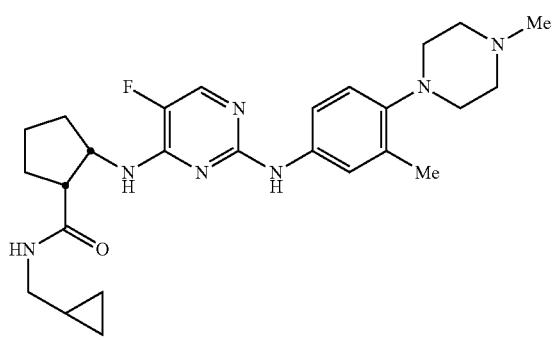 [SMILES: Cc1cc(Nc2ncc(F)c(N[C@H]3CCC[C@H]3C(=O)NCC3CC3)n2)ccc1N1CCN(C)CC1] | Racemic-cis-N4-[2-(N-cyclopropylmethyl) aminocarbonylcyclopent-1-yl]-5-fluoro-N2-[4-(4-methylpiperazin-1-yl)-3-methylphenyl]-2,4-pyrimidinediamine |
| 159 | 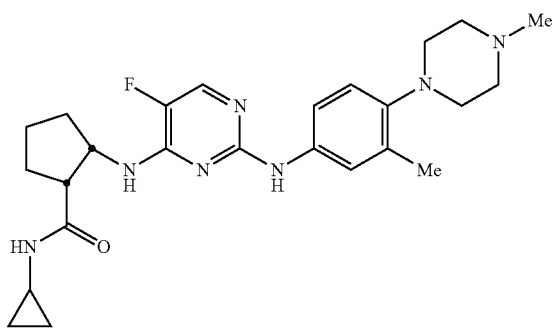 [SMILES: Cc1cc(Nc2ncc(F)c(N[C@H]3CCC[C@H]3C(=O)NC3CC3)n2)ccc1N1CCN(C)CC1] | Racemic-cis-N4-[2-(N-cyclopropyl) aminocarbonylcyclopent-1-yl]-5-fluoro-N2-[4-(4-methylpiperazin-1-yl)-3-methylphenyl]-2,4-pyrimidinediamine |

| 160 | Mixture of IVa + IVb type | 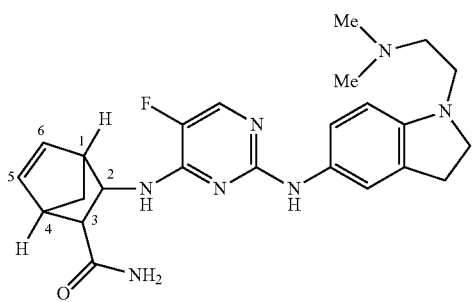 | Racemic-(2-exo,3-exo)-N4-[3-aminocarbonylbicyclo[2.2.1]hept-5-en-2-yl)-N2-[1-(2-dimethylaminoethyl)-2,3-dihydroindol-5-yl]-5-fluoro-2,4-pyrimidinediamine |
| --- | --- | --- | --- |
| 161 | Mixture of IVa + IVb type | 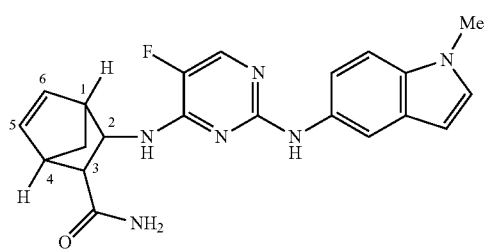 | Racemic-(2-exo,3-exo)-N4-[3-aminocarbonylbicyclo[2.2.1]hept-5-ene-2-yl)-5-fluoro-N2-(1-methylindol-5-yl)-2,4-pyrimidinediamine |
| 162 | Mixture of IVa + IVb type | 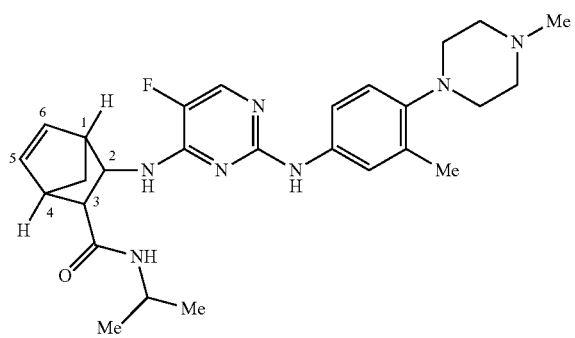 | Racemic-(2-exo,3-exo)-5-fluoro-N4-[2-(N-isopropyl)aminocarbonylbicyclo[2.2.1]hept-5-en-2-yl]-N2-[3-methyl-4-(4-methylpiperazin-1-yl)phenyl]-2,4-pyrimidinediamine |
| 163 | Mixture of IVa + IVb type | 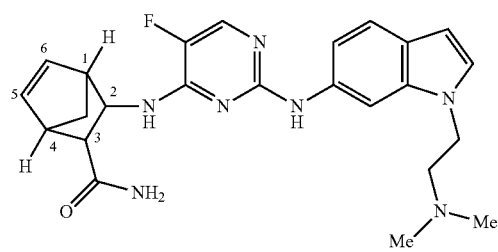 | Racemic-(2-exo,3-exo)-N4-[3-aminocarbonylbicyclo[2.2.1]hept-5-en-2-yl)-N2-[1-(2-dimethylaminoethyl)indol-6-yl]-5-fluoro-2,4-pyrimidinediamine |

TABLE 1-continued

| 164 | Mixture of IVa + IVb type | 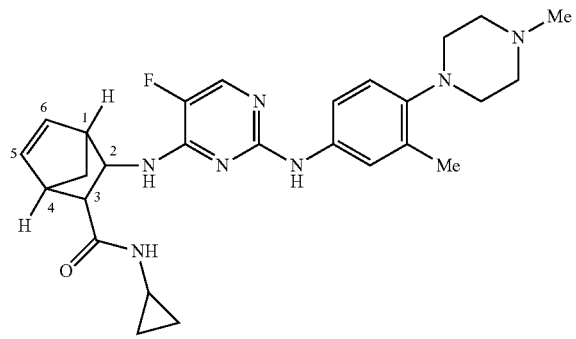 | Racemic-(2-exo,3-exo)-N4-[3-(N-cyclopropyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |
| --- | --- | --- | --- |
| 165 | Mixture of IVa + IVb type | 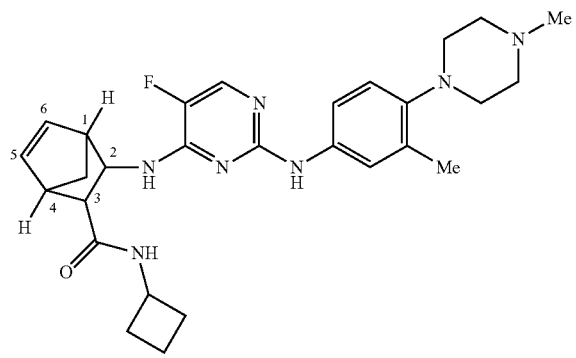 | Racemic-(2-exo,3-exo)-N4-[3-(N-cyclobutyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |
| 166 | Mixture of IVa + IVb type | 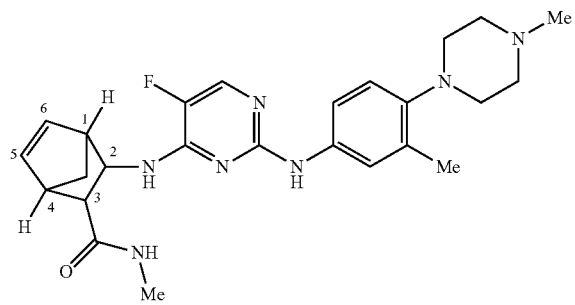 | Racemic-(2-exo,3-exo)-N4-[3-(N-methyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |
| 167 | Mixture of IVa + IVb type | 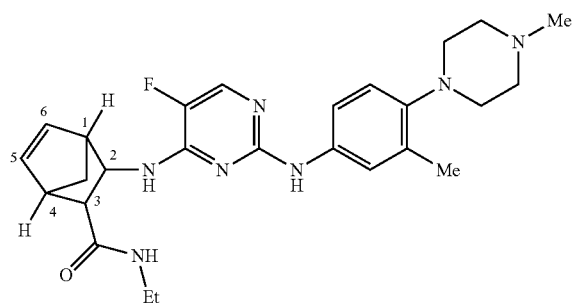 | Racemic-(2-exo,3-exo)-N4-[3-(N-ethyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |

| | | | |
|---|---|---|---|
| 168 | Mixture of IVa + IVb type | 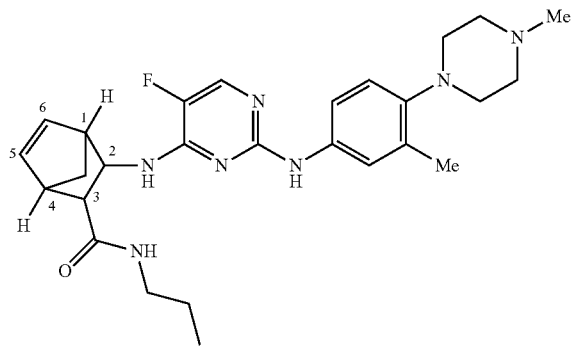 | Racemic-(2-exo,3-exo)-5-fluoro-N2-[4-(4-methylpiperazin-1-yl)-3-methylphenyl]-N4-[3-(N-n-propyl)aminocarbonyl bicyclo[2.2.1]hept-5-en-2-yl]-2,4-pyrimidinediamine |
| 169 | Mixture of IVa + IVb type | 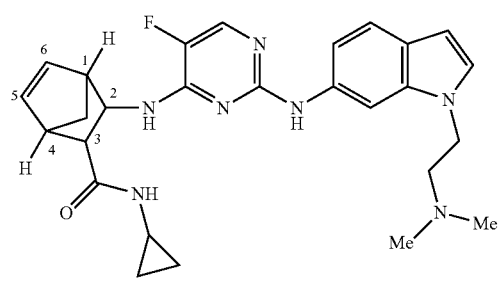 | Racemic-(2-exo,3-exo)-N4-[3-cyclopropylaminocarbonylbicyclo[2.2.1]hept-5-en-2-yl]-N2-[1-(2-dimethyl aminoethyl)indol-6-yl]-5-fluoro-2,4-pyrimidinediamine |
| 170 | Mixture of IVa + IVb type | 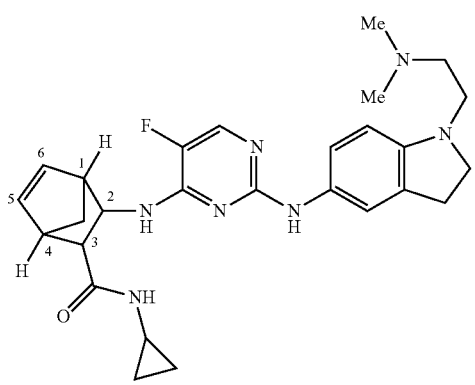 | Racemic-(2-exo,3-exo)-N4-[3-cyclopropylaminocarbonylbicyclo[2.2.1]hept-5-en-2-yl]-N2-[1-(2-dimethyl aminoethyl)-2,3-dihydroindol-5-yl]-5-fluoro-2,4-pyrimidinediamine |
| 171 | Mixture of IVa + IVb type | 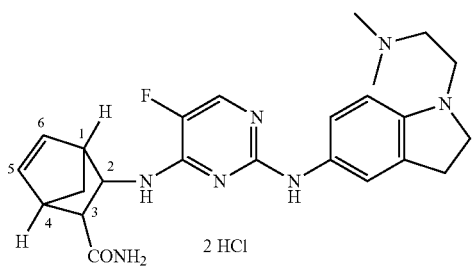 | Racemic-(2-exo,3-exo)-N4-(3-aminocarbonylbicyclo[2.2.1]hept-5-en-2-yl)-5-fluoro-N2-[N-(2-dimethylaminoethyl)-2,3-dihydro-indol-5-yl]-2,4-pyrimidinediamine Bis Hydrogen Chloride Salt |

| | | |
|---|---|---|
| 172 | Mixture of IVa + IVb type 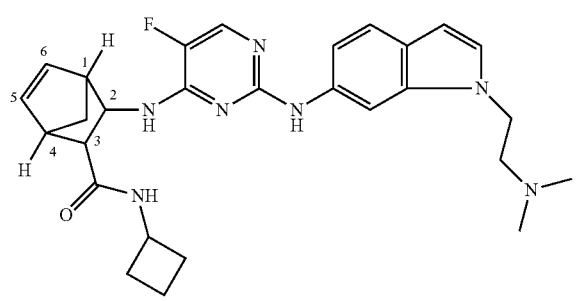 | Racemic-(2-exo,3-exo)-N4-[3-cyclobutylaminocarbonylbicyclo[2.2.1]hept-5-en-2-yl]-N2-[1-(2-dimethylaminoethyl)indol-5-yl]-5-fluoro-2,4-pyrimidinediamine |
| 173 | Mixture of IVa + IVb type 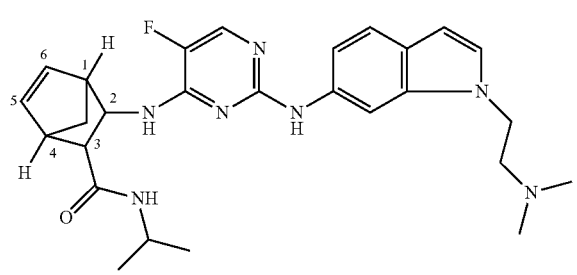 | Racemic-(2-exo,3-exo)-N2-[1-(2-dimethylaminoethyl)indol-5-yl]-5-fluoro-N4-[3-isopropylaminocarbonylbicyclo[2.2.1]hept-5-en-2-yl]-2,4-pyrimidinediamine |
| 174 | Mixture of IVa + IVb type 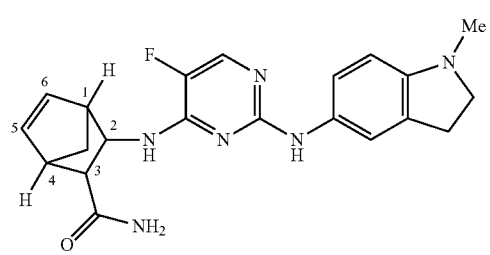 | Racemic-(2-exo,3-exo)-N4-[3-aminocarbonylbicyclo[2.2.1]hept-5-en-2-yl]-5-fluoro-N2-(1-methyl-2,3-dihydroindol-5-yl)-2,4-pyrimidinediamine |
| 175 | Mixture of IVa + IVb type 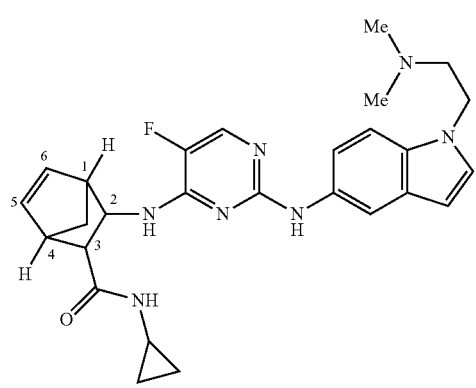 | Racemic-(2-exo,3-exo)-N4-[3-cyclopropylaminocarbonylbicyclo[2.2.1]hept-5-en-2-yl]-N2-[1-(2-dimethylaminoethyl)indol-5-yl]-5-fluoro-2,4-pyrimidinediamine |

TABLE 1-continued

| 176 | Mixture of IVa + IVb type 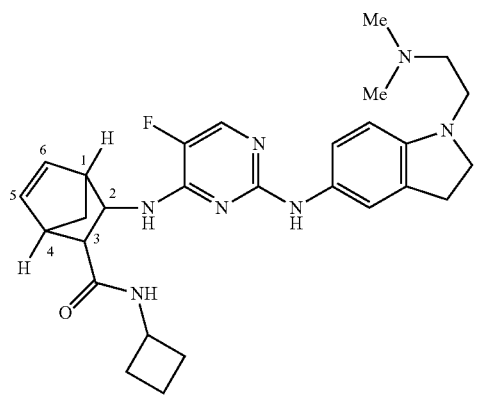 | Racemic-(2-exo,3-exo)-N4-[3-cyclobutylaminocarbonylbicyclo[2.2.1]hept-5-en-2-yl]-N2-[1-(2-dimethylaminoethyl)-2,3-dihydroindol-5-yl]-5-fluoro-2,4-pyrimidinediamine |
| --- | --- | --- |
| 177 | Mixture of IVa + IVb type 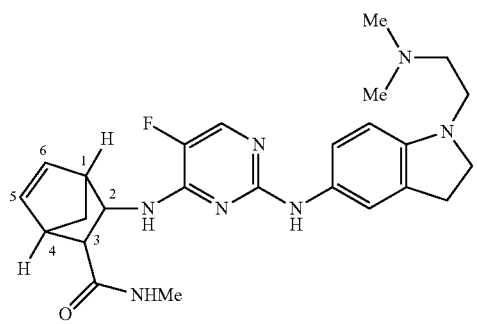 | Racemic-(2-exo,3-exo)-N2-[1-(2-dimethylaminoethyl)-2,3-dihydroindol-5-yl]-5-fluoro-N4-[3-N-methylaminocarbonylbicyclo[2.2.1]hept-5-en-2-yl]-2,4-pyrimidinediamine |
| 178 | Mixture of IVa + IVb type 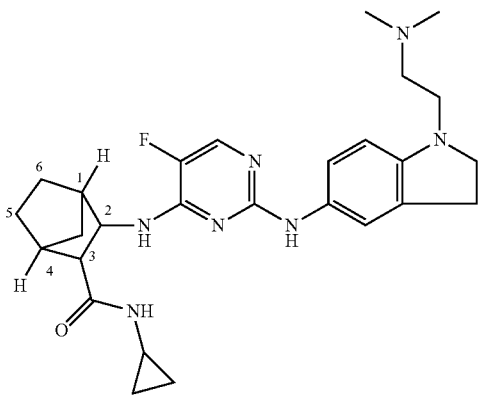 | Racemic-(2-exo,3-exo)-N4-[3-cyclopropylaminocarbonylbicyclo[2.2.1]hept-2-yl]-N2-[1-(2-dimethylaminoethyl)-2,3-dihydro-indol-5-yl]-5-fluoro-2,4-pyrimidinediamine |
| 179 | Mixture of IVa + IVb type 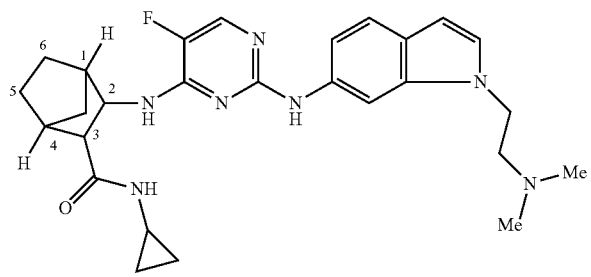 | Racemic-(2-exo,3-exo)-N4-[3-cyclopropylaminocarbonylbicyclo[2.2.1]hept-2-yl]-N2-[1-(2-dimethylaminoethyl)indol-6-yl]-5-fluoro-2,4-pyrimidinediamin |

| | | |
|---|---|---|
| 180 | Mixture of IVa + IVb type 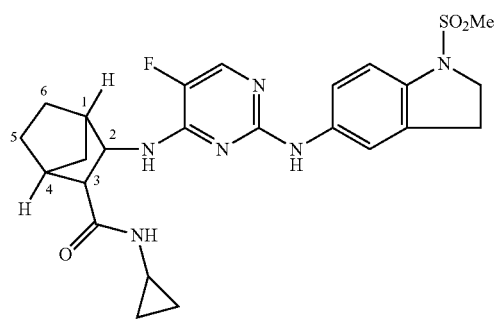 | Racemic-(2-exo,3-exo)-N4-[3-cyclopropylaminocarbonylbicyclo[2.2.1]hept-2-yl)-5-fluoro-N2-[1-methylsulfonyl-2,3-dihydro-indol-5-yl]-2,4-pyrimidinediamine |
| 181 | Mixture of IVa + IVb type 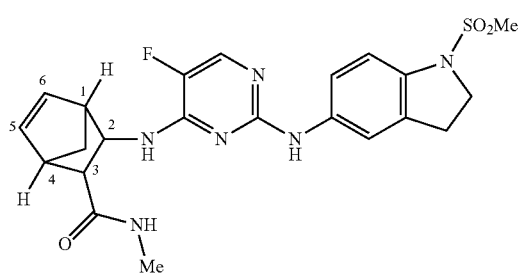 | Racemic-(2-exo,3-exo)-5-fluoro-N4-[3-methylaminocarbonyl bicyclo[2.2.1]hept-5-en-2-yl)-N2-[1-methylsulfonyl-2,3-dihydroindol-5-yl]-2,4-pyrimidinediamine |
| 182 | Mixture of IVa + IVb type 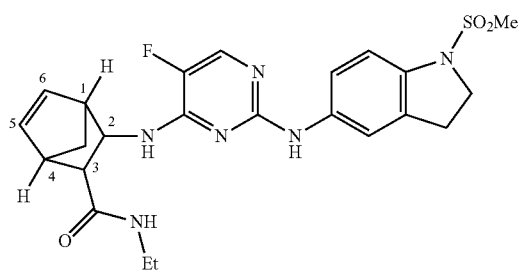 | Racemic-(2-exo,3-exo)-N4-[3-ethylaminocarbonylbicyclo[2.2.1]hept-5-en-2-yl)-5-fluoro-N2-[1-methylsulfonyl-2,3-dihydro-indol-5-yl]-2,4-pyrimidinediamine |
| 183 | Mixture of IVa + IVb type 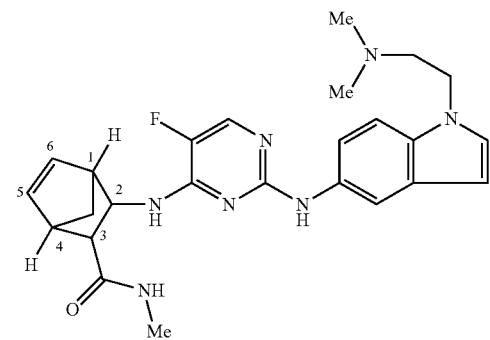 | Racemic-(2-exo,3-exo)-N2-[1-(2-dimethylaminoethyl)indol-5-yl]-5-fluoro-N4-[3-methylaminocarbonyl bicyclo[2.2.1]hept-5-en-2-yl)-2,4-pyrimidinediamin |

| 184 | Mixture of IVa + IVb type | 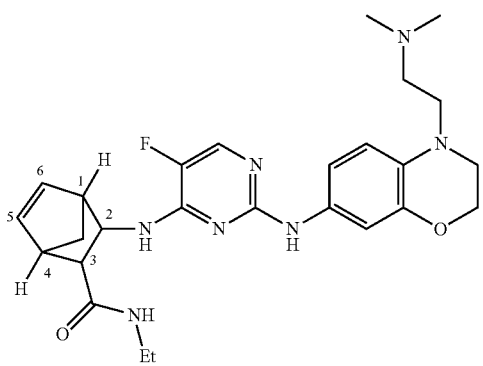 | Racemic-(2-exo,3-exo)-N4-[3-N-ethylminocarbonylbicyclo[2.2.1]hept-5-en-2-yl)-5-fluoro-N2-{1-[2-(dimethylamino)ethyl]-3,4-dihydro-4H-benz[1,4]oxazin-6-yl}-2,4-pyrimidinediamine |
|---|---|---|---|
| 185 | Mixture of IVa + IVb type | 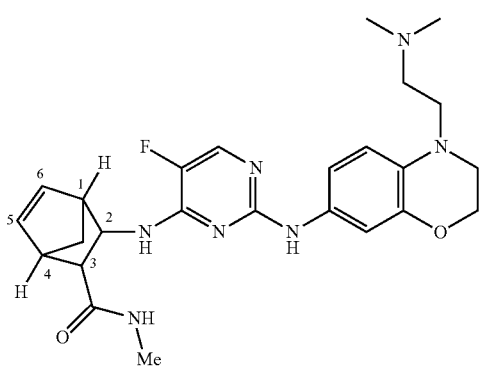 | Racemic-(2-exo,3-exo)-N4-(3-N-methylaminocarbonylbicyclo[2.2.1]hept-5-en-2-yl)-5-fluoro-N2-{1-[2-(dimethylamino)ethyl]-3,4-dihydro-4H-benz[1,4]oxazin-6-yl}-2,4-pyrimidinediamine |
| 186 | | 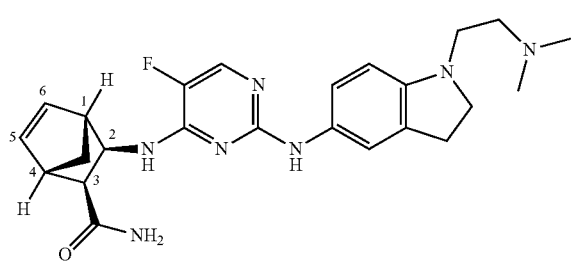 [SMILES: CN(C)CCN1CCc2cc(Nc3ncc(F)c(N[C@H]4[C@@H](C(N)=O)[C@@H]5C=C[C@H]4C5)n3)ccc21] | (1R,2R,3S,4S)-N4-[3-Aminocarbonylbicyclo[2.2.1]hept-5-en-2-yl]-N2-[1-(2-dimethylaminoethyl)-2,3-dihydroindol-5-yl]-5-fluoro-2,4-pyrimidinediamine |
| 187 | | 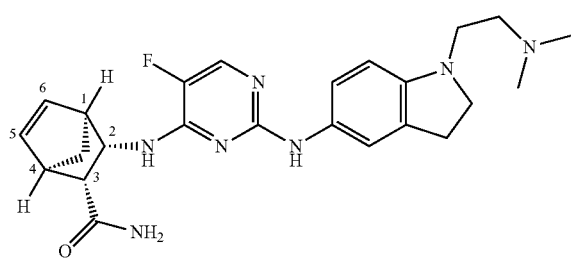 [SMILES: CN(C)CCN1CCc2cc(Nc3ncc(F)c(N[C@@H]4[C@H](C(N)=O)[C@H]5C=C[C@@H]4C5)n3)ccc21] | (1S,2S,3R,4R)-N4-[3-Aminocarbonyl bicyclo[2.2.1]hept-5-en-2-yl]-N2-[1-(2-dimethylaminoethyl)-2,3-dihydroindol-5-yl]-5-fluoro-2,4-pyrimidinediamine |
| 188 | | 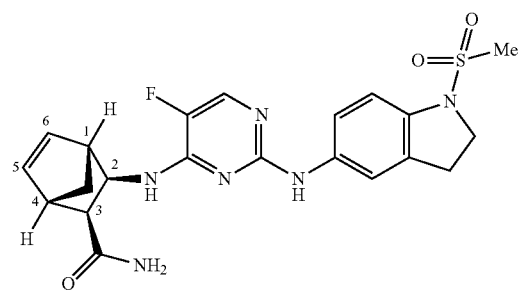 [SMILES: CS(=O)(=O)N1CCc2cc(Nc3ncc(F)c(N[C@H]4[C@@H](C(N)=O)[C@@H]5C=C[C@H]4C5)n3)ccc21] | (1R,2R,3S,4S)-N4-(3-Aminocarbonyl bicyclo[2.2.1]hept-5-en-2-yl)-5-fluoro-N2-[1-methylsulfonyl-2,3-dihydro-indol-5-yl]-2,4-pyrimidinediamine |

TABLE 1-continued

| | | |
|---|---|---|
| 189 | 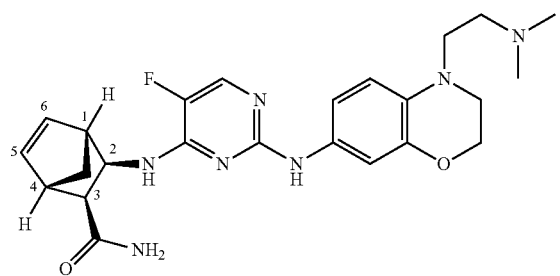 [SMILES: CN(C)CCN1CCOc2cc(Nc3ncc(F)c(N[C@H]4[C@@H](C(N)=O)[C@@H]5C=C[C@H]4C5)n3)ccc21] | (1R,2R,3S,4S)-N4-(3-Aminocarbonyl bicyclo[2.2.1]hept-5-en-2-yl)-5-fluoro-N2-{1-[2-(dimethylamino)ethyl]-3,4-dihydro-4H-benz[1,4]oxazin-6-yl}-2,4-pyrimidinediamine |
| 190 | 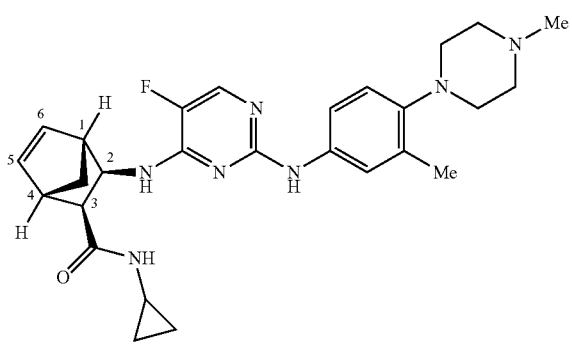 [SMILES: Cc1cc(Nc2ncc(F)c(N[C@H]3[C@@H](C(=O)NC4CC4)[C@@H]4C=C[C@H]3C4)n2)ccc1N1CCN(C)CC1] | (1R,2R,3S,4S)-N4-[3-(N-Cyclopropyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |
| 191 | 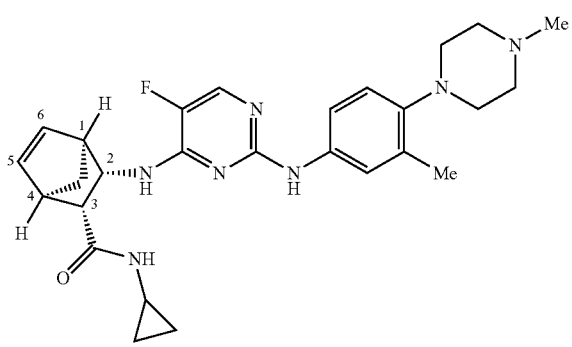 [SMILES: Cc1cc(Nc2ncc(F)c(N[C@@H]3[C@H](C(=O)NC4CC4)[C@H]4C=C[C@@H]3C4)n2)ccc1N1CCN(C)CC1] | (1S,2S,3R,4S)-N4-[3-(N-Cyclopropyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |
| 192 | 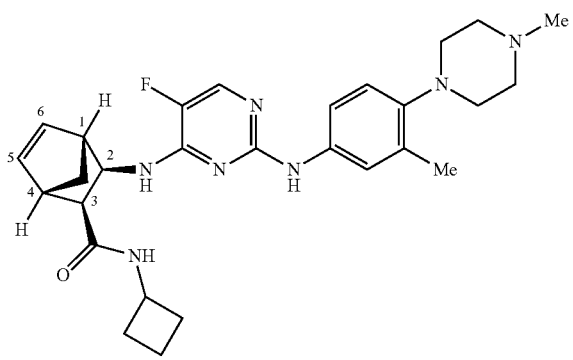 [SMILES: Cc1cc(Nc2ncc(F)c(N[C@H]3[C@@H](C(=O)NC4CCC4)[C@@H]4C=C[C@H]3C4)n2)ccc1N1CCN(C)CC1] | (1R,2R,3S,4S)-N4-[3-(N-Cyclobutyl)aminocarbonylbicyclo[2.2.1]hept-5-en-2-yl]-5-fluoro-N2-[3-methyl-4-(4-methylpiperazin-1-yl)phenyl]-2,4-pyrimidinediamine |

TABLE 1-continued

| 193 | 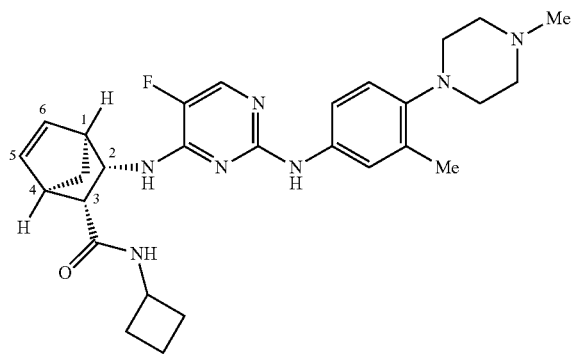 [SMILES: Cc1cc(Nc2ncc(F)c(N[C@@H]3[C@H](C(=O)NC4CCC4)[C@H]4C=C[C@@H]3C4)n2)ccc1N1CCN(C)CC1] | (1S,2S,3R,4R)-N4-[3-(N-Cyclobutyl) aminocarbonylbicyclo[2.2.1]hept-5-en-2-yl]-5-fluoro-N2-[3-methyl-4-(4-methylpiperazin-1-yl)phenyl]-2,4-pyrimidinediamine |
| --- | --- | --- |
| 194 | 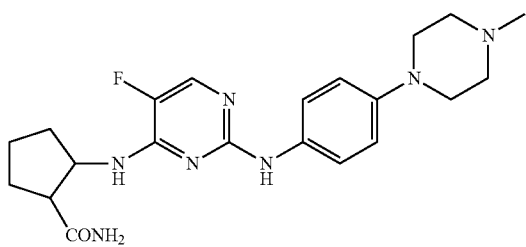 [SMILES: CN1CCN(c2ccc(Nc3ncc(F)c(NC4CCCC4C(N)=O)n3)cc2)CC1] | N4-(2-Carboxamidocyclopentyl)-5-fluoro-N2-[4-(4-methylpiperazino)phenyl]-2,4-pyrimidinediamine |
| 195 | 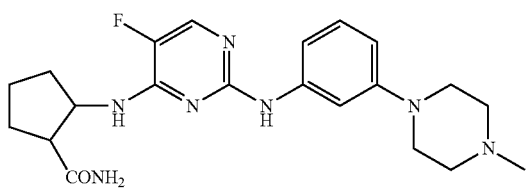 [SMILES: CN1CCN(c2cccc(Nc3ncc(F)c(NC4CCCC4C(N)=O)n3)c2)CC1] | N4-(2-Carboxamidocyclopentyl))-5-fluoro-N2-[3-(4-methylpiperazino)phenyl]-2,4-pyrimidinediamine |
| 196 | 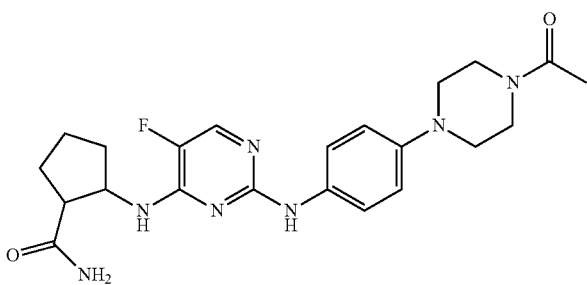 [SMILES: CC(=O)N1CCN(c2ccc(Nc3ncc(F)c(NC4CCCC4C(N)=O)n3)cc2)CC1] | N2-[4-(4-Acetylpiperazino)phenyl]-N4-(2-carboxamidocyclopentyl)-5-fluoro-2,4-pyrimidinediamine |
| 197 | 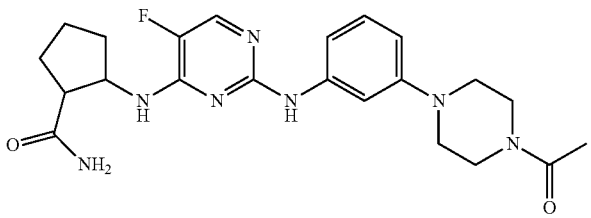 [SMILES: CC(=O)N1CCN(c2cccc(Nc3ncc(F)c(NC4CCCC4C(N)=O)n3)c2)CC1] | N2-[3-(4-Acetylpiperazino)phenyl]-N4-(2-carboxamidocyclopentyl)-5-fluoro-2,4-pyrimidinediamine |
| 198 | 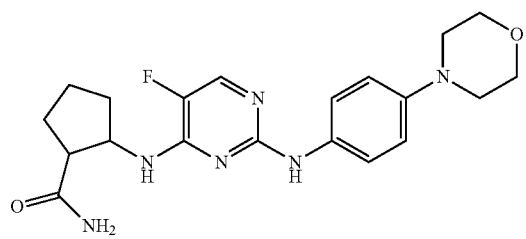 [SMILES: NC(=O)C1CCCC1Nc1nc(Nc2ccc(N3CCOCC3)cc2)ncc1F] | N4-(2-Carboxamidocyclopentyl)-5-fluoro-N2-(4-morpholinophenyl)-2,4-pyrimidinediamine |

TABLE 1-continued

| | | |
|---|---|---|
| 199 | 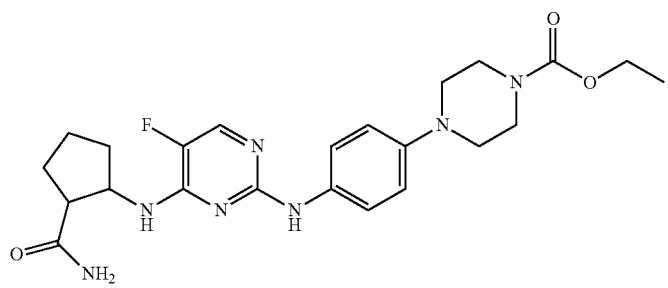 [SMILES: CCOC(=O)N1CCN(c2ccc(Nc3ncc(F)c(NC4CCCC4C(N)=O)n3)cc2)CC1] | N4-(2-Carboxamidocyclopentyl)-N2-[4-(4-ethoxycarbonylpiperazino)phenyl]-5-fluoro-2,4-pyrimidinediamine |
| 200 | 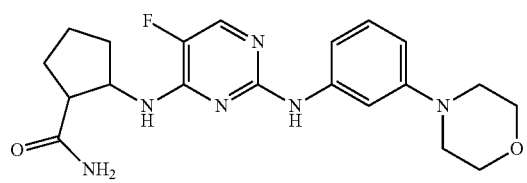 [SMILES: NC(=O)C1CCCC1Nc1nc(Nc2cccc(N3CCOCC3)c2)ncc1F] | N4-(2-Carboxamidocyclopentyl)-5-fluoro-N2-(3-morpholinophenyl)-2,4-pyrimidinediamine |
| 201 | 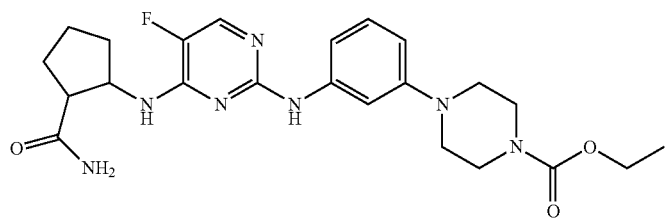 [SMILES: CCOC(=O)N1CCN(c2cccc(Nc3ncc(F)c(NC4CCCC4C(N)=O)n3)c2)CC1] | N4-(2-Carboxamidocyclopentyl)-N2-[3-(4-ethoxycarbonylpiperazino)phenyl]-5-fluoro-2,4-pyrimidinediamine |
| 202 | 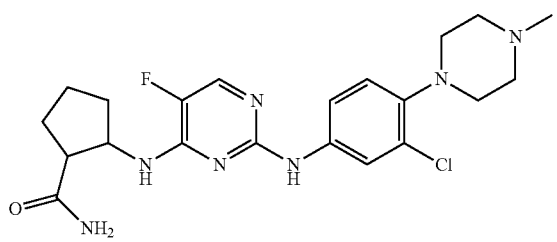 [SMILES: CN1CCN(c2ccc(Nc3ncc(F)c(NC4CCCC4C(N)=O)n3)cc2Cl)CC1] | N4-(2-Carboxamidocyclopentyl)-N2-[3-chloro-4-(4-methylpiperazino)phenyl]-5-fluoro-2,4-pyrimidinediamine |
| 203 | 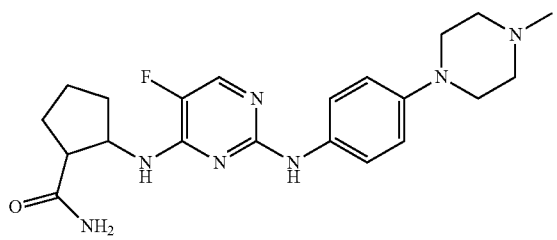 [SMILES: CN1CCN(c2ccc(Nc3ncc(F)c(NC4CCCC4C(N)=O)n3)cc2)CC1] | N4-(2-Carboxamidocyclopentyl)-5-fluoro-N2-[4-(4-methylpiperazino)phenyl]-2,4-pyrimidinediamine Monohydrochloride Salt |
| 15 | 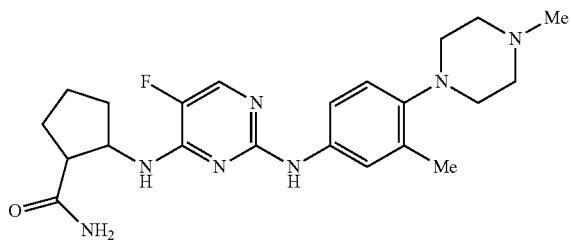 [SMILES: Cc1cc(Nc2ncc(F)c(NC3CCCC3C(N)=O)n2)ccc1N1CCN(C)CC1] | (cis)-N4-(2-Carboxamidocyclopent-1-yl)-5-fluoro-N2-[4-(4-methylpiperazino)-3-trifluoromethylphenyl]-2,4-pyrimidinediamine |

TABLE 1-continued

| | | |
|---|---|---|
| 204 | 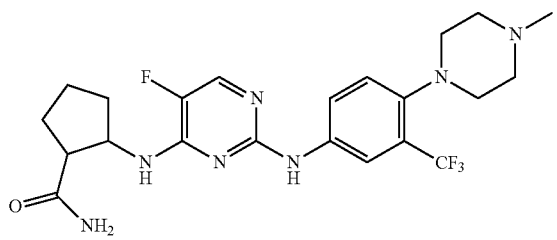 [SMILES: CN1CCN(c2ccc(Nc3ncc(F)c(NC4CCCC4C(N)=O)n3)cc2C(F)(F)F)CC1] | (cis)-N4-(2-Carboxamidocyclopent-1-yl)-5-fluoro-N2-[4-(4-methylpiperazino)-3-trifluoromethylphenyl]-2,4-pyrimidinediamine |
| 205 | 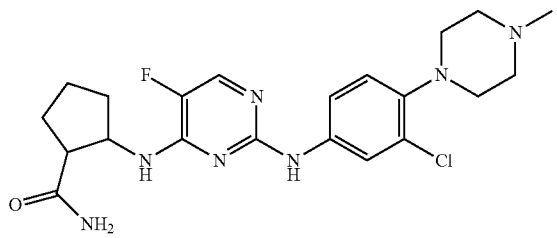 [SMILES: CN1CCN(c2ccc(Nc3ncc(F)c(NC4CCCC4C(N)=O)n3)cc2Cl)CC1] | (cis)-N4-(2-Carboxamidocyclopent-1-yl)-N2-[3-chloro-4-(4-methylpiperazino)phenyl]-5-fluoro-2,4-pyrimidinediamine |
| 206 | 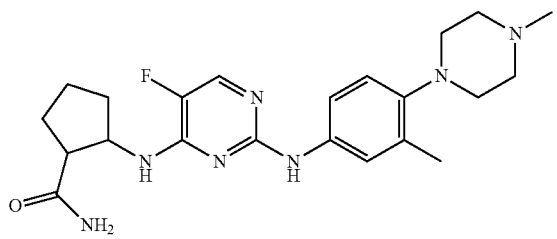 [SMILES: Cc1cc(Nc2ncc(F)c(NC3CCCC3C(N)=O)n2)ccc1N1CCN(C)CC1] | (cis)-N4-(2-Carboxamidocyclopenty-1-yl)-5-fluoro-N2-[3-methyl-4-(4-methylpiperazino)phenyl]-2,4-pyrimidinediamine |
| 207 | 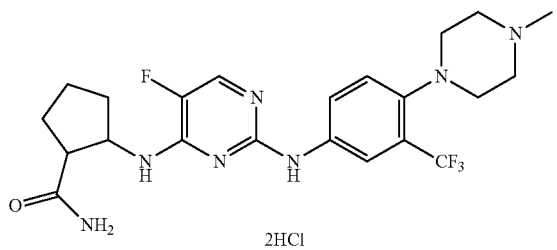 [SMILES: CN1CCN(c2ccc(Nc3ncc(F)c(NC4CCCC4C(N)=O)n3)cc2C(F)(F)F)CC1] | (cis)-N4-(2-Carboxamidocyclopent-1-yl)-5-fluoro-N2-[4-(4-methylpiperazino)-3-trifluoromethylphenyl]-2,4-pyrimidinediamine Bis Hydrogen Chloride Salt |
| 15a | 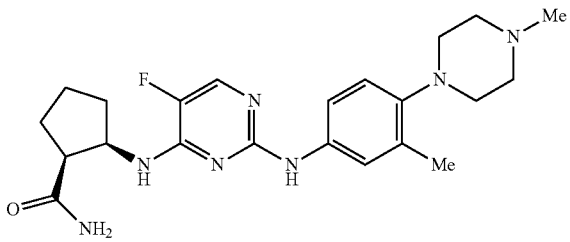 [SMILES: Cc1cc(Nc2ncc(F)c(N[C@@H]3CCC[C@@H]3C(N)=O)n2)ccc1N1CCN(C)CC1] | (1S,2R)-N4-(2-Aminocarbonylcyclopent-1-yl)-5-fluoro-N2-[4-(4-methylpiperazin-1-yl)-3-methylphenyl]-2,4-pyrimidinediamine |
| 208 | 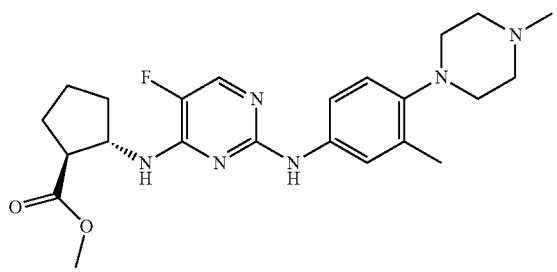 [SMILES: COC(=O)[C@H]1CCC[C@@H]1Nc1nc(Nc2ccc(N3CCN(C)CC3)c(C)c2)ncc1F] | (1S,2S)-5-fluoro-N4-(2-methoxycarbonylcyclopent-1-yl)-N2-[3-methyl-4-(4-methylpiperazino)phenyl]-2,4-pyrimidinediamine |

TABLE 1-continued

| | | |
|---|---|---|
| 209 | 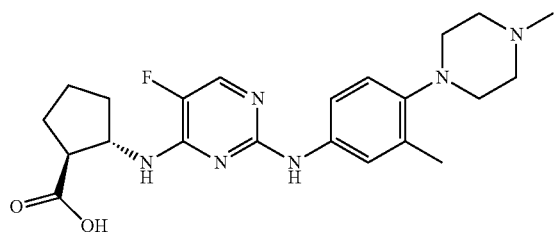 [SMILES: Cc1cc(Nc2ncc(F)c(N[C@H]3CCC[C@@H]3C(=O)O)n2)ccc1N1CCN(C)CC1] | (1S,2S)-5-fluoro-N4-(2-hydroxycarbonylcyclopent-1-yl)-N2-[3-methyl-4-(4-methylpiperazino)phenyl]-2,4-pyrimidinediamine |
| 15d | 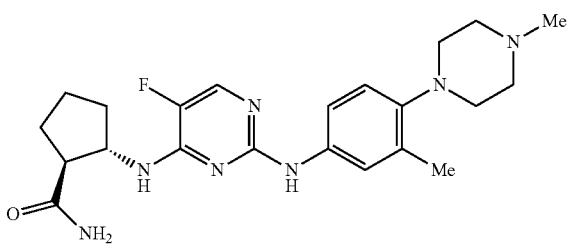 [SMILES: Cc1cc(Nc2ncc(F)c(N[C@H]3CCC[C@@H]3C(N)=O)n2)ccc1N1CCN(C)CC1] | (1S,2S)-N4-(2-Aminocarbonylcyclopent-1-yl)-5-fluoro-N2-[4-(4-methylpiperazin-1-yl)-3-methylphenyl]-2,4-pyrimidinediamine |
| 15b | 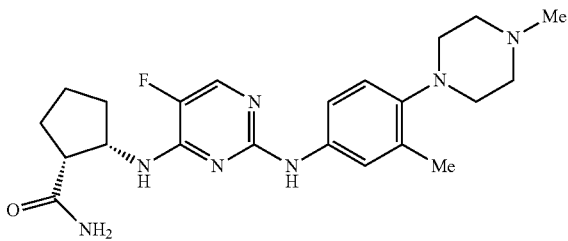 [SMILES: Cc1cc(Nc2ncc(F)c(N[C@H]3CCC[C@H]3C(N)=O)n2)ccc1N1CCN(C)CC1] | (1R,2S)-N4-(2-Aminocarbonylcyclopent-1-yl)-5-fluoro-N2-[4-(4-methylpiperazin-1-yl)-3-methylphenyl]-2,4-pyrimidinediamine |
| 210 | 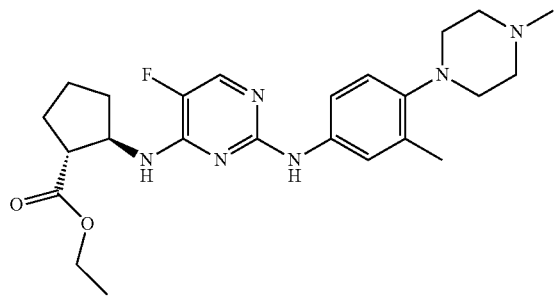 [SMILES: CCOC(=O)[C@@H]1CCC[C@H]1Nc1nc(Nc2ccc(N3CCN(C)CC3)c(C)c2)ncc1F] | (1R,2R)-N4-(2-Ethoxycarbonylcyclopent-1-yl)-5-fluoro-N2-[3-methyl-4-(4-methylpiperazino)phenyl]-2,4-pyrimidinediamine |
| 211 | 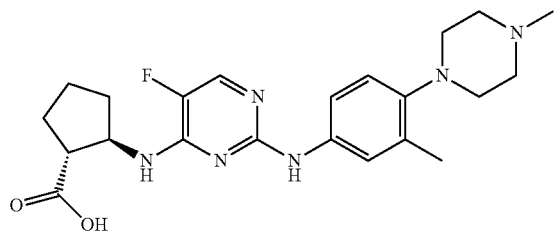 [SMILES: Cc1cc(Nc2ncc(F)c(N[C@@H]3CCC[C@H]3C(=O)O)n2)ccc1N1CCN(C)CC1] | (1R,2R)-5-fluoro-N4-(2-hydroxycarbonylcyclopent-1-yl)-N2-[3-methyl-4-(4-methylpiperazino)phenyl]-2,4-pyrimidinediamine |
| 15c | 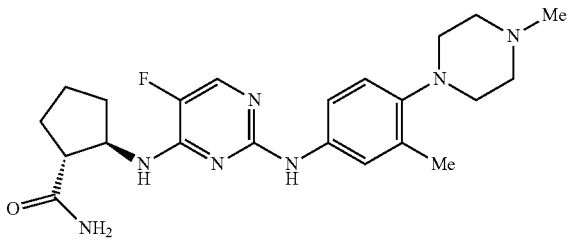 [SMILES: Cc1cc(Nc2ncc(F)c(N[C@@H]3CCC[C@H]3C(N)=O)n2)ccc1N1CCN(C)CC1] | (1R,2R)-N4-(2-Aminocarbonylcyclopent-1-yl)-5-fluoro-N2-[4-(4-methylpiperazin-1-yl)-3-methylphenyl]-2,4-pyrimidinediamine |

TABLE 1-continued

| | | |
|---|---|---|
| 212 | 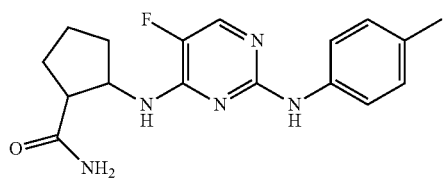 [SMILES: Cc1ccc(Nc2ncc(F)c(NC3CCCC3C(N)=O)n2)cc1] | (cis)-N4-(2-Carboxamidocyclopent-1-yl)-5-fluoro-N2-(4-methylphenyl)-2,4-pyrimidinediamine |
| 213 | 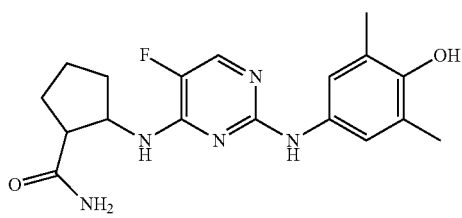 [SMILES: Cc1cc(Nc2ncc(F)c(NC3CCCC3C(N)=O)n2)cc(C)c1O] | (cis)-N4-(2-Carboxamidocyclopent-1-yl)-N2-(3,5-dimethyl-4-hydroxyphenyl)-5-fluoro-2,4-pyrimidinediamine |
| 214 | 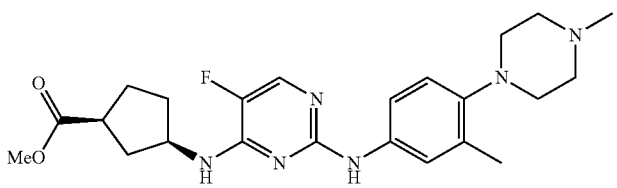 [SMILES: COC(=O)[C@H]1CC[C@@H](Nc2nc(Nc3ccc(N4CCN(C)CC4)c(C)c3)ncc2F)C1] | (1R,3S)-N4-(3-Methoxycarbonylcyclopent-1-yl)-5-fluoro-N2-[3-methyl-4-(4-methylpiperazin-1-yl)phenyl]-2,4-pyrimidinediamine |
| 215 | 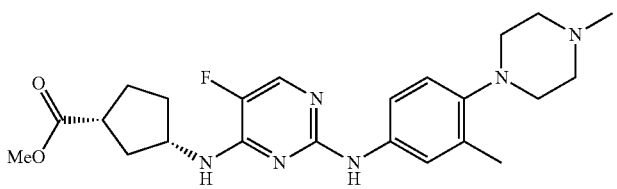 [SMILES: COC(=O)[C@@H]1CC[C@H](Nc2nc(Nc3ccc(N4CCN(C)CC4)c(C)c3)ncc2F)C1] | (1S,3R)-N4-(3-Methoxycarbonyl-cyclopent-1-yl)-5-fluoro-N2-[3-methyl-4-(4-methylpiperazin-1-yl)phenyl]-2,4-pyrimidinediamine |
| 216 | 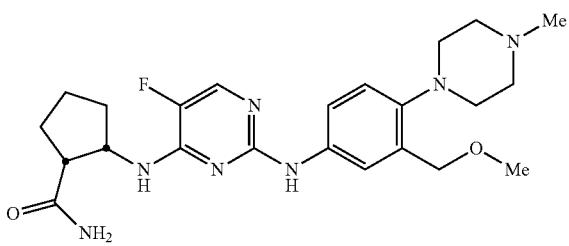 [SMILES: COCc1cc(Nc2ncc(F)c(N[C@H]3CCC[C@H]3C(N)=O)n2)ccc1N1CCN(C)CC1] | Racemic-cis-N4-(2-aminocarbonylcyclopent-1-yl)-5-fluoro-N2-[4-(4-methylpiperazin-1-yl)-3-methoxymethylenephenyl]-2,4-pyrimidinediamine |
| 217 | 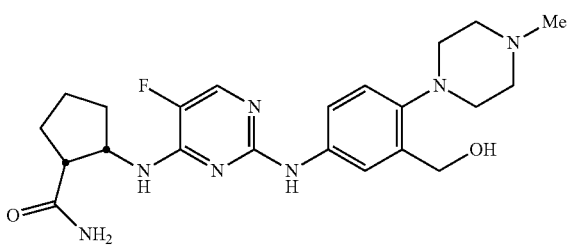 [SMILES: CN1CCN(c2ccc(Nc3ncc(F)c(N[C@H]4CCC[C@H]4C(N)=O)n3)cc2CO)CC1] | Racemic-cis-N4-(2-aminocarbonylcyclopent-1-yl)-5-fluoro-N2-[3-hydroxymethylene-4-(4-methylpiperazin-1-yl)phenyl]-2,4-pyrimidinediamine |
| 218 | 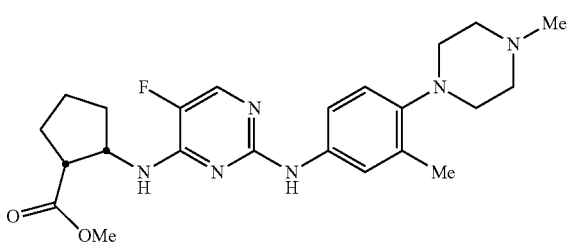 [SMILES: COC(=O)[C@@H]1CCC[C@@H]1Nc1nc(Nc2ccc(N3CCN(C)CC3)c(C)c2)ncc1F] | Racemic-cis-5-fluoro-N2-[3-methyl-4-(4-methylpiperazin-1-yl)phenyl]-N4-(2-methoxycarbonylcyclopent-1-yl)-2,4-pyrimidinediamine |

TABLE 1-continued

| | | |
|---|---|---|
| 219 | 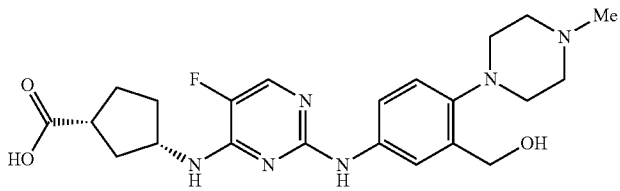 [SMILES: CN1CCN(c2ccc(Nc3ncc(F)c(N[C@H]4CC[C@@H](C(=O)O)C4)n3)cc2CO)CC1] | (1S,3R)-N4-(3-Carboxycyclopent-1-yl)-5-fluoro-N2-[3-methyl-4-(4-methylpiperazin-1-yl)phenyl]-2,4-pyrimidinediamine |
| 220 | 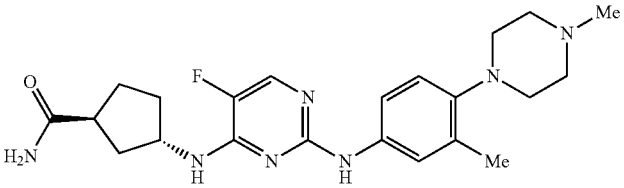 [SMILES: Cc1cc(Nc2ncc(F)c(N[C@H]3CC[C@H](C(N)=O)C3)n2)ccc1N1CCN(C)CC1] | (1S,3S)-N4-(3-Aminocarbonylcyclopent-1-yl)-5-fluoro-N2-[3-methyl-4-(4-methylpiperazin-1-yl)phenyl]-2,4-pyrimidinediamine |
| 221 | Mixture of IVa + IVb type<br>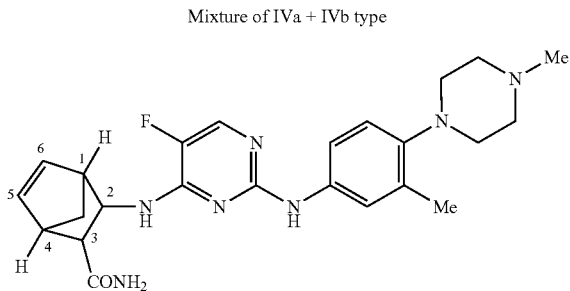 [SMILES: Cc1cc(Nc2ncc(F)c(NC3C4C=CC(C4)C3C(N)=O)n2)ccc1N1CCN(C)CC1] | Racemic-(2-exo, 3-exo)-N4-(3-aminocarbonylbicyclo[2.2.1]hept-5-en-2-yl)-5-fluoro-N2-[3-methyl-4-(4-methylpiperazin-1-yl)phenyl]-2,4-pyrimidinediamine |
| 222 | 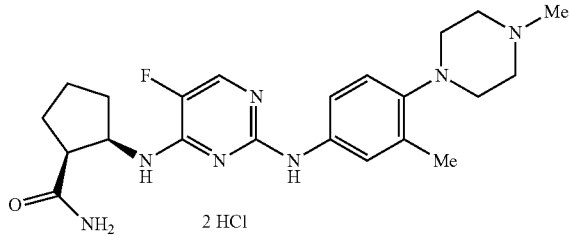 [SMILES: Cc1cc(Nc2ncc(F)c(N[C@@H]3CCC[C@@H]3C(N)=O)n2)ccc1N1CCN(C)CC1]2 HCl | (1R,2S)-N4-(2-Aminocarbonylcyclopent-1-yl)-5-fluoro-N2-[3-methyl-4-(4-methylpiperazin-1-yl)phenyl]-2,4-pyrimidinediamine Bis Hydrogen Chloride Salt |
| 223 | 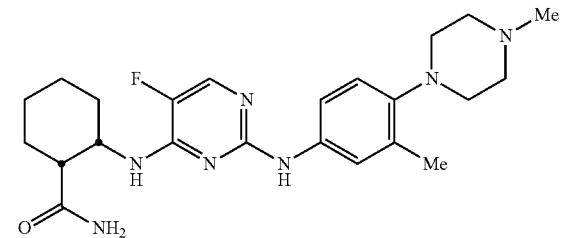 | Racemic-cis-N4-(2-aminocarbonylcyclohex-1-yl)-5-fluoro-N2-[3-methyl-4-(4-methylpiperazin-1-yl)phenyl]-2,4-pyrimidinediamine |
| 224 | 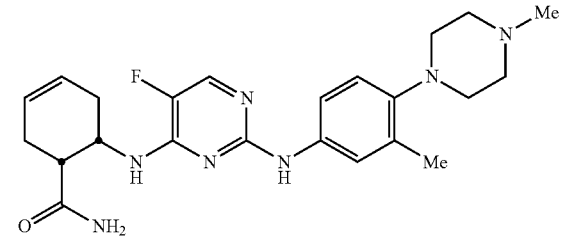 | Racemic-(cis)-N4-(2-aminocarbonyl cyclohex-4-en-1-yl)-5-fluoro-N2-[3-methyl-4-(4-methylpiperazin-1-yl)phenyl]-2,4-pyrimidinediamine |
| 225 | 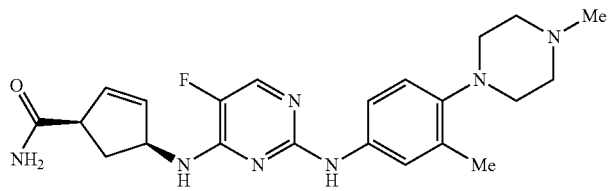 [SMILES: Cc1cc(Nc2ncc(F)c(N[C@@H]3C=C[C@H](C(N)=O)C3)n2)ccc1N1CCN(C)CC1] | (1S,4R)-cis-N4-(4-Aminocarbonyl cyclopent-2-ene-1-yl)-5-fluoro-N2-[3-methyl-4-(4-methylpiperazin-1-yl)phenyl]-2,4-pyrimidinediamine |

| | | |
|---|---|---|
| 226 | 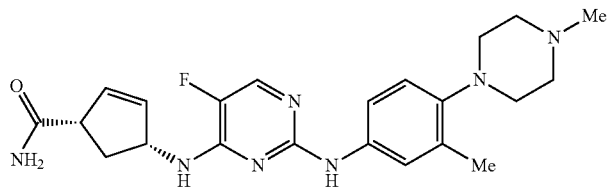 [SMILES: Cc1cc(Nc2ncc(F)c(N[C@H]3C=C[C@@H](C(N)=O)C3)n2)ccc1N1CCN(C)CC1] | (1R,4S)-cis-N4-(4-Aminocarbonyl cyclopent-2-ene-1-yl)-5-fluoro-N2-[3-methyl-4-(4-methylpiperazin-1-yl)phenyl]-2,4-pyrimidinediamine |
| 227 | 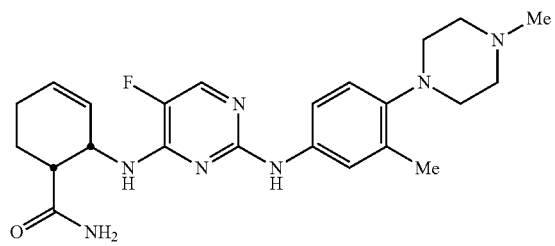 | Racemic-cis-N4-(2-aminocarbonyl cyclohex-5-ene-1-yl)-5-fluoro-N2-[3-methyl-4-(4-methylpiperazin-1-yl)phenyl]-2,4-pyrimidinediamine |
| 228 | Mixture of IVa + IVb Type<br>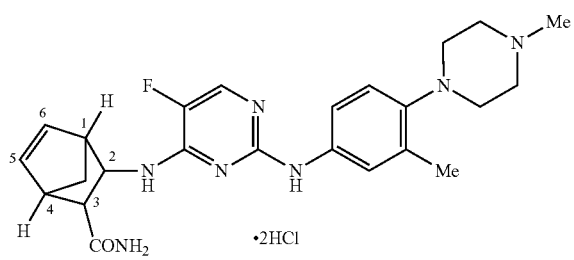•2HCl | Racemic-(2-exo,3-exo)-N4-(3-aminocarbonylbicyclo[2.2.1]hept-5-en-2-yl)-5-fluoro-N2-[3-methyl-4-(4-methylpiperazin-1-yl)phenyl]-2,4-pyrimidinediamine Bis-Hydrochloride Salt |
| 229 | 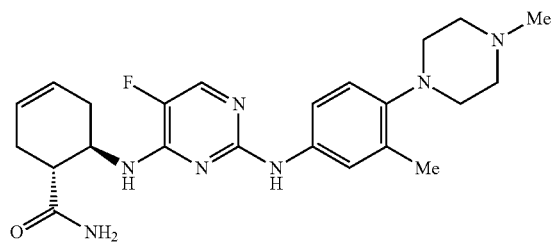 [SMILES: Cc1cc(Nc2ncc(F)c(N[C@@H]3CC=CC[C@H]3C(N)=O)n2)ccc1N1CCN(C)CC1] | Racemic-N4-(2-aminocarbonylcyclohex-4-ene-1-yl)-5-fluoro-N2-[3-methyl-4-(4-methylpiperazin-1-yl)phenyl]-2,4-pyrimidinediamine |
| 60r2 | Mixture of IVc + IVd Type<br>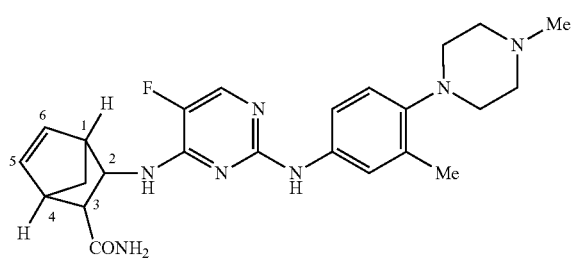 | Racemic-(2-endo,3-endo)-N4-(3-aminocarbonylbicyclo[2.2.1]hept-5-en-2-yl)-5-fluoro-N2-[3-methyl-4-(4-methylpiperazin-1-yl)phenyl]-2,4-pyrimidinediamine |
| 60a | 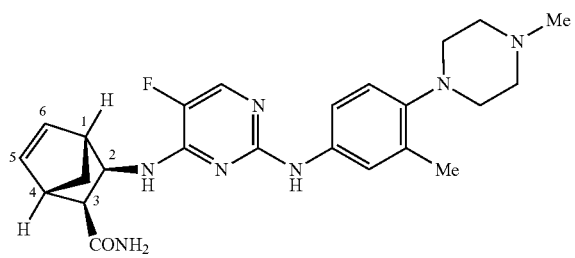 [SMILES: Cc1cc(Nc2ncc(F)c(N[C@H]3[C@@H](C(N)=O)[C@@H]4C=C[C@H]3C4)n2)ccc1N1CCN(C)CC1] | (1R,2R,3S,4S)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine |

TABLE 1-continued

| | | | |
|---|---|---|---|
| 60b | 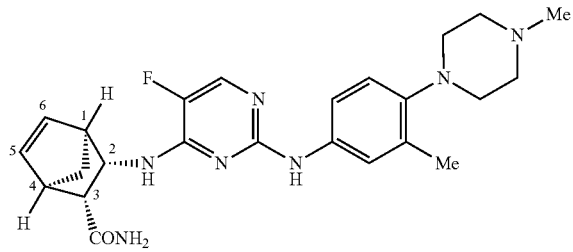 [SMILES: Cc1cc(Nc2ncc(F)c(N[C@@H]3[C@H](C(N)=O)[C@H]4C=C[C@@H]3C4)n2)ccc1N1CCN(C)CC1] | | (1S,2S,3R,4R)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine |
| 230 | Mixture of IVa + IVb type | 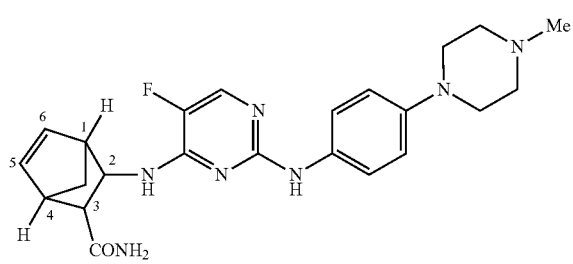 | Racemic-(2-exo,3-exo)-N4-(3-aminocarbonylbicyclo[2.2.1]hept-5-en-2-yl)-5-fluoro-N2-[4-(4-methylpiperazin-1-yl)phenyl]-2,4-pyrimidinediamine |
| 231 | Mixture of IVa + IVb type | 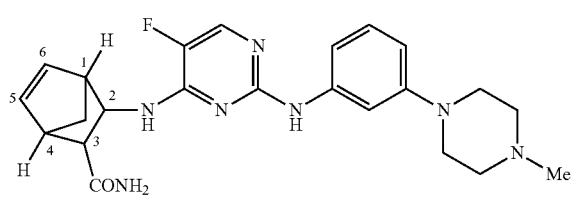 | Racemic-(2-exo,3-exo)-N4-(3-aminocarbonylbicyclo[2.2.1]hept-5-en-2-yl)-5-fluoro-N2-[3-(4-methylpiperazin-1-yl)phenyl]-2,4-pyrimidinediamine |
| 232 | Mixture of IVa + IVb type | 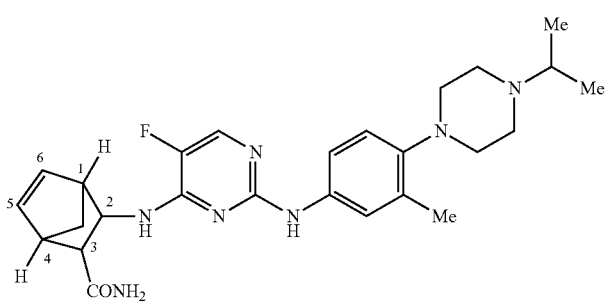 | Racemic-(2-exo,3-exo)-N4-(3-aminocarbonylbicyclo[2.2.1]hept-5-en-2-yl)-5-fluoro-N2-[4-(4-isopropylpiperazin-1-yl)-3-methylphenyl]-2,4-pyrimidinediamine |
| 233 | Mixture of type IVa + IVb | 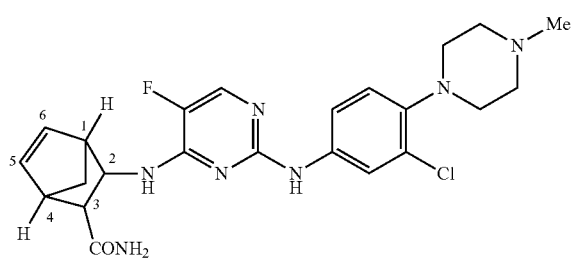 | Racemic-(2-exo,3-exo)-N4-(3-aminocarbonylbicyclo[2.2.1]hept-5-en-2-yl)-N2-[3-chloro-4-(4-methylpiperazin-1-yl)phenyl]-5-fluoro-2,4-pyrimidinediamine |

TABLE 1-continued

| | | |
|---|---|---|
| 234 | 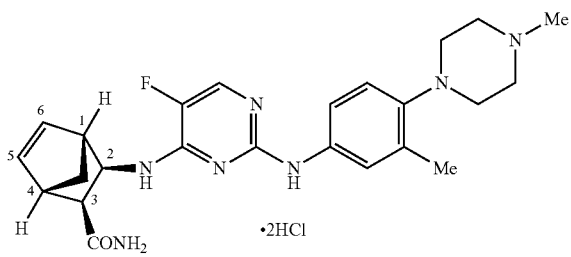 [SMILES: Cc1cc(Nc2ncc(F)c(N[C@H]3[C@@H](C(N)=O)[C@@H]4C=C[C@H]3C4)n2)ccc1N1CCN(C)CC1] | (1R,2R,3S,4R)-N4-(3-Aminocarbonyl bicyclo[2.2.1]hept-5-en-2-yl)-5-fluoro-N2-[3-methyl-4-(4-methylpiperazin-1-yl)phenyl]-2,4-pyrimidinediamine Bis-Hydrochloride Salt |
| 235 | Mixture of IVa + IVb type 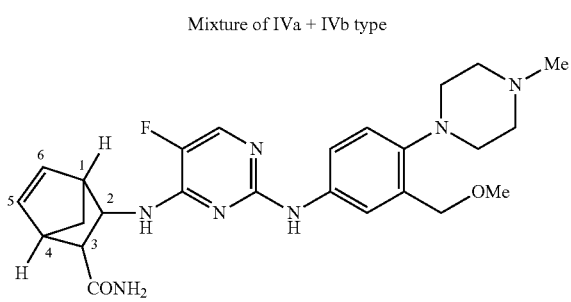 [SMILES: COCc1cc(Nc2ncc(F)c(NC3C4C=CC(C4)C3C(N)=O)n2)ccc1N1CCN(C)CC1] | Racemic-(2-exo,3-exo)-N4-(3-aminocarbonylbicyclo[2.2.1]hept-5-en-2-yl)-5-fluoro-N2-[3-methoxymethyl-4-(4-methylpiperazin-1-yl)phenyl]2,4-pyrimidinediamine |
| 236 | Mixture of IVa + IVb type 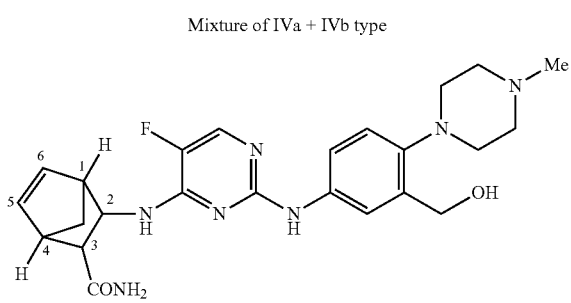 [SMILES: CN1CCN(c2ccc(Nc3ncc(F)c(NC4C5C=CC(C5)C4C(N)=O)n3)cc2CO)CC1] | Racemic-(2-exo,3-exo)-N4-(3-aminocarbonylbicyclo[2.2.1]hept-5-en-2-yl)-5-fluoro-N2-[3-hydroxymethyl-4-(4-methylpiperazin-1-yl)phenyl]-2,4-pyrimidinediamine |
| 237 | 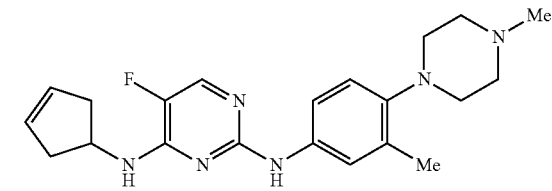 [SMILES: Cc1cc(Nc2ncc(F)c(NC3CC=CC3)n2)ccc1N1CCN(C)CC1] | N4-(Cyclopent-3-ene-1-yl)-5-fluoro-N2-[3-methyl-4-(4-methylpiperazin-1-yl)phenyl]-2,4-pyrimidinediamine |
| 238 | 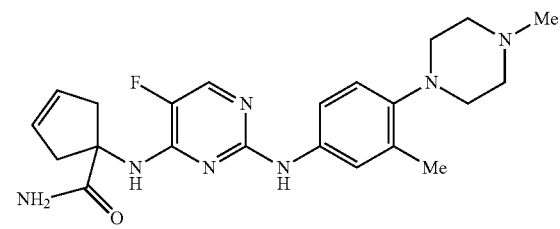 [SMILES: Cc1cc(Nc2ncc(F)c(NC3(C(N)=O)CC=CC3)n2)ccc1N1CCN(C)CC1] | N4-(1-Aminocarbonylcyclopent-3-ene-1-yl)-5-fluoro-N2-[3-methyl-4-(4-methylpiperazin-1-yl)phenyl]-2,4-pyrimidinediamine |
| 239 | Mixture of IVa + IVb type 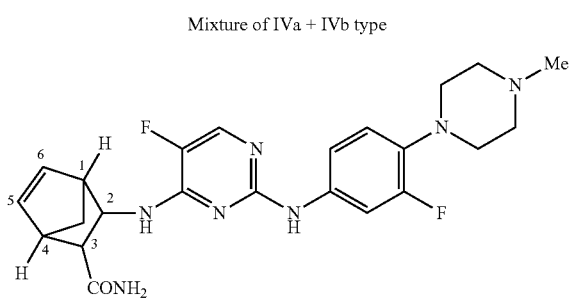 [SMILES: CN1CCN(c2ccc(Nc3ncc(F)c(NC4C5C=CC(C5)C4C(N)=O)n3)cc2F)CC1] | Racemic-(2-exo,3-exo)-N4-(3-aminocarbonylbicyclo[2.2.1]hept-5-en-2-yl)-5-fluoro-N2-[3-fluoro-4-(4-methylpiperazin-1-yl)phenyl]-2,4-pyrimidinediamine |

TABLE 1-continued

| 240 | Mixture of IVa + IVb type 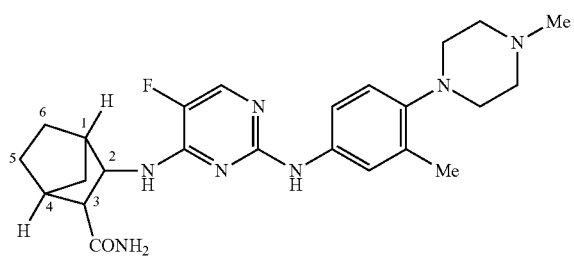 | Racemic-(2-exo,3-exo)-N4-(3-aminocarbonylbicyclo[2.2.1]hept-2-yl)-5-fluoro-N2-[3-methyl-4-(4-methylpiperazin-1-yl)phenyl]-2,4-pyrimidinediamine |
| 241 | Mixture of IVa + IVb type 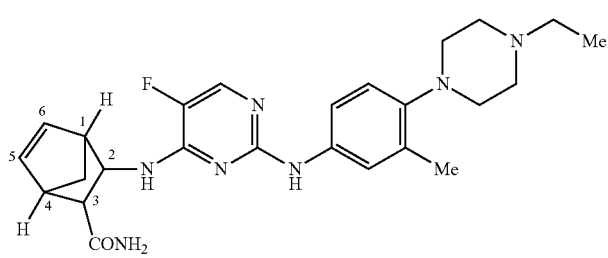 | Racemic-(2-exo,3-exo)-N4-(3-aminocarbonylbicylo[2.2.1]hept-5-en-2-yl)-N2-[4-(4-ethylpiperazin-1-yl)-3-methylphenyl]-5-fluoro-2,4-pyrimidinediamine |
| 242 | 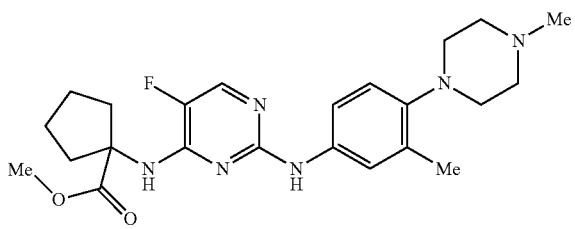 [SMILES: COC(=O)C1(Nc2nc(Nc3ccc(N4CCN(C)CC4)c(C)c3)ncc2F)CCCC1] | 5-Fluoro-N4-(1-methoxycarbonyl cyclopent-1-yl)-N2-[3-methyl-4-(4-methylpiperazin-1-yl)phenyl]-2,4-pyrimidinediamine |
| 243 | Mixture of IVa + IVb type 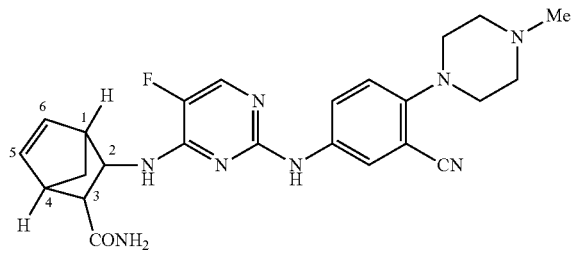 | Racemic-(2-exo,3-exo)-N4-(3-aminocarbonylbicyclo[2.2.1]hept-5-en-2-yl)-N2-[3-cyano-4-(4-methylpiperazin-1-yl)phenyl]-5-fluoro-2,4-pyrimidinediamine |
| 244 | 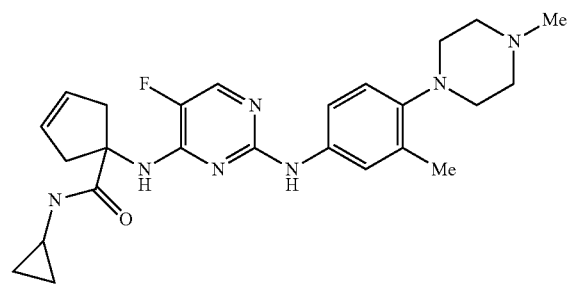 [SMILES: Cc1cc(Nc2ncc(F)c(NC3(C(=O)NC4CC4)CC=CC3)n2)ccc1N1CCN(C)CC1] | N4-(1-Cyclopropylaminocarbonylcyclopent-3-en-1-yl)-5-fluoro-N2-[3-methyl-4-(4-methylpiperazin-1-yl)phenyl]-2,4-pyrimidinediamine |

| | | |
|---|---|---|
| 245 | Mixture of IVa + IVb type 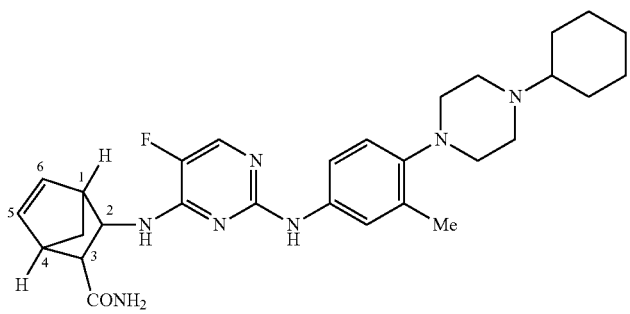 | Racemic-(2-exo,3-exo)-N4-(3-aminocarbonylbicyclo[2.2.1]hept-5-en-2-yl)-N2-[4-(4-cyclohexylpiperazin-1-yl)-3-methylphenyl]-5-fluoro-2,4-pyrimidinediamine |
| 246 | 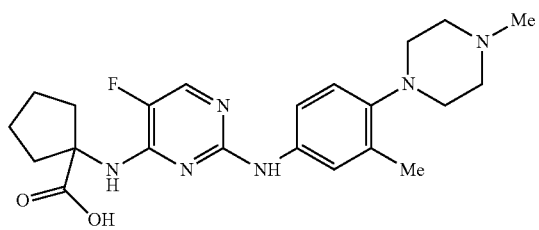 [SMILES: Cc1cc(Nc2ncc(F)c(NC3(C(=O)O)CCCC3)n2)ccc1N1CCN(C)CC1] | N4-(1-Carboxycyclopent-1-yl)-5-fluoro-N2-[3-methyl-4-(4-methylpiperazin-1-yl)phenyl]-2,4-pyrimidinediamine |
| 247 | 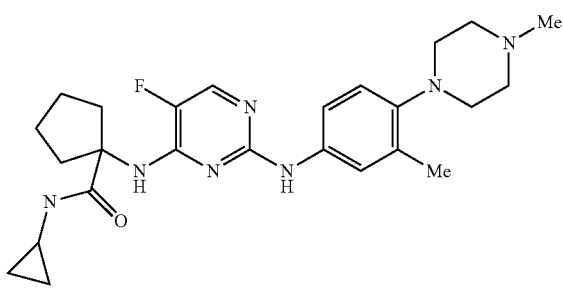 [SMILES: Cc1cc(Nc2ncc(F)c(NC3(C(=O)NC4CC4)CCCC3)n2)ccc1N1CCN(C)CC1] | N4-(1-Cyclopropylaminocarbonyl cyclopent-1-yl)-5-fluoro-N2-[3-methyl-4-(4-methylpiperazin-1-yl)phenyl]-2,4-pyrimidinediamine |
| 248 | 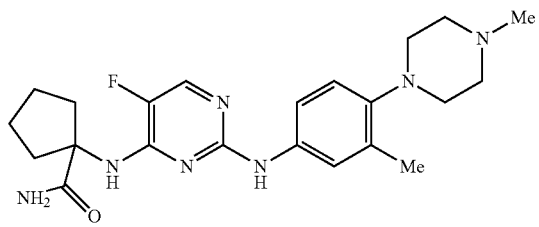 [SMILES: Cc1cc(Nc2ncc(F)c(NC3(C(N)=O)CCCC3)n2)ccc1N1CCN(C)CC1] | N4-(1-Aminocarbonylcyclopent-1-yl)-5-fluoro-N2-[3-methyl-4-(4-methylpiperazin-1-yl)phenyl]-2,4-pyrimidinediamine |
| 249 | 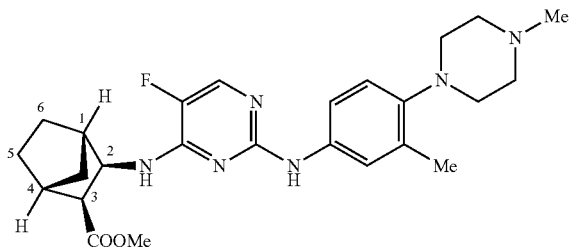 [SMILES: COC(=O)[C@H]1[C@@H]2CC[C@@H](C2)[C@H]1Nc1nc(Nc2ccc(N3CCN(C)CC3)c(C)c2)ncc1F] | (1S,2R,3S,4R)-5-Fluoro-N4-(3-methoxycarbonylbicyclo[2.2.1]hept-2-yl)-N2-[3-methyl-4-(4-methylpiperazin-1-yl)phenyl]-2,4-pyrimidinediamine |
| 250 | Mixture of IVa + IVb type 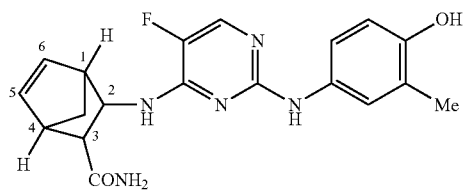 | Racemic-(2-exo,3-exo)-N4-(3-aminocarbonylbicyclo[2.2.1]hept-5-en-2-yl)-5-fluoro-N2-[(4-hydroxy-3-methyl)phenyl]-2,4-pyrimidinediamine |

TABLE 1-continued

| 251 | Mixture of IVa + IVb type 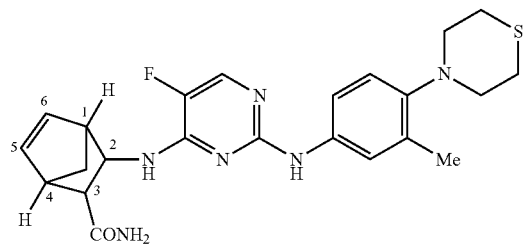 | Racemic-(2-exo,3-exo)-N4-(3-aminocarbonylbicyclo[2.2.1]hept-5-en-2-yl)-5-en-2-yl)-5-fluoro-N2-[(3-methyl-1-thiomorpholin-4-yl)phenyl]-2,4-pyrimidinediamine |
| --- | --- | --- |
| 252 | Mixture of IVa + IVb type 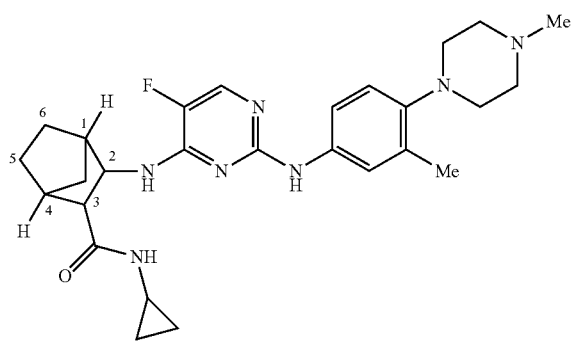 | Racemic-(2-exo,3-exo)-N4-(3-N-cyclopropylaminocarbonyl-bicyclo[2.2.1]hept-2-yl)-5-fluoro-N2-[3-methyl-4-(4-methylpiperazin-1-yl)phenyl]-2,4-pyrimidinediamine |
| 253 | 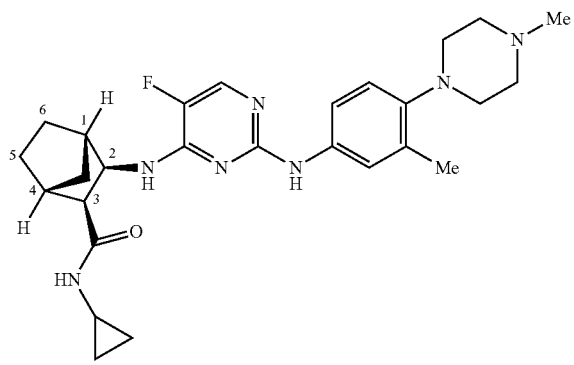 [SMILES: Cc1cc(Nc2ncc(F)c(N[C@@H]3[C@H]4CC[C@H](C4)[C@@H]3C(=O)NC3CC3)n2)ccc1N1CCN(C)CC1] | (1S,2R,3S,4R)-N4-(3-N-Cyclopropyl aminocarbonylbicyclo[2.2.1]hept-2-yl)-5-fluoro-N2-[3-methyl-4-(4-methylpiperazin-1-yl)phenyl]-2,4-pyrimidinediamine |
| 254 | Mixture of IVa + IVb type 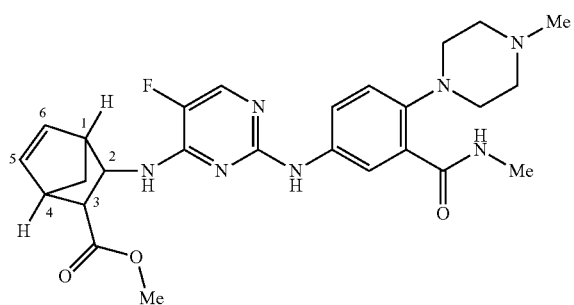 | Racemic-(2-exo,3-exo)-5-fluoro-N4-(3-methoxycarbonylbicyclo[2.2.1]hept-5-en-2-yl)-N2-[3-methylaminocarbonyl-4-(4-methylpiperazin-1-yl)phenyl]-2,4-pyrimidinediamine |

TABLE 1-continued

| | | | |
|---|---|---|---|
| 255 | Mixture of IVa + IVb type | 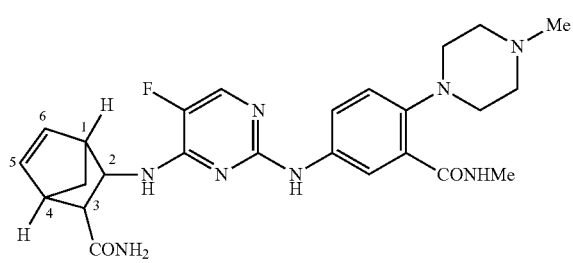 | Racemic-(2-exo,3-exo)-N4-(3-aminocarbonylbicyclo[2.2.1]hept-5-en-2-yl)-5-fluoro-N2-[3-methylaminocarbonyl-4-(4-methylpiperazin-1-yl)phenyl]-2,4-pyrimidinediamine |
| 256 | Mixture of IVa + IVb type | 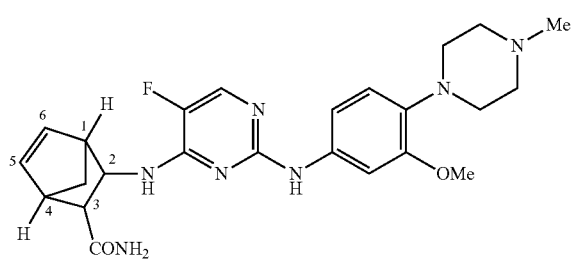 | Racemic-(2-exo,3-exo)-N4-(3-aminocarbonylbicyclo[2.2.1]hept-5-en-2-yl)-5-fluoro-N2-[3-methoxy-4-(4-methylpiperazin-1-yl)phenyl]-2,4-pyrimidinediamine |
| 257 | | 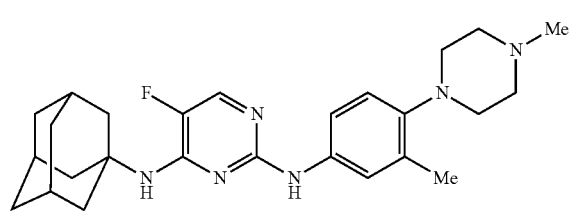 [SMILES: Cc1cc(Nc2ncc(F)c(NC34CC5CC(CC(C5)C3)C4)n2)ccc1N1CCN(C)CC1] | N4-(1-Adamantyl)-5-fluoro-N2-[3-methyl-4-(4-methylpiperazin-1-yl)phenyl]-2,4-pyrimidinediamine |
| 258 | | | N4-(2-Adamantyl)-5-fluoro-N2-[3-methyl-4-(4-methylpiperazin-1-yl)phenyl]-2,4-pyrimidinediamine |
| 259 | | 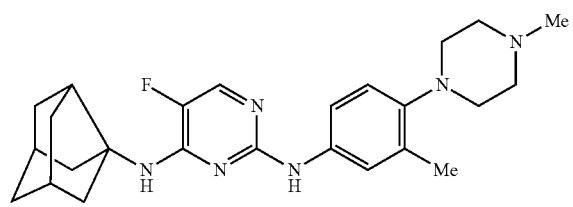 [SMILES: Cc1cc(Nc2ncc(F)c(NC34CC5CC(CC3C5)C4)n2)ccc1N1CCN(C)CC1] | 5-Fluoro-N2-[3-methyl-4-(4-methylpiperazin-1-yl)phenyl]-N4-(3-noradamantyl)-2,4-pyrimidinediamine |
| 260 | Mixture of IVa + IVb type | 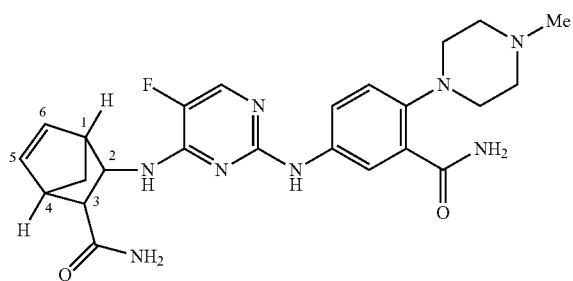 | Racemic-(2-exo,3-exo)-N2-[3-aminocarbonyl-4-(4-methylpiperazin-1-yl)phenyl]-N4-(3-aminocarbonylbicyclo[2.2.1]hept-5-en-2-yl)-5-fluoro-2,4-pyrimidinediamine |

TABLE 1-continued

| | | |
|---|---|---|
| 261 | Mixture of IVa + IVb type 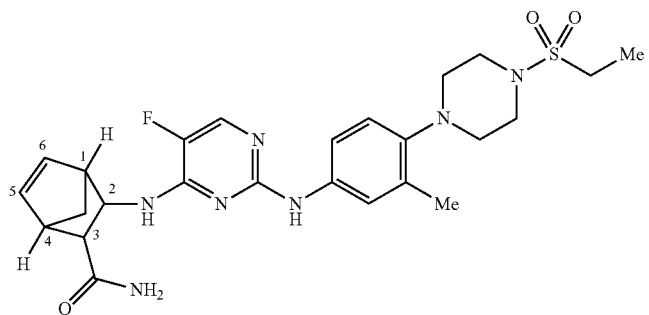 | Racemic-(2-exo,3-exo)-N4-(3-aminocarbonylbicylco[2.2.1]hept-5-en-2-yl)-N2-[4-(4-ethylsulfonylpiperazin-1-yl)-3-methylphenyl]-5-fluoro-2,4-pyrimidinediamine |
| 262 | Mixture of IVa + IVb type 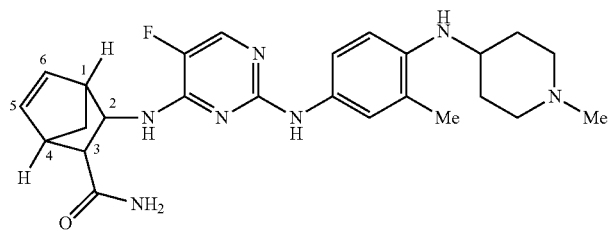 | Racemic-(2-exo,3-exo)-N4-(3-aminocarbonylbicyclo[2.2.1]hept-5-en-2-yl)-5-fluoro-N2-[3-methyl-4-(1-methylpiperidin-4-ylamino)phenyl]-2,4-pyrimidinediamine |
| 263 | Mixture of IVa + IVb type 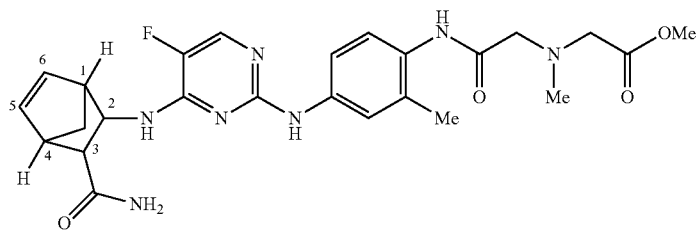 | Racemic-(2-exo,3-exo)-N4-(3-aminocarbonylbicyclo[2.2.1]hept-5-en-2-yl)-5-fluoro-N2-{3-methoxy-4-[2-(N-methyl-N-methoxyacet-2-yl)iminoacetylamino]phenyl}-2,4-pyrimidinediamine |
| 264 | Mixture of IVa + IVb type 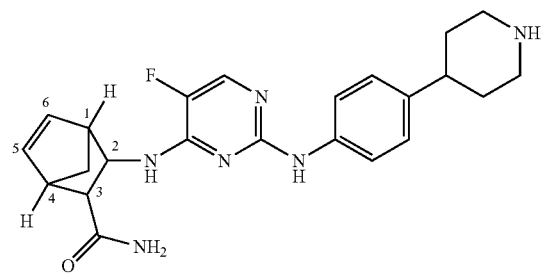 | Racemic-(2-exo,3-exo)-N4-(3-aminocarbonylbicyclo[2.2.1]hept-5-en-2-yl)-5-fluoro-N2-[4-(piperidin-4-yl)phenyl]-2,4-pyrimidinediamine |
| 265 | Mixture of IVa + IVb type 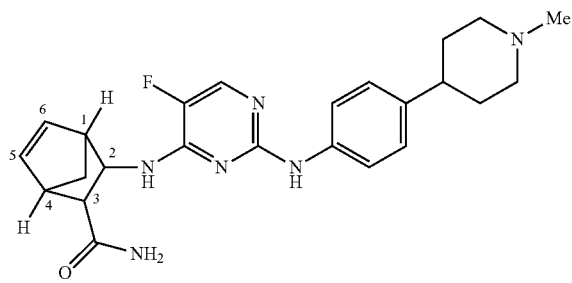 | Racemic-(2-exo,3-exo)-N4-(3-aminocarbonylbicyclo[2.2.1]hept-5-en-2-yl)-5-fluoro-N2-[4-(1-methylpiperidin-4-yl)phenyl]-2,4-pyrimidinediamine |

TABLE 1-continued

| | | | |
|---|---|---|---|
| 266 | Mixture of IVa + IVb type | 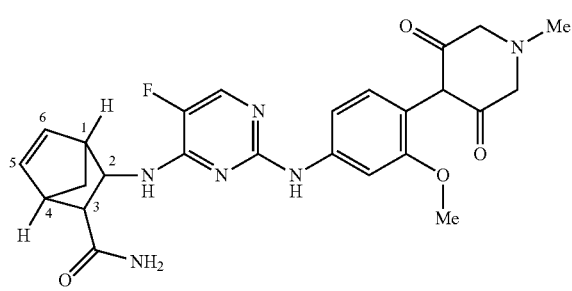 | Racemic-(2-exo,3-exo)-N4-(3-aminocarbonylbicyclo[2.2.1]hept-5-en-2-yl)-5-fluoro-N2-[3-methoxy-4-(4-methyl-2,6-dioxopiperazino)phenyl]-2,4-pyrimidinediamine |
| 267 | Mixture of IVa + IVb type | 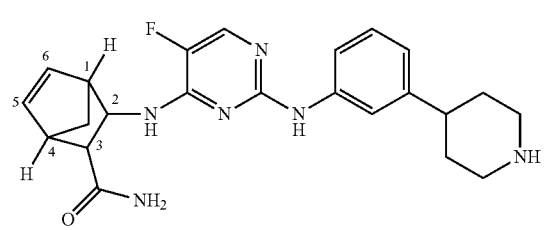 | Racemic-(2-exo,3-exo)-N4-(3-aminocarbonylbicyclo[2.2.1]hept-5-en-2-yl)-5-fluoro-N2-[3-(piperidin-4-yl)phenyl]-2,4-pyrimidinediamine |
| 268 | Mixture of IVa + IVb type | 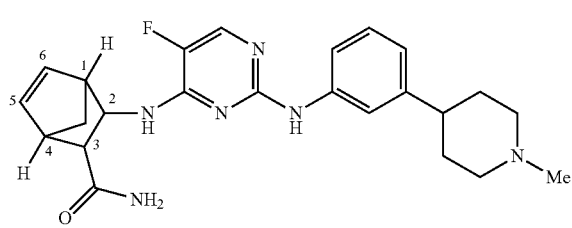 | Racemic-(2-exo,3-exo)-N4-(3-aminocarbonylbicyclo[2.2.1]hept-5-en-2-yl)-5-fluoro-N2-[3-(1-methylpiperadin-4-yl)phenyl]-2,4-pyrimidinediamine |
| 269 | | 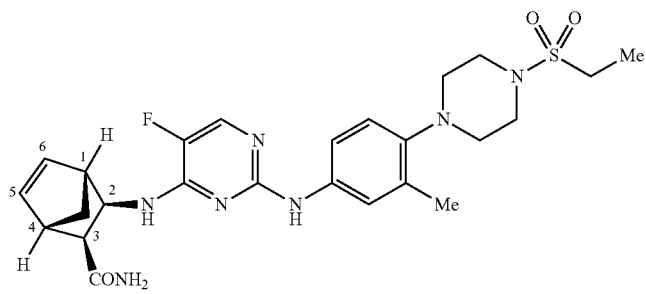 [SMILES: CCS(=O)(=O)N1CCN(c2ccc(Nc3ncc(F)c(N[C@H]4[C@@H](C(N)=O)[C@@H]5C=C[C@H]4C5)n3)cc2C)CC1] | (1R,2R,3S,4S)-N4-(3-Aminocarbonylbicyclo[2.2.1]hept-5-en-2-yl)-N2-[3-methyl-4-(4-ethylsulfonylpiperazin-1-yl)phenyl]-5-fluoro-2,4-pyrimidinediamine |
| 270 | | 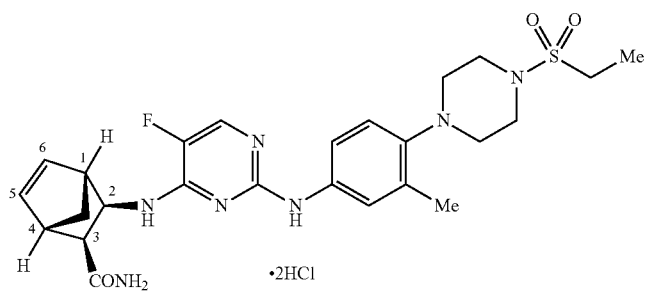 [SMILES: CCS(=O)(=O)N1CCN(c2ccc(Nc3ncc(F)c(N[C@H]4[C@@H](C(N)=O)[C@@H]5C=C[C@H]4C5)n3)cc2C)CC1] | (1R,2S,3S,4S)-N4-(3-aminocarbonylbicyclo[2.2.1]hept-5-en-2-yl)-N2-[3-methyl-4-(4-ethylsulfonylpiperazin-1-yl)phenyl]-5-fluoro-2,4-pyrimidinediamine Bis-Hydrochloride Salt |

TABLE 1-continued

| | | |
|---|---|---|
| 271 | 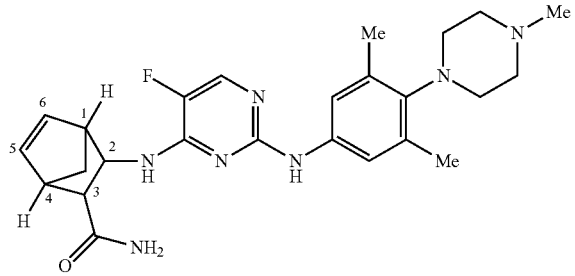 [SMILES: Cc1cc(Nc2ncc(F)c(NC3C4C=CC(C4)C3C(N)=O)n2)cc(C)c1N1CCN(C)CC1] | Racemic-(2-exo,3-exo)-N4-(3-aminocarbonylbicyclo[2.2.1]hept-5-en-2-yl)-N2-[3,5-dimethyl-4-(4-methylpiperazin-1-yl)phenyl]-5-fluoro-2,4-pyrimidinediamine |
| 272 | 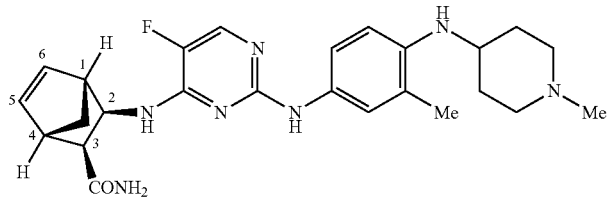 [SMILES: Cc1cc(Nc2ncc(F)c(N[C@H]3[C@@H](C(N)=O)[C@@H]4C=C[C@H]3C4)n2)ccc1NC1CCN(C)CC1] | (1R,2R,3S,4S)-N4-(3-Aminocarbonylbicyclo[2.2.1]hept-5-en-2-yl)-5-fluoro-N2-[3-methyl-4-(1-methylpiperidin-4-ylamino)phenyl]-2,4-pyrimidinediamine |
| 273 | 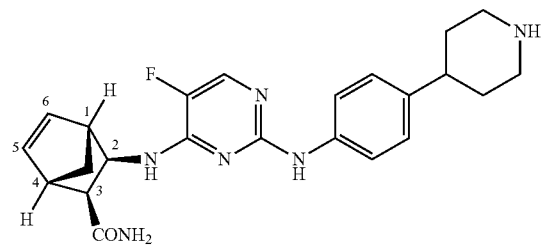 [SMILES: NC(=O)[C@@H]1[C@H](Nc2nc(Nc3ccc(C4CCNCC4)cc3)ncc2F)[C@H]2C=C[C@@H]1C2] | (1R,2R,3S,4S)-N4-(3-Aminocarbonylbicyclo[2.2.1]hept-5-en-2-yl)-5-fluoro-N2-[4-(piperidin-4-yl)phenyl]-2,4-pyrimidinediamine |
| 274 | 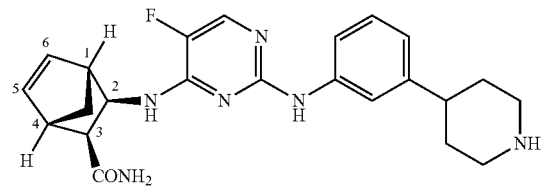 [SMILES: NC(=O)[C@@H]1[C@H](Nc2nc(Nc3cccc(C4CCNCC4)c3)ncc2F)[C@H]2C=C[C@@H]1C2] | (1R,2R,3S,4S)-N4-(3-Aminocarbonylbicyclo[2.2.1]hept-5-en-2-yl)-5-fluoro-N2-[3-(piperidin-4-yl)phenyl]-2,4-pyrimidinediamine |
| 275 | 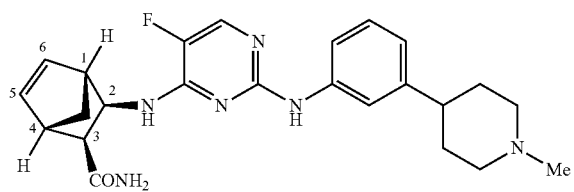 [SMILES: CN1CCC(c2cccc(Nc3ncc(F)c(N[C@H]4[C@@H](C(N)=O)[C@@H]5C=C[C@H]4C5)n3)c2)CC1] | (1R,2R,3S,4S)-N4-(3-Aminocarbonylbicyclo[2.2.1]hept-5-en-2-yl)-5-fluoro-N2-[3-(1-methylpiperidin-4-yl)phenyl]-2,4-pyrimidinediamine |
| 276 | 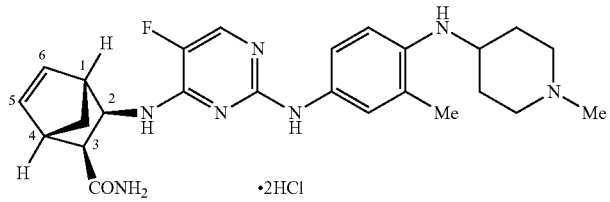 [SMILES: Cc1cc(Nc2ncc(F)c(N[C@H]3[C@@H](C(N)=O)[C@@H]4C=C[C@H]3C4)n2)ccc1NC1CCN(C)CC1] | (1R,2R,3S,4S)-N4-(3-Aminocarbonylbicyclo[2.2.1]hept-5-en-2-yl)-5-fluoro-N2-[3-methyl-4-(1-methylpiperidin-4-ylamino)phenyl]-2,4-pyrimidinediamine Bis-Hydrochloride Salt |
| 277 | Mixture of IVa + IVb type<br>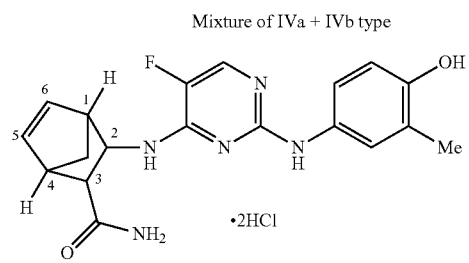 [SMILES: Cc1cc(Nc2ncc(F)c(NC3C4C=CC(C4)C3C(N)=O)n2)ccc1O] | Racemic-(2-exo,3-exo)-N4-(3-aminocarbonylbicyclo[2.2.1]hept-5-en-2-yl)-5-fluoro-N2-(4-hydroxy-3-methylphenyl)-2,4-pyrimidinediamine Bis-Hydrochloride Salt |

TABLE 1-continued

| | | |
|---|---|---|
| 278 | | Racemic-cis-N4-(2-aminocarbonyl cyclopent-1-yl)-5-fluoro-N2-{4-[(4-methylpiperazin-1-yl)-butan-1-one-4-yl]phenyl}-2,4-pyrimidinediamine |
| 279 | | Racemic-cis-N4-(2-aminocarbonyl cyclopent-1-yl)-5-fluoro-N2-{4-[(4-methylpiperazin-1-yl)-ethan-1-one-2-yl]phenyl}-2,4-pyrimidinediamine |
| 280 | | Racemic-cis-N4-(2-aminocarbonyl cyclopent-1-yl)-5-fluoro-N2-{4-[(4-methylpiperazin-1-yl)-propan-1-one-3-yl]}phenyl-2,4-pyrimidinediamine |
| 281 | | Racemic-cis-N4-(2-aminocarbonyl cyclopent-1-yl)-5-fluoro-N2-[4-(4-methylpiperaino-1-yl-carbonyl)phenyl]-2,4-pyrimidinediamine |
| 282 | | Racemic-cis-N4-(2-aminocarbonyl cyclopent-1-yl)-5-fluoro-N2-[3-methyl-4-(5-methyl-(1S,4S)2,5-diazabicyclo[2.2.1]heptan-2-yl)phenyl]-2,4-pyrimidinediamine |
| 283 | | Racemic-cis-N4-(2-aminocarbonyl cyclopent-1-yl)-N2-[4-(2,6-dimethylmorpholino)-3-methyl]phenyl-5-fluoro-2,4-pyrimidinediamine |

| | | |
|---|---|---|
| 284 | Mixture of type IVa + IVb 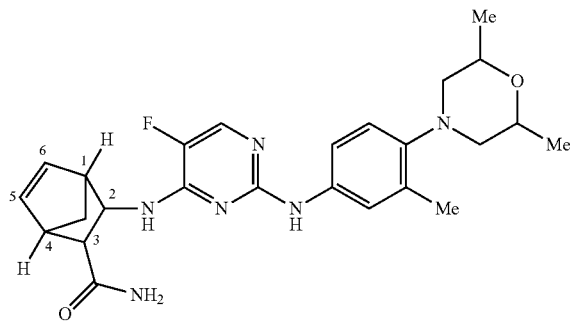 | Racemic-(2-exo,3-exo)-N4-(3-aminocarbonylbicyclo]2.2.1]hept-5-en-2-yl)-N2-[4-(2,5-dimethylmorpholino)-3-methylphenyl]-5-fluoro-2,4-pyrimidinediamine |
| 285 | Mixture of IVa + IVb type 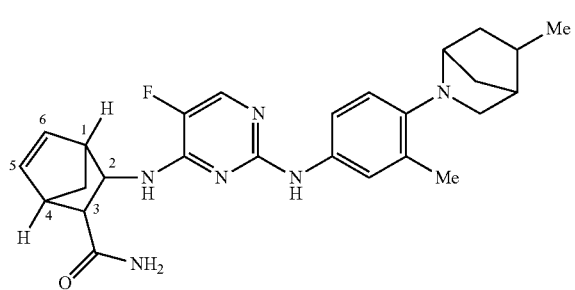 | Racemic-(2-exo,3-exo)-N4-(3-aminocarbonylbicyclo[2.2.1]hept-5-en-2-yl)-5-fluoro-N2-[3-methyl-4-(5-methyl-(1S,4S)-2,5-diazabicyclo[2.2.1]heptan-2-yl)]phenyl-2,4-pyrimidinediamine |
| 286 | 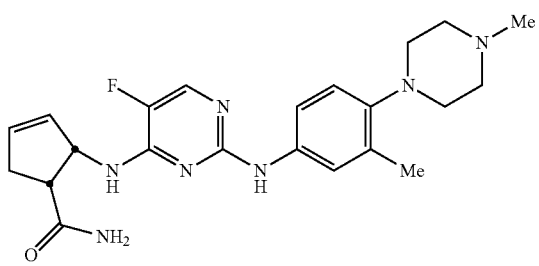 [SMILES: Cc1cc(Nc2ncc(F)c(N[C@H]3C=CC[C@H]3C(N)=O)n2)ccc1N1CCN(C)CC1] | Racemic-cis-N4-(2-aminocarbonyl cyclopent-4-en-1-yl)-5-fluoro-N2-{3-methyl-4-(4-methylpiperazin-1-yl)phenyl]-2,4-pyrimidinediamine |
| 287 | 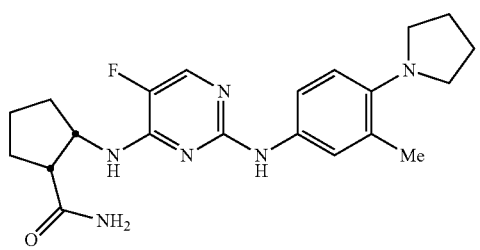 [SMILES: Cc1cc(Nc2ncc(F)c(N[C@H]3CCC[C@H]3C(N)=O)n2)ccc1N1CCCC1] | Racemic-cis-N4-(2-aminocarbonyl cyclopent-1-yl)-5-fluoro-N2-[3-methyl-4-(pyrrolidino)phenyl]2,4-pyrimidinediamine |
| 288 | Mixture of IVa + IVb type 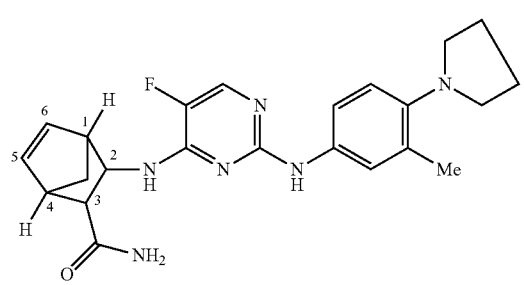 | Racemic-(2-exo,3-exo)-N4-(3-aminocarbonylbicyclo[2.2.1]hept-5-en-2-yl)-5-fluoro-N2-[3-methyl-4-(pyrrolidino)phenyl]-2,4-pyrimidinediamine |

TABLE 1-continued

| Compound No. | NMR and LCMS | A549, 6 pt | H1299, 6 pt |
|---|---|---|---|
| 102 | LCMS: purity: 99%; MS (m/e): 487 (MH+) | + | + |
| 103 | LCMS: purity: 91%; MS (m/e): 498 (MH+) | ++ | +++ |
| 104 | LCMS: purity: 98%; MS (m/e): 484 (MH+) | +++ | +++ |
| 105 | LCMS: purity: 94%; MS (m/e): 414 (MH+) | + | + |
| 106 | LCMS: purity: 99%; MS (m/e): 418 (MH+) | + | + |
| 107 | 1H NMR (CDCl$_3$): δ 7.63 (d, 1H, J = 3.9 Hz), 6.85 (d, 1H, J = 8.4 Hz), 6.16 (d, 1H, J = 2.7 Hz), 6.54 (dd, J = 2.7 and 8.4 Hz), 4.63 (m, 1H), 3.76 (m, 4H), 3.00 (m, 1H), 2.83 (m, 4H), 2.27 (s, 3H), 2.06-1.86 (m, 5H), 1.65 (m, 1H); LCMS: purity: 96%; MS (m/e): 415 (MH+) | + | + |
| 108 | LCMS: purity: 98%; MS (m/e): 438 (MH+) | − | + |
| 109 | 1H NMR (DMSO-d6): δ 8.85 (s, 1H), 8.55 (d, 8.55 (d, 1H, J = 7.8 Hz), 7.78 (d, 1H, J = 0.9 Hz), 7.50 (d, 1H, J = 2.4 Hz), 7.42 (dd, 1H, J = 2.4 and 8.7 Hz), 7.15 (m, 5H), 6.89 (d, 1H, J = 8.7 Hz), 6.80 (d, 1H, J = 7.8 Hz), 6.34 (m, 1H), 6.27 (m, 1H), 4.94 (m, 1H), 4.23 (t, 1H, J = 7.8 Hz), 2.88 (s, 1H), 2.75 (m, 5H), 2.62 (d, 1H, J = 8.1 Hz), 2.44 (m, 5H), 2.21 (s, 3H), 2.19 (s, 3H), 1.43 (d, 1H, J = 8.7 Hz), 1.34 (d, 3H, J = 7.5 Hz); LCMS: purity: 93%; MS (m/e): 556 (M+) | ++ | ++ |
| 110 | 1H NMR (DMSO-d6): δ 8.85 (s, 1H), 8.35 (d, 1H, J = 7.8 Hz), 7.85 (d, 1H, J = 3.6 Hz), 7.50 (d, 1H, J = 2.4 Hz), 7.43 (dd, 1H, J = 2.4 and 8.4 Hz), 7.31-7.19 (m, 5H), 6.90 (d, 1H, J = 9.3 Hz), 6.32 (m, 1H), 6.26 (m, 1H), 4.86 (t, 1H, J = 7.2 Hz), 4.16 (t, 1H, J = 7.5 Hz), 2.75 (m, 5H), 2.61 (d, 1H, J = 7.5 Hz), 2.46 (m, 5H), 2.22 (s, 3H), 2.19 (s, 3H), 2.14 (d, 1H, J = 10.5 Hz), 1.34 (d, 1H, J = 6.6 Hz), 1.14 (d, 3H, J = 6.6 Hz); LCMS: purity: 95%; MS (m/e): 556 (M+), 557 (MH+) | ++ | ++ |
| 111 | 1H NMR (DMSO-d6): δ 8.86 (s, 1H), 7.84 (d, 1H, J = 3.3 Hz), 7.68 (bs, 1H), 7.45 (m, 2H), 7.36 (d, 1H, J = 7.2 Hz), 7.19 (s, 1H), 6.89 (d, 1H, J = 9.3 Hz), 6.32 (m, 1H), 6.25 (m, 1H), 4.38 (t, 1H, J = 5.4 Hz), 4.11 (bt, 1H, J = 8.1 Hz), 3.52 (q, 2H, J = 5.7 Hz), 2.86 (bs, 1H), 2.76 (m, 5H), 2.53 (m, 4H), 2.43 (t, 2H, J = 6.6 Hz), 2.19 (s, 3H), 2.12 (d, 1H, J = 8.4 Hz), 1.40 (d, 1H, J = 8.7 Hz); LCMS: purity: 93%; MS (m/e): 483 (MH+) | +++ | +++ |
| 112 | LCMS: purity: 98%; MS (m/e): 541 (MH+) | | |
| 113 | 1H NMR (DMSO-d6): δ 8.89 (s, 1H), 7.8 (d, 1H, J = 3.9 Hz), 7.66 (1H, bs), 7.37 (d, 1H, J = 9.0 Hz), 7.16 (bs, 1H), 7.08 (s, 1H), 6.9 (d, 1H, J = 8.4 Hz), 6.29 (m, 2H), 4.69 (s, 2H), 4.07 (m, 2H), 3.58 (bs, 2H), 3.46 (bs, 2H), 2.85 (bs, 1H), 2.77 (s, 1H), 2.5 (s, 3H), 1.40 (m, 1H); LCMS: purity: 88%; MS (m/e): 510 (MH+); | | |
| 114 | LCMS: purity: 97%; MS (m/e): 496 (MH+) | | |
| 115 | 1H NMR (DMSO-d6): δ 8.90 (s, 1H), 7.85 (d, 1H, J = 3.6 Hz), 7.66 (s, 1H), 7.36 (d, 1H, J = 7.5 Hz), 7.2 (s, 1H), 7.16 (s, 1H), 6.93 (d, 1H, J = 7.8 Hz), 6.2 (m, 2H), 4.12 (t, 2H, J = 8.4 Hz), 3.99 (t, 2H, J = 5.7 Hz), 3.56 (t, 4H, J = 4.8 Hz), 3.28 (m, 4H), 2.85 (s, 1H), 2.76 (s, 1H), 2.70 (t, 2H, J = 5.4), 2.12 (d, 1H, J = 11.7 Hz), 2.05 (s, 3H), 1.39 (d, 1H, J = 7.5 Hz); LCMS: purity: 98%; MS (m/e): 484 (MH+) | +++ | +++ |
| 116 | 1H NMR (DMSO-d6): δ 8.85 (s, 1H), 7.82 (d, 1H, J = 3.3 Hz), 7.67 (bs, 1H), 7.47 (s, 1H), 7.37 (d, 1H, J = 7.8 Hz), 7.184 (bs, 1H), 6.88 (d, 1H, J = 9.3 Hz), 6.3 (m, 2H), 4.38 (t, 2H, J = 5.7 Hz), 4.08 (m, 2H), 3.49 (m, 2H), 3.2 (m, 4H), 3.1 (m, 4H), 2.85 (bs, 1H), 2.76 (bs, 2H), 2.18 (s, 3H), 2.10 (d, 1H, J = 5.92 Hz), 1.38 (d, 1H, J = 9.6 Hz); LCMS: purity: 98%; MS (m/e): 482 (MH+) | +++ | +++ |
| 117 | 1H NMR (DMSO-d6): δ 8.87 (s, 1H), 7.84 (d, 1H, J = 3.3 Hz) 7.68 (bs, 1H), 7.45 (m, 2H), 7.36 (bd, 1H, J = 7.3 Hz), 7.19 (bs, 1H), 6.89 (d, 1H, J = 8.1 Hz), 6.32 (m, 1H), 6.25 (m, 1H), 4.12 (t, 1H), 2.85 (bs, 1H), 2.80 (m, 4H), 2.5 (m, 6H), 2.40 (s, 4H), 2.28 (s, 3H), 2.11 (d, 1H), 1.40 (d, 1H)" LCMS: purity: 99%; MS (m/e): 452 (MH+) | | |
| 118 | 1H NMR (DMSO-d6): δ 8.85 (s, H), 7.83 (d, 1H, J = 3.3 Hz), 7.67 (bs, 1H), 7.46 (m, 3H), 7.36 (bd, 1H, J = 7.5 Hz), 7.18 (bs, 1H), 6.89 (d, 1H, J = 8.1 Hz), 6.33 (m, 1H), 6.25 (m, 1H), 4.15 (t, 1H), 2.85 (bs, 1H), 2.81 (m, 4H), 2.52 (m, 6H), 2.3 (s, 2H), 2.25 (s, 3H), 2.20 (s, 3H), 2.15 (d, 1H), 1.40 (d, 1H); LCMS: purity: 98%; MS (m/e): 452 (MH+) | | |
| 119 | 1H NMR (DMSO-d6): δ 8.86 (s, 1H), 7.84 (d, 1H, J = 3.3 Hz), 7.67 (bs, 1H), 7.45 (m, 3H), 7.37 (bd, 1H, J = 7.8 Hz), 7.18 (bs, 1H), 6.89 (d, 1H, J = 8.4 Hz), 6.56 (s, >2H), 6.32 (m, 1H), 6.25 (m, 1H), 4.18 (t, 1H), 2.82 (s, 1H), 2.80 (m, 5H), 2.48 (m, 5H), 2.23 (s, 3H), 2.20 (s, 3H), 2.15 (d, 1H), 1.40 (d, 1H); LCMS: purity: 96%; MS (m/e): 452 (MH+) | | |
| 120 | 1H NMR (DMSO-d6): δ 8.85 (s, 1H), 8.76 (m, 2H), 8.83 (d, 1H, J = 3.3 Hz), 7.65 (bs, 1H), 7.45 (m, 5H), 7.35 (bd, 1H, J = 7.8 Hz), 7.18 (bs, 1H), 6.88 (d, 1H, J = 8.1 Hz), 6.35 (m, 1H), 6.25 (m, 1H), 4.11 (t, 1H, J = 7.5 Hz), 2.86 (s, 1H), 2.77 (m, 4H), 2.49 (m, 6H), 2.22 (s, 3H), 2.19 (s, 3H), 2.12 (d, 1H), J = 9 Hz), 1.40 (d, 1H, J = 9 Hz); LCMS: purity: 99%; MS (m/e): 452 (MH+). | | |
| 121 | 1H NMR (DMSO-d6): δ 8.84 (s, 1H), 7.83 (d, 1H, J = 3.3 Hz), 7.67 (s, 1H), 7.45 (m, 2H), 7.35 (d, 1H, J = 7.5 Hz), 7.18 (bs, 1H), 6.88 (d, 1H, J = 8.4 Hz), 6.33 (m, 2H), 6.25 (m, 1H), 4.15 (t, 1H, J = 7.5 Hz), 2.86 (s, 1H), 2,78 (m, 4H), 2.45 (m, 6H), 2.20 (m, 10H), 2.12 (d, 1H, J = 9 Hz), 1.48 (m, 4H), 1.40 (d, 1H, J = 9 Hz) LCMS: purity: 99%; MS (m/e): 452 (MH+) | +++ | +++ |

TABLE 1-continued

| | | | |
|---|---|---|---|
| 122 | 1H NMR (DMSO-d6): δ 8.89 (s, 1H), 7.84 (d, 1H, J = 3.3 Hz), 7.68 (s, 1H), 7.48 (m, 2H), 7.38 (d, 1H, J = 7.2 Hz), 7.17 (s, 1H), 6.90 (d, 1H, J = 8.1 Hz), 6.32 (m, 1H), 6.25 (m, 1H), 4.14 (m, 3H), 2.86 (m, 5H), 2.78 (m, 5H), 2.53 (s, 1H), 2.46 (s, 3H), 2.20 (s, 3H), 2.12 (d, 1H, J = 8.4 Hz), 1.40 (d, 1H, J = 9 Hz) LCMS: purity: 99%; MS (m/e): 452 (MH+) | +++ | +++ |
| 123 | LCMS: purity: 92%; MS (m/e): 506 (MH+); | +++ | +++ |
| 124 | 1H NMR (DMSO-d6): δ 8.86 (s, 1H), 8.45 (d, 1H, J = 8.1 Hz), 7.78 (d, 1H, J = 3.0 Hz), 7.52 (d, 1H, J = 2.4 Hz), 7.44 (dd, 2H, J = 2.7 and 6.9 Hz), 7.04 (bdd, 2H, J = 8.7 Hz), 6.90 (bdd, 2H, J = 8.4 Hz), 6.83 (d, 1H, J = 8.4 Hz), 6.69 (bdd, 2H, J = 8.4 Hz), 6.33 (m, 1H), 6.26 (m, 1H), 4.89 (m, 1H, J = 4.2 Hz), 4.21 (t, 1H, J = 8.1 Hz), 3.65 (s, 3H), 2.88-2.74 (m, 7H), 2.57 (d, 1H, J = 8.1 Hz), 2.43 (m, 4H), 2.20 (s, 3H), 1.43 (d, 1H, J = 8.7 Hz), 1.31 (d, 3H, J = 6.9 Hz); LCMS: purity: 94%; MS (m/e): 587 (MH+) | ++ | ++ |
| 125 | LCMS: purity: 97%; MS (m/e): 497 (MH+); | +++ | +++ |
| 126 | LCMS: purity: 97%; MS (m/e): 356 (MH+) | | |
| 127 | LCMS: purity: 97%; MS (m/e): 400 (MH+) | | |
| 128 | LCMS: purity: 99%; MS (m/e): 430 (MH+) | | |
| 129 | LCMS: purity: 99%; MS (m/e): 427 (MH+) | | |
| 130 | LCMS: purity: 97%; MS (m/e): 483 (MH+) | + | + |
| 131 | LCMS: purity: 96%; MS (m/e): 469 (MH+) | + | + |
| 132 | 1H NMR (DMSO-d6): δ 8.92 (s, 1H), 7.83 (d, J = 3.0 Hz, 1H), 7.53 (s, 1H), 7.40-7.28 (m, 2H), 6.98-6.94 (m, 1H), 6.92 (d, J = 8.7 Hz, 1H), 6.88 (d, J = 6.0 Hz, 1H), 4.44 (t, J = 6.9 Hz, 1H), 3.65-3.58 (m, 5H), 3.39 (s, 2H), 2.91 (q, J = 7.2 Hz), 2.80-2.69 (m, 4H), 2.00-1.70 (m, 5H), 1.62-1.49 (m, 1H); LCMS: purity: 94%; MS (m/e): 443 (MH+). | ++ | ++ |
| 133 | 1H NMR (DMSO-d6): δ 9.47 (s, 1H), 7.94 (d, J = 3.3 Hz, 1H), 7.67 (s, 1H), 7.58-7.42 (m, 4H), 7.17 (s, 1H), 6.83 (s, 2H), 6.36-6.31 (m, 1H), 6.26-6.21 (m, 1H), 4.17 (t, J = 8.1 Hz, 1H), 3.82 (s, 3H), 2.87 (s, 1H), 2.78 (s, 1H), 2.54-2.47 (m, 1H), 2.16 (d, J = 8.74 Hz, 1H), 1.41 (d, J = 9.3 Hz, 1H),.; LCMS: purity: 94%; MS (m/e): 449 (MH+). | + | + |
| 134 | 1H NMR (DMSO-d6): δ 8.82 (s, 1H), 7.94 (d, J = 0.90 Hz, 1H), 7.83 (dd, J = 1.0 and 3.3 Hz, 1H), 7.97 (s, 1H), 7.36-7.24 (m, 3H), 7.19 (s, 1H), 6.36-6.22 (m, 3H), 5.73 (d, J = 1.2 Hz, 1H), 4.19 (d, J = 6.6 Hz, 2H), 4.11 (t, J = 7.8 Hz, 1H), 2.86 (s, 1H), 2.82 (s, 1H), 2.61 (t, J = 6.6 Hz, 1H), 2.52 (s, 1H), 2.47-2.38 (m, 4H), 2.0-2.1 (m, 4H), 1.40 (d, J = 8.1 Hz, 1H); LCMS: purity: 95%; MS (m/e): 505 (MH+) | ++ | ++ |
| 135 | LCMS: purity: 95%; MS (m/e): 592 (MH+) | + | + |
| 136 | 1H NMR (DMSO-d6): δ 8.94 (s, 1H), 7.89 (d, J = 3.6 Hz, 1H), 7.77 (s, 1H), 7.69-7.60 (m, 2H), 7.47 (d, J = 7.8 Hz, 1H), 7.25 (s, 1H), 6.92-6.83 (m, 2H), 6.42-6.32 (m, 2H), 4.13 (t, J = 8.1 Hz, 1H), 3.97 (dd, J = 5.1 and 9.6 Hz, 1H), 3.81 (dd, J = 6.0 and 9.3 Hz, 1H), 3.04-2.97 (m, 1H), 2.92 (s, 1H), 2.85 (s, 1H), 2.41 (s, 2H), 2.27-2.15 (m, 3H), 2.07-1.94 (m, 2H), 1.78-1.60 (m, 3H), 1.46 (d, J = 8.4 Hz, 1H); LCMS: purity: 96%; MS (m/e): 453 (MH+). | +++ | +++ |
| 137 | 1H NMR (DMSO-d6): δ 8.99 (s, 1H), 7.85 (d, J = 3.6 Hz, 1H), 7.71 (s, 1H), 7.61 (d, J = 8.7 Hz, 2H), 7.46 (d, J = 7.5 Hz, 1H), 7.20 (s, 1H), 7.06 (d, J = 8.4 Hz, 2H), 6.36-6.27 (m, 2H), 4.07 (t, J = 7.8 Hz, 1H), 2.88-2.79 (m, 4H), 2.42-2.30 (m, 2H), 2.16 (s, 3H), 2.10 (d, J = 8.4 Hz, 1H), 1.97-1.86 (m, 1H), 1.73-1.54 (m, 4H), 1.40 (d, J = 8.4 Hz, 1H); LCMS: purity: 94%; MS (m/e): 437 (MH+). | +++ | +++ |
| 138 | 1H NMR (DMSO-d6): δ 8.05 (d, J = 4.5 Hz, 1H), 7.87 (s, 1H), 7.58 (d, J = 8.4 Hz, 2H), 7.32 (s, 1H), 7.18 (d, J = 8.7 Hz, 2H), 6.37-6.32 (m, 1H), 6.25-6.21 (m, 1H), 4.02-3.94 (m, 1H), 3.50-3.39 (m, 2H), 2.03 (d, J = 9.6 Hz, 1H), 2.00-1.89 (m, 5H), 1.41 (d, J = 8.1 Hz, 1H), 3.08-2.98 (m, 2H), 2.93-2.86 (m, 2H), 2.78-2.72 (m, 4H) | +++ | +++ |
| 139 | 1H NMR (DMSO-d6): δ 7.89 (d, J = 3.9 Hz, 1H), 7.71 (s, 1H), 7.52-7.46 (m, 2H), 7.23 (s, 1H), 6.94 (d, J = 8.4 Hz, 1H), 6.36-6.31 (m, 1H), 6.27-6.23 (m, 1H), 4.12-4.04 (m, 1H), 3.50-3.44 (m, 5H), 3.22-3.09 (m, 4H), 2.94-2.77 (m, 6H), 2.22 (s, 3H), 2.11 (d, J = 8.1 Hz, 1H), 1.41 (d, J = 9.3 Hz, 1H). | +++ | +++ |
| 140 | 1H NMR (DMSO-d6): δ 7.89 (d, J = 3.9 Hz, 1H), 7.71 (s, 1H), 7.52-7.46 (m, 2H), 7.23 (s, 1H), 6.94 (d, J = 8.4 Hz, 1H), 6.36-6.31 (m, 1H), 6.27-6.23 (m, 1H), 4.07 (t, J = 7.2 Hz, 1H), 3.53-3.30 (m, 5H), 3.24-3.08 (m, 4H), 2.96-2.79 (m, 7H), 2.30 (s, 3H), 2.23 (s, 3H), 2.10 (d, J = 8.7 Hz, 1H), 1.41 (d, J = 8.7 Hz, 1H). | +++ | +++ |
| 141 | 1H NMR (DMSO-d6): δ 7.97 (s, 1H), 7.78 (s, 1H), 7.45-7.35 (m, 2H), 7.30 (s, 1H), 7.01 (d, J = 8.1 Hz, 1H), 6.36-6.31 (m, 1H), 6.23-6.18 (m, 1H), 4.06-3.98 (m, 1H), 3.60-3.30 (m, 5H), 3.22-3.12 (m, 4H), 2.98-2.83 (m, 7H), 2.24 (s, 3H), 2.06 (d, J = 8.4 Hz, 1H), 1.41 (d, J = 8.4 Hz, 1H) | +++ | +++ |
| 142 | 1H NMR (CD3OD): δ 7.80 (d, J = 4.8 Hz, 1H), 7.45-7.40 (m, 1H), 7.36 (dd, J = 2.1 and 8.7 Hz, 1H), 6.95 (d, J = 8.7 Hz, 1H), 6.38-6.34 (m, 1H), 6.24-6.21 (m, 1H), 4.15 (d, J = 7.2 Hz, 1H), 3.62-3.58 (m, 3H), 3.27-3.10 (m, 5H), 3.01-2.93 (m, 4H), 2.88 (s, 1H), 2.61 (d, J = 8.1 Hz, 1H), 2.29 (s, 3H), 2.15 (d, J = 9.3 Hz, 1H), 1.52 (d, J = 9.6 Hz, 1H). | +++ | +++ |
| 143 | 1H NMR (DMSO-d6): δ 8.87 (s, 1H), 7.83 (d, J = 3.3 Hz, 1H), 7.68 (s, 1H), 7.51-7.42 (m, 2H), 7.40-7.16 (m, 8H), 6.89 (d, J = 8.1 Hz, 1H), 6.36-6.31 (m, 1H), 6.28-6.24 (m, 1H), 4.92 (s, 1H), 4.11 (t, J = 7.2 Hz, 1H), 2.86-2.78 (m, 6H), 2.63-2.53 (m, 3H), 2.32 (s, 3H), 2.19 (s, 3H), 2.12 (d, J = 9.0 Hz, 1H), 1.40 (d, J = 8.7 Hz, 1H). | +++ | +++ |
| 144 | 1H NMR (DMSO-d6): δ 7.89 (d, J = 3.9 Hz, 1H), 7.72 (s, 1H), 7.49 (s, 2H), 7.45 (d, J = 7.8 Hz, 2H), 7.23 (s, 1H), 7.08 (d, J = 8.4 Hz, 2H), 6.95 (d, J = 8.4 Hz, 1H), 6.36-6.31 (m, 1H), 6.28-6.23 (m, 1H), 4.08 (t, J = 9.0 Hz, 1h), 3.53- | +++ | +++ |

TABLE 1-continued

| | | | |
|---|---|---|---|
| | 3.44 (m, 3H), 3.23-3.10 (m, 4H), 2.96-2.76 (m, 7H), 2.28 (s, 3H), 2.23 (s, 3H), 2.11 (d, J = 8.4 Hz, 1H), 1.98 (s, 1H), 1.41 (d, J = 8.7 Hz, 1H). | | |
| 145 | 1H NMR (DMSO-d6): δ 10.30 (s, 1H), 9.54 (s, 1H), 7.97 (d, J = 3.9 Hz, 1H), 7.78 (s, 1H), 7.62 (d, J = 7.8 Hz, 1H), 7.41 (s, 1H), 7.27-7.20 (m, 2H), 6.82 (d, J = 7.5 Hz, 1H), 6.36-6.32 (m, 1H), 6.24-6.20 (m, 1H), 4.11 (t, J = 7.5 Hz, 1H), 3.51-3.40 (m, 3H), 3.12-2.96 (m, 2H), 2.89-2.86 (m, 1H), 2.80-2.72 (m, 4H), 2.57 (d, J = 8.1 Hz, 1H), 2.11 (d, J = 9.0 Hz, 1H), 1.99-1.88 (m, 4H), 1.40 (d, J = 9.3 Hz, 1H). | +++ | +++ |
| 146 | 1H NMR (CDCl$_3$): δ 7.61 (d, J = 3.3 Hz, 1H), 7.36 (d, J = 9.0 Hz, 2H), 7.07 (s, 1H), 6.76 (d, J = 9.0 Hz, 2H), 6.46 (d, J = 7.5 Hz, 1H), 6.23-6.15 (m, 2H), 5.81 (s, 1H), 5.72 (s, 1H), 4.24-4.08 (m, 2H), 2.94 (s, 1H), 2.80 (s, 1H), 2.68-2.56 (m, 2H), 2.37 (d, J = 7.5 Hz, 1H), 2.25-2.10 (m, 6H), 1.96-1.86 (m, 3H), 1.82-1.69 (m, 3H), 1.53 (d, J = 9.3 Hz, 1H); LCMS: purity: 98%; MS (m/e): 454 (MH$^+$). | +++ | +++ |
| 147 | LCMS: purity: 95%; MS (m/e): 468 (MH$^+$). | +++ | +++ |
| 148 | 1H NMR (DMSO-d6): δ 9.53 (s, 1H), 8.18 (d, J = 2.7 Hz, 1H), 7.94 (d, J = 3.6 Hz, 1H), 7.76-7.69 (m, 1H), 7.67-7.62 (m, 1H), 7.61 (d, J = 2.7 and 9.3 Hz, 1H), 7.40 (dd, J = 1.2 and 9.0 Hz, 1H), 7.23 (s, 1H), 6.36-6.28 (m, 2H), 4.09 (t, J = 7.8 Hz, 1H), 2.87 (s, 1H), 2.80 (s, 1H), 2.53 (d, J = 8.1 Hz, 1H), 2.12 (d, J = 8.7 Hz, 1H), 1.41 (d, J = 9.3 Hz, 1H); LCMS: purity: 94%; MS (m/e): 459 (MH$^+$). | + | + |
| 149 | 1H NMR (CDCl$_3$): δ 7.73 (dd, J = 1.2 and 3.3 Hz, 1H), 7.50-7.45 (m, 1H), 7.25-7.17 (m, 1H), 7.15 (t, J = 7.8 Hz, 1H), 6.94 (dd, J = 1.2 and 7.8 Hz, 1H), 6.64-6.55 (m, 1H), 6.51 (dd, J = 2.4 and 8.1 Hz, 1H), 6.42-6.37 (m, 1H), 6.28-6.24 (m, 1H), 5.91-5.68 (m, 2H), 4.37-4.26 (m, 2H), 3.04 (bs, 1H), 2.91 (bs, 1H), 2.79-2.67 (m, 2H), 2.52 (d, J = 8.1 Hz, 1H), 2.39-2.27 (m, 5H), 2.24 (d, J = 9.3 Hz, 1H), 2.09-1.97 (m, 2H), 1.94-1.78 (m,2H ), 1.62 (d, J = 9.3 Hz, 1H); LCMS: purity: 98%; MS (m/e): 454 (MH$^+$). | +++ | +++ |
| 150 | 1H NMR (DMSO-d6): δ 8.79 (s, 1H), 7.82 (d, J = 3.6 Hz, 1H), 7.67 (s, 1H), 7.44 (d, J = 2.4 Hz, 1H), 7.40 (dd, J = 2.7 and 8.7 Hz, 1H), 7.34 (d, J = 7.2 Hz, 1H), 7.18 (s, 1H), 6.82 (d, J = 8.7 Hz, 1H), 6.34-6.30 (m, 1H), 6.27-6.22 (m, 1H), 4.27-4.18 (m, 1H), 4.10 (t, J = 7.8 Hz, 1H), 2.85 (s, 1H), 2.77 (s, 1H), 2.60-2.49 (m, 3H), 2.23-2.09 (m, 3H), 2.16 (s, 3H), 2.12 (s, 3H), 1.92-1.80 (m, 2H), 1.71-1.57 (m, 2H), 1.40 (d, J = 8.7 Hz, 1H); LCMS purity: 98%; MS (m/e): 468 (MH$^+$). | +++ | +++ |
| 151 | 1H NMR (CDCl$_3$): δ 7.93 (d, J = 2.4 Hz, 1H), 7.60 (d, J = 3.3 Hz, 1H), 7.48-7.41 (m, 1H), 7.35 (dd, J = 2.7 and 9.0 Hz, 1H), 6.82 (d, J = 8.7 Hz, 1H), 6.45 (d, J =0 8.7 Hz, 1H), 6.22-6.14 (m, 2H), 5.95 (s, 1H), 5.69 (s, 1H), 4.38-4.29 (m, 1H), 4.25 (t, J = 7.8 Hz, 1H), 2.95 (s, 1H), 2.75 (s, 1H), 2.62-2.49 (m, 2H), 2.40 (d, J = 7.8 Hz, 1H), 2.35-2.22 (m, 3H), 2.22 (s, 3H), 2.14 (d, J = 9.0 Hz, 1H), 1.97-1.78 (m, 4H), 1.53 (d, J = 9.6 Hz, 1H); LCMS: purity: 97%; MS (m/e): 521 (MH$^+$). | +++ | +++ |
| 152 | 1H NMR (CDCl$_3$): δ 7.84 (d, J = 2.1 Hz, 1H), 7.64 (d, J = 2.7 Hz, 1H), 7.04 (dd, J = 2.7 and 9.0 Hz, 1H), 6.85 (s, 1H), 6.81 (d, J = 8.7 Hz, 1H), 6.48 (d, J = 7.8 Hz, 1H), 6.34-6.29 (m, 1H), 6.23-6.17 (m, 1H), 5.56 (s, 1H), 5.47 (s, 1H), 4.25 (t, J = 7.8 Hz, 1H), 4.24-4.14 (m, 1H), 2.97 (s, 1H), 2.81 (s, 1H), 2.73-2.60 (m, 2H), 2.43 (d, J = 8.1 Hz, 1H), 2.33-2.22 (m, 2H), 2.26 (s, 3H), 2.16 (d, J = 9.0 Hz, 1H), 2.00-1.81 (m, 5H), 1.55 (d, J = 9.0 Hz, 1H),; LCMS: purity: 98%; MS (m/e): 488 (MH$^+$). | +++ | +++ |
| 153 | 1H NMR (CDCl$_3$): δ 7.69 (d, J = 3.6 Hz, 1H), 7.32-7.25 (m, 2H), 6.90 (s, 1H), 6.71 (d, J = 9.6 Hz, 1H), 6.33 (d, J = 8.4 Hz, 1H), 6.29-6.24 (m, 2H), 5.72 (s, 1H), 5.67 (s, 1H), 4.32 (t, J = 7.5 Hz, 1H), 3.78 (d, J = 5.7 Hz, 2H), 3.06-2.85 (m, 5H), 2.46 (d, J = 7.8 Hz, 1H), 2.33 (s, 3H), 2.21 (s, 3H), 2.04 (t, J = 11.7 Hz, 2H), 1.91-1.72 (m, 3H), 1.61 (d, J = 9.3 Hz, 1H), 1.52 (dt, J = 3.6 and 12.3 Hz, 2H); LCMS: purity: 97%; MS (m/e): 481 (MH$^+$) | +++ | +++ |
| 154 | LCMS: purity: 99%; MS (m/e): 452 (MH+) | ++ | ++ |
| 155 | LCMS: purity: 99%; MS (m/e): 452 (MH+) | + | + |
| 156 | 1H NMR (CDCl$_3$): δ 7.72 (d, 1H, J = 3.3 Hz), 7.03 (d, 1H, J = 1.8 Hz), 6.96 (d, 1H, J = 7.8 Hz), 6.87 (s, 1H), 6.75 (dd, 1H, J = 1.8 and 7.6 Hz), 5.71 (d, 1H, J = 7.5 Hz), 5.52 (s, 1H), 5.36 (s, 1H), 4.56 (m, 1H), 4.21 (m, 1H), 3.55 (t, 2H, J = 8.7 Hz), 2.98 (q, 2H, J = 8.4 Hz), 2.01 (m, 4H); LCMS: purity: 89%; MS (m/e): 357 (MH+) | + | + |
| 157 | 1H NMR (CDCl$_3$): δ 7.71 (d, 1H, J = 3.3 Hz), 7.01 (d, 1H, J = 1.8 Hz), 6.98 (d, 1H, J = 7.8 Hz), 6.87 (s, 1H), 6.75 (dd, 1H, J = 1.8 and 7.6 Hz), 5.71 (d, 1H, J = 7.5 Hz), 5.52 (s, 1H), 5.36 (s, 1H), 4.56 (m, 1H), 4.21 (m, 1H), 3.55 (t, 2H, J = 8.7 Hz), 2.98 (q, 2H, J = 8.4 Hz), 2.01 (m, 4H); LCMS: purity: 90%; MS (m/e): 357 (MH+) | + | + |
| 158 | 1H NMR (CDCl$_3$): δ 8.46 (s, 1H), 7.68 (d, 1H, J = 3.3 Hz), 7.33-7.40 (m, 2H), 7.07 (s, 1H), 6.98 (d, 1H, J = 8.4 Hz), 5.83 (d, 1H, J = 6.9 Hz), 5.59 (s, 1H), 4.54 (q, 1H, J = 6.9 Hz), 3.05-2.88 (m, 2H), 2.96 (t, 2H, J = 4.8 Hz), 2.78 (bs, 3H), 2.47 (s, 3H), 2.42 (s, 4H), 2.29 (s, 3H), 2.12 (m, 2H), 1.95 (m, 2H), 1.64 (m, 1H), 0.73 (m, 1H), 0.39 (m, 2H), 0.06 (m, 2H); LCMS: purity: 94%; MS (m/e): 482 (MH+) | ++ | + |
| 159 | 1H NMR (CDCl$_3$): δ 8.45 (s, 1H), 7.68 (d, 1H, J = 3.6 Hz), 7.59 (bs, 1H), 7.38 (m, 2H), 6.98 (d, 1H, J = 9.6 Hz), 5.98 (d, 1H, J = 6.9 Hz), 5.70 (s, 1H), 4.53 (q, 1H, J = 7.2 Hz), 3.03 (t, 3H, J = 4.5 Hz), 2.92-2.79 (m, 4H), 2.58 (m, 1H), 2.56 (s, 3H), 2.27 (s, 3H), 2.09 (m, 3H), 1.94 (m, 3H), 1.63 (m, 1H), 1.26 (m, 1H), 0.68 (m, 2H), 0.27 (m, 2H); LCMS: purity: 97%; MS (m/e): 468 (MH+) | ++ | ++ |
| 160 | 1H NMR (CDCl$_3$): δ 8.46 (s, 1H), 7.99 (bs, 1H), 7.61 (d, 1H, J = 3.6 Hz), 7.28 (m, 2H), 6.75 (d, 1H, J = 7.8 Hz), 6.45 (d, 1H, J = 8.4 Hz), 6.27 (m, 2H), 5.81 (s, 1H), 5.45 (s, 1H), 4.26 (t, 1H, J = 8.1 Hz), 3.32 (m, 4H), 3.03 (s, 1H), 2.94 | ++ | +++ |

| | | | |
|---|---|---|---|
| | (t, 2H, J = 7.8 Hz), 2.86 (t, 2H, J = 6.9 Hz), 2.56 (s, 6H), 2.47 (d, 1H, J = 8.1 Hz), 2.19 (d, 1H, J = 9 Hz), 1.62 (d, 1H, J = 9 Hz); LCMS: purity: 99%; MS (m/e): 452 (MH+) | | |
| 161 | 1H NMR (CDCl₃): δ 7.89 (s, 1H), 7.71 (d, 1H, J = 3.6 Hz), 7.51 (m, 1H), 7.23 (d, 2H, J = 4.8 Hz), 7.01 (d, 1H, J = 3.0 Hz), 6.38 (d, 1H, J = 3.0 Hz), 6.30 (m, 2H), 5.54 (s, 1H), 5.28 (s, 1H), 4.33 (m, 2H), 3.77 (s, 3H), 3.04 (s, 1H), 2.90 (s, 1H), 2.46 (d, 1H, J = 8.4 Hz), 2.21 (d, 1H, J = 9.3 Hz); LCMS: purity: 90%; MS (m/e): 393 (MH+) | ++ | ++ |
| 162 | 1H NMR (CDCl₃): δ 7.70 (d, 1H, J = 2.4 Hz), 7.35 (s, 1H), 7.33 (d, 1H, J = 7.8 Hz), 6.97 (d, 1H, J = 8.1 Hz), 6.72 (s, 1H), 6.27 (bs, 2H), 6.12 (d, 1H, J = 7.5 Hz), 5.38 (d, 1H, J = 8.4 Hz), 4.30 (t, 1H, J = 9 Hz), 3.95 (m, 1H), 2.90 (m, 6H), 2.57 (bs, 4H), 2.36 (s, 3H), 2.28 (t, 5H, J = 7.8 Hz), 1.62 (d, 1H, J = 9.6 Hz), 1.03 (d, 3H, J = 6.3 Hz), 0.87 (d, 3H, J = 6.3 Hz); LCMS: purity: 94%; MS (m/e): 494 (MH+) | +++ | +++ |
| 163 | 1H NMR (CDCl₃): δ 7.78 (s, 1H), 7.75 (d, 1H, J = 3 Hz), 7.47 (d, 1H, J = 8.7 Hz), 7.07 (dd, 1H, J = 1.8 and 8.2 Hz), 7.04 (d, 1H, J = 3 Hz), 6.99 (s, 1H), 6.41 (d, 1H, J = 3.4 Hz), 6.26 (m, 2H), 6.06 (d, 1H, J = 8.1 Hz), 5.81 (s, 1H), 5.38 (s, 1H), 4.42 (t, 1H, J = 8.1 Hz), 4.15 (t, 2H, J = 7.2 Hz), 3.03 (s, 1H), 2.83 (s, 1H), 2.68 (m, 2H), 2.50 (d, 1H, J = 7.8 Hz), 2.28 (s, 6H), 2.24 (d, 1H, J = 9.3 Hz), 1.63 (d, 1H, J = 9.3 Hz); LCMS: purity: 92%; MS (m/e): 450 (MH+) | ++ | ++ |
| 164 | 1H NMR (CDCl₃): δ 7.72 (d, 1H, J = 3.3 Hz), 7.34 (m,2 H), 6.97 (d, 1H, J = 9.3 Hz), 6.68 (s, 1H), 6.26 (m, 2H), 6.11 (d, 1H, J = 7.5 Hz), 5.66 (s, 1H), 4.29 (t, 1H, J = 7.5 Hz), 2.90 (m, 6H), 2.57 (m, 4H), 2.36 (s, 3H), 2.28 (s, 3H), 2.25 (m, 2H), 1.62 (d, 1H, J = 9.6 Hz), 1.25 (m, 1H), 0.66 (m, 2H), 0.24 (m, 2H); LCMS: purity: 90%; MS (m/e): 492 (MH+) | +++ | +++ |
| 165 | 1H NMR (CDCl₃, 300 MHz): δ 7.71 (d, 1H, J = 3 Hz), 7.34 (m, 2H), 6.98 (d, 1H, J = 7.8 Hz), 6.68 (s, 1H), 6.27 (m, 2H), 6.01 (d, 1H, J = 7.5 Hz), 5.67 (d, 1H, J = 7.8 Hz), 4.28 (m, 2H), 2.91 (m, 6H), 2.58 (s, 4H), 2.36 (s, 3H), 2.29 (s, 3H), 2.25 (m, 2H), 1.62 (m, 7H); LCMS: purity: 97%; MS (m/e): 506 (MH+) | +++ | +++ |
| 166 | 1H NMR (CDCl₃): δ 7.71 (d, 1H, J = 3.0 Hz), 7.36 (d, 1H, J = 8.7 Hz), 7.32 (s, 1H), 6.97 (d, 1H, J = 8.1 Hz), 6.69 (s, 1H), 6.44 (d, 1H, J = 8.7 Hz), 6.27 (m, 2H), 5.56 (s, 1H), 4.29 (t, 1H, J = 8.1 Hz), 2.90 (m, 6H), 2.71 (d, 3H, J = 4.8 Hz), 2.57 (s, 4H), 2.35 (s, 3H), 2.28 (s, 3H), 1.61 (d, 1H, J = 9.0 Hz), 0.96 (d, 1H, J = 6.3 Hz), 0.88 (m, 1H); LCMS: purity: 92%; MS (m/e): 466 (MH+) | +++ | +++ |
| 167 | ¹H NMR (CDCl₃): δ 7.71 (d, 1H, J = 3.0 Hz), 7.34 (m, 2H), 6.97 (d, 1H, J = 9 Hz), 6.67 (s, 1H), 6.27 (m, 3H), 6.28 (m, 3H), 5.53 (s, 1H), 4.31 (t, 1H, J = 9.6 Hz), 3.18 (m, 2H), 2.90 (m, 5H), 2.57 (s, 4H), 2.38 (s, 3H), 2.31 (m, 2H), 2.28 (s, 3H), 1.62 (m, 2H), 0.97 (t, 3H, J = 5.1 Hz); LCMS: purity: 96%; MS (m/e): 480 (MH⁺) | +++ | +++ |
| 168 | 1H NMR (CDCl₃): δ 7.71 (d, 1H, J = 3.0 Hz), 7.36 (m, 2H), 6.97 (d, 1H, J = 8.1 Hz), 6.69 (s, 1H), 6.44 (d, 1H, J = 8.1 Hz), 6.67 (s, 1H), 6.28 (m, 3H), 5.56 (t, 1H, J = 6.5 Hz), 4.31 (t, 1H, J = 7.5 Hz), 3.11 (m, 2H), 2.91 (m, 5H), 2.58 (s, 4H), 2.36 (s, 3H), 2.33 (m, 1H), 2.26 (s, 3H), 1.62 (m, 2H), 1.37 (m, 3H), 0.82 (t, 3H, J = 7.8 Hz); LCMS: purity: 92%; MS (m/e): 494 (MH+) | +++ | +++ |
| 169 | 1H NMR (CDCl₃): δ 7.75 (m, 2H), 7.48 (d, 1H, J = 8.4 Hz), 7.06 (m, 2H), 6.91 (s, 1H), 6.41 (d, 1H, J = 3.3 Hz), 6.25 (m, 2H), 5.90 (d, 1H, J = 9 Hz), 5.81 (s, 1H), 4.35 (t, 1H, J = 8.1 Hz), 4.15 (t, 2H, J = 7.2 Hz), 2.99 (s, 1H), 2.83 (s, 1H), 2.67 (m, 2H), 2.54 (m, 1H), 2.35 (d, 1H, J = 8.4 Hz), 2.28 (s, 6H), 1.64 (m, 1H), 0.96 (d, 1H, J = 6.3 Hz), 0.63 (m, 2H), 0.19 (m, 2H); LCMS: purity: 97%; MS (m/e): 490 (MH+) | +++ | ++ |
| 170 | 1H NMR (CDCl₃): δ 7.69 (d, 1H, J = 3.3 Hz), 7.26 (s, 1H), 7.11 (d, 1H, J = 9.3 Hz), 6.57 (s, 1H), 6.42 (d, 1H, J = 8.4 Hz), 6.24 (m, 2H), 5.94 (m, 1H, J = 7.2 Hz), 5.66 (s, 1H), 4.24 (t, 1H, J = 8.1 Hz), 3.34 (t, 2H, J = 8.1 Hz), 3.15 (t, 2H, J = 6.9 Hz), 2.95 (m, 3H), 2.82 (s, 1H), 2.53 (t, 2H, J = 6.9 Hz), 2.56 (s, 6H), 1.73 (s, 2H), 1.62 (d, 1H, J = 9.6 Hz), 0.97 (d, 1H, J = 6.6 Hz), 0.65 (m, 2H), 0.23 (m, 2H); LCMS: purity: 94%; MS (m/e): 492 (MH+) | +++ | +++ |
| 171 | LCMS: purity: 94%; MS (m/e): 453 (MH+) | ++ | ++ |
| 172 | 1H NMR (CDCl₃): δ 7.77 (s, 1H), 7.74 (d, 1H, J = 3.3 Hz), 7.49 (d, 1H, J = 8.4 Hz), 7.10 (dd, 1H, J = 1.8 and 8.1 Hz), 7.05 (d, 1H, J = 3.3 Hz), 6.94 (s, 1H), 6.42 (d, 1H, J = 3.3 Hz), 6.25 (m, 2H), 5.85 (d, 1H, J = 8.1 Hz), 5.73 (d, 1H, J = 7.5 Hz), 4.36 (t, 1H, J = 8.1 Hz), 4.20 (m, 1H), 4.15 (t, 2H, J = 7.5 Hz), 2.99 (s, 1H), 2.83 (s, 1H), 2.68 (t, 2H, J = 6.6 Hz), 2.37 (d, 1H, J = 8.1 Hz), 2.28 (s, 6H), 1.73 (m, 2H), 1.60 (m, 6H); LCMS: purity: 93%; MS (m/e): 504 (MH+) | ++ | ++ |
| 173 | 1H NMR (CDCl₃): δ 7.76 (s, 1H), 7.74 (d, 1H, J = 3.3 Hz), 7.48 (d, 1H, J = 8.4 Hz), 7.11 (dd, 1H, J = 1.8 and 8.4 Hz), 7.06 (d, 1H, J = 3.0 Hz), 6.89 (s, 1H), 6.42 (d, 1H, J = 3.3 Hz), 6.26 (q, 2H, J = 3 Hz), 5.95 (d, 1H, J = 7.8 Hz), 5.41 (d, 1H, J = 7.8 Hz), 4.35 (t, 1H, J = 9.6 Hz), 4.16 (t, 2H, J = 6.9 Hz), 3.94 (m, 1H), 2.99 (s, 1H), 2.83 (s, 1H), 2.68 (t, 2H, J = 7.2 Hz), 2.35 (d, 1H, J = 6.6 Hz), 2.32 (s, 6H), 1.64 (d, 2H, J = 9.3 Hz), 1.01 (d, 3H, J = 6.9 Hz), 0.86 (d, 3H, J = 6.9 Hz); LCMS: purity: 92%; MS (m/e): 492 (MH+) | ++ | ++ |
| 174 | 1H NMR (CDCl₃): δ 7.68 (d, 1H, J = 3.3 Hz), 7.29 (s, 1H), 7.13 (d, 1H, J = 8.1 Hz), 6.63 (s, 1H), 6.42 (d, 1H, J = 8.1 Hz), 6.27 (m, 2H), 6.15 (d, 1H, J = 6.5 Hz), 5.54 (s, 1H), 5.28 (s, 1H), 4.31 (t, 1H, J = 9.0 Hz), 3.26 (t, 2H, J = 8.1 Hz), 3.03 (s, 1H), 2.92 (t, 2H, J = 7.8 Hz), 2.85 (s, 1H), 2.73 (s, 3H), 2.44 (d, 1H, J = 7.8 Hz), 1.63 (m, 2H); LCMS: purity: 90%; MS (m/e): 395 (MH+) | ++ | ++ |

TABLE 1-continued

| | | | |
|---|---|---|---|
| 175 | 1H NMR (CDCl₃): δ 7.88 (s, 1H), 7.72 (bs, 1H), 7.24 (m, 2H), 7.09 (d, 1H, J = 3.0 Hz), 6.83 (s, 1H), 6.38 (d, 1H, J = 2.7 Hz), 5.30 (m, 1H), 6.24 (m, 1H), 5.99 (d, 1H, J = 7.8 Hz), 5.64 (s, 1H), 4.30 (t, 1H, J = 8.7 Hz), 4.20 (t, 2H, J = 7.2 Hz), 2.98 (s, 1H), 2.86 (s, 1H), 2.69 (t, 2H, J = 6.6 Hz), 2.55 (m, 1H), 2.32 (s, 6H), 1.66 (m, 3H), 0.64 (m, 2H), 0.20 (m, 2H); LCMS: purity: 90%; MS (m/e): 490 (MH+) | +++ | +++ |
| 176 | 1H NMR (CDCl₃): δ 7.68 (d, 1H, J = 3.3 Hz), 7.28 (s, 1H), 7.12 (dd, 1H, J = 2.1 and 8.1 Hz), 6.55 (s, 1H), 6.43 (d, 1H, J = 8.4 Hz), 6.25 (m, 2H), 5.87 (d, 1H, J = 7.5 Hz), 5.67 (d, 1H, J = 8.1 Hz), 4.24 (m, 2H), 3.35 (t, 2H, J = 8.1 Hz), 3.16 (t, 2H, J = 7.5 Hz), 2.99 (s, 1H), 2.94 (t, 2H, J = 8.1 Hz), 2.82 (s, 1H), 2.54 (t, 2H, J = 6.9 Hz), 2.31 (s, 6H), 2.29 (m, 1H), 2.23 (d, 1H, J = 9.3 Hz), 1.63 (m, 7H); LCMS: purity: 93%; MS (m/e): 466 (MH+) | +++ | +++ |
| 177 | 1H NMR (CDCl₃): δ 7.68 (d, 1H, J = 3.6 Hz), 7.27 (bs, 1H), 7.12 (dd, 1H, J = 2.1 and 8.2 Hz), 6.57 (s, 1H), 6.42 (d, 1H, J = 8.4 Hz), 6.26 (m, 3H), 5.58 (s, 1H), 4.25 (t, 1H, J = 7.4 Hz), 3.34 (t, 2H, J = 8.1 Hz), 3.15 (t, 2H, J = 7.5 Hz), 2.96 (s, 1H), 2.94 (t, 2H, J = 8.1 Hz), 2.84 (s, 1H), 2.69 (d, 3H, J = 5.1 Hz), 2.53 (t, 2H, J = 7.2 Hz), 2.28 (m, 1H), 2.27 (s, 6H), 1.60 (d, 1H, J = 9.0 Hz), 0.98 (d, 1H, J = 7.8 Hz); LCMS: purity: 93%; MS (m/e): 466 (MH+) | +++ | ++ |
| 178 | 1H NMR (CDCl₃): δ 7.68 (d, 1H, J = 3.0 Hz), 7.29 (s, 1H), 7.10 (d, 1H, J = 7.8 Hz), 6.59 (s, 1H), 6.42 (d, 1H, J = 8.7 Hz), 5.96 (d, 1H, J = 7.2 Hz), 5.61 (s, 1H), 4.25 (t, 1H, J = 8.1 Hz), 3.34 (t, 2H, J = 7.4 Hz), 3.15 (t, 2H, J = 6.9 Hz), 2.95 (t, 2H, J = 8.1 Hz), 2.53 (m, 3H), 2.31 (s, 6H), 2.09 (d, 1H, J = 10.2 Hz), 1.60 (m, 2H), 1.26 (m, 4H), 0.87 (m, 3H), 0.63 (m, 2H); LCMS: purity: 93%; MS (m/e): 494 (MH+) | +++ | +++ |
| 179 | 1H NMR (CDCl₃): δ 7.72 (m, 2H), 7.48 (d, 1H, J = 8.4 Hz), 7.14 (d, 1H, J = 8.7 Hz), 7.05 (d, 1H, J = 7.8 Hz), 6.92 (s, 1H), 6.42 (d, 1H, J = 3.3 Hz), 5.90 (d, 1H, J = 8.4 Hz), 5.74 (s, 1H), 4.35 (t, 1H, J = 8.1 Hz), 4.19 (t, 2H, J = 6.9 Hz), 2.70 (t, 2H, J = 7.8 Hz), 2.49 (s, 2H), 2.38 (d, 1H, J = 8.4 Hz), 2.38 (s, 6H), 2.13 (d, 1H, J = 9.9 Hz), 1.61 (m, 1H), 1.29 (m, 4H), 0.62 (m, 2H), 0.17 (m, 2H); LCMS: purity: 96%; MS (m/e): 492 (MH+ | ++ | ++ |
| 180 | 1H NMR (CDCl₃): δ 7.71 (d, 1H, J = 3.0 Hz), 7.55 (s, 1H), 7.30 (m, 2H), 6.78 (s, 1H), 6.44 (d, 1H, J = 6.0 Hz), 5.66 (s, 1H), 4.24 (t, 1H, J = 7.8 Hz), 3.96 (t, 2H, J = 8.1 Hz), 3.13 (t, 2H, J = 8.4 Hz), 2.82 (s, 3H), 2.58 (m, 1H), 2.46 (s, 1H), 2.35 (d, 1H, J = 8.7 Hz), 2.31 (m, 1H), 2.12 (d, 1H, J = 10.2 Hz), 1.66 (d, 1H, J = 6.0 Hz), 1.27 (m, 4H), 0.69 (d, 2H, J = 7.2 Hz), 0.29 (m, 2H); LCMS: purity: 99%; MS (m/e): 501 (MH+) | +++ | +++ |
| 181 | 1H NMR (CDCl₃): δ 7.72 (d, 1H, J = 3.3 Hz), 7.53 (s, 1H), 7.31 (d, 2H, J = 1.2 Hz), 6.74 (m, 1H), 6.27 (m, 2H), 5.62 (bs, 1H), 4.24 (t, 1H, J = 7.5 Hz), 3.97 (t, 2H, J = 8.4 Hz), 3.13 (t, 2H, J = 8.4 Hz), 2.98 (s, 1H), 2.87 (s, 1H), 2.82 (s, 3H), 2.76 (d, 3H, J = 4.8 Hz), 2.36 (d, 1H, J = 9.6 Hz), 2.27 (d, 1H, J = 9.0 Hz), 1.61 (d, 1H, J = 9.3 Hz); LCMS: purity: 95%; MS (m/e): 473 (MH+) | +++ | +++ |
| 182 | 1H NMR (CDCl₃): δ 7.71 (d, 1H, J = 3.0 Hz), 7.53 (s, 1H), 7.30 (s, 2H), 6.85 (s, 1H), 6.58 (d, 1H, J = 7.2 Hz), 6.27 (bs, 2H), 5.64 (bs, 1H), 4.25 (t, 1H, J = 8.4 Hz), 3.96 (t, 2H, J = 8.4 Hz), 3.22 (m, 2H), 3.12 (t, 2H, J = 8.7 Hz), 2.98 (s, 1H), 2.86 (s, 1H), 2.82 (s, 3H), 2.34 (d, 1H, J = 8.1 Hz), 2.27 (d, 1H, J = 9 Hz), 1.61 (d, 1H, J = 9.0 Hz), 1.02 (t, 3H, J = 7.5 Hz); LCMS: purity: 98%; MS (m/e): 487 (MH+) | +++ | +++ |
| 183 | 1H NMR (CDCl₃): δ 7.88 (s, 1H), 7.71 (s, 2H), 7.09 (d, 2H, J = 2.7 Hz), 6.83 (s, 1H), 6.38 (m, 2H), 6.32 (s, 1H), 6.24 (s, 1H), 5.53 (s, 1H), 4.31 (t, 1H, J = 7.5 Hz), 4.20 (t, 2H, J = 6.6 Hz), 2.97 (s, 1H), 2.89 (s, 1H), 2.68 (m, 4H), 2.34 (m, 2H), 2.29 (s, 6H), 1.68 (m, 1H), 1.28 (bs, 1H); LCMS: purity: 90%; MS (m/e): 464 (MH+) | +++ | +++ |
| 184 | 1H NMR (CDCl₃): δ 7.68 (d, 1H, J = 3.3 Hz), 7.18 (d, 1H, J = 2.4 Hz), 6.84 (dd, 1H, J = 2.4 and 8.5 Hz), 6.60 (d, 2H, J = 8.4 Hz), 6.36 (dd, 2H, J = 2.6 and 5.7 Hz), 6.24 (dd, 1H, J = 2.7 and 5.8 Hz), 5.60 (bs, 1H), 4.24 (m, 3H), 3.24 (m, 3H), 3.18 (m, 2H), 2.97 (s, 1H), 2.87 (s, 1H), 2.49 (t, 2H, J = 7.5 Hz), 2.32 (m, 1H), 2.28 (s, 6H), 1.71 (s, 1H), 1.61 (d, 1H, J = 9.0 Hz), 0.98 (t, 3H, J = 7.2 Hz); LCMS: purity: 94%; MS (m/e): 496 (MH+) | +++ | +++ |
| 185 | 1H NMR (CDCl₃): δ 7.68 (d, 1H, J = 3.3 Hz), 7.20 (d, 1H, J = 2.4 Hz), 6.83 (dd, 1H, J = 2.1 and 8.7 Hz), 6.66 (bs, 1H), 6.60 (d, 1H, J = 7.5 Hz), 6.46 (d, 1H, J = 8.1 Hz), 6.38 (dd, 1H, J = 2.7 and 5.7 Hz), 6.21 (dd, 1H, J = 2.7 and 5.8 Hz), 5.66 (s, 1H), 4.22 (m, 3H), 3.33 (m, 4H), 2.96 (s, 1H), 2.89 (s, 1H), 2.71 (d, 3H, J = 4.5 Hz), 2.49 (t, 2H, J = 7.5 Hz), 2.33 (m, 1H), 2.28 (s, 6H), 1.58 (d, 1H, J = 9.6 Hz), 1.26 (d, 1H, J = 2.7 Hz); LCMS: purity: 96%; MS (m/e): 482 (MH+) | +++ | +++ |
| 186 | 1H NMR (CDCl₃): δ 7.64 (s, 1H), 7.62 (d, 1H, J = 3.3 Hz), 7.28 (s, 1H), 7.21 (dd, 1H, J = 1.8 and 8.5 Hz), 6.53 (d, 1H, J = 7.5 Hz), 6.44 (d, 1H, J = 8.4 Hz), 6.26 (m, 2H), 5.72 (s, 1H), 5.51 (s, 1H), 4.27 (t, 1H, J = 8.1 Hz), 3.31 (m, 4H), 3.02 (s, 1H), 2.93 (t, 2H, J = 8.1 Hz), 2.86 (s, 1H), 2.78 (t, 2H, J = 7.2 Hz), 2.48 (s, 6H), 2.45 (d, 1H, J = 9.0 Hz), 2.20 (d, 1H, J = 9 Hz), 1.61 (d, 1H, J = 9.3 Hz); LCMS: purity: 100%; MS (m/e): 452 (MH+) | +++ | +++ |
| 187 | 1H NMR (CDCl₃): δ 7.62 (d, 1H, J = 3.3 Hz), 7.58 (s, 1H), 7.29 (s, 1H), 7.21 (dd, 1H, J = 1.8 and 8.5 Hz), 6.51 (d, 1H, J = 7.5 Hz), 6.44 (d, 1H, J = 8.4 Hz), 6.26 (m, 2H), 5.72 (s, 1H), 5.51 (s, 1H), 4.27 (t, 1H, J = 8.1 Hz), 3.31 (m, 4H), 3.02 (s, 1H), 2.93 (t, 2H, J = 8.1 Hz), 2.86 (s, 1H), 2.78 (t, 2H, J = 7.2 Hz), 2.48 (s, 6H), 2.45 (d, 1H, J = 9.0 Hz), 2.20 (d, 1H, J = 9 Hz), 1.61 (d, 1H, J = 9.3 Hz); LCMS: purity: 97%; MS (m/e): 452 (MH+) | + | + |
| 188 | 1H NMR (CDCl₃ + CD₃OD): δ 7.66 (d, 1H, J = 3.3 Hz), 7.51 (s, 1H), 7.39 (dd, 1H, J = 2.1 and 9.7 Hz), 7.28 (d, 1H, J = 8.7 Hz), 6.29 (q, 2H, J = 2.7 | +++ | +++ |

TABLE 1-continued

| | | | |
|---|---|---|---|
| | Hz), 4.21 (d, 1H, J = 8.4 Hz), 3.98 (t, 2H, J = 8.4 Hz), 3.35 (s, 1H), 3.15 (t, 2H, J = 8.1 Hz), 3.01 (s, 1 H), 2.89 (s, 1H), 2.85 (s, 3H), 2.53 (d, 1H, J = 8.4 Hz), 2.19 (d, 1H, J = 8.7 Hz), 1.60 (d, 1H, J = 9 Hz); LCMS: purity: 98%; MS (m/e): 459 (MH+) | | |
| 189 | 1H NMR (CDCl$_3$): δ 7.69 (d, 1H, J = 3.0 Hz), 7.20 (d, 1H, J = 2.1 Hz), 6.83 (dd, 1H, J = 1.5 and 8.8 Hz), 6.61 (m, 2H), 6.38 (m, 1H), 6.24 (m, 2H), 5.63 (s, 1H), 5.36 (s, 1H), 4.31 (t, 1H, J = 8.1 Hz), 4.22 (t, 1H, J = 3.9 Hz), 3.34 (t, 3H, J = 6.6 Hz), 3.30 (s, 1H), 2.89 (s, 1H), 2.50 (m, 2H), 2.28 (s, 6H), 2.21 (d, 1H, J = 9.3 Hz), 1.68 (s, 2H), 1.60 (d, 1H, J = 9 Hz); LCMS: purity: 93%; MS (m/e): 468 (MH+) | +++ | +++ |
| 190 | 1H NMR (CDCl$_3$): δ 7.72 (d, 1H, J = 3.3 Hz), 7.34 (m, 2H), 6.97 (d, 1H, J = 9.3 Hz), 6.68 (s, 1H), 6.26 (m, 2H), 6.11 (d, 1H, J = 7.5 Hz), 5.66 (s, 1H), 4.29 (t, 1H, J = 7.5 Hz), 2.90 (m, 6H), 2.57 (m, 4H), 2.36 (s, 3H), 2.28 (s, 3H), 2.25 (m, 2H), 1.62 (d, 1H, J = 9.6 Hz), 1.25 (m, 1H), 0.66 (m, 2H), 0.24 (m, 2H); LCMS: purity: 98%; MS (m/e): 492 (MH+) | ++++ | ++ |
| 191 | 1H NMR (CDCl$_3$): δ 7.72 (d, 1H, J = 3.3 Hz), 7.34 (m, 2H), 6.97 (d, 1H, J = 9.3 Hz), 6.68 (s, 1H), 6.26 (m, 2H), 6.11 (d, 1H, J = 7.5 Hz), 5.66 (s, 1H), 4.29 (t, 1H, J = 7.5 Hz), 2.90 (m, 6H), 2.57 (m, 4H), 2.36 (s, 3H), 2.28 (s, 3H), 2.25 (m, 2H), 1.62 (d, 1H, J = 9.6 Hz), 1.25 (m, 1H), 0.66 (m, 2H), 0.24 (m, 2H); LCMS: purity: 95%; MS (m/e): 492 (MH+) | ++ | + |
| 192 | 1H NMR (CDCl$_3$, 300 MHz): δ 7.71 (d, 1H, J = 3 Hz), 7.34 (m, 2H), 6.98 (d, 1H, J = 7.8 Hz), 6.68 (s, 1H), 6.27 (m, 2H), 6.01 (d, 1H, J = 7.5 Hz), 5.67 (d, 1H, J = 7.8 Hz), 4.28 (m, 2H), 2.91(m, 6H), 2.58 (m, 4H), 2.36 (s, 3H), 2.29 (s, 3H), 2.25 (m, 2H), 1.62 (m, 7H); LCMS: purity: 100%; MS (m/e): 506 (MH+) | +++ | +++ |
| 193 | 1H NMR (CDCl$_3$, 300 MHz): δ 7.71 (d, 1H, J = 3 Hz), 7.34 (m, 2H), 6.98 (d, 1H, J = 7.8 Hz), 6.68 (s, 1H), 6.27 (m, 2H), 6.01 (d, 1H, J = 7.5 Hz), 5.67 (d, 1H, J = 7.8 Hz), 4.28 (m, 2H), 2.91 (m, 6H), 2.58 (m, 4H), 2.36 (s, 3H), 2.29 (s, 3H), 2.25 (m, 2H), 1.62 (m, 7H); LCMS: purity: 99%; MS (m/e): 506 (MH+) | − | + |
| 194 | 1H NMR (DMSO-d6): d 1.57 (m, 1H), 1.88 (m, 5H), 2.20 (s, 3H), 2.43 (t, J = 4.8 Hz, 4H), 2.89 (q, J = 7.8 Hz, 1H), 3.01 (t, J = 4.2 Hz, 4H), 4.44 (m, J = 7.5 Hz, 1H), 6.80 (d, J = 9.0 Hz, 3H), 6.98 (s, 1H), 7.39 (s, 1H), 7.52 (d, J = 8.4 Hz, 2H), 7.79 (d, J = 3.9 Hz, 1H), 8.76 (s, 1H); 19° F. NMR (282 MHz, DMSO-d6: d −169.58; LCMS: ret. time: 1.42 min.; purity: 99.92%; MS ( | ++ | ++ |
| 195 | 1H NMR (DMSO-d6): d 1.55 (m, 1H), 1.88 (m, 5H), 2.21 (s, 3H), 2.43 (m, 4H), 2.89 (q, J = 7.8 Hz, 1H), 3.07 (t, J = 4.8 Hz, 4H), 4.50 (m, J = 6.6 Hz, 1H), 6.45 (d, J = 8.1 Hz, 1H), 6.85 (d, J = 5.7 Hz, 1H), 6.97 (s, 1H), 7.01 (t, J = 7.8 Hz, 1H), 7.09 (d, J = 8.7 Hz, 1H), 7.40 (m, 2H), 7.84 (d, J = 3.6 Hz, 1H), 8.85 (s, 1H); 19° F. NMR (282 MHz, DMSO-d6): d −168.45; LCMS: ret. time: 1.43 min.; purity: 99.96%; MS (m/e): 414.22 (MH+). | ++ | ++ |
| 196 | 1H NMR (DMSO-d6): d 1.57 (m, 1H), 1.89 (m, 5H), 2.02 (s, 3H), 2.89 (q, J = 7.5 Hz, 1H), 2.96 (t, J = 5.1 Hz, 2H), 3.02 (t, 2H), 3.55 (m, 4H), 4.44 (m, 1H), 6.84 (d, J = 9.0 Hz, 3H), 6.97 (s, 1H), 7.38 (s, 1H), 7.55 (d, J = 9.3 Hz, 2H), 7.80 (d, J = 3.6 Hz, 1H), 8.79 (s, 1H); 19° F. NMR (282 MHz, DMSO-d6): d −169.17; LCMS: ret. time: 1.63 min.; purity: 93.76%; MS (m/e): 442.21 (MH+). | ++ | ++ |
| 197 | 1H NMR (DMSO-d6): d 1.55 (m, 1H), 1.88 (m, 5H), 2.03 (s, 3H), 2.90 (q, J = 7.5 Hz, 1H), 3.03 (t, J = 5.1 Hz, 2H), 3.09 (t, J = 4.8 Hz, 2H), 3.56 (t, 4H), 4.50 (m, J = 6.6 Hz, 1H), 6.49 (d, J = 7.8 Hz, 1H), 6.86 (d, J = 5.7 Hz, 1H), 6.98 (s, 1H), 7.04 (t, J = 8.1 Hz, 1H), 7.15 (d, J = 8.7 Hz, 1H), 7.40 (m, 2H), 7.84 (d, J = 3.6 Hz, 1H), 8.89 (s, 1H); 19° F. NMR (282 MHz, DMSO-d6): d −168.30; LCMS: ret. time: 1.54 min.; purity: 98.90%; MS (m/e): 442.22 (MH+). | + | ++ |
| 198 | 1H NMR (DMSO-d6): d 1.57 (m, 1H), 1.87 (m, 5H), 2.89 (q, J = 7.8 Hz, 1H), 2.99 (t, J = 4.8 Hz, 4H), 3.71 (t, J = 4.5 Hz, 4H), 4.44 (m, J = 6.6 Hz, 1H), 6.82 (d, J = 9.0 Hz, 3H), 6.98 (s, 1H), 7.38 (s, 1H), 7.54 (d, J = 9.0 Hz, 2H), 7.79 (d, J = 3.6 Hz, 1H), 8.77 (s, 1H); 19° F. NMR (282 MHz, DMSO-d6): d −169.26; LCMS: ret. time: 11.74 min.; purity: 98.31%; MS (m/e): 401.14 (MH+). | ++ | ++ |
| 199 | 1H NMR (DMSO-d6): d 1.19 (t, J = 6.9 Hz, 3H), 1.56 (m, 1H), 1.86 (m, 5H), 2.88 (q, J = 7.8 Hz, 1H), 2.98 (t, J = 5.1 Hz, 4H), 3.48 (t, J = 4.8 Hz, 4H), 4.04 (q, J = 6.9 Hz, 2H), 4.44 (m, J = 6.6 Hz, 1H), 6.80 (s, 1H), 6.84 (d, J = 9.0 Hz, 2H), 6.98 (s, 1H), 7.38 (s, 1H), 7.55 (d, J = 9.0 Hz, 2H), 7.80 (d, J = 3.6 Hz, 1H), 8.80 (s, 1H); 19° F. NMR (282 MHz, DMSO-d6): d −169.16; LCMS: ret. time: 15.87 min.; purity: 95.16%; MS (m/e): 472.14 (MH+). | ++ | ++ |
| 200 | 1H NMR (DMSO-d6): d 1.54 (m, 1H), 1.88 (m, 5H), 2.90 (q, J = 7.5 Hz, 1H), 3.05 (t, J = 4.8 Hz, 4H), 3.72 (t, J = 4.8 Hz, 4H), 4.49 (m, J = 6.9 Hz, 1H), 6.46 (dd, J = 2.4, 7.8 Hz, 1H), 6.86 (d, J = 6.0 Hz, 1H), 6.98 (s, 1H), 7.04 (t, J = 7.8 Hz, 1H), 7.13 (d, J = 8.7 Hz, 1H), 7.40 (m, 2H), 7.84 (d, J = 3.6 Hz, 1H), 8.88 (s, 1H); 19°F. NMR (282 MHz, DMSO-d6): d −168.35; LCMS: ret. time: 14.87 min.; purity 98.88%; MS (m/e): 400.87 (MH+). | ++ | + |
| 201 | 1H NMR (DMSO-d6): d 1.19 (t, J = 6.9 Hz, 3H), 1.54 (m, 1H), 1.88 (m, 5H), 2.90 (q, J = 7.5 Hz, 1H), 3.05 (t, J = 4.8 Hz, 4H), 3.49 (t, J = 4.8 Hz, 4H), 4.05 (q, J = 7.2 Hz, 2H), 4.50 (m, J = 6.9 Hz, 1H), 6.48 (dd, J = 1.5, 7.8 Hz, 1H), 6.86 (d, J = 5.4 Hz, 1H), 6.97 (s, 1H), 7.04 (t, J = 7.8 Hz, 1H), 7.13 (d, J = 9.0 Hz, 1H), 7.38 (s, 1H), 7.44 (t, J = 2.1 Hz, 1H), 7.84 (d, J = 3.6 Hz, 1H), 8.90 (s, 1H); 19° F. NMR (282 MHz, DMSO-d6): d −168.30; LCMS: ret. time: 15.57 min.; purity: 99.00%; MS (m/e): 472.22 (MH+). | ++ | + |

TABLE 1-continued

| | | | |
|---|---|---|---|
| 202 | 1H NMR (DMSO-d6): d 1.58 (m, 1H), 1.91 (m, 5H), 2.21 (s, 3H), 2.45 (m, 4H), 2.88 (t, 4H), 2.92 (q, J = 7.8 Hz, 1H), 4.44 (m, J = 6.6 Hz, 1H), 6.98 (m, 2H), 7.03 (d, J = 8.7 Hz, 1H), 7.39 (s, 1H), 7.43 (dd, J = 2.4, 8.7 Hz, 1H), 7.86 (d, J = 3.6 Hz, 1H), 8.04 (d, J = 2.7 Hz, 1H), 9.12 (br, 1H); 19° F. NMR (282 MHz, DMSO-d6): d −167.96; LCMS: ret. time: 8.87 min.; purity: 91.11%; MS (m/e): 448 (MH+). | ++ | ++ |
| 203 | | ++ | ++ |
| 15 | LCMS: purity: 94%; MS (m/e): 428 (MH+). | ++ | ++ |
| 204 | LCMS: ret. time: 12.17 min.; purity: 94.13%; MS (m/e): 482 (MH+). | ++ | + |
| 205 | LCMS: ret. time: 9.14 min.; purity: 91.57%; MS (m/e): 448 (MH+). | ++ | ++ |
| 206 | LCMS: ret. time: 5.84 min.; purity: 93.28%; MS (m/e): 427.92 (MH+). | ++ | ++ |
| 207 | LCMS: ret. time: 13.56 min.; purity: 91.36%; MS (m/e): 482 (MH+). | ++ | + |
| 15a | LCMS: purity: 91%; MS (m/e): 429 (MH+) | ++ | ++ |
| 208 | | + | + |
| 209 | | − | − |
| 15d | LCMS: purity: 91%; MS (m/e): 429 (MH+) | − | − |
| 15b | LCMS: purity: 95%; MS (m/e): 429 (MH+) | + | + |
| 210 | LCMS: ret. time: 13.50.; purity: 86.14%; MS (m/e): 457.23 (MH+). | + | + |
| 211 | | − | − |
| 15c | LCMS: purity: 93%; MS (m/e): 429 (MH+) | + | + |
| 212 | LCMS: ret. time: 8.68 min.; purity: 95.24%; MS (m/e): 330.19 (MH+). | + | + |
| 213 | LCMS: ret. time: 7.70 min.; purity: 95.96%; MS (m/e): 360.20 (MH+). | ++ | ++ |
| 214 | LCMS: purity: 82%; MS (m/e): 444 (MH+) | + | + |
| 215 | LCMS: purity: 92%; MS (m/e): 444 (MH+) | + | + |
| 216 | LCMS: purity: 92%; MS (m/e): 459 (MH+) | ++ | ++ |
| 217 | LCMS: purity: 92%; MS (m/e): 445 (MH+) | ++ | + |
| 218 | LCMS: purity: 99%; MS (m/e): 444 (MH+) | + | + |
| 219 | LCMS: purity: 86%; MS (m/e): 430 (MH+) | − | − |
| 220 | LCMS: purity: 74%; MS (m/e): 429 (MH+) | + | + |
| 221 | LCMS: purity: 94%; MS (m/e): 453 (MH+) | +++ | +++ |
| 222 | LCMS: purity: 87%; MS (m/e): 429 (MH+) | ++ | ++ |
| 223 | LCMS: purity: 98%; MS (m/e): 443 (MH+) | ++ | + |
| 224 | 1H NMR (DMSO-d6): δ 2.18 (s, 3H), 2.21 (s, 3H), 2.26-2.32 (m, 2H), 2.44 (m, 5H), 2.76 (t, J = 4.5 Hz, 4H), 2.81 (m, 2H), 4.38 (m, 1H), 5.63 (m, 2H), 6.63 (d, J = 6.3 Hz, 1H), 6.87 (d, J = 8.7 Hz, 1H), 7.02 (s, 1H), 7.32 (s, 1H), 7.37 (dd, J = 2.4, 8.4 Hz, 1H), 7.51 (d, J = 2.4 Hz, 1H), 7.84 (d, J = 3.6 Hz, 1H), 8.84 (br, 1H); 19° F. NMR (282 MHz, DMSO-d6): δ −168.84; LCMS: ret. time: 10.61 min.; LCMS: purity: 99.22%; MS (m/e): 440.12 (MH+) | + | + |
| 225 | LCMS: purity: 76.31%; MS (m/e): 426.35 (MH+) | ++ | ++ |
| 226 | LCMS: purity: 96.83%; MS (m/e): 426.30 (MH+) | + | + |
| 227 | 1H NMR (DMSO-d6): δ 1.73 (m, 1H), 2.03 (m, 2H), 2.18 (s, 3H), 2.21 (s, 3H), 2.44 (m, 6H), 2.76 (t, J = 4.5 Hz, 4H), 4.87 (m, 1H), 5.79 (m, 2H), 6.79 (d, J = 8.4 Hz, 1H), 6.89 (d, J = 8.4 Hz, 1H), 6.96 (s, 1H), 7.31 (s, 1H), 7.41 (dd, J = 2.4, 8.4 Hz, 1H), 7.48 (d, J = 2.7 Hz, 1H), 7.82 (d, J = 3.6 Hz, 1H), 8.80 (br, 1H); 19° F. NMR (282 MHz, DMSO-d6): δ −168.35; LCMS: purity: 93.08%; MS (m/e): 440.25 (MH+) | + | + |
| 228 | LCMS: purity: 98.89%; MS (m/e): 452 (MH+) | +++ | +++ |
| 229 | 1H NMR (DMSO-d6): δ 1.98 (m, 1H), 2.17 (s, 3H), 2.21 (s, 3H), 2.25 (m, 2H), 2.43 (m, 5H), 2.63 (m, 1H), 2.75 (t, J = 4.5 Hz, 4H), 4.36 (m, 1H), 5.64 (m, 2H), 6.84 (d, J = 8.7 Hz, 1H), 6.86 (s, 1H), 7.03 (d, J = 8.4 Hz, 1H), 7.04 (s, 1H), 7.26 (dd, J = 2.4, 8.4 Hz, 1H), 7.66 (d, J = 2.1 Hz, 1H), 7.79 (d, J = 3.9 Hz, 1H), 8.76 (br, 1H); 19° F. NMR (282 MHz, DMSO-d6): δ −168.02; LCMS: purity: 96.90%; MS (m/e): 440.06 (MH+) | − | − |
| 60r2 | LCMS: purity: 69.47%; MS (m/e): 452 (MH+) | ++ | ++ |
| 60a | LCMS: purity: 99.83%; MS (m/e): 452 (MH+) | +++ | +++ |
| 60b | LCMS: purity: 99.80%; MS (m/e): 452 (MH+) | + | + |
| 230 | 1H NMR (DMSO-d6): δ 1.40 (d, J = 8.4 Hz, 1H), 2.11 (d, J = 8.1 Hz, 1H), 2.21 (s, 3H), 2.44 (m, 5H), 2.80 (s, 1H), 2.87 (s, 1H), 3.03 (t, J = 4.8 Hz, 4H), 4.07 (m, 1H), 6.31 (m, 2H), 6.82 (d, J = 9.3 Hz, 2H), 7.20 (s, 1H), 7.39 (d, J = 5.4 Hz, 1H), 7.53 (d, J = 9.3 Hz, 2H), 7.72 (s, 1H), 7.82 (d, J = 3.6 Hz, 1H), 8.82 (br, 1H); 19° F. NMR (282 MHz, DMSO-d6): δ −209.32; LCMS: purity: 90.38%; MS (m/e): 438.24 (MH+) | +++ | +++ |
| 231 | LCMS: purity: 91.84%; MS (m/e): 438.06 (MH+) | +++ | +++ |
| 232 | 1H NMR (DMSO-d6): δ 1.01 (d, J = 6.3 Hz, 6H), 1.41 (d, J = 8.7 Hz, 1H), 2.12 (d, J = 8.4 Hz, 1H), 2.20 (s, 3H), 2.57 (m, 6H), 2.67 (m, 1H), 2.77 (m, 4H), 2.86 (s, 1H), 4.12 (m, 1H), 6.30 (m, 2H), 6.90 (d, J = 9.6 Hz, 1H), 7.19 (s, 1H), 7.37 (d, J = 8.1 Hz, 1H), 7.47 (m, 2H), 7.69 (s, 1H), 7.84 (d, J = 3.6 Hz, 1H), 8.86 (br, 1H); 19° F. NMR 282 MHz, DMSO-d6): δ −208.84; LCMS: purity: 97.87%; MS (m/e): 480.05 (MH+) | +++ | +++ |
| 233 | LCMS: purity: 96.33%; MS (m/e): 472.21 (MH+) | +++ | +++ |
| 234 | LCMS: purity: 98.34%; MS (m/e): 452.15 (MH+) | +++ | ++ |
| 235 | 1H NMR (DMSO-d6): δ 1.40 (d, J = 9.0 Hz, 1H), 2.13 (d, J = 8.4 Hz, 1H), 2.22 (s, 3H), 2.45 (m, 5H), 2.79 (t, J = 4.5 Hz, 5H), 2.86 (s, 1H), 3.30 (s, 3H), 4.10 (t, J = 7.8 Hz, 1H), 4.39 (s, 2H), 6.30 (m, 2H), 6.98 (d, J = 8.4 Hz, 1H), 7.19 (s, 1H), 7.38 (d, J = 7.8 Hz, 1H), 7.58 (dd, J = 2.7, 9.0 Hz, 2H), 7.70 (m, 2H), 7.85 (d, J = 3.6 Hz, 1H), 8.96 (br, 1H); 19° F. NMR (282 MHz, DMSO-d6): δ −208.59; LCMS: purity: 86.56%; MS (m/e): 482.05 (MH+) | +++ | +++ |
| 236 | LCMS: purity: 86.59%; MS (m/e): 468.02 (MH+) | +++ | +++ |
| 237 | 1H NMR (DMSO-d6): δ 2.18 (s, 3H), 2.22 (s, 3H), 2.36 (m, 2H), 2.44 (m, 4H), 2.71 (m, 2H), 2.76 (t, J = 4.5 Hz, 4H), 4.63 (q, J = 7.2 Hz, 1H), 5.74 (s, | ++ | + |

TABLE 1-continued

| # | Data | Col A | Col B |
|---|---|---|---|
| | 2H), 6.88 (d, J = 8.7 Hz, 1H), 7.42 (m, 2H), 7.57 (d, J = 2.4 Hz, 1H), 7.80 (d, J = 3.9 Hz, 1H), 8.79 (br, 1H); 19° F. NMR (282 MHz, DMSO-d6): δ −206.34; LCMS: purity: 92.23%; MS (m/e): 383.07 (MH+) | | |
| 238 | LCMS: purity: 79.55%; MS (m/e): 426.16 (MH+) | + | − |
| 239 | LCMS: purity: 86.34%; MS (m/e): 456.14 (MH+) | +++ | +++ |
| 240 | 1H NMR (DMSO-d6): δ 1.25 (m, 2H), 1.55 (m, 2H), 1.94 (d, J = 8.4 Hz, 1H), 2.20 (s, 3H), 2.22 (s, 3H), 2.28 (s, 2H), 2.45 (m, 4H), 2.60 (s, 1H), 2.62 (s, 1H), 2.76 (t, J = 4.5 Hz, 4H), 4.12 (t, J = 7.8 Hz, 1H), 6.88 (d, J = 8.4 Hz, 1H), 7.11 (s, 1H), 7.46 (m, 3H), 7.62 (s, 1H), 7.82 (d, J = 3.6 Hz, 1H), 8.84 (br, 1H); 19° F. NMR (282 MHz, DMSO-d6): δ −208.92; LCMS: purity: 87.88%; MS (m/e): 454.23 (MH+) | +++ | +++ |
| 241 | LCMS: purity: 83.54%; MS (m/e): 466.19 (MH+) | +++ | +++ |
| 242 | 1H NMR (DMSO-d6): δ 1.71 (m, 4H), 2.23 (s, 6H), 2.50 (m, 4H), 2.87 (m, 8H), 3.45 (s, 3H), 6.86 (d, J = 9.0 Hz, 1H), 7.30 (d, J = 9.0 Hz, 1H), 7.39 (s, 1H), 7.52 (s, 1H), 7.86 (d, J = 3.9 Hz, 1H), 8.74 (br, 1H); 19° F. NMR (282 MHz, DMSO-d6): δ −205.12; LCMS: purity: 86.63%; MS (m/e): 443.13 (MH+) | + | + |
| 243 | LCMS: purity: 97.00%; MS (m/e): 463.32 (MH+) | +++ | +++ |
| 244 | LCMS: purity: 64.55%; MS (m/e): 465.95 (MH+) | − | − |
| 245 | LCMS: purity: 79.37%; MS (m/e): 520.37 (MH+) | +++ | +++ |
| 246 | LCMS: purity: 95.44%; MS (m/e): 429.06 (MH+) | − | − |
| 247 | LCMS: purity: 97.47%; MS (m/e): 468.34 (MH+) | − | − |
| 248 | LCMS: purity: 94.24%; MS (m/e): 428.63 (MH+) | − | − |
| 249 | LCMS: purity: 76.81%; MS (m/e): 469.36 (MH+) | + | + |
| 250 | LCMS: purity: 98.66%; MS (m/e): 370.57 (MH+) | +++ | +++ |
| 251 | LCMS: purity: 96.69%; MS (m/e): 455.44 (MH+) | +++ | +++ |
| 252 | LCMS: purity: 96.67%; MS (m/e): 494.04 (MH+) | +++ | +++ |
| 253 | LCMS: purity: 61.04%; MS (m/e): 493.98 (MH+) | ++ | ++ |
| 254 | 1H NMR (DMSO-d6): δ 1.49 (d, J = 9.3 Hz, 1H), 2.23 (s, 3H), 2.28 (d, J = 9.6 Hz, 1H), 2.49 (m, 4H), 2.75-2.86 (m, 9H), 2.95 (s, 1H), 3.36 (s, 3H), 4.42 (t, J = 7.8 Hz, 1H), 6.26 (s, 2H), 6.97 (d, J = 7.5 Hz, 1H), 7.10 (d, J = 8.7 Hz, 1H), 7.70 (dd, J = 3.0, 8.7 Hz, 1H), 7.85 (d, J = 3.6 Hz, 1H), 8.15 (d, J = 2.7 Hz, 1H), 9.07 (br, 1H), 9.34 (d, J = 5.1 Hz, 1H); 19° F. NMR (282 MHz, DMSO-d6): δ −206.01; LCMS: purity: 96.25%; MS (m/e): 511.30 (MH+) | + | + |
| 255 | LCMS: purity: 94.35%; MS (m/e): 495.10 (MH+) | ++ | ++ |
| 256 | LCMS: purity: 83.00%; MS (m/e): 468.09 (MH+) | +++ | +++ |
| 257 | LCMS: purity: 95.23%; MS (m/e): 451.28 (MH+) | | |
| 258 | LCMS: purity: 91.37%; MS (m/e): 451.13 (MH+) | + | + |
| 259 | LCMS: purity: 86.81%; MS (m/e): 437.17 (MH+) | + | + |
| 260 | LCMS: purity: 76.75%; MS (m/e): 481.17 (MH+) | ++ | ++ |
| 261 | LCMS: purity: 88.67%; MS (m/e): 530.41 (MH+) | +++ | +++ |
| 262 | 1H NMR (DMSO-d6): δ 1.42 (m, 4H), 1.86-2.13 (m, 5H), 2.05 (s, 3H), 2.16 (s, 3H), 2.75 (m, 3H), 2.85 (s, 1H), 3.17 (m, 1H), 3.97 (d, J = 7.8 Hz, 1H), 4.09 (t, J = 8.7 Hz, 1H), 6.22 (m, 1H), 6.31 (m, 1H), 6.46 (d, J = 9.6 Hz, 1H), 7.18 (s, 1H), 7.25 (m, 3H), 7.66 (s, 1H), 7.78 (d, J = 3.6 Hz, 1H), 8.54 (br, 1H); 19° F. NMR (282 MHz, DMSO-d6): δ −209.98; LCMS: purity: 83.23%; MS (m/e): 466.03 (MH+) | +++ | +++ |
| 263 | 1H NMR (DMSO-d6): δ 1.42 (d, 1H), 2.16 (d, 1H), 2.40 (s, 3H), 2.78 (m, 1H), 2.86 (m, 2H), 3.26 (s, 2H), 3.50 (s, 2H), 3.64 (s, 3H), 3.79 (s, 3H), 4.16 (m, 1H), 6.25 (m, 1H), 6.33 (m, 1H), 7.17 (m, 1H), 7.35 (m, 2H), 7.44 (d, 1H), 7.67 (m, 1H), 7.88 (d, J = 3.3 Hz, 1H), 7.97 (d, J = 8.4 Hz, 1H), 9.04 (s, 1H), 9.33 (s, 1H); 19° F. NMR (282 MHz, DMSO-d6): δ −208.06; LCMS: purity: 70.02%; MS (m/e): 528.50 (MH+) | +++ | ++ |
| 264 | 1H NMR (DMSO-d6): δ 1.41 (d, J = 9.3 Hz, 1H), 1.77 (m, 2H), 1.89 (m, 2H), 2.11 (d, J = 8.7 Hz, 1H), 2.72-3.00 (m, 5H), 4.08 (t, J = 7.5 Hz, 1H), 6.28 (dd, J = 2.7, 5.4 Hz, 1H), 6.34 (dd, J = 3.0, 5.7 Hz, 1H), 7.07 (d, J = 8.7 Hz, 2H), 7.23 (s, 1H), 7.53 (d, J = 7.8 Hz, 1H), 7.66 (d, J = 8.4 Hz, 2H), 7.73 (s, 1H), 7.87 (d, J = 3.6 Hz, 1H), 8.33 (br, 1H), 8.56 (br, 1H), 9.09 (s, 1H); 19° F. NMR (282 MHz, DMSO-d6): δ −208.28; LCMS: purity: 85.27%; MS (m/e): 423.52 (MH+) | +++ | ++ |
| 265 | 1H NMR (DMSO-d6): δ 1.42 (d, 1H), 1.67 (m, 5H), 1.92 (m, 2H), 2.10 (d, J = 8.4 Hz, 1H), 2.17 (s, 3H), 2.36 (m, 2H), 2.81-2.87 (m, 3H), 4.08 (m, 1H), 6.31 (m, 2H), 7.07 (d, J = 8.4 Hz, 2H), 7.21 (s, 1H), 7.46 (d, 1H), 7.61 (d, J = 8.4 Hz, 2H), 7.73 (s, 1H), 7.85 (d, J = 3.3 Hz, 1H), 9.00 (s, 1H); 19° F. NMR (282 MHz, DMSO-d6): δ −208.59; LCMS: purity: 80.17%; MS (m/e): 437.15 (MH+) | +++ | +++ |
| 266 | LCMS: purity: 88.11%; MS (m/e): 496.24 (MH+) | ++ | ++ |
| 267 | 1H NMR (DMSO-d6): δ 1.41 (d, J = 9.6 Hz, 1H), 1.78 (m, 2H), 1.89 (m, 2H), 2.12 (d, J = 8.7 Hz, 1H), 2.72-3.01 (m, 5H), 3.36 (m, 3H), 4.12 (t, J = 7.5 Hz, 1H), 6.26 (dd, J = 3.0, 8.1 Hz, 1H), 6.33 (dd, J = 2.7, 5.7 Hz, 1H), 6.75 (d, J = 7.8 Hz, 1H), 7.20 (m, 3H), 7.43 (s, 1H), 7.61 (m, 1H), 7.69 (m, 1H), 7.90 (d, J = 3.6 Hz, 1H), 8.65 (br, 1H), 9.20 (s, 1H); 19° F. NMR (282 MHz, DMSO-d6): δ −207.57; LCMS: purity: 93.52%; MS (m/e): 423.25 (MH+) | +++ | +++ |
| 268 | LCMS: purity: 80.24%; MS (m/e): 437.06 (MH+) | +++ | +++ |
| 269 | LCMS: purity: 92.11%; MS (m/e): 530.59 (MH+) | +++ | +++ |
| 270 | LCMS: purity: 85.03%; MS (m/e): 530.14 (MH+) | + | + |
| 271 | LCMS: purity: 93.55%; MS (m/e): 466.71 (MH+) | + | + |
| 272 | LCMS: purity: 93.05%; MS (m/e): 466.28 (MH+) | +++ | +++ |
| 273 | LCMS: purity: 90.63%; MS (m/e): 423.17 (MH+) | +++ | ++ |
| 274 | LCMS: purity: 95.60%; MS (m/e): 423.26 (MH+) | +++ | +++ |
| 275 | LCMS: purity: 90.25%; MS (m/e): 437.26 (MH+) | +++ | +++ |
| 276 | LCMS: purity: 86.74%; MS (m/e): 465.99 (MH+) | +++ | +++ |

TABLE 1-continued

| # | Data | Col3 | Col4 |
|---|---|---|---|
| 277 | LCMS: purity: 97.45%; MS (m/e): 370.11 (MH+) | +++ | +++ |
| 278 | 1H NMR (DMSO-d6): δ 8.928 (s, 1H), 7.83-7.82 (d, J = 3.6 Hz, 1H), 7.61-7.58 (d, J = 8.7 Hz, 1H), 7.37 (s, 1H), 7.03-7.00 (d, J = 8.4 Hz, 1H), 6.97 (s, 1H), 6.87-6.85 (bd, J = 5.7 Hz, 1H), 4.05-3.98 (m, 1H), 3.42 (m, 2H), 3.37 (m, 2H), 2.94-2.86 (m, 1H), 2.29-2.22 (m, 1H), 2.16 (s, 3H), 1.92-1.83 (m, 2H), 1.81-1.71 (m, 2H), 1.59-1.50 (m, 1H); LCMS: purity: 94% MS (m/e): 484 (MH+) | + | + |
| 279 | 1H NMR (DMSO-d6): δ 8.99 (s, 1H), 7.85-7.83 (dd, J = 4.8 Hz, 1H), 7.63-7.60 (d, J = 7.8 Hz, 1H), 7.38 (s, 1H), 7.06-7.03 (d, J = 8.7 Hz, 1H), 6.97 (s, 1H), 6.89-6.87 (d, J = 6.9 Hz, 1H), 4.48-4.43 (m, 1H), 3.59 (s, 1H), 3.45-3.41 (m, 2H), 2.92 (m, 1H) 2.20-2.14 (m, 4H), 2.12 (s, 3H), 1.95-1.75 (m, 4H); LCMS: purity: 94% MS (m/e): 456 (MH+) | + | + |
| 280 | 1H NMR (DMSO-d6): δ 8.92 (s, 1H), 7.83-7.82 (d, J = 3.6 Hz, 1H), 7.59-7.56 (d, J = 8.7 Hz, 1H), 7.38 (s, 1H), 7.06-7.03 (d, J = 8.4 Hz, 1H), 6.98 (s, 1H), 6.87-6.85 (d, J = 6.3 Hz, 1H), 6.84-6.81 (d, J = 8.1 Hz, 1H), 6.45-6.42 (d, J = 8.4 Hz, 1H), 4.47-4.42 (m, 1H), 3.40-3.34 (m, 4H) 2.92-2.86 (m, 1H), 2.73-2.68 (t, 1H, 2.59-2.52 (m, 1H), 2.20-2.17 (m, 2H), 2.13 (s, 3H), 1.96-1.76 (m, 2H), 1.57-1.53 (m, 2H); LCMS: purity: 100% MS (m/e): 470 (MH+) | + | + |
| 281 | 1H NMR (DMSO-d6): δ 9.28 (s, 1H), 7.88-7.87 (d, J = 3.3 Hz, 1H), 7.38 (s, 1H), 7.27-7.24 (d, J = 8.4 Hz, 1H), 6.99-6.97 (d, J = 7.8 Hz, 1H), 4.49-4.45 (m, 1H), 3.46 (bs, 4H), 3.15 (s, 4H), 2.94-2.87 (m, 1H), 2.29 (bs, 2H), 2.17 (s, 3H), 1.96-1.86 (m, 4H); LCMS: purity: 94.32% MS (m/e): 442 (MH+) | + | + |
| 282 | 1H NMR (DMSO-d6): δ 8.66 (s, 1H), 7.78-7.77 (d, J = 3.6 Hz, 1H), 7.46 (s, 1H), 7.36 (s, 1H), 7.28-7.25 (d, J = 9.0 Hz, 1H) 6.96 (s, 1H), 6.78-6.76 (d, J = 6.3 Hz, 1H), 6.67-6.65 (d, J = 8.4 Hz, 1H), 4.44 (m, 1H), 3.83 (s, 1H), 2.91-2.89 (m, 2H), 2.70-2.62 (m, 3H), 2.26 (s, 3H), 2.15 (s, 3H), 1.87 (bs, 6H), 1.77-1.75 (d, J = 7.8 Hz, 1H), 1.68-1.65 (d, J = 8.7 Hz, 1H); LCMS: purity: 95.60% MS (m/e): 440 (MH+) | ++ | ++ |
| 283 | 1H NMR (DMSO-d6): δ 8.82 (s, 1H), 7.82-7.81 (d, J = 3.3 Hz, 1H), 7.57-7.56 (d, J = 2.4 Hz, 1H), 7.42-7.38 (dd, J = 6.3 Hz, 2H), 6.97 (s, 1H), 6.88-6.85 (d, J = 9 Hz, 2H), 4.47-4.43 (m, 1H), 3.72-3.67 (m, 1H), 2.92-2.89 (m, 1H), 2.84-2.80 (d, J = 10.2 Hz, 2H), 2.30-2.23 (m, 2H), 2.20 (s, 3H), 1.95-1.75 (m, 5H), 1.57-1.53 (m, 1H), 1.10 (s, 3H), 1.08 (s, 3H); LCMS: purity: 92.59% MS (m/e): 443 (MH+) | ++ | ++ |
| 284 | 1H NMR (DMSO-d6): δ 8.85 (s, 1H), 7.84-7.83 (d, J = 3.6 Hz, 1H), 7.67 (s, 1H), 7.46 (s, 2H), 7.38-7.35 (d, J = 8.1 Hz, 1H), 7.17 (s, 1H), 6.88-6.85 (d, J = 9.3 Hz, 1H), 6.32-6.27 (d, J = 11.1 Hz, 2H), 4.13-4.08 (m, 1H), 3.70-3.67 (m, 2H), 2.84 (s, 2H), 2.80-2.77 (d, J = 9.6 Hz, 2H), 2.31-2.24 (m, 2H), 2.20 (s, 3H), 2.10-2.06 (d, J = 12.9 Hz, 1H), 2.05 (s, 3H), 1.41-1.38 (d, J = 9.3 Hz, 1H), 1.106 (s, 3H), 1.08 (s, 3H); LCMS: purity: 98.27% (m/e): 467 (MH+) | +++ | +++ |
| 285 | 1H NMR (DMSO-d6): δ 8.73 (s, 1H) 7.81-7.80 (d, J = 3.6 Hz, 1H), 7.67 (s, 1H), 7.39 (m, 1H), 7.36-7.31 (m, 2H), 7.18 (s, 2H), 6.71-6.68 (d, J = 8.4 Hz, 1H), 6.30 (m, 2H), 6.26 (m, 1H), 4.12-4.07 (m, 1H), 3.88 (s, 2H), 3.49 (m, 2H), 3.24-3.17 (m, 2H), 2.85 (s, 1H), 2.77 (bs, 2H), 2.37 (bs, 2H), 2.15 (s, 3H), 1.83 (m, 1H), 1.76 (m, 1H), 1.41-1.38 (d, J = 9 Hz, 1H), 1.23 (bs, 1H); LCMS: purity: 96.89% (m/e): 478 (MH+) | +++ | +++ |
| 286 | 1H NMR (DMSO-d6): δ 8.79 (s, 1H), 7.80 (s, 1H), 7.51 (s, 1H), 7.46 (s, 1H), 7.41-7.38 (d, J = 8.4 Hz, 2H), 7.25-7.23 (d, J = 8.1 Hz, 2H), 6.97 (s, 2H), 6.88-6.86 (d, J = 8.7 Hz, 2H), 5.07 (s, 1H), 3.38 (bs, 2H), 2.75 (m, 4H), 2.23 (s, 3H), 2.16 (s, 3H), 1.89 (s, 2H); LCMS: purity: 95.49% (m/e): 426 (MH+) | ++ | ++ |
| 287 | 1H NMR (DMSO-d6): δ 8.71 (s, 1H), 7.80-7.79 (d, J = 3.9 Hz, 1H), 7.49 (s, 1H), 7.37 (s, 1H), 7.34-7.30 (dd, J = 6.6 Hz, 1H), 6.96 (s, 1H), 6.80-6.77 (d, J = 8.4 Hz, 2H), 4.47-4.42 (m, 1H), 2.98 (bs, 4H), 2.92-2.87 (m, 1H), 2.19 (s, 3H), 1.95-1.85 (m, 10H), 1.59-1.53 (m, 1H); LCMS: purity: 90.98% (m/e): 399 (M+) | + | + |
| 288 | 1H NMR (DMSO-d6): δ 8.75 (s, 1H), 7.82-7.81 (d, J = 3.6 Hz, 1H), 7.66 (s, 1H), 7.39 (s, 2H), 7.33-7.31 (d, J = 7.8 Hz, 2H), 7.17 (s, 1H), 6.80-6.77 (d, J = 9.6 Hz, 1H), 6.34-6.23 (d, J = 14.1 Hz, 2H), 4.13-4.08 (m, 1H), 2.99 (bs, 4H), 2.85 (s, 1H), 2.77 (s, 1H), 2.19 (s, 3H), 2.13-2.10 (d, J = 8.7 Hz, 1H), 1.84 (bs, 4H), 1.41-1.38 (d, J = 8.1 Hz, 1H); LCMS: purity: 96.70% (m/e): 423 (M+) | ++ | ++ |

Cis racemic Compound 15, (1S,2R) enantiomeric Compound 15a and (1R,2R) enantiomeric Compound 15b were also tested against DU145 (prostate carcinoma), HCT116 (colorectal carcinoma) and MiaPaCa-2 (pancreatic carcinoma) cell lines. The racemate (Compound 15) and the (1S,2R) enantiomer (Compound 15a) exhibited $IC_{50}$s of <1 µM against these cell lines. The (1R,2R) enantiomer (Compound 15b) exhibited $IC_{50}$s of <5 µM.

Certain compounds were tested against other cell types for their ability to inhibit proliferation in standard antiproliferation assays. The various cells lines tested included: A549 (lung carcinoma); ASPC-1 (pancreatic adenocarcinoma); BXPC-3 (pabcreatic adenocarcinoma); CaOV-3 (ovarian adenocarcinoma); COLO 205 (colorectal adenocarcinoma); DU145 (prostate carcinoma); ES-2 (ovarian clear cell carcinoma); H1299 (non-small cell lung carcinoma); H1155 (non-small cell lung carcinoma); H460 (large cell lung carcinoma); HELA (cervical adenocarcinoma); HL160 (promyeloblast promyelocytic leukemia); K562 (bone marrow chronic myelogenous leukemia); L1210 (mouse lymphocytic leukemia); MiaPaCa-2 (pancreatic carcinoma); MOLT4 (T lymphoblast acute lymphoblastic leukemia); OVCAR-3 (ovarian adenocarcinoma); MOLT3 (T lymphoblast acute lymphoblastic leukemia); OVCAR-8 (ovarian carcinoma); PC3 (prostate adenocarcinoma); SK-OV-3 (ovarian adenocarcinoma); SU86.86 (pancreatic carcinoma); SW620 (colorectal adenocarcinoma); THP-1 (monocyte acute monocytic leukemia); TOV-21G (ovarian clear cell carcinoma); U20S (bone osteosarcoma); and U937 (histiocytic lymphoma).

The IC$_{50}$ values obtained with racemate 60 and its bis HCl salt (Compound 228; racdemate R3), racemate 60r2, diasteromer 60a and its bis HCl salt (Compound 234; enantiomer E3), and diastereomer 60b are provided in TABLE 2, below. In TABLE 2, a "+" indicates an IC$_{50}$ value of ≤1 μM, a "++" indicates an IC$_{50}$ value of ≤20 nM, "+++" indicates an IC$_{50}$ value of ≤10 nM, and a "–" indicates an IC$_{50}$ value of >1 μM. A blank indicates that the compound was not tested against the specific cell line.

TABLE 2

In Vitro IC$_{50}$ Values of Selected Compounds

| | 60 | 228 | 60a | 60b | 234 | 60r2 | 221 | 222 | 206 |
|---|---|---|---|---|---|---|---|---|---|
| A549 | ++ | + | +++ | -- | +++ | + | +++ | + | + |
| ASPC1 | ++ | | +++ | | | | ++ | | |
| BxPC-3 | | | +++ | | | | | | |
| CaOV-3 | | | +++ | | | | | | |
| Colo205 | +++ | | +++ | -- | +++ | | +++ | + | |
| DU145 | ++ | | ++ | + | + | | +++ | | |
| ES-2 | | | | | | | | | |
| H1299 | | + | +++ | -- | + | | ++ | + | |
| H1155 | +++ | | +++ | | | | | | |
| H460 | | | | | +++ | | | | |
| H7299 | ++ | + | ++ | -- | + | + | | | |
| HELA | +++ | | +++ | -- | +++ | | +++ | | |
| HL160 | +++ | | +++ | -- | | | +++ | + | |
| K562 | + | | + | -- | | | + | -- | |
| L1210 | + | | ++ | -- | | | + | + | |
| Miapaca2 | +++ | | +++ | -- | +++ | | +++ | + | |
| MOLT3 | +++ | | +++ | -- | | | +++ | + | |
| MOLT4 | +++ | | +++ | -- | | | +++ | + | |
| OVCAR-3 | | | | | | | | | |
| OVCAR-8 | | | | | | | | | |
| PC3 | ++ | | +++ | -- | | | | | |
| SKOV3 | | | ++ | | | | | | |
| Su86.86 | | | ++ | | | | | | |
| SW620 | + | | ++ | -- | | | ++ | + | |
| THP-1 | + | | + | + | | | ++ | + | |
| TOV-G21 | | | +++ | | | | | | |
| U20S | ++ | | +++ | + | | | ++ | | |
| U937 | | | +++ | -- | | | +++ | + | |

7.17 Inhibition of Aurora Kinases in Functional Cellular Assays

Enantiomers E1 and E2 (Compounds 60a and 60b, respectively) were tested for their ability to inhibit Aurora kinase-B in a functional cellular assay involving phosphorylation of its substrate, histone H3. For the assay, A549 cells were seeded into the wells of a microtiter tray (5000 cells/well in 100 μl F12K media) late in the afternoon on Day 1. The cells were grown overnight (37° C., 5% CO$_2$). On Day 2, 50 μl nocodazole (1 μM in media) was added to each well, giving a final concentration of 333 nM. Cells were grown for an additional 18 hrs under the same conditions.

On Day 3, 50 μl aliquots of varying concentrations of test compound were added to the wells. Test compounds were prepared by 2-fold serial dilution of a 2 mM stock (in DMSO). The diluted compounds in DMSO were then further diluted 1:50 with media to yield a final solution containing 4× test compound, 98% media, 2% DMSO. After incubation, the media/test compound was washed and the cells fixed with 2% para-formaldehyde (in Dulbecco's phosphate buffered saline "DPBS"; 25 μl per well; >20 min incubation). The fixed cells were washed once with DPBS (200 μl/well), stained with phospho-Histone H3 (Cell Signaling Technology; 1:500 in DPBS, 10% normal goat serum "NGS", 0.05% Triton X-100; 1-2 hrs at room temperature), and washed twice with DPBS (200 μl/well). The cells were then stained with a secondary antibody labeled with a fluorescent dye (secondary antibody donkey anti-mouse AlexFluor 488 (Invitrogen Molecular Probes; 1:2000) and DAPI (1:15,000 of 1 mg/ml stock) for 1 hr at room temperature, washed three times with DPBS (200 μl/well) and stored under DPBS (100 μl/well) at 4° C. until ready for analysis.

A Zeiss Axiovert S100 inverted fluorescent microscope with a Plan-NEOFLUAR 10× objective, a Hamamatsu Lightningcure 200 Mercury-Xenon light source and an Omega Optical XF57 quad filter was used for all data collection. The system was equipped with a Ludl Mac2000 motorized stage with X/Y/Z control, a Ludl filter wheel, a Zymark Twister robot arm and a Quantix digital camera from Roper Scientific. All hardware was controlled with ImagePro 4.5 with the ScopePro/StagePro 4.1 module (Media Cybernetics) on a PC running Win2000. Visual Basic Scripts were written for ImagePro to automate hardware control and image collection. Focusing was performed with a software auto-focus routine contained with StagePro that used the maximum local contrast to determine the best plane of focus from a Z series captured once in each well. Once proper focus was achieved images were captured in a 3×3 grid pattern of adjacent images next to, but not including, the position of focusing. Images were captured and analyzed in 12-bit format using segmentation and morphological routines contained in the Image Pro software package. Identified nuclei were counted and pixel data for each cell along with experimental conditions was stored in a database using MySQL 4.0.14. Subsequent analysis of experimental results and graph creation was done using Matlab 6.5.

For phospho-histone H3 analysis the data is converted to Facs files and analysed using FlowJo. The percent Phospho-H3 cells are plotted at each compound concentration to determine an EC50 for Aurora B inhibition.

Results. The enantiomer E1 (Compound 60a) inhibited Aurora kinase-B with an IC$_{50}$ of about 7 nM in this assay. By contrast, the IC$_{50}$ of the enantiomer E2 (Compound 60b) was 2.49 µM, approx. 350 times greater.

7.18 Compound 60a Shrinks Tumors In Vivo

The ability of the bis HCl salt of Compound 60a (enantiomer E3; Compound 234) was tested for its ability to shrink A549 and Colo205 tumors in a standard xenograft therapeutic model in SCID mice, and Colo205 and MiaPaCa tumors in a standard xenograph regression model in SCID mice. When palpable tumors appeared and were of a pre-selected volume (approx. 100 mm3 for treatment model; >300 mm3 for regression model), the mice were administered test compounds in the amounts and according to the dosing regimens specified in TABLE 3 (treatment protocol) and TABLE 4 (regression protocol), below.

TABLE 3

Summary of Treatment Model Experiments (Mean tumor size 100 mm³)

| Cell Line | Dose (mg/kg/day) | Schedule (day on/day off) | Route |
|---|---|---|---|
| Colo205 | 2 | 4/3 | oral |
| Colo205 | 10 | 4/3 | oral |
| Colo205 | 10 | 2/1 | oral |
| Colo205 | 10 | 5/2 | oral |
| Colo205 | 10 | 7/7 | oral |
| Colo205 | 10 | 3/11 | oral |
| Colo205 | 10 | 1/6 | oral |
| Colo205 | 10 | daily | oral |
| A549 | 10 | 5/2 | oral |
| A549 | 10 | 2/1 | oral |
| A549 | 10 | 7/7 | oral |
| A549 | 10 | daily (13 days) | i.p. |
| A549 | 20 | daily (5 days) | i.p. |

TABLE 4

Summary of Progression Model Experiments (Mean tumor size > 300 mm³)

| Cell Line | Dose (mg/kg/day) | Schedule | Route |
|---|---|---|---|
| Colo205 | 10 | daily (13 days) | oral |
| MiaPaCa | 10 | daily (3 cycles) | oral |
| MiaPaCa | 10 | daily (3 cycles) | i.p. |

Figure 2:
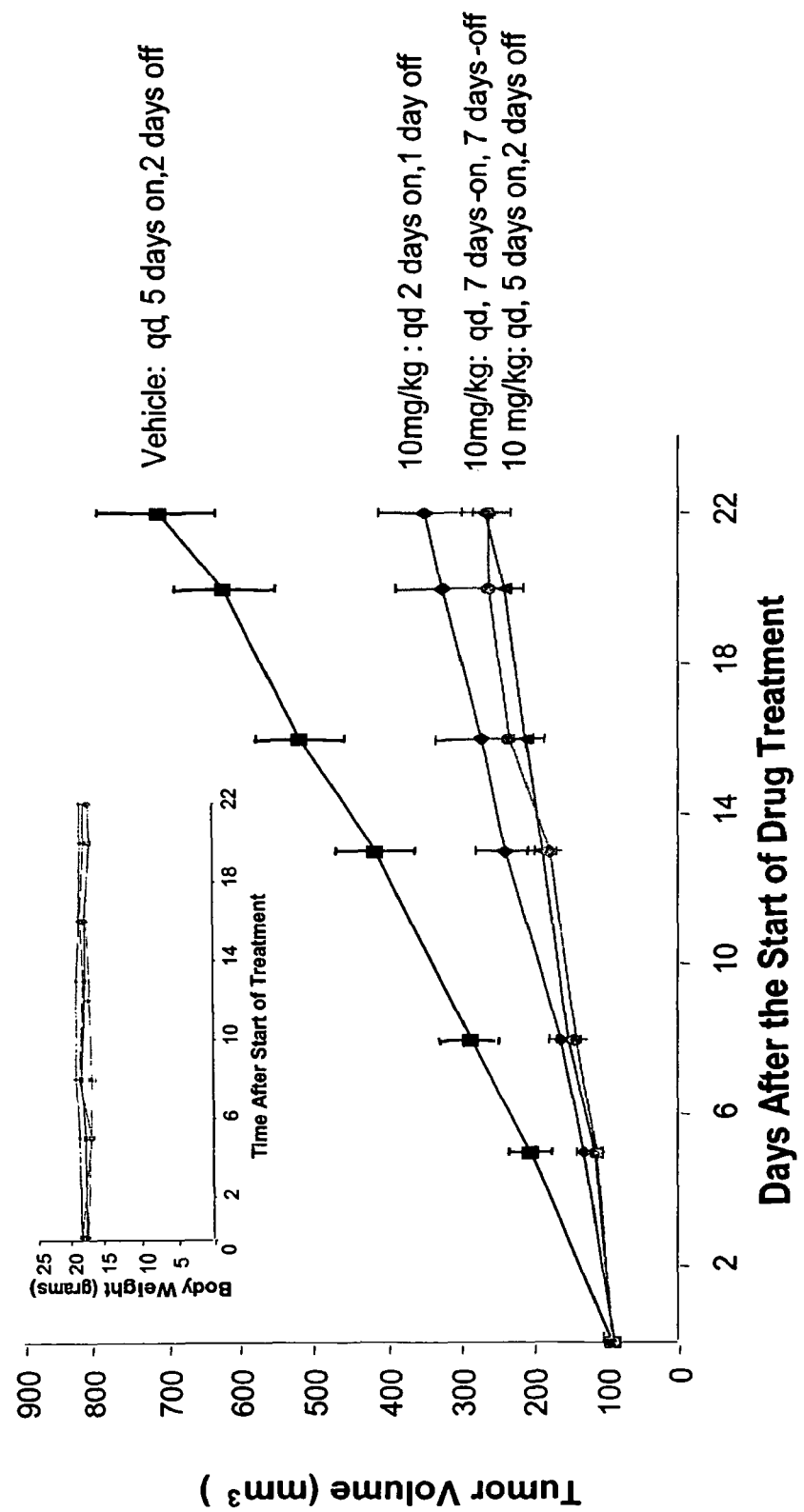

Results. The inhibitory effects of Compound 234 on Colo205 tumor growth in the treatment model are illustrated in FIGS. 1 and 2. The results of the daily dosing regimen are illustrated in FIG. 1; the results of the pulsed dosing regimens in FIG. 2. Both dosing regimens yielded significant (p<0.050) reductions in tumor growth rate as compared to a vehicle control for all dosage levels tested. A 549 tumors were less responsive to treatment resulting in an approximate 40% reduction in mean tumor volume following a dosing regimen of 5 days on/2 days off and a dose level of 10 mg/kg qd (p>0.05).

Figure 3:
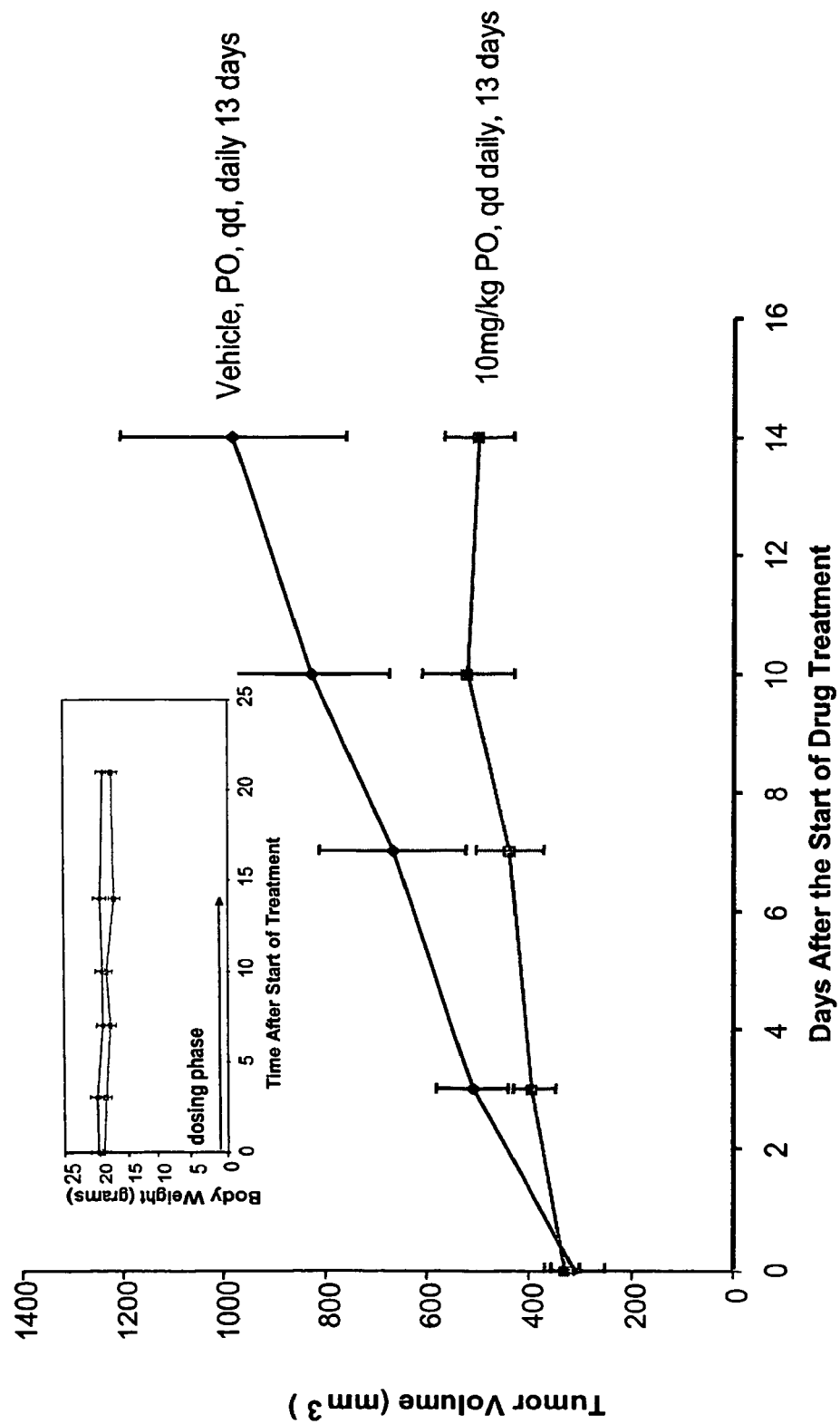
Figure 4:
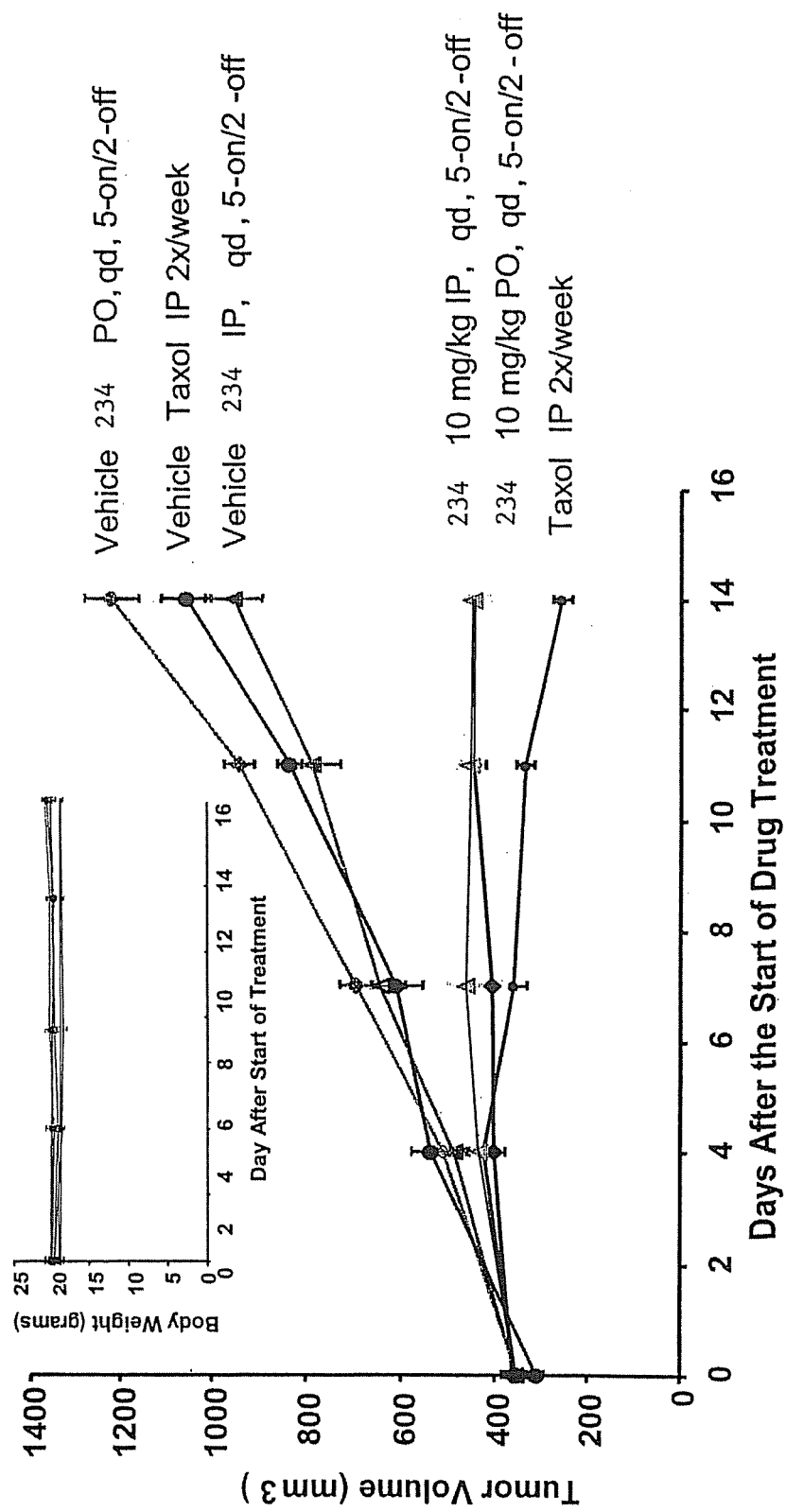

The inhibitory effects of Compound 234 on Colo205 tumor growth in the regression model are illustrated in FIG. 3. The effects of Compound 234 on MiaPaCa tumors in the regression model are illustrated in FIG. 4. Significant reductions in tumor growth rate were observed with both tumor lines. These reductions were independent of the mode of administration. Moreover, the reductions observed in MiaPaCa tumors were similar to those observed with taxol (see FIG. 4).

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated into the application by reference for all purposes.

What is claimed is:

1. A method of inhibiting an Aurora kinase in a cell, the method comprising contacting the cell with an effective amount of a compound according to structural formula (I):

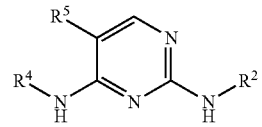

or an active salt or N-oxide thereof, wherein:
$R^2$ is an optionally substituted heteroaryl, or heteroarylalkyl group;
$R^4$ is a saturated or unsaturated, bridged or unbridged cycloalkyl ring including an $R^7$ substituent, with the proviso that when the cycloalkyl ring is a saturated bridged cycloalkyl, or an unsaturated bridged or unbridged cycloalkyl, this $R^7$ substituent is optional;
$R^5$ is selected from hydrogen, an optionally substituted lower alkyl and a group selected from the group consisting of —CN, —NC, —NO$_2$, halo, (C1-C3) haloalkyl, (C1-C3) perhaloalkyl, (C1-C3) fluoroalkyl, (C1-C3) perfluoroalkyl, —CF$_3$, (C1-C3) haloalkoxy, (C1-C3) perhaloalkoxy, (C1-C3) fluoroalkoxy, (C1-C3) perfluoroalkoxy, —OCF$_3$, OC(O)R$^a$, —C(O)OR$^a$, —C(O)CF$_3$, and —C(O)CF$_3$;
$R^7$ is an amide or an ester group,
wherein each R$^a$ is independently selected from hydrogen, lower alkyl, lower cycloalkyl, (C6-C14) aryl, phenyl, naphthyl, (C7-C20) arylalkyl and benzyl.

2. The method according to claim 1 wherein the cell is a human cancer cell.

3. The method according to claim 2 wherein the cell is a breast, colon, renal, cervical, neuroblastomer, melanoma, pancreatic, prostate, or other type of solid tumor.

* * * * *